(12) United States Patent
Dooley et al.

(10) Patent No.: US 7,138,542 B2
(45) Date of Patent: Nov. 21, 2006

(54) METHOD OF TREATING TINNITUS

(75) Inventors: David James Dooley, South Lyon, MI (US); David Juergen Wustrow, Ann Arbor, MI (US)

(73) Assignee: Warner Lambert Company, Morris Plains, NJ (US)

( * ) Notice: Subject to any disclaimer, the term of this patent is extended or adjusted under 35 U.S.C. 154(b) by 0 days.

(21) Appl. No.: 11/314,126

(22) Filed: Dec. 21, 2005

(65) Prior Publication Data

US 2006/0100281 A1    May 11, 2006

Related U.S. Application Data

(62) Division of application No. 10/353,367, filed on Jan. 29, 2003.

(60) Provisional application No. 60/353,632, filed on Jan. 31, 2002.

(51) Int. Cl.
| C07C 61/06 | (2006.01) |
| C07C 61/08 | (2006.01) |
| C07C 53/126 | (2006.01) |
| C07C 53/134 | (2006.01) |
| C07C 53/136 | (2006.01) |
| A61K 31/131 | (2006.01) |

(52) U.S. Cl. .................. 562/400; 562/507; 562/512; 514/561; 514/568

(58) Field of Classification Search ............... 562/400, 562/507, 512; 514/561, 568
See application file for complete search history.

(56) References Cited

U.S. PATENT DOCUMENTS

| 4,024,175 A | 5/1977 | Satzinger et al. ........ 260/468 J |
| 4,087,544 A | 5/1978 | Satzinger et al. ........... 424/305 |
| 5,563,175 A | 10/1996 | Silverman et al. .......... 514/561 |
| 6,316,638 B1 | 11/2001 | Bryans et al. .............. 548/408 |
| 2002/0072533 A1* | 6/2002 | Schrier et al. .............. 514/364 |

FOREIGN PATENT DOCUMENTS

| GB | 2 342 043 | 4/2000 |
| WO | WO 98/17627 | 4/1998 |
| WO | WO 99/31057 | 6/1999 |
| WO | WO 99/31074 | 6/1999 |
| WO | WO 99/31075 | 6/1999 |
| WO | WO 99/61424 | 12/1999 |
| WO | WO 00/76958 | 12/2000 |
| WO | WO 01/28978 | 4/2001 |

OTHER PUBLICATIONS

PCT International Search Report, PCT/IB03/00232.
Zapp, "Gabapentin for the treatment of tinnitus: A case report", Database accession No. EMB-2001-077211, abstract.
Szczepaniak and Moller, Hearing Research, 97 (1996) 46-53.
Menkes and Larson, J. Neurol. Neurosurg. Psychiatry, 1998; 65:803.
Shulman et al., "Benzodiazepine receptor deficiency and tinnitus", Database accession No. EMB-2001-049123, abstract.
Gee et al., "The Novel Anticonvulsant Drug, Gabapentin (Neurontin), Binds to the alpha2delta Subunit of a Calcium Channel", J. Biol. Chem., 271(10):5768-5776, 1996.
C. A. Bauer, et al., "Assessing Tinnitus and Prospective Tinnitus Therapeutics Using a Psychophysical Animal Model", Journal of the Association for Research in Otalaryngolgy, 2001, 2/1:054-064.
N. S. Gee et al., "The Novel Anticonvulsant Drug, Gabapentin (Neurontin), Bi9nds to the alpha2delta Subunit of a Calcium Channel", Journal of Biological Chemistry, 1996, 271, 5879-5776.

* cited by examiner

*Primary Examiner*—Elvis O. Price
(74) *Attorney, Agent, or Firm*—Charles W. Ashbrook; David R. Kurlandsky; Paul M. Misiak

(57) ABSTRACT

The invention relates to a method of treating tinnitus by administering an alpha2delta ligand such as, for example, a compound of Formula

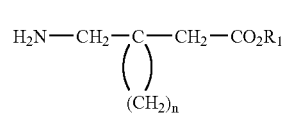

I and pharmaceutically acceptable salts thereof, wherein $R_1$ is hydrogen or straight or branched lower alkyl, and n is an integer of from 4 to 6.

2 Claims, No Drawings

METHOD OF TREATING TINNITUS

This application is a Divisional application of U.S. Ser. No. 10/353,367, filed Jan. 29, 2003 which claims benefit of U.S. Provisional Application 60/353,632 filed Jan. 31, 2002; under 35 USC 119(e)(i), which is hereby incorporated herein by reference.

This invention relates to a method of preventing or treating tinnitus by administering a compound that exhibits activity as an alpha2delta ligand ($\alpha2\delta$ ligand). These compounds have affinity for the $\alpha2\delta$ subunit of a calcium channel. Such compounds have also been referred to in the literature as gamma-aminobutyric acid (GABA) analogs.

BACKGROUND OF THE INVENTION

Tinnitus is a medical disorder affecting between 10 and 13 percent of the population. Thus, approximately 36 million Americans and 40 million Europeans suffer from this disorder. Tinnitus can be defined as the sensation of sound perceived in the head or the ear without an evident external stimulus. It is subjective in nature and is a manifestation of malfunction in the processing of auditory signals involving both perceptual and psychological components.

Tinnitus can be triggered anywhere along the auditory pathway. The emergence of persistent annoying tinnitus is usually considered to have psychological components. Tinnitus can be associated with any form of sensorineural hearing impairment, especially difficulty in hearing, ageing and exposure to noise. Middle ear surgery, myringoplasty, chronic supporative otitis media and otosclerosis can all give rise to conductive hearing impairment and tinnitus.

Several alpha2delta ligands are known. Gabapentin, a cyclic alpha2delta ligand, is now commercially available (Neurontin®, Warner-Lambert Company) and extensively used clinically for treatment of epilepsy and neuropathic pain. Such cyclic alpha2delta ligands are described in U.S. Pat. No. 4,024,175 and its divisional U.S. Pat. No. 4,087,544. Other series of alpha2delta ligands are described in U.S. Pat. No. 5,563,175 and U.S. Pat. No. 6,316,638. these patents are incorporated herein by reference in their entirties.

SUMMARY OF THE INVENTION

This invention provides a method of preventing or treating tinnitus in a mammal suffering therefrom, comprising administering a therapeutically effective amount of an alpha2delta ligand or a pharmaceutically acceptable salt thereof.

A preferred embodiment of the invention method utilizes an alpha2delta ligand that is a cyclic amino acid compound of Formula I

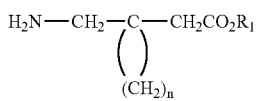

wherein $R_1$ is hydrogen or lower alkyl and n is an integer of from 4 to 6, and the pharmaceutically acceptable salts thereof. An especially preferred embodiment utilizes a compound of Formula I where $R_1$ is hydrogen and n is 5, which compound is 1-(aminomethyl)-cyclohexane acetic acid, known generically as gabapentin. Other preferred Alpha2delta ligands, or a pharmaceutically acceptable salt thereof, are compounds of Formula I wherein the cyclic ring is substituted, for example with alkyl such as methyl or ethyl. Typical of such compounds include (1-aminomethyl-3-methylcyclohexyl) acetic acid, (1-aminomethyl-3-methyl-cyclopentyl) acetic acid, and (1-aminomethyl-3,4-dimethylcyclopentyl) acetic acid.

In another preferred embodiment, the invention method utilizes an alpha2delta ligand of Formula II

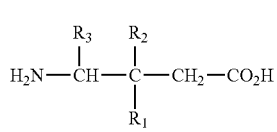

or a pharmaceutically acceptable salt thereof, wherein:

$R_1$ is a straight or branched unsubstituted alkyl of from 1 to 6 carbon atoms, unsubstituted phenyl, or unsubstituted cycloalkyl of from 3 to 6 carbon atoms;

$R_2$ is hydrogen or methyl; and $R_3$ is hydrogen, methyl, or carboxyl.

Diastereomers and enantiomers of compounds of Formula II can be utilized in the invention method.

An especially preferred embodiment of the invention method employs a compound of Formula II where $R_2$ and $R_3$ are both hydrogen, and $R_1$ is $—(CH_2)_{0-2}\text{-}i\,C_4H_9$ as an (R), (S), or (R,S) isomer.

A more preferred embodiment of the invention method utilizes a compound of Formula II named 3-aminomethyl-5-methyl-hexanoic acid, or especially (S)-3-(aminomethyl)-5-methylhexanoic acid, now known generically as pregabalin. Pregabalin is also known as "Cl-1008" and "S-(+)-3-IBG."

Another preferred embodiment of the invention method utilizes a compound of Formula II named 3-(1-aminoethyl)-5-methylheptanoic acid or 3-(1-aminoethyl)-5-methylhexanoic acid.

Another preferred embodiment of the invention method utilizes an alpha2delta ligand that is a compound of the Formula III, IIIC, IIIF, IIIG, or IIIH

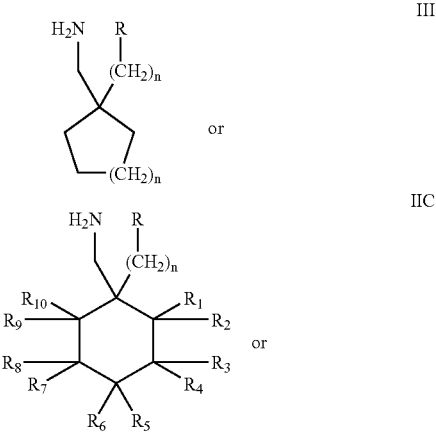

-continued

IIF
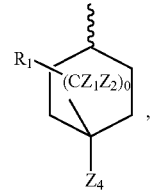

IIG
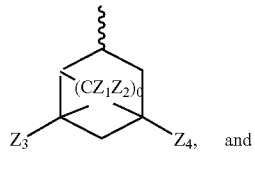

IIH
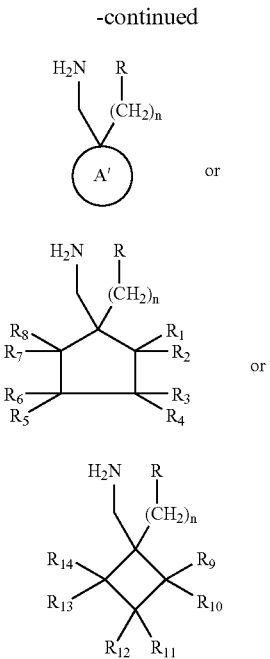

or a pharmaceutically acceptable salt thereof wherein:

n is an integer of from 0 to 2;

m is an integer of from 0 to 3;

R is sulfonamide, amide, phosphonic acid, heterocycle, sulfonic acid, or hydroxamic acid;

$R_1$ to $R_{14}$ are each independently selected from hydrogen or straight or branched alkyl of from 1 to 6 carbons, unsubstituted or substituted benzyl or phenyl which substituents are selected from halogen, alkyl, alkoxy, hydroxy, carboxy, carboalkoxy, trifluoromethyl, and nitro;

/*

A' is a bridged ring selected from (1)
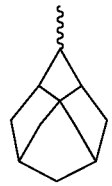

(2)
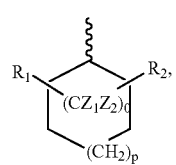

-continued (3)
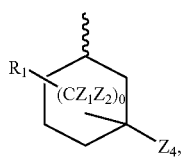

(4)

(5)

wherein

§ is the point of attachment;

$Z_1$ to $Z_4$ are each independently selected from hydrogen and methyl;

o is an integer of from 1 to 4; and p is an integer of from 0 to 2.

In Formula I above R cannot be sulfonic acid when m is 2 and n is 1. (Suman-Chaulan N., et al., *European Journal of Pharmacology,* 1993; 244:293–301).

Another preferred embodiment of the invention method utilizes a compound of Formulas III, IIIC, IIIF, IIIG, or IIIH selected from:

(1-Aminomethyl-cyclohexylmethyl)-phosphonic acid;

(1R-trans)(1-Aminomethyl-3-methyl-cyclohexylmethyl)-phosphonic acid;

(trans)(1-Aminomethyl-3,4-dimethyl-cyclopentylmethyl)-phosphonic acid;

(1R-trans)(1-Aminomethyl-3-methyl-cyclopentylmethyl)-phosphonic acid;

(1S-cis)(1-Aminomethyl-3-methyl-cyclopentylmethyl)-phosphonic acid;

(1S-trans)(1-Aminomethyl-3-methyl-cyclopentylmethyl)-phosphonic acid;

(1R-cis)(1-Aminomethyl-3-methyl-cyclopentylmethyl)-phosphonic acid;

(1α,3α,4α)(1-Aminomethyl-3,4-dimethyl-cyclopentylmethyl)-phosphonic acid;

(1α,3β,4β)(1-Aminomethyl-3,4-dimethyl-cyclopentylmethyl)-phosphonic acid;

(R)(1-Aminomethyl-3,3-dimethyl-cyclopentylmethyl)-phosphonic acid;

(S)(1-Aminomethyl-3,3-dimethyl-cyclopentylmethyl)-phosphonic acid;

(1-Aminomethyl-3,3-dimethyl-cyclobutylmethyl)-phosphonic acid;

2-(1-Aminomethyl-cyclohexyl)-N-hydroxy-acetamide;

(1S-trans)2-(1-Aminomethyl-3-methyl-cyclohexyl)-N-hydroxy-acetamide;

(trans)2-(1-Aminomethyl-3,4-dimethyl-cyclopentyl)-N-hydroxy-acetamide;
(1S-cis)2-(1-Aminomethyl-3-methyl-cyclopentyl)-N-hydroxy-acetamide;
(1R-trans)2-(1-Aminomethyl-3-methyl-cyclopentyl)-N-hydroxy-acetamide;
(1R-cis)2-(1-Aminomethyl-3-methyl-cyclopentyl)-N-hydroxy-acetamide;
(1S-trans)2-(1-Aminomethyl-3-methyl-cyclopentyl)-N-hydroxy-acetamide;
(1α,3α,4α)2-(1-Aminomethyl-3,4-dimethyl-cyclopentyl)-N-hydroxy-acetamide;
(1α,3β,4β)2-(1-Aminomethyl-3,4-dimethyl-cyclopentyl)-N-hydroxy-acetamide;
(S)2-(1-Aminomethyl-3,3-dimethyl-cyclopentyl)-N-hydroxy-acetamide;
(R)2-(1-Aminomethyl-3,3-dimethyl-cyclopentyl)-N-hydroxy-acetamide;
2-(1-Aminomethyl-3,3-dimethyl-cyclobutyl)-N-hydroxy-acetamide;
N-[2-(1-Aminomethyl-cyclohexyl)-ethyl]-methanesulfonamide;
(1S-cis)N-[2-(1-Aminomethyl-3-methyl-cyclohexyl)-ethyl]-methanesulfonamide;
(trans)N-[2-(1-Aminomethyl-3,4-dimethyl-cyclopentyl)-ethyl]-methanesulfonamide;
(1S-cis)N-[2-(1-Aminomethyl-3-methyl-cyclopentyl)-ethyl]-methanesulfonamide;
(1R-trans)N-[2-(1-Aminomethyl-3-methyl-cyclopentyl)-ethyl]-methanesulfonamide;
(1R-cis)N-[2-(1-Aminomethyl-3-methyl-cyclopentyl)-ethyl]-methanesulfonamide;
(1S-cis)N-[2-(1-Aminomethyl-3-methyl-cyclopentyl)-ethyl]-methanesulfonamide;
(1α,3α,4α)N-[2-(1-Aminomethyl-3,4-dimethyl-cyclopentyl)-ethyl]-methanesulfonamide;
(1α,3β,4β)N-[2-(1-Aminomethyl-3,4-dimethyl-cyclopentyl)-ethyl]-methanesulfonamide;
(S)N-[2-(1-Aminomethyl-3,3-dimethyl-cyclopentyl)-ethyl]-methanesulfonamide;
(R)N-[2-(1-Aminomethyl-3,3-dimethyl-cyclopentyl)-ethyl]-methanesulfonamide;
N-[2-(1-Aminomethyl-3,3-dimethyl-cyclobutyl)-ethyl]-methanesulfonamide;
(1S-cis)3-(1-Aminomethyl-3-methyl-cyclohexylmethyl)-4H-[1,2,4]oxadiazol-5-one;
(trans)3-(1-Aminomethyl-3,4-dimethyl-cyclopentylmethyl)-4H-[1,2,4]oxadiazol-5-one;
(1S-cis)3-(1-Aminomethyl-3-methyl-cyclopentylmethyl)-4H-[1,2,4]oxadiazol-5-one;
(1R-trans)3-(1-Aminomethyl-3-methyl-cyclopentylmethyl)-4H-[1,2,4]oxadiazol-5-one;
(1R-cis)3-(1-Aminomethyl-3-methyl-cyclopentylmethyl)-4H-[1,2,4]oxadiazol-5-one;
(1S-trans)3-(1-Aminomethyl-3-methyl-cyclopentylmethyl)-4H-[1,2,4]oxadiazol-5-one;
(1α,3α,4α)3-(1-Aminomethyl-3,4-dimethyl-cyclopentylmethyl)-4H-[1,2,4]oxadiazol-5-one,
(1α,3β,4β)3-(1-Aminomethyl-3,4-dimethyl-cyclopentylmethyl)-4H-[1,2,4]oxadiazol-5-one;
(S)3-(1-Aminomethyl-3,3-dimethyl-cyclopentylmethyl)-4H-[1,2,4]oxadiazol-5-one;
(R)3-(1-Aminomethyl-3,3-dimethyl-cyclopentylmethyl)-4H-[1,2,4]oxadiazol-5-one;
3-(1-Aminomethyl-3,3-dimethyl-cyclobutylmethyl)-4H-[1,2,4]oxadiazol-5-one;
3-(1-Aminomethyl-cyclohexylmethyl)-4H-[1,2,4]oxadiazole-5-thione;
(1S-cis)3-(1-Aminomethyl-3-methyl-cyclohexylmethyl)-4H-[1,2,4]oxadiazole-5-thione;
(trans)3-(1-Aminomethyl-3,4-dimethyl-cyclopentylmethyl)-4H-[1,2,4]oxadiazole-5-thione;
(1S-cis)3-(1-Aminomethyl-3-methyl-cyclopentylmethyl)-4H-[1,2,4]oxadiazole-5-thione;
(1R-trans)3-(1-Aminomethyl-3-methyl-cyclopentylmethyl)-4H-[1,2,4]oxadiazole-5-thione;
(1R-cis)3-(1-Aminomethyl-3-methyl-cyclopentylmethyl)-4H-[1,2,4]oxadiazole-5-thione;
(1S-trans)3-(1-Aminomethyl-3-methyl-cyclopentylmethyl)-4H-[1,2,4]oxadiazole-5-thione;
(1α,3α,4α)3-(1-Aminomethyl-3,4-dimethyl-cyclopentylmethyl)-4H-[1,2,4]oxadiazole-5-thione;
(1α,3β,4β)3-(1-Aminomethyl-3,4-dimethyl-cyclopentylmethyl)-4H-[1,2,4]oxadiazole-5-thione;
(S)3-(1-Aminomethyl-3,3-dimethyl-cyclopentylmethyl)-4H-[1,2,4]oxadiazole-5-thione;
(R)3-(1-Aminomethyl-3,3-dimethyl-cyclopentylmethyl)-4H-[1,2,4]oxadiazole-5-thione;
3-(1-Aminomethyl-3,3-dimethyl-cyclobutylmethyl)-4H-[1,2,4]oxadiazole-5-thione;
C-[1-(1H-Tetrazol-5-ylmethyl)-cyclohexyl]-methylamine;
(1S-cis)C-[3-Methyl-1-(1H-tetrazol-5-ylmethyl)-cyclohexyl]-methylamine;
(trans)C-[3,4-Dimethyl-1-(1H-tetrazol-5-ylmethyl)-cyclopentyl]-methylamine;
(1S-cis)C-[3-Methyl-1-(1H-tetrazol-5-ylmethyl)-cyclopentyl]-methylamine;
(1R-trans)C-[3-Methyl-1-(1H-tetrazol-5-ylmethyl)-cyclopentyl]-methylamine;
(1R-cis)C-[3-Methyl-1-(1H-tetrazol-5-ylmethyl)-cyclopentyl]-methylamine;
(1S-trans)C-[3-Methyl-1-(1H-tetrazol-5-ylmethyl)-cyclopentyl]-methylamine;
(1α,3α,4α)C-[3,4-Dimethyl-1-(1H-tetrazol-5-ylmethyl)-cyclopentyl]-methylamine;
(1α,3β,4β)C-[3,4-Dimethyl-1-(1H-tetrazol-5-ylmethyl)-cyclopentyl]-methylamine;
(S) C-[3,3-Dimethyl-1-(1H-tetrazol-5-ylmethyl)-cyclopentyl]-methylamine;
(R)C-[3,3-Dimethyl-1-(1H-tetrazol-5-ylmethyl)-cyclopentyl]-methylamine;
C-[3,3-Dimethyl-1-(1H-tetrazol-5-ylmethyl)-cyclobutyl]-methylamine;
N-[2-(1-Aminomethyl-cyclohexyl)-ethyl]-C,C,C-trifluoro-methanesulfonamide;
(1S-cis)N-[2-(1-Aminomethyl-3-methyl-cyclohexyl)-ethyl]-C,C,C-trifluoro-methanesulfonamide;
(trans)N-[2-(1-Aminomethyl-3,4-dimethyl-cyclopentyl)-ethyl]-C,C,C-trifluoro-methanesulfonamide;
(1R-cis)N-[2-(1-Aminomethyl-3-methyl-cyclopentyl)-ethyl]-C,C,C-trifluoro-methanesulfonamide;
(1S-trans)N-[2-(1-Aminomethyl-3-methyl-cyclopentyl)-ethyl]-C,C,C-trifluoro-methanesulfonamide;
(1S-cis)N-[2-(1-Aminomethyl-3-methyl-cyclopentyl)-ethyl]-C,C,C-trifluoro-methanesulfonamide;
(1R-trans)N-[2-(1-Aminomethyl-3-methyl-cyclopentyl)-ethyl]-C,C,C-trifluoro-methanesulfonamide;
(1α,3α,4α)N-[2-(1-Aminomethyl-3,4-dimethyl-cyclopentyl)-ethyl]-C,C,C-trifluoro-methanesulfonamide;
(1α,3β,4β)N-[2-(1-Aminomethyl-3,4-dimethyl-cyclopentyl)-ethyl]-C,C,C-trifluoro-methanesulfonamide;
(S) N-[2-(1-Aminomethyl-3,3-dimethyl-cyclopentyl)-ethyl]-C,C,C-trifluoro-methanesulfonamide;

(R)N-[2-(1-Aminomethyl-3,3-dimethyl-cyclopentyl)-ethyl]-C,C,C-trifluoro-methanesulfonamide;
N-[2-(1-Aminomethyl-3,3-dimethyl-cyclobutyl)-ethyl]-C,C,C-trifluoro-methanesulfonamide;
3-(1-Aminomethyl-cyclohexylmethyl)-4H-[1,2,4]thiadiazol-5-one;
(1S-cis)3-(1-Aminomethyl-3-methyl-cyclohexylmethyl)-4H-[1,2,4]thiadiazol-5-one;
(trans)3-(1-Aminomethyl-3,4-dimethyl-cyclopentylmethyl)-4H-[1,2,4]thiadiazol-5-one;
(1R-cis)3-(1-Aminomethyl-3-methyl-cyclopentylmethyl)-4H-[1,2,4]thiadiazol-5-one;
(1S-trans)3-(1-Aminomethyl-3-methyl-cyclopentylmethyl)-4H-[1,2,4]thiadiazol-5-one;
(1S-cis)3-(1-Aminomethyl-3-methyl-cyclopentylmethyl)-4H-[1,2,4]thiadiazol-5-one;
(1R-trans)3-(1-Aminomethyl-3-methyl-cyclopentylmethyl)-4H-[1,2,4]thiadiazol-5-one;
(1α,3α,4α)3-(1-Aminomethyl-3,4-dimethyl-cyclopentylmethyl)-4H-[1,2,4]thiadiazol-5-one;
(1α,3β,4β)3-(1-Aminomethyl-3,4-dimethyl-cyclopentylmethyl)-4H-[1,2,4]thiadiazol-5-one;
(S)3-(1-Aminomethyl-3,3-dimethyl-cyclopentylmethyl)-4H-[1,2,4]thiadiazol-5-one;
(R)3-(1-Aminomethyl-3,3-dimethyl-cyclopentylmethyl)-4H-[1,2,4]thiadiazol-5-one;
3-(1-Aminomethyl-3,3-dimethyl-cyclobutylmethyl)-4H-[1,2,4]thiadiazol-5-one;
C-[1-(2-Oxo-2,3-dihydro-2$\lambda^{4+}$[1,2,3,5]oxathiadiazol-4-ylmethyl)-cyclohexyl]-methylamine;
(1S-cis)C-[3-Methyl-1-(2-oxo-2,3-dihydro-2$\lambda^{4+}$[1,2,3,5]oxathiadiazol-4-ylmethyl)-cyclohexyl]methylamine;
(trans)C-[3,4-Dimethyl-1-(2-oxo-2,3-dihydro-2$\lambda^{4+}$[1,2,3,5]oxathiadiazol-4-ylmethyl)-cyclohexyl]-methylamine;
(1S-cis)C-[3-Methyl-1-(2-oxo-2,3-dihydro-2$\lambda^{4+}$[1,2,3,5]oxathiadiazol-4-ylmethyl)-cyclohexyl]-methylamine;
(1R-trans)C-[3-Methyl-1-(2-oxo-2,3-dihydro-2$\lambda^{4+}$[1,2,3,5]oxathiadiazol-4-ylmethyl)-cyclohexyl]-methylamine;
(1R-cis)C-[3-Methyl-1-(2-oxo-2,3-dihydro-2$\lambda^{4+}$[1,2,3,5]oxathiadiazol-4-ylmethyl)-cyclohexyl]-methylamine;
(1S-trans)C-[3-Methyl-1-(2-oxo-2,3-dihydro-2$\lambda^{4+}$[1,2,3,5]oxathiadiazol-4-ylmethyl)-cyclohexyl]-methylamine;
(1α,3α,4α)C-[3,4-Dimethyl-1-(2-oxo-2,3-dihydro-2$\lambda^{4+}$[1,2,3,5]oxathiadiazol-4-ylmethyl)-cyclohexyl]-methylamine;
(1α,3β,4β)C-[3,4-Dimethyl-1-(2-oxo-2,3-dihydro-2$\lambda^{4+}$[1,2,3,5]oxathiadiazol-4-ylmethyl)-cyclohexyl]-methylamine;
(S) C-[3,3-Dimethyl-1-(2-oxo-2,3-dihydro-2$\lambda^{4+}$[1,2,3,5]oxathiadiazol-4-ylmethyl)-cyclohexyl]-methylamine;
(R)C-[3,3-Dimethyl-1-(2-oxo-2,3-dihydro-2$\lambda^{4+}$[1,2,3,5]oxathiadiazol-4-ylmethyl)-cyclohexyl]-methylamine;
C-[3,3-Dimethyl-1-(2-oxo-2,3-dihydro-2$\lambda^{4+}$[1,2,3,5]oxathiadiazol-4-ylmethyl)-cyclobutyl]-methylamine;
(1-Aminomethyl-cyclohexyl)-methanesulfonamide;
(1R-trans)(1-Aminomethyl-3-methyl-cyclohexyl)-methanesulfonamide;
(trans)(1-Aminomethyl-3,4-dimethyl-cyclopentyl)-methanesulfonamide;
(1S-trans)(1-Aminomethyl-3-methyl-cyclopentyl)-methanesulfonamide;
(1R-cis)(1-Aminomethyl-3-methyl-cyclopentyl)-methanesulfonamide;
(1R-trans)(1-Aminomethyl-3-methyl-cyclopentyl)-methanesulfonamide;
(1S-cis)(1-Aminomethyl-3-methyl-cyclopentyl)-methanesulfonamide;
(1α,3β,4β)(1-Aminomethyl-3,4-dimethyl-cyclopentyl)-methanesulfonamide;
(1α,3α,4α)(1-Aminomethyl-3,4-dimethyl-cyclopentyl)-methanesulfonamide;
(R)(1-Aminomethyl-3,3-dimethyl-cyclopentyl)-methanesulfonamide;
(S)(1-Aminomethyl-3,3-dimethyl-cyclopentyl)-methanesulfonamide;
(1-Aminomethyl-3,3-dimethyl-cyclobutyl)-methanesulfonamide;
(1-Aminomethyl-cyclohexyl)-methanesulfonic acid;
(1R-trans)(1-Aminomethyl-3-methyl-cyclohexyl)-methanesulfonic acid;
(trans)(1-Aminomethyl-3,4-dimethyl-cyclopentyl)-methanesulfonic acid;
(1S-trans)(1-Aminomethyl-3-methyl-cyclopentyl)-methanesulfonic acid;
(1S-cis)(1-Aminomethyl-3-methyl-cyclopentyl)-methanesulfonic acid;
(1R-trans)(1-Aminomethyl-3-methyl-cyclopentyl)-methanesulfonic acid;
(1R-cis)(1-Aminomethyl-3-methyl-cyclopentyl)-methanesulfonic acid;
(1α,3β,4β)(1-Aminomethyl-3,4-dimethyl-cyclopentyl)-methanesulfonic acid;
(1α,3α,4α)(1-Aminomethyl-3,4-dimethyl-cyclopentyl)-methanesulfonic acid;
(R)(1-Aminomethyl-3,3-dimethyl-cyclopentyl)-methanesulfonic acid;
(S)(1-Aminomethyl-3,3-dimethyl-cyclopentyl)-methanesulfonic acid;
(1-Aminomethyl-3,3-dimethyl-cyclobutyl)-methanesulfonic acid;
(1-Aminomethyl-cyclopentylmethyl)-phosphonic acid;
2-(1-Aminomethyl-cyclopentyl)-N-hydroxy-acetamide;
N-[2-(1-Aminomethyl-cyclopentyl)-ethyl]-methanesulfonamide;
3-(1-Aminomethyl-cyclopentylmethyl)-4H-[1,2,4]oxadiazol-5-one;
3-(1-Aminomethyl-cyclopentylmethyl)-4H-[1,2,4]oxadiazole-5-thione;
C-[1-(1H-Tetrazol-5-ylmethyl)-cyclopentyl]-methylamine;
N-[2-(1-Aminomethyl-cyclopentyl)-ethyl]-C,C,C-trifluoro-methanesulfonamide;
3-(1-Aminomethyl-cyclopentylmethyl)-4H-[1,2,4]thiadiazol-5-one;
C-[1-(2-Oxo-2,3-dihydro-2$\lambda^{4+}$[1,2,3,5]oxathiadiazol-4-ylmethyl)-cyclopentyl]-methylamine;
(1-Aminomethyl-cyclopentyl)-methanesulfonamide;
(1-Aminomethyl-cyclopentyl)-methanesulfonic acid;
(9-Aminomethyl-bicyclo[3.3.1]non-9-ylmethyl)-phosphonic acid;
2-(9-Aminomethyl-bicyclo[3.3.1]non-9-yl)-N-hydroxy-acetamide;
N-[2-(9-Aminomethyl-bicyclo[3.3.1]non-9-yl)-ethyl]-methanesulfonamide;
3-(9-Aminomethyl-bicyclo[3.3.1]non-9-ylmethyl)-4H-[1,2,4]oxadiazol-5-one;
3-(9-Aminomethyl-bicyclo[3.3.1]non-9-ylmethyl)-4H-[1,2,4]oxadiazole-5-thione;
C-[9-(1H-Tetrazol-5-ylmethyl)-bicyclo[3.3.1]non-9-yl]-methylamine;
N-[2-(9-Aminomethyl-bicyclo[3.3.1]non-9-yl)-ethyl]-C,C,C-trifluoro-methanesulfonamide;
3-(9-Aminomethyl-bicyclo[3.3.1]non-9-ylmethyl)-4H-[1,2,4]thiadiazol-5-one;
C-[9-(2-Oxo-2,3-dihydro-2$\lambda^{4+}$[1,2,3,5]oxathiadiazol-4-ylmethyl)-bicyclo[3.3.1]non-9-yl]-methylamine;

(9-Aminomethyl-bicyclo[3.3.1]non-9-yl)-methanesulfonamide;
(9-Aminomethyl-bicyclo[3.3.1]non-9-yl)-methanesulfonic acid;
(2-Aminomethyl-adamantan-2-ylmethyl)-phosphonic acid;
2-(2-Aminomethyl-adamantan-2-yl)-N-hydroxy-acetamide;
N-[2-(2-Aminomethyl-adamantan-2-yl)-ethyl]-methanesulfonamide;
3-(2-Aminomethyl-adamantan-2-ylmethyl)-4H-[1,2,4]oxadiazol-5-one;
3-(2-Aminomethyl-adamantan-2-ylmethyl)-4H-[1,2,4]oxadiazole-5-thione;
C-[2-(1H-Tetrazol-5-ylmethyl)-adamantan-2-yl]-methylamine;
N-[2-(2-Aminomethyl-adamantan-2-yl)-ethyl]-C,C,C-trifluoro-methanesulfonamide;
3-(2-Aminomethyl-adamantan-2-ylmethyl)-4H-[1,2,4]thiadiazol-5-one;
C-[2-(2-Oxo-2,3-dihydro-2λ$^{4+}$[1,2,3,5]oxathiadiazol-4-ylmethyl)-adamantan-2-yl]-methylamine;
(2-Aminomethyl-adamantan-2-yl)-methanesulfonamide;
(2-Aminomethyl-adamantan-2-yl)-methanesulfonic acid;
(1-Aminomethyl-cycloheptylmethyl)-phosphonic acid;
2-(1-Aminomethyl-cycloheptyl)-N-hydroxy-acetamide;
N-[2-(1-Aminomethyl-cycloheptyl)-ethyl]-methanesulfonamide;
3-(1-Aminomethyl-cycloheptylmethyl)-4H-[1,2,4]oxadiazole-5-thione;
N-[2-(1-Aminomethyl-cycloheptyl)-ethyl]-C,C,C-trifluoromethanesulfonamide;
C-[1-(2-Oxo-2,3-dihydro-2l4-[1,2,3,5]oxathiadiazol-4-ylmethyl)-cycloheptyl]-methylamine;
(1-Aminomethyl-cycloheptyl)-methanesulfonamide; and
(1-Aminomethyl-cycloheptyl)-methanesulfonic acid.

Another preferred embodiment of the invention method utilizes a compound of Formulas III, IIIC, IIIF, IIIG, or IIIH, wherein preferred compounds are those wherein R is a sulfonamide selected from —NHSO$_2$R$^{15}$ or —SO$_2$NHR$^{15}$ wherein R$^{15}$ is straight or branched alkyl or trifluoromethyl.

Another preferred embodiment of the invention method utilizes a compound of Formulas III, IIIC, IIIF, IIIG, or IIIH, wherein especially preferred is N-[2-(1-aminomethyl-cyclohexyl)-ethyl]-methanesulfonamide.

Another preferred embodiment of the invention method utilizes a compound of Formulas III, IIIC, IIIF, IIIG, or IIIH, wherein other preferred compounds are those wherein R is a phosphonic acid, —PO$_3$H$_2$.

Another preferred embodiment of the invention method utilizes a compound of Formulas III, IIIC, IIIF, IIIG, or IIIH, wherein especially preferred are (1-aminomethyl-cyclohexylmethyl)-phosphonic acid and (2-aminomethyl-4-methyl-pentyl)-phosphonic acid.

Another preferred embodiment of the invention method utilizes a compound of Formulas III, IIIC, IIIF, IIIG, or IIIH, wherein other preferred compounds are those wherein R is a heterocycle selected from:

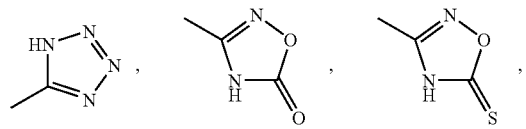

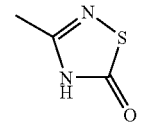 , and 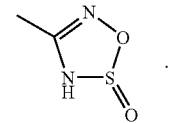 .

Another preferred embodiment of the invention method utilizes a compound of Formulas III, IIIC, IIIF, IIIG, or IIIH, wherein especially preferred are C-[1-(1H-tetrazol-5-ylmethyl)cyclohexyl]-methylamine and 4-methyl-2-(1H-tetrazol-5-yl methyl)-pentylamine.

An especially preferred embodiment of the invention method utilizes a compound of Formula III wherein:
m is an integer of from 0 to 2;
p is an integer of 2; and R is 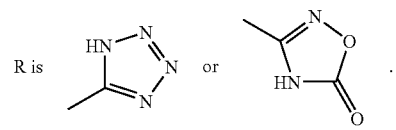

Still more preferred is an embodiment of the invention method which utilizes a compound of Formulas III, IIIC, IIIF, IIIG, or IIIH named 3-(1-aminomethyl-cyclohexylmethyl)-4H-[1,2,4]oxadiazol-5-one, or a pharmaceutically acceptable salt thereof.

Still more preferred is an embodiment of the invention method which utilizes a compound of Formulas III, IIIC, IIIF, IIIG, or IIIH named 3-(1-aminomethyl-cyclohexylmethyl)-4H-[1,2,4]oxadiazol-5-one hydrochloride.

Also preferred is an embodiment of the invention method which utilizes a compound of Formulas III, IIIC, IIIF, IIIG, or IIIH named 3-(1-aminomethyl-cycloheptylmethyl)-4H-[1,2,4]oxadiazol-5-one, or a pharmaceutically acceptable salt thereof.

Also more preferred is an embodiment of the invention method which utilizes a compound of Formulas III, IIIC, IIIF, IIIG, or IIIH named 3-(1-aminomethyl-cycloheptylmethyl)-4H-[1,2,4]oxadiazol-5-one hydrochloride.

Also preferred is an embodiment of the invention method which utilizes a compound of Formulas III, IIIC, IIIF, IIIG, or IIIH named C-[1-(1H-tetrazol-5-ylmethyl)-cycloheptyl]-methylamine, or a pharmaceutically acceptable salt thereof.

Also more preferred is an embodiment which utilizes a compound of Formulas III, IIIC, IIIF, IIIG, or IIIH named C-[1-(1H-tetrazol-5-ylmethyl)-cycloheptyl]-methylamine.

Another preferred embodiment of the invention method utilizes an alpha2delta ligand that is a compound of Formula IV

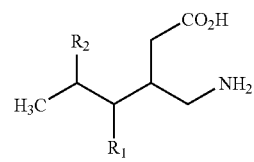

or a pharmaceutically acceptable salt thereof wherein:
R$^1$ is hydrogen, straight or branched alkyl of from 1 to 6 carbon atoms or phenyl;

R² is straight or branched alkyl of from 1 to 8 carbon atoms,
straight or branched alkenyl of from 2 to 8 carbon atoms,
cycloalkyl of from 3 to 7 carbon atoms,
alkoxy of from 1 to 6 carbon atoms,
-alkylcycloalkyl,
-alkylalkoxy,
-alkyl OH
-alkylphenyl,
-alkylphenoxy,
-phenyl or substituted phenyl; and
R¹ is straight or branched alkyl of from 1 to 6 carbon atoms
or phenyl when R² is methyl.

Preferred is an embodiment of the invention method employing a compound of Formula IV wherein R¹ is hydrogen, and R² is alkyl.

Another preferred embodiment of the invention method employing a compound of Formula IV wherein R¹ is methyl, and R² is alkyl.

Still another preferred embodiment of the invention method utilizes a compound of Formula IV wherein R¹ is methyl, and R² is methyl or ethyl.

Especially preferred is an embodiment of the invention method utilizing a compound of Formula IV selected from:
3-Aminomethyl-5-methylheptanoic acid;
3-Aminomethyl-5-methyl-octanoic acid;
3-Aminomethyl-5-methyl-nonanoic acid;
3-Aminomethyl-5-methyl-decanoic acid;
3-Aminomethyl-5-methyl-undecanoic acid;
3-Aminomethyl-5-methyl-dodecanoic acid;
3-Aminomethyl-5-methyl-tridecanoic acid;
3-Aminomethyl-5-cyclopropyl-hexanoic acid;
3-Aminomethyl-5-cyclobutyl-hexanoic acid;
3-Aminomethyl-5-cyclopentyl-hexanoic acid;
3-Aminomethyl-5-cyclohexyl-hexanoic acid;
3-Aminomethyl-5-trifluoromethyl-hexanoic acid;
3-Aminomethyl-5-phenyl-hexanoic acid;
3-Aminomethyl-5-(2-chlorophenyl)-hexanoic acid;
3-Aminomethyl-5-(3-chlorophenyl)-hexanoic acid;
3-Aminomethyl-5-(4-chlorophenyl)-hexanoic acid;
3-Aminomethyl-5-(2-methoxyphenyl)-hexanoic acid;
3-Aminomethyl-5-(3-methoxyphenyl)-hexanoic acid;
3-Aminomethyl-5-(4-methoxyphenyl)-hexanoic acid; and
3-Aminomethyl-5-(phenylmethyl)-hexanoic acid.

Another especially preferred embodiment of the invention method uses a compound of Formula IV selected from:
(3R,4S)-3-Aminomethyl-4,5-dimethyl-hexanoic acid;
3-Aminomethyl-4,5-dimethyl-hexanoic acid;
(3R,4S)-3-Aminomethyl-4,5-dimethyl-hexanoic acid MP;
(3S,4S)-3-Aminomethyl-4,5-dimethyl-hexanoic acid;
(3R,4R)-3-Aminomethyl-4,5-dimethyl-hexanoic acid MP;
3-Aminomethyl-4-isopropyl-hexanoic acid;
3-Aminomethyl-4-isopropyl-heptanoic acid;
3-Aminomethyl-4-isopropyl-octanoic acid;
3-Aminomethyl-4-isopropyl-nonanoic acid;
3-Aminomethyl-4-isopropyl-decanoic acid; and
3-Aminomethyl-4-phenyl-5-methyl-hexanoic acid.

Another preferred embodiment of the invention method uses a compound of Formula IV selected from:
(3S,5S)-3-Aminomethyl-5-methoxy-hexanoic acid;
(3S,5S)-3-Aminomethyl-5-ethoxy-hexanoic acid;
(3S,5S)-3-Aminomethyl-5-propoxy-hexanoic acid;
(3S,5S)-3-Aminomethyl-5-isopropoxy-hexanoic acid;
(3S,5S)-3-Aminomethyl-5-tert-butoxy-hexanoic acid;
(3S,5S)-3-Aminomethyl-5-fluoromethoxy-hexanoic acid;
(3S,5S)-3-Aminomethyl-5-(2-fluoro-ethoxy)-hexanoic acid;
(3S,5S)-3-Aminomethyl-5-(3,3,3-trifluoro-propoxy)-hexanoic acid;
(3S,5S)-3-Aminomethyl-5-phenoxy-hexanoic acid;
(3S,5S)-3-Aminomethyl-5-(4-chloro-phenoxy)-hexanoic acid;
(3S,5S)-3-Aminomethyl-5-(3-chloro-phenoxy)-hexanoic acid;
(3S,5S)-3-Aminomethyl-5-(2-chloro-phenoxy)-hexanoic acid;
(3S,5S)-3-Aminomethyl-5-(4-fluoro-phenoxy)-hexanoic acid;
(3S,5S)-3-Aminomethyl-5-(3-fluoro-phenoxy)-hexanoic acid;
(3S,5S)-3-Aminomethyl-5-(2-fluoro-phenoxy)-hexanoic acid;
(3S,5S)-3-Aminomethyl-5-(4-methoxy-phenoxy)-hexanoic acid;
(3S,5S)-3-Aminomethyl-5-(3-methoxy-phenoxy)-hexanoic acid;
(3S,5S)-3-Aminomethyl-5-(2-methoxy-phenoxy)-hexanoic acid;
(3S,5S)-3-Aminomethyl-5-(4-nitro-phenoxy)-hexanoic acid;
(3S,5S)-3-Aminomethyl-5-(3-nitro-phenoxy)-hexanoic acid;
(3S,5S)-3-Aminomethyl-5-(2-nitro-phenoxy)-hexanoic acid;
(3S,5S)-3-Aminomethyl-6-hydroxy-5-methyl-hexanoic acid;
(3S,5S)-3-Aminomethyl-6-methoxy-5-methyl-hexanoic acid;
(3S,5S)-3-Aminomethyl-6-ethoxy-5-methyl-hexanoic acid;
(3S,5S)-3-Aminomethyl-5-methyl-6-propoxy-hexanoic acid;
(3S,5S)-3-Aminomethyl-6-isopropoxy-5-methyl-hexanoic acid;
(3S,5S)-3-Aminomethyl-6-tert-butoxy-5-methyl-hexanoic acid;
(3S,5S)-3-Aminomethyl-6-fluoromethoxy-5-methyl-hexanoic acid;
(3S,5S)-3-Aminomethyl-6-(2-fluoro-ethoxy)-5-methyl-hexanoic acid;
(3S,5S)-3-Aminomethyl-5-methyl-6-(3,3,3-trifluoro-propoxy)-hexanoic acid;
(3S,5S)-3-Aminomethyl-5-methyl-6-phenoxy-hexanoic acid;
(3S,5S)-3-Aminomethyl-6-(4-chloro-phenoxy)-5-methyl-hexanoic acid;
(3S,5S)-3-Aminomethyl-6-(3-chloro-phenoxy)-5-methyl-hexanoic acid;
(3S,5S)-3-Aminomethyl-6-(2-chloro-phenoxy)-5-methyl-hexanoic acid;
(3S,5S)-3-Aminomethyl-6-(4-fluoro-phenoxy)-5-methyl-hexanoic acid;
(3S,5S)-3-Aminomethyl-6-(3-fluoro-phenoxy)-5-methyl-hexanoic acid;
(3S,5S)-3-Aminomethyl-6-(2-fluoro-phenoxy)-5-methyl-hexanoic acid;
(3S,5S)-3-Aminomethyl-6-(4-methoxy-phenoxy)-5-methyl-hexanoic acid;
(3S,5S)-3-Aminomethyl-6-(3-methoxy-phenoxy)-5-methyl-hexanoic acid;
(3S,5S)-3-Aminomethyl-6-(2-methoxy-phenoxy)-5-methyl-hexanoic acid;
(3S,5S)-3-Aminomethyl-5-methyl 6-(4-trifluoromethyl-phenoxy)-hexanoic acid;
(3S,5S)-3-Aminomethyl-5-methyl 6-(3-trifluoromethyl-phenoxy)-hexanoic acid;

(3S,5S)-3-Aminomethyl-5-methyl 6-(2-trifluoromethyl-phenoxy)-hexanoic acid;
(3S,5S)-3-Aminomethyl-5-methyl 6-(4-nitro-phenoxy)-hexanoic acid;
(3S,5S)-3-Aminomethyl-5-methyl 6-(3-nitro-phenoxy)-hexanoic acid;
(3S,5S)-3-Aminomethyl-5-methyl 6-(2-nitro-phenoxy)-hexanoic acid;
(3S,5S)-3-Aminomethyl-6-benzyloxy-5-methyl-hexanoic acid;
(3S,5S)-3-Aminomethyl-7-hydroxy-5-methyl-heptanoic acid;
(3S,5S)-3-Aminomethyl-7-methoxy-5-methyl-heptanoic acid;
(3S,5S)-3-Aminomethyl-7-ethoxy-5-methyl-heptanoic acid;
(3S,5S)-3-Aminomethyl-5-methyl-7-propoxy-heptanoic acid;
(3S,5S)-3-Aminomethyl-7-isopropoxy-5-methyl-heptanoic acid;
(3S,5S)-3-Aminomethyl-7-tert-butoxy-5-methyl-heptanoic acid;
(3S,5S)-3-Aminomethyl-7-fluoromethoxy-5-methyl-heptanoic acid;
(3S,5S)-3-Aminomethyl-7-(2-fluoro-ethoxy)-5-methyl-heptanoic acid;
(3S,5S)-3-Aminomethyl-5-methyl-7-(3,3,3-trifluoro-propoxy)-heptanoic acid;
(3S,5S)-3-Aminomethyl-7-benzyloxy-5-methyl-heptanoic acid;
(3S,5S)-3-Aminomethyl-5-methyl-7-phenoxy-heptanoic acid;
(3S,5S)-3-Aminomethyl-7-(4-chloro-phenoxy)-5-methyl-heptanoic acid;
(3S,5S)-3-Aminomethyl-7-(3-chloro-phenoxy)-5-methyl-heptanoic acid;
(3S,5S)-3-Aminomethyl-7-(2-chloro-phenoxy)-5-methyl-heptanoic acid;
(3S,5S)-3-Aminomethyl-7-(4-fluoro-phenoxy)-5-methyl-heptanoic acid;
(3S,5S)-3-Aminomethyl-7-(3-fluoro-phenoxy)-5-methyl-heptanoic acid;
(3S,5S)-3-Aminomethyl-7-(2-fluoro-phenoxy)-5-methyl-heptanoic acid;
(3S,5S)-3-Aminomethyl-7-(4-methoxy-phenoxy)-5-methyl-heptanoic acid;
(3S,5S)-3-Aminomethyl-7-(3-methoxy-phenoxy)-5-methyl-heptanoic acid;
(3S,5S)-3-Aminomethyl-7-(2-methoxy-phenoxy)-5-methyl-heptanoic acid;
(3S,5S)-3-Aminomethyl-5-methyl-7-(4-trifluoromethyl-phenoxy)-heptanoic acid;
(3S,5S)-3-Aminomethyl-5-methyl-7-(3-trifluoromethyl-phenoxy)-heptanoic acid;
(3S,5S)-3-Aminomethyl-5-methyl-7-(2-trifluoromethyl-phenoxy)-heptanoic acid;
(3S,5S)-3-Aminomethyl-5-methyl-7-(4-nitro-phenoxy)-heptanoic acid;
(3S,5S)-3-Aminomethyl-5-methyl-7-(3-nitro-phenoxy)-heptanoic acid;
(3S,5S)-3-Aminomethyl-5-methyl-7-(2-nitro-phenoxy)-heptanoic acid;
(3S,5S)-3-Aminomethyl-5-methyl-6-phenyl-hexanoic acid;
(3S,5S)-3-Aminomethyl-6-(4-chloro-phenyl)-5-methyl-hexanoic acid;
(3S,5S)-3-Aminomethyl-6-(3-chloro-phenyl)-5-methyl-hexanoic acid;
(3S,5S)-3-Aminomethyl-6-(2-chloro-phenyl)-5-methyl-hexanoic acid;
(3S,5S)-3-Aminomethyl-6-(4-methoxy-phenyl)-5-methyl-hexanoic acid;
(3S,5S)-3-Aminomethyl-6-(3-methoxy-phenyl)-5-methyl-hexanoic acid;
(3S,5S)-3-Aminomethyl-6-(2-methoxy-phenyl)-5-methyl-hexanoic acid;
(3S,5S)-3-Aminomethyl-6-(4-fluoro-phenyl)-5-methyl-hexanoic acid;
(3S,5S)-3-Aminomethyl-6-(3-fluoro-phenyl)-5-methyl-hexanoic acid;
(3S,5S)-3-Aminomethyl-6-(2-fluoro-phenyl)-5-methyl-hexanoic acid;
(3S,5R)-3-Aminomethyl-5-methyl-7-phenyl-heptanoic acid;
(3S,5R)-3-Aminomethyl-7-(4-chloro-phenyl)-5-methyl-heptanoic acid;
(3S,5R)-3-Aminomethyl-7-(3-chloro-phenyl)-5-methyl-heptanoic acid;
(3S,5R)-3-Aminomethyl-7-(2-chloro-phenyl)-5-methyl-heptanoic acid;
(3S,5R)-3-Aminomethyl-7-(4-methoxy-phenyl)-5-methyl-heptanoic acid;
(3S,5R)-3-Aminomethyl-7-(3-methoxy-phenyl)-5-methyl-heptanoic acid;
(3S,5R)-3-Aminomethyl-7-(2-methoxy-phenyl)-5-methyl-heptanoic acid;
(3S,5R)-3-Aminomethyl-7-(4-fluoro-phenyl)-5-methyl-heptanoic acid;
(3S,5R)-3-Aminomethyl-7-(3-fluoro-phenyl)-5-methyl-heptanoic acid;
(3S,5R)-3-Aminomethyl-7-(2-fluoro-phenyl)-5-methyl-heptanoic acid;
(3S,5R)-3-Aminomethyl-5-methyl-oct-7-enoic acid;
(3S,5R)-3-Aminomethyl-5-methyl-non-8-enoic acid;
(E)-(3S,5S)-3-Aminomethyl-5-methyl-oct-6-enoic acid;
(Z)-(3S,5S)-3-Aminomethyl-5-methyl-oct-6-enoic acid;
(Z)-(3S,5S)-3-Aminomethyl-5-methyl-non-6-enoic acid;
(E)-(3S,5S)-3-Aminomethyl-5-methyl-non-6-enoic acid;
(E)-(3S,5R)-3-Aminomethyl-5-methyl-non-7-enoic acid;
(Z)-(3S,5R)-3-Aminomethyl-5-methyl-non-7-enoic acid;
(Z)-(3S,5R)-3-Aminomethyl-5-methyl-dec-7-enoic acid;
(E)-(3S,5R)-3-Aminomethyl-5-methyl-undec-7-enoic acid;
(3S,5S)-3-Aminomethyl-5,6,6-trimethyl-heptanoic acid;
(3S,5S)-3-Aminomethyl-5,6-dimethyl-heptanoic acid;
(3S,5S)-3-Aminomethyl-5-cyclopropyl-hexanoic acid;
(3S,5S)-3-Aminomethyl-5-cyclobutyl-hexanoic acid;
(3S,5S)-3-Aminomethyl-5-cyclopentyl-hexanoic acid; and
(3S,5S)-3-Aminomethyl-5-cyclohexyl-hexanoic acid.

Still another more preferred embodiment of the invention method utilizes a compound of Formula IV selected from:
(3S,5R)-3-Aminomethyl-5-methyl-heptanoic acid;
(3S,5R)-3-Aminomethyl-5-methyl-octanoic acid;
(3S,5R)-3-Aminomethyl-5-methyl-nonanoic acid;
(3S,5R)-3-Aminomethyl-5-methyl-decanoic acid;
(3S,5R)-3-Aminomethyl-5-methyl-undecanoic acid;
(3S,5R)-3-Aminomethyl-5-methyl-dodecanoic acid;
(3S,5R)-3-Aminomethyl-5,9-dimethyl-decanoic acid;
(3S,5R)-3-Aminomethyl-5,7-dimethyl-octanoic acid;
(3S,5R)-3-Aminomethyl-5,8-dimethyl-nonanoic acid;
(3S,5R)-3-Aminomethyl-6-cyclopropyl-5-methyl-hexanoic acid;
(3S,5R)-3-Aminomethyl-6-cyclobutyl-5-methyl-hexanoic acid;
(3S,5R)-3-Aminomethyl-6-cyclopentyl-5-methyl-hexanoic acid;

(3S,5R)-3-Aminomethyl-6-cyclohexyl-5-methyl-hexanoic acid;
(3S,5R)-3-Aminomethyl-7-cyclopropyl-5-methyl-heptanoic acid;
(3S,5R)-3-Aminomethyl-7-cyclobutyl-5-methyl-heptanoic acid;
(3S,5R)-3-Aminomethyl-7-cyclopentyl-5-methyl-heptanoic acid;
(3S,5R)-3-Aminomethyl-7-cyclohexyl-5-methyl-heptanoic acid;
(3S,5R)-3-Aminomethyl-8-cyclopropyl-5-methyl-octanoic acid;
(3S,5R)-3-Aminomethyl-8-cyclobutyl-5-methyl-octanoic acid;
(3S,5R)-3-Aminomethyl-8-cyclopentyl-5-methyl-octanoic acid;
(3S,5R)-3-Aminomethyl-8-cyclohexyl-5-methyl-octanoic acid;
(3S,5S)-3-Aminomethyl-6-fluoro-5-methyl-hexanoic acid;
(3S,5S)-3-Aminomethyl-7-fluoro-5-methyl-heptanoic acid;
(3S,5R)-3-Aminomethyl-8-fluoro-5-methyl-octanoic acid;
(3S,5R)-3-Aminomethyl-9-fluoro-5-methyl-nonanoic acid;
(3S,5S)-3-Aminomethyl-7,7,7-trifluoro-5-methyl-heptanoic acid;
(3S,5R)-3-Aminomethyl-8,8,8-trifluoro-5-methyl-octanoic acid;
(3S,5R)-3-Aminomethyl-5-methyl-8-phenyl-octanoic acid;
(3S,5S)-3-Aminomethyl-5-methyl-6-phenyl-hexanoic acid; and
(3S,5R)-3-Aminomethyl-5-methyl-7-phenyl-heptanoic acid.

Another preferred embodiment of the invention method utilizes an alpha2delta ligand which is a compound of Formulas (1A) or (1B)

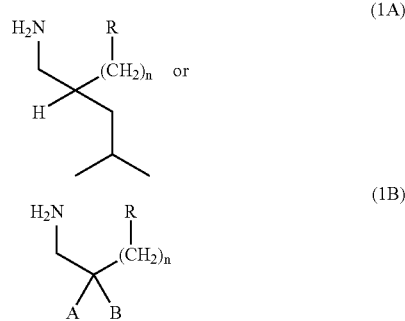

or a pharmaceutically acceptable salt thereof wherein:
n is an integer of from 0 to 2;
R is sulfonamide,
  amide,
  phosphonic acid,
  heterocycle,
  sulfonic acid, or
  hydroxamic acid;
A is hydrogen or methyl; and B is 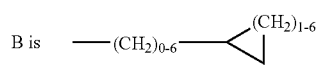

straight or branched alkyl of from 1 to 11 carbons, or
$-(CH_2)_{1-4}-Y-(CH_2)_{0-4}$-phenyl wherein Y is $-O-$, $-S-$, $-NR'_3$ wherein:
R'$_3$ is alkyl of from 1 to 6 carbons, cycloalkyl of from 3 to 8 carbons, benzyl or phenyl wherein benzyl or phenyl can be unsubstituted or substituted with from 1 to 3 substituents each independently selected from alkyl, alkoxy, halogen, hydroxy, carboxy, carboalkoxy, trifluoromethyl, and nitro.

A preferred embodiment utilizes an alpha2delta ligand which is a compound of Formulas (1A) or (1B), wherein R is a sulfonamide selected from $-NHSO_2R^{15}$ and $-SO_2NHR^{15}$, wherein $R^{15}$ is straight or branched alkyl or trifluoromethyl.

An especially preferred embodiment utilizes a compound of Formulas (1A) or (1B) selected from:
4-Methyl-2-(1H-tetrazol-5-ylmethyl)-pentylamine;
3-(2-Aminomethyl-4-methyl-pentyl)-4H-[1,2,4]oxadiazole-5-thione, HCl;
(2-Aminomethyl-4-methyl-pentyl)-phosphonic acid;
3-(3-Amino-2-cyclopentyl-propyl)-4H-[1,2,4]oxadiazol-5-one;
3-(3-Amino-2-cyclopentyl-propyl)-4H-[1,2,4]thiadiazol-5-one;
2-Cyclopentyl-3-(2-oxo-2,3-dihydro-2$\lambda^4$-[1,2,3,5]oxathiadiazol-4-yl)-propylamine;
3-(3-Amino-2-cyclobutyl-propyl)-4H-[1,2,4]oxadiazol-5-one;
3-(3-Amino-2-cyclobutyl-propyl)-4H-[1,2,4]thiadiazol-5-one; and
2-Cyclobutyl-3-(2-oxo-2,3-dihydro-2$\lambda^4$-[1,2,3,5]oxathiadiazol-4-yl)-propylamine.

Another preferred embodiment utilizes a compound of Formulas (1A) or (1B), wherein R is a phosphonic acid, $-PO_3H_2$.

Another preferred embodiment utilizes a compound of Formulas (1A) or (1B), wherein R is

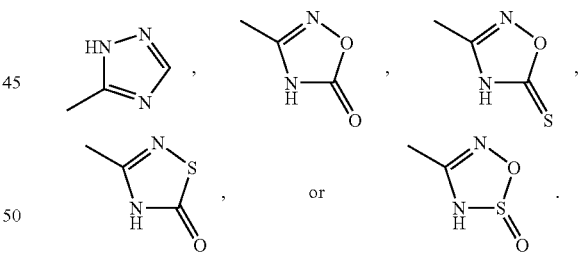

More preferred is an embodiment that utilizes a compound of Formulas (1A) or (1B), wherein R is

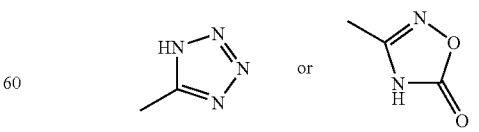

Still more preferred is an embodiment that utilizes a compound of Formulas (1A) or (1B) named 3-(2-aminomethyl-4-methyl-pentyl)-4H-[1,3,4]oxadiazol-5-one, or a pharmaceutically acceptable salt thereof.

Still more preferred is an embodiment that utilizes a compound of Formulas (1A) or (1B) named 3-(2-aminomethyl-4-methyl-pentyl)-4H-[1,2,4]oxadiazol-5-one hydrochloride.

Another embodiment of the present invention utilizes an alpha2delta ligand that is a compound of Formulas V, VI, VII, or VIII

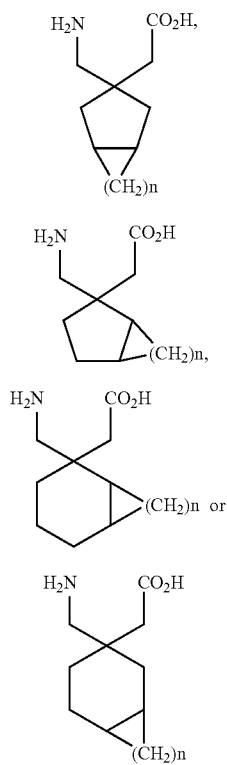

or a pharmaceutically acceptable salt thereof, wherein n is integer of from 1 to 4, where there are stereocenters, each center may be independently R or S.

A preferred embodiment utilizes a compound of Formulas V, VI, VII, or VIII, wherein n is an integer of from 2 to 4.

Another preferred embodiment utilizes a compound of Formula V.

A still more preferred embodiment utilizes a compound of Formulas V, VI, VII, or VIII selected from:
(1α,6α,8β)(2-Aminomethyl-octahydro-inden-2-yl)-acetic acid;
(2-Aminomethyl-octahydro-inden-2-yl)-acetic acid;
(2-Aminomethyl-octahydro-pentalen-2-yl)-acetic acid;
(2-Aminomethyl-octahydro-pentalen-2-yl)-acetic acid;
(3-Aminomethyl-bicyclo[3.2.0]hept-3-yl)-acetic acid; and;
(3-Aminomethyl-bicyclo[3.2.0]hept-3-yl)-acetic acid.
(2-Aminomethyl-octahydro-inden-2-yl)-acetic acid;

Another still more preferred embodiment utilizes a compound of Formulas V, VI, VII, or VIII selected from:
(1α,5β)(3-Aminomethyl-bicyclo[3.1.0]hex-3-yl)-acetic acid,
(1α,5β)(3-Aminomethyl-bicyclo[3.2.0]hept-3-yl)-acetic acid,
(1α,5β)(2-Aminomethyl-octahydro-pentalen-2-yl)-acetic acid,
(1α,6β)(2-Aminomethyl-octahydro-inden-2-yl)-acetic acid,
(1α,7β)(2-Aminomethyl-decahydro-azulen-2-yl)-acetic acid,
(1α,5β)(3-Aminomethyl-bicyclo[3.1.0]hex-3-yl)-acetic acid,
(1α,5β)(3-Aminomethyl-bicyclo[3.2.0]hept-3-yl)-acetic acid,
(1α,5β)(2-Aminomethyl-octahydro-pentalen-2-yl)-acetic acid,
(1α,6β)(2-Aminomethyl-octahydro-inden-2-yl)-acetic acid,
(1α,7β)(2-Aminomethyl-decahydro-azulen-2-yl)-acetic acid,
(1α,3α,5α)(3-Aminomethyl-bicyclo[3.1.0]hex-3-yl)-acetic acid,
(1α,3α,5α)(2-Aminomethyl-octahydro-pentalen-2-yl)-acetic acid,
(1α,6α,8α)(2-Aminomethyl-octahydro-inden-2-yl)-acetic acid,
(1α,7α,9α)(2-Aminomethyl-decahydro-azulen-2-yl)-acetic acid,
(1α,3β,5α)(3-Aminomethyl-bicyclo[3.1.0]hex-3-yl)-acetic acid,
(1α,3β,5α)(3-Aminomethyl-bicyclo[3.2.0]hept-3-yl)-acetic acid,
(1α,3β,5α)(2-Aminomethyl-octahydro-pentalen-2-yl)-acetic acid,
(1α,6α,8β)(2-Aminomethyl-octahydro-inden-2-yl)-acetic acid,
(1α,7α,9β)(2-Aminomethyl-decahydro-azulen-2-yl)-acetic acid,
((1R,3R,6R)-3-Aminomethyl-bicyclo[4.1.0]hept-3-yl)-acetic acid,
((1R,3S,6R)-3-Aminomethyl-bicyclo[4.1.0]hept-3-yl)-acetic acid,
((1S,3S,6S)-3-Aminomethyl-bicyclo[4.1.0]hept-3-yl)-acetic acid,
((1S,3R,6S)-3-Aminomethyl-bicyclo[4.1.0]hept-3-yl)-acetic acid,
((1R,3R,6S)-3-Aminomethyl-bicyclo[4.2.0]oct-3-yl)-acetic acid,
((1R,3S,6S)-3-Aminomethyl-bicyclo[4.2.0]oct-3-yl)-acetic acid,
((1S,3S,6R)-3-Aminomethyl-bicyclo[4.2.0]oct-3-yl)-acetic acid,
((1S,3R,6R)-3-Aminomethyl-bicyclo[4.2.0]oct-3-yl)-acetic acid,
((3αR,5R,7αS)-5-Aminomethyl-octahydro-inden-5-yl)-acetic acid,
((3αR,5S,7αS)-5-Aminomethyl-octahydro-inden-5-yl)-acetic acid,
((3αS,5S,7αR)-5-Aminomethyl-octahydro-inden-5-yl)-acetic acid,
((3αS,5R,7αR)-5-Aminomethyl-octahydro-inden-5-yl)-acetic acid,
((2R,4αS,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-decahydro-naphthalen-2-yl)-acetic acid,
((2R,4αR,8αS)-2-Aminomethyl-decahydro-naphthalen-2-yl)-acetic acid,
((2R,4αS,9αR)-2-Aminomethyl-decahydro-benzocyclophepten-2-yl)-acetic acid,
((2S,4αS,9αR)-2-Aminomethyl-decahydro-benzocyclophepten-2-yl)-acetic acid,
((2S,4αR,9αS)-2-Aminomethyl-decahydro-benzocyclophepten-2-yl)-acetic acid, ((2R,4αR,9αS)-2-Aminomethyl-decahydro-benzocyclo-hepten-2-yl)-acetic acid,
((1R,3R,6S)-3-Aminomethyl-bicyclo[4.1.0]hept-3-yl)-acetic acid,
((1R,3S,6S)-3-Aminomethyl-bicyclo[4.1.0]hept-3-yl)-acetic acid,
((1S,3S,6R)-3-Aminomethyl-bicyclo[4.1.0]hept-3-yl)-acetic acid,
((1S,3R,6R)-3-Aminomethyl-bicyclo[4.1.0]hept-3-yl)-acetic acid,
((1R,3R,6R)-3-Aminomethyl-bicyclo[4.2.0]oct-3-yl)-acetic acid,
((1R,3S,6R)-3-Aminomethyl-bicyclo[4.2.0]oct-3-yl)-acetic acid,
((1S,3S,6S)-3-Aminomethyl-bicyclo[4.2.0]oct-3-yl)-acetic acid,
((1S,3R,6S)-3-Aminomethyl-bicyclo[4.2.0]oct-3-yl)-acetic acid,
((3αR,5R,7αR)-5-Aminomethyl-octahydro-inden-5-yl)-acetic acid,
((3αR,5S,7αR)-5-Aminomethyl-octahydro-inden-5-yl)-acetic acid,
((3αS,5S,7αS)-5-Aminomethyl-octahydro-inden-5-yl)-acetic acid,
((3αS,5R,7αS)-5-Aminomethyl-octahydro-inden-5-yl)-acetic acid,
((2R,4αR,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-decahydro-naphthalen-2-yl)-acetic acid,
((2R,4αS,8αS)-2-Aminomethyl-decahydro-naphthalen-2-yl)-acetic acid,
((2R,4αR,9αR)-2-Aminomethyl-decahydro-benzocyclo-hepten-2-yl)-acetic acid,
((2S,4αR,9αR)-2-Aminomethyl-decahydro-benzocyclo-hepten-2-yl)-acetic acid,
((2S,4αS,9αS)-2-Aminomethyl-decahydro-benzocyclo-hepten-2-yl)-acetic acid, and
((2R,4αS,9αS)-2-Aminomethyl-decahydro-benzocyclo-hepten-2-yl)-acetic acid.

A more preferred embodiment utilizes a compound of Formulas V, VI, VII, or VIII named (1α,3α,5α)(3-aminomethyl-bicyclo[3.2.0]hept-3-yl)-acetic acid, or a pharmaceutically acceptable salt thereof.

A still more preferred embodiment utilizes a compound of Formulas V, VI, VII, or VIII named (1α,3α,5α)(3-aminomethyl-bicyclo[3.2.0]hept-3-yl)-acetic acid hydrochloride.

Other preferred embodiments of this invention relate to the above described method of treating tinnitus wherein the alpha2delta ligand that is employed is selected from the following compounds and their pharmaceutically acceptable salts:
3-(1-aminomethyl-cyclohexylmethyl)-4H-[1,2,4]oxadiazol-5-one;
(S,S)-(1-aminomethyl-3,4-dimethyl-cyclopentyl)-acetic acid;
(R,S)-3-aminomethyl-5-methyl-octanoic acid;
(S,R)-3-aminomethyl-5-methyl-octanoic acid;
(3-aminomethyl-bicyclo[3.2.0]hept-3-yl)-acetic acid;
(3-aminomethyl-bicyclo[3.2.0]hept-3-yl)-acetic acid, wherein the cyclobutyl ring is trans to the methylamine group; and
C-[1-(1H-tetrazol-5-ylmethyl)-cycloheptyl]-methylamine.

These compounds can be prepared as describrd below or in World Patent Application WO 99/21824, published May 6, 1999, World Patent Application WO 00/76958, published Dec. 21, 2000, or World Patent Application WO 01/28978, published Apr. 26, 2001. These applications are incorporated herein by reference in their entireties.

A more preferred embodiment utilizes the hydrochloride salt of the compound 3-(1-aminomethyl-cyclohexylmethyl)-4H-[1,2,4]oxadiazol-5-one.

DETAILED DESCRIPTION OF THE INVENTION

A preferred alpha2delta ligand to be utilized in the method of this invention is selected from the cyclic amino acids of Formula I. These are described in U.S. Pat. No. 4,024,175 and its divisional U.S. Pat. No. 4,087,544, which are both incorporated herein by reference.

Another preferred method utilizes an alpha2delta ligand of Formula II, and these compounds are described in U.S. Pat. No. 5,563,175, which is incorporated herein by reference.

Another preferred method utilizes an alpha2delta ligand of Formula III, IIIC, IIIF, IIIG, or IIIH, and these compounds are described in PCT International Application Publication No. WO 99/31075, which is herein incorporated by reference.

Another preferred method utilizes an alpha2delta ligand of Formula IV, which are described in PCT International Application Publication No. WO 00/76958, which is herein incorporated by reference.

Other preferred alpha2delta ligands to be utilized in the method of the present invention are compounds of Formulas (1A) and (1B), which are described in PCT International Application Publication No. WO 99/31074, which is herein incorporated by reference.

PCT International Application Publication No. WO 01/28978, which is herein incorporated by reference, describes other preferred alpha2delta ligands to be utilized in the method of the present invention, which are compounds of Formulas V, VI, VII, and VIII.

Other preferred alpha2delta ligands for use in the present invention method are described in PCT International Application No. WO 99/31057, which is herein incorporated by reference. Such alpha2delta ligands are compounds of Formula (1D) and (1E)

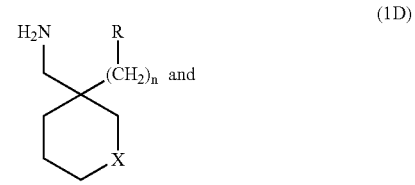

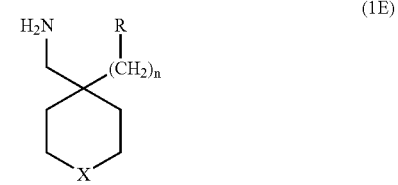

or a pharmaceutically acceptable salt thereof wherein:
n is an integer of from 0 to 2;
R is sulfonamide, amide,
phosphonic acid,
heterocycle,
sulfonic acid, or
hydroxamic acid; and X is —O—, —S—, —S(O)—, —S(O)$_2$—, or NR'$_1$ wherein R'$_1$ is hydrogen, straight or branched alkyl of from 1 to 6 carbons, benzyl, —C(O)R'$_2$ wherein R'$_2$ is straight or branched alkyl of 1 to 6 carbons, benzyl or phenyl or —CO$_2$R'$_3$ wherein R'$_3$ is straight or branched alkyl of from 1 to 6 carbons, or benzyl wherein the benzyl or phenyl groups can be unsubstituted or substituted by from 1 to 3 substituents selected from halogen, trifluoromethyl, and nitro.

Other preferred alpha2delta ligands that may be utilized in the method of the present invention are described in PCT International Application No. WO 98/17627, which is herein incorporated by reference. This embodiment uses an alpha2delta ligand that is a compound of formula

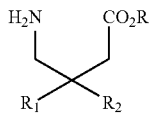

or a pharmaceutically acceptable salt thereof wherein:
R is hydrogen or lower alkyl;
R$_1$ is hydrogen or lower alkyl;

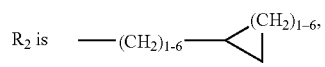

straight or branched alkyl of from 7 to 11 carbon atoms, or
—(CH$_2$)$_{(1-4)}$—X—(CH$_2$)$_{(0-4)}$-phenyl wherein
X is —O—, —S—, —NR$_3$- wherein
R$_3$ is alkyl of from 1 to 6 carbons, cycloalkyl of from 3 to 8 carbons, benzyl or phenyl;
wherein phenyl and benzyl can be unsubstituted or substituted with from 1 to 3 substituents each independently selected from alkyl, alkoxy, halogen, hydroxy, carboxy, carboalkoxy, trifluoromethyl, amino, and nitro.

Other preferred alpha2delta ligands that may be utilized in the method of the present invention are described in PCT International Application No. WO 99/61424, which is herein incorporated by reference. This embodiment of the invention method uses an alpha2delta ligand that is a compound of formula (1), (2), (3), (4), (5), (6), (7), or (8)

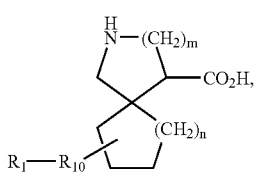

(1)

-continued

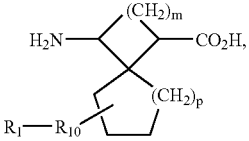

(2)

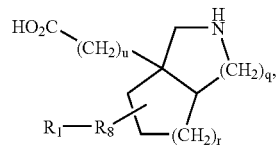

(3)

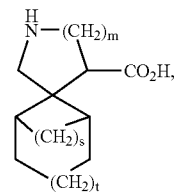

(4)

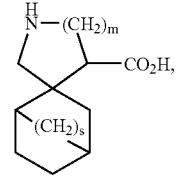

(5)

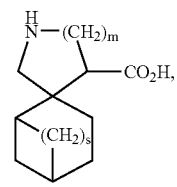

(6)

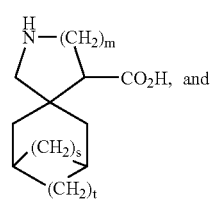

(7)

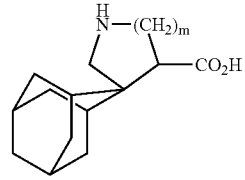

(8)

or a pharmaceutically acceptable salt thereof or a prodrug thereof wherein:
R$_1$ to R$_{10}$ are each independently selected from hydrogen or a straight or branched alkyl of from 1 to 6 carbons, benzyl, or phenyl;
m is an integer of from 0 to 3;
n is an integer of from 1 to 2;
o is an integer of from 0 to 3;
p is an integer of from 1 to 2;
q is an integer of from 0 to 2;
r is an integer of from 1 to 2;
s is an integer of from 1 to 3;

t is an integer of from 0 to 2; and u is an integer of from 0 to 1.

All US patents and WO publications referenced above are hereby incorporated by reference.

The terms are as defined below or as they otherwise occur in the specification.

It should be appreciated that the terms "uses", "utilizes", and "employs", and their derivatives thereof, are used interchangeably when describing an embodiment of the present invention.

The phrase "lower alkyl" means a straight or branched alkyl group or radical having from 1 to 6 carbon atoms, and includes methyl, ethyl, n-propyl, i-propyl, n-butyl, i-butyl, sec-butyl, tert-butyl, n-pentyl, n-hexyl, and the like.

The term "alkyl" is a straight or branched group of from 1 to 8 carbon atoms, unless stated otherwise, including but not limited to methyl, ethyl, propyl, n-propyl, isopropyl, butyl, 2-butyl, tert-butyl, and octyl. Alkyl can be unsubstituted or substituted by hydroxy or from 1 to 3 fluorine atoms. Preferred groups are methyl and ethyl.

The term "alkenyl" is a straight or branched group of from 2 to 8 carbon atoms containing 1 or 2 or 3 double bonds including but not limited to ethenyl, propen-1-yl, propen-2-yl, propen-3-yl, 1-hexen-3-yl, and hept-1,3-dien-7-yl. Alkenyl can be unsubstituted or substituted by from 1 to 3 fluorine atoms.

The term "cycloalkyl" means a cyclic group of from 3 to 7 carbon atoms including but not limited to cyclopropyl, cyclobutyl, and cycloheptyl.

The benzyl and phenyl groups may be unsubstituted or substituted with from 1 to 3 groups each independently selected from halogen, especially fluoro, alkoxy, alkyl, and $NH_2$.

Halogen includes fluorine, chlorine, bromine, and iodine.

The term "alkoxy" means the group —O-alkyl wherein alkyl is as defined above.

The terms used to define the invention of compounds of Formulas (1A), (1B), III, IIIC, IIIF, IIIG, and IIIH are as described below.

Sulfonamides are those of formula —$NHSO_2R^{15}$ or —$SO_2NHR^{15}$ wherein $R^{15}$ is a straight or branched alkyl group of from 1 to 6 carbons or a trifluoromethyl.

Amides are compounds of formula —$NHCOR^{12}$ wherein $R^{12}$ is straight or branched alkyl of from 1 to 6 carbons, benzyl, and phenyl.

Phosphonic acids are —$PO_3H_2$.

Sulfonic acids are —$SO_3H$.

Hydroxamic acid is

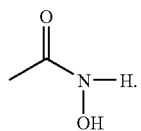

Heterocycles are groups of from 1 to 2 rings, with from 1 to 6 heteroatoms selected from oxygen, nitrogen, and sulfur.

Preferred heterocycles are

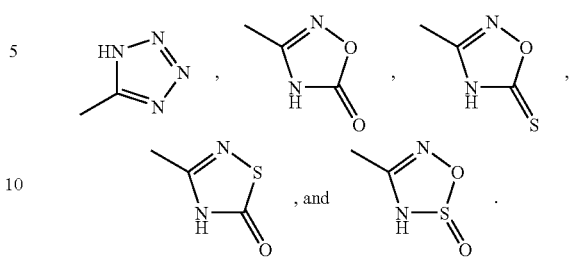

The term alkyl is a straight or branched group of from 1 to 11 carbon atoms including but not limited to methyl, ethyl, propyl, n-propyl, isopropyl, butyl, 2-butyl, tert-butyl, pentyl, hexyl, and n-hexyl, heptyl, octyl, nonyl, decyl, and undecyl except as where otherwise stated.

The cycloalkyl groups are from 3 to 8 carbons and are cyclopropyl, cyclobutyl, cyclopentyl, cyclohexyl, cycloheptyl, and cyclooctyl unless otherwise stated.

The benzyl and phenyl groups may be unsubstituted or substituted by from 1 to 3 substituents selected from hydroxy, carboxy, carboalkoxy, halogen, $CF_3$, nitro, alkyl, and alkoxy. Preferred are halogens.

Alkoxy is as defined above for alkyl.

Halogen is fluorine, chlorine, and bromine and preferred are fluorine and chlorine.

Carboalkoxy is —COOalkyl wherein alkyl is as described above. Preferred are carbomethoxy and carboethoxy.

The degree of binding to the α2δ subunit can be determined using the radioligand binding assay using [3H]gabapentin and the α2δ subunit derived from porcine brain tissue, as described by N. S. Gee et al., *J. Biol. Chem.*, 1996, 271:5879–5776.

The ability of a compound to treat tinnitus can be evaluated using the method described by Carol A. Bauer in "Assessing Tinnitus and Prospective Tinnitus Therapeutics Using a Psychological Animal Model", Journal of the Association for Research in Otolaryngology, 2/1:054–064 (2001).

All that is required to practice the method of this invention is to administer an alpha2delta ligand, or a pharmaceutically acceptable salt thereof, in an amount that is therapeutically effective to treat tinnitus. Such tinnitus-treating amount will generally be from about 1 to about 300 mg/kg of subject body weight. Typical doses will be from about 10 to about 5000 mg/day for an adult subject of normal weight. In a clinical setting, regulatory agencies such as, for example, the Food and Drug Administration ("FDA") in the U.S. may require a particular therapeutically effective amount.

In determining what constitutes an effective amount or a therapeutically effective amount of an alpha2delta ligand, or a pharmaceutically acceptable salt thereof, for treating tinnitus according to the invention method, a number of factors will generally be considered by the medical practitioner or veterinarian in view of the experience of the medical practitioner or veterinarian, published clinical studies, the subject's (ie, mammal's) age, sex, weight and general condition, as well as the type and extent of the disease, disorder or condition being treated, and the use of other medications, if any, by the subject. As such, the administered dose may fall within the ranges or concentrations recited above, or may vary outside, i.e., either below or above, those ranges depending upon the requirements of the individual subject, the severity of the condition being treated, and the particular therapeutic formulation being employed. Determination of a proper dose for a particular situation is within the skill of the medical or veterinary arts. Generally, treatment may be initiated using smaller dosages of the alpha2delta ligand that are less than optimum for a particular subject. Thereafter, the dosage can be increased by small increments until the optimum effect under the circumstance is reached. For convenience, the total daily dosage may be divided and administered in portions during the day, if desired.

Pharmaceutical compositions of an alpha2delta ligand, or a pharmaceutically acceptable salt thereof, are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses.

Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol, glycerin; sorbitol; polyethylene glycol; water; agar; alginic acid; isotonic saline, and phosphate buffer solutions; as well as other compatible substances normally used in pharmaceutical formulations.

The compositions to be employed in the invention can also contain other components such as coloring agents, flavoring agents, and/or preservatives. These materials, if present, are usually used in relatively small amounts. The compositions can, if desired, also contain other therapeutic agents commonly employed to treat tinnitus. Further, the compositions can, if desired, also contain other therapeutic agents commonly employed to treat secondary symptoms such as, for example, depression or anxiety that may or may not accompany tinnitus. For example, the compositions may contain aspirin, naprosyn, or similar anti-inflammatory analgesic agents.

The percentage of the active ingredients in the foregoing compositions can be varied within wide limits, but for practical purposes it is preferably present in a concentration of at least 10% in a solid composition and at least 2% in a primary liquid composition. The most satisfactory compositions are those in which a much higher proportion of the active ingredient is present, for example, up to about 95%.

Preferred routes of administration of an alpha2delta ligand, or a pharmaceutically acceptable salt thereof, are oral or parenteral. For example, a useful intravenous dose is between 5 and 50 mg, and a useful oral dosage is between 20 and 800 mg. The dosage is within the dosing range used in treatment of diseases resulting in tinnitus such as osteoarthritis, or as would be determined by the needs of the patient as described by the physician.

The alpha2delta ligand, or a pharmaceutically acceptable salt thereof, may be administered in any form. Preferably, administration is in unit dosage form. A unit dosage form of the alpha2delta ligand, or a pharmaceutically acceptable salt thereof, to be used in this invention may also comprise other compounds useful in the therapy of diseases resulting in tinnitus.

The advantages of using a compound of Formulas I, II, III, IIIC, IIIF, IIIG, IIIH, IV, (1A), (1B), V, VI, VII, or VIII, or a pharmaceutically acceptable salt thereof, including gabapentin, pregabalin, 3-(1-aminomethyl-cyclohexylmethyl)-4H-[1,2,4]oxadiazol-5-one hydrochloride, 3-(1-aminomethyl-cycloheptylmethyl)-4H-[1,2,4]oxadiazol-5-one hydrochloride, C-[1-(1H-tetrazol-5-ylmethyl)-cycloheptyl]-methylamine, 3-(2-aminomethyl-4-methyl-pentyl)-4H-[1,2,4]oxadiazol-5-one hydrochloride, (1α,3α,5α)(3-aminomethyl-bicyclo[3.2.0]hept-3-yl)-acetic acid hydrochloride, or (3S,5R)-3-aminomethyl-5-methyl-octanoic acid, in the instant invention include the relatively nontoxic nature of the compounds, the ease of preparation, the fact that the compounds are well-tolerated, and the ease of IV and oral administration of the drugs. Further, typically the drugs are not metabolized in the body.

The invention method is useful in human and veterinary medicines for treating or preventing tinnitus in a mammal. A mammal includes humans, cats, dogs, horses, cows, pigs, and sheep.

Some of the compounds utilized in a method of the present invention are capable of further forming pharmaceutically acceptable salts, including, but not limited to, acid addition and/or base salts. The acid addition salts are formed from basic compounds, whereas the base addition salts are formed from acidic compounds. All of these forms are within the scope of the compounds useful in the method of the present invention.

Pharmaceutically acceptable acid addition salts of the basic compounds useful in the method of the present invention include nontoxic salts derived from inorganic acids such as hydrochloric, nitric, phosphoric, sulfuric, hydrobromic, hydroiodic, hydrofluoric, phosphorous, and the like, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like. Also contemplated are salts of amino acids such as arginate and the like and gluconate, galacturonate (see, for example, Berge S. M. et al., "Pharmaceutical Salts," *J. of Pharma. Sci.*, 1977; 66:1).

An acid addition salt of a basic compound useful in the method of the present invention is prepared by contacting the free base form of the compound with a sufficient amount of a desired acid to produce a nontoxic salt in the conventional manner. The free base form of the compound may be regenerated by contacting the acid addition salt so formed with a base, and isolating the free base form of the compound in the conventional manner. The free base forms of compounds prepared according to a process of the present invention differ from their respective acid addition salt forms somewhat in certain physical properties such as solubility, crystal structure, hygroscopicity, and the like, but otherwise free base forms of the compounds and their respective acid addition salt forms are equivalent for purposes of the present invention.

A pharmaceutically acceptable base addition salt of an acidic compound useful in the method of the present invention may be prepared by contacting the free acid form of the compound with a nontoxic metal cation such as an alkali or alkaline earth metal cation, or an amine, especially an organic amine. Examples of suitable metal cations include sodium cation (Na+), potassium cation (K+), magnesium cation (Mg$^{2+}$), calcium cation (Ca$^{2+}$), and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, supra., 1977).

A base addition salt of an acidic compound useful in the method of the present invention may be prepared by contacting the free acid form of the compound with a sufficient amount of a desired base to produce the salt in the conventional manner. The free acid form of the compound may be regenerated by contacting the salt form so formed with an acid, and isolating the free acid of the compound in the conventional manner. The free acid forms of the compounds useful in the method of the present invention differ from their respective salt forms somewhat in certain physical properties such as solubility, crystal structure, hygroscopicity, and the like, but otherwise the salts are equivalent to their respective free acid for purposes of the present invention.

Certain of the compounds useful in the method of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds useful in the method of the present invention possess one or more chiral centers, and each center may exist in the R or S configuration. A method of the present invention may utilize any diastereomeric, enantiomeric, or epimeric form of an alpha2delta ligand, or a pharmaceutically acceptable salt thereof, as well as mixtures thereof.

Additionally, certain compounds useful in the method of the present invention may exist as geometric isomers such as the entgegen (E) and zusammen (Z) isomers of alkenyl groups. A method of the present invention may utilize any cis, trans, syn, anti, entgegen (E), or zusammen (Z) isomer of an alpha2delta ligand, or a pharmaceutically acceptable salt thereof, as well as mixtures thereof.

Certain compounds useful in the method of the present invention can exist as two or more tautomeric forms. Tautomeric forms of the compounds may interchange, for example, via enolization/de-enolization and the like. A method of the present invention may utilize any tautomeric form of an alpha2delta ligand, or a pharmaceutically acceptable salt thereof, as well as mixtures thereof.

Intermediates for the synthesis of an alpha2delta ligand, or a pharmaceutically acceptable salt thereof, useful in the invention method, and pharmaceutically acceptable salts thereof, may be prepared by one of ordinary skill in the art of organic chemistry by adapting various synthetic procedures that are well-known in the art of organic chemistry. These synthetic procedures may be found in the literature in, for example, *Reagents for Organic Synthesis*, by Fieser and Fieser, John Wiley & Sons, Inc, New York, 2000; *Comprehensive Organic Transformations*, by Richard C. Larock, VCH Publishers, Inc, New York, 1989; the series *Compendium of Organic Synthetic Methods,* 1989, by Wiley-Interscience; the text *Advanced Organic Chemistry, 4$^{th}$* edition, by Jerry March, Wiley-Interscience, New York, 1992; or the *Handbook of Heterocyclic Chemistry* by Alan R. Katritzky, Pergamon Press Ltd, London, 1985, to name a few. Alternatively, a skilled artisan may find methods useful for preparing the intermediates in the chemical literature by searching widely available databases such as, for example, those available from the *Chemical Abstracts Service*, Columbus, Ohio, or *MDL Information Systems GmbH* (formerly *Beilstein Information Systems GmbH*), Frankfurt, Germany.

Preparations of the compounds useful in a method of the present invention may use starting materials, reagents, solvents, and catalysts that may be purchased from commercial sources or they may be readily prepared by adapting procedures in the references or resources cited above. Commercial sources of starting materials, reagents, solvents, and catalysts useful in preparing invention compounds include, for example, *The Aldrich Chemical Company*, and other subsidiaries of Sigma-Aldrich Corporation, St. Louis, Mo., *BACHEM*, BACHEM A. G., Switzerland, or *Lancaster Synthesis Ltd*, United Kingdom.

Syntheses of some compounds useful in the method of the present invention may utilize starting materials, intermediates, or reaction products that contain a reactive functional group. During chemical reactions, a reactive functional group may be protected using protecting groups that render the reactive group substantially inert to the reaction conditions employed. A protecting group is introduced onto a starting material prior to carrying out the reaction step for which a protecting group is needed. Once the protecting group is no longer needed, the protecting group can be removed. It is well within the ordinary skill in the art to introduce protecting groups during a synthesis of an alpha2delta ligand, or a pharmaceutically acceptable salt thereof, and then later remove them. Procedures for introducing and removing protecting groups are known and referenced such as, for example, in *Protective Groups in Organic Synthesis, 2$^{nd}$* ed., Greene T. W. and Wuts P. G., John Wiley & Sons, New York: N.Y., 1991, which is hereby incorporated by reference. Thus, for example, protecting groups such as the following may be utilized to protect amino, hydroxyl, and other groups: carboxylic acyl groups such as, for example, formyl, acetyl, and trifluoroacetyl; alkoxycarbonyl groups such as, for example, ethoxycarbonyl, tert-butoxycarbonyl (BOC), β,β,β-trichloroethoxycarbonyl (TCEC), and β-iodoethoxycarbonyl; aralkyloxycarbonyl groups such as, for example, benzyloxycarbonyl (CBZ), para-methoxybenzyloxycarbonyl, and 9-fluorenylmethyloxycarbonyl (FMOC); trialkylsilyl groups such as, for example, trimethylsilyl (TMS) and tert-butyldimethylsilyl (TBDMS); and other groups such as, for example, triphenylmethyl (trityl), tetrahydropyranyl, vinyloxycarbonyl, ortho-nitrophenylsulfenyl, diphenylphosphinyl, para-toluenesulfonyl (Ts), mesyl, trifluoromethanesulfonyl, and benzyl. Examples of procedures for removal of protecting groups include hydrogenolysis of CBZ groups using, for example, hydrogen gas at 50 psi in the presence of a hydrogenation catalyst such as 10% palladium on carbon, acidolysis of BOC groups using, for example, hydrogen chloride in dichloromethane, trifluoroacetic acid (TFA) in dichloromethane, and the like, reaction of silyl groups with fluoride ions, and reductive cleavage of TCEC groups with zinc metal.

Preparations of an alpha2delta ligand, or a pharmaceutically acceptable salt thereof, useful in the method of the present invention are incorporated by reference to the patents or patent application publications described above, or are illustrated in the Schemes below.

Compounds of Formulas III, IIIC, IIIF, IIIG, and IIIH may be prepared according to the following methods. Sulfonamides can be synthesized by the general route outlined in Scheme 1.

Scheme 1

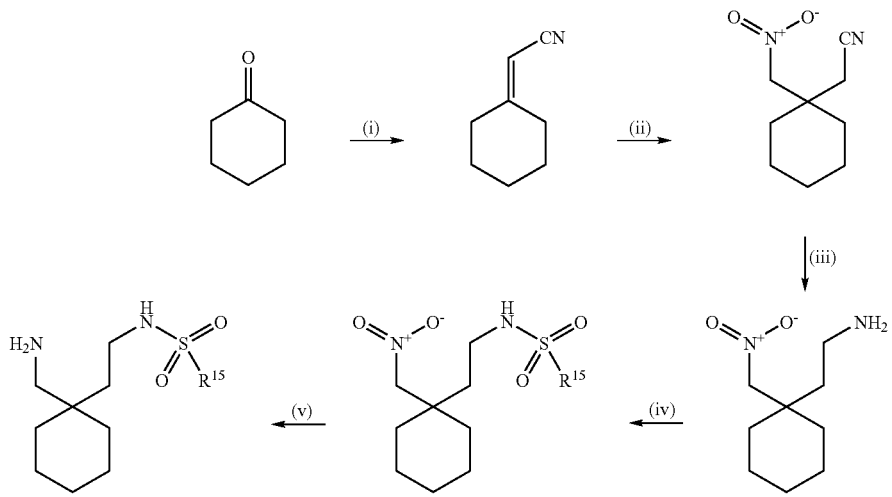

Reagents:
(i) Diethylcyanomethyl phosphonate, NaH, tetrahydrofuran;
(ii) Nitromethane, tetrabutylammonium fluoride, tetrahydrofuran;
(iii) Borane methyl sulphide, toluene;
(iv) Triethylamine, $R^{15}SO_2Cl$, tetrahydrofuran;
(v) 10% Pd—C, hydrogen gas, methanol.

Tetrazoles can be synthesized by the general route outlined in Scheme 2.

Scheme 2

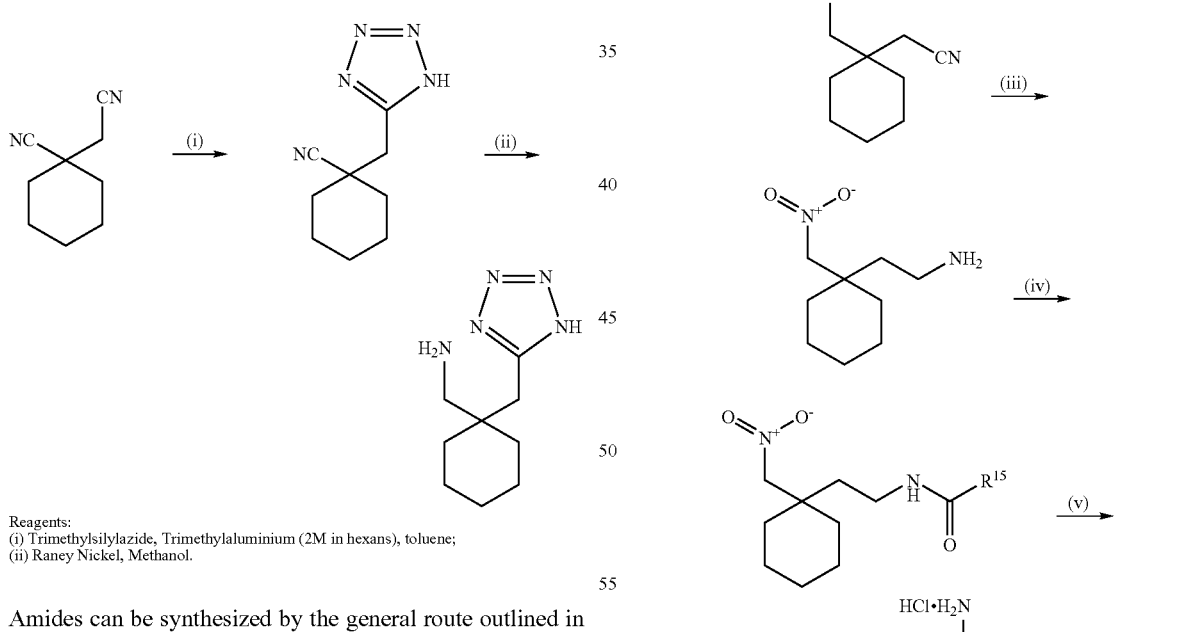

Reagents:
(i) Trimethylsilylazide, Trimethylaluminium (2M in hexans), toluene;
(ii) Raney Nickel, Methanol.

Amides can be synthesized by the general route outlined in Scheme 3.

Scheme 3

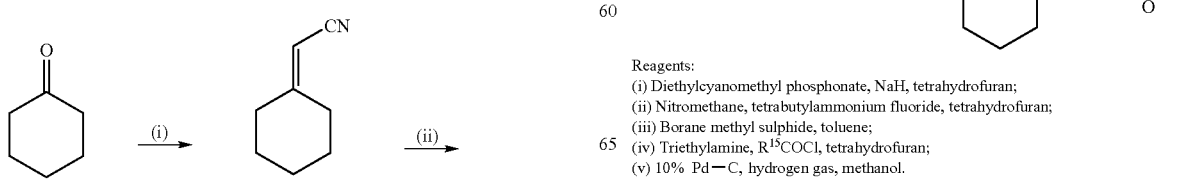

Reagents:
(i) Diethylcyanomethyl phosphonate, NaH, tetrahydrofuran;
(ii) Nitromethane, tetrabutylammonium fluoride, tetrahydrofuran;
(iii) Borane methyl sulphide, toluene;
(iv) Triethylamine, $R^{15}COCl$, tetrahydrofuran;
(v) 10% Pd—C, hydrogen gas, methanol.

Heterocycles such as

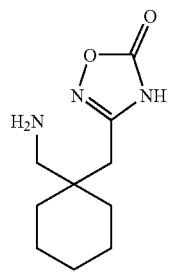

can be synthesized by the general route outlined in Scheme 4.

Scheme 4

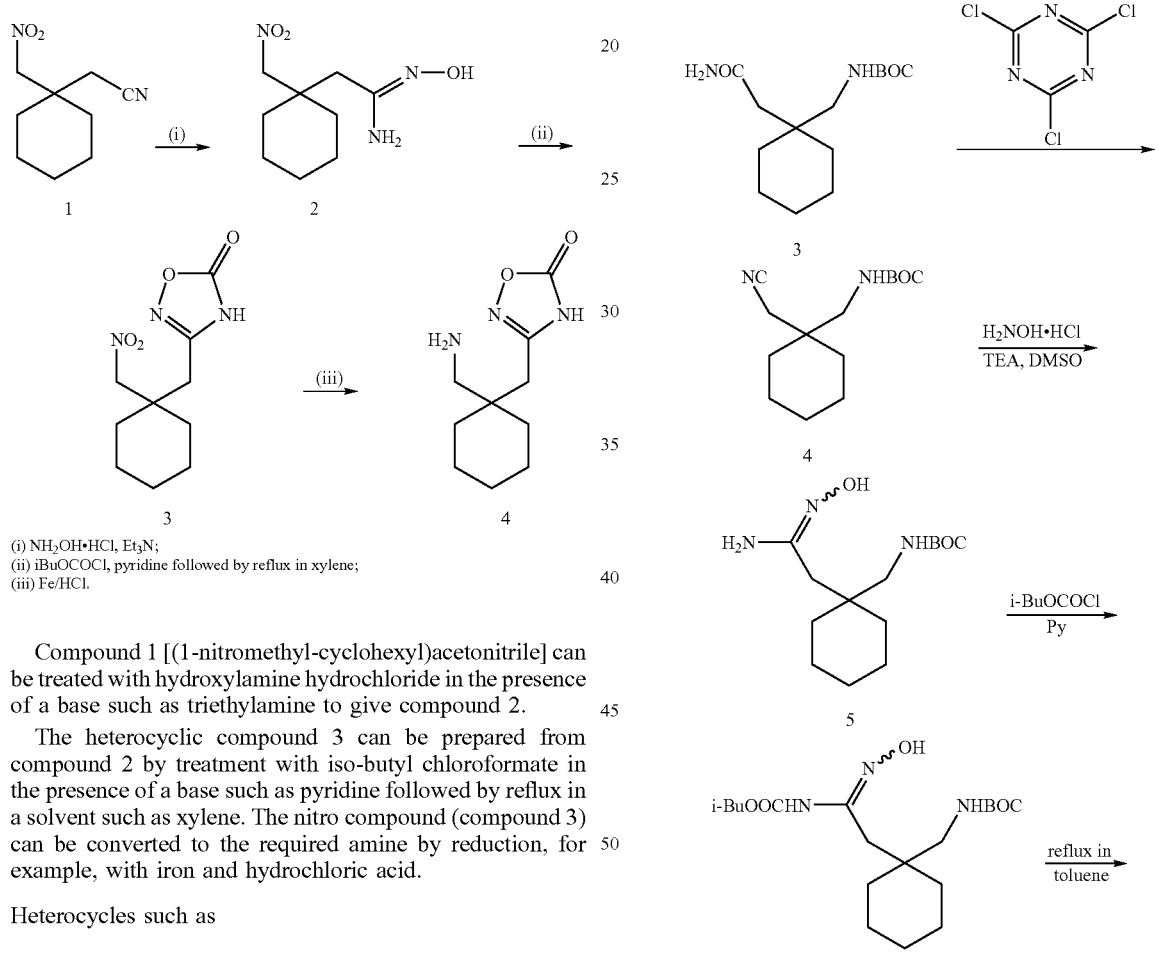

(i) NH$_2$OH·HCl, Et$_3$N;
(ii) iBuOCOCl, pyridine followed by reflux in xylene;
(iii) Fe/HCl.

Compound 1 [(1-nitromethyl-cyclohexyl)acetonitrile] can be treated with hydroxylamine hydrochloride in the presence of a base such as triethylamine to give compound 2.

The heterocyclic compound 3 can be prepared from compound 2 by treatment with iso-butyl chloroformate in the presence of a base such as pyridine followed by reflux in a solvent such as xylene. The nitro compound (compound 3) can be converted to the required amine by reduction, for example, with iron and hydrochloric acid.

Heterocycles such as

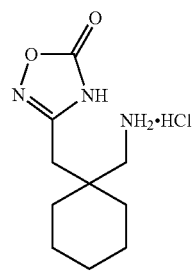

can be synthesized by the general route outlined in Scheme 5a.

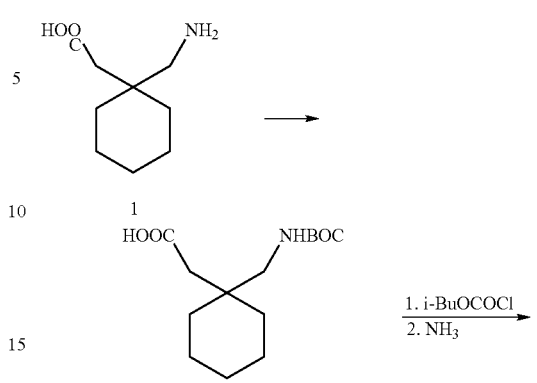

-continued

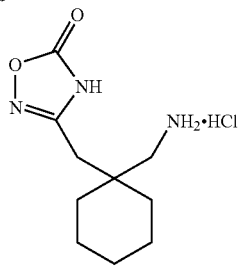

Heterocycles such as

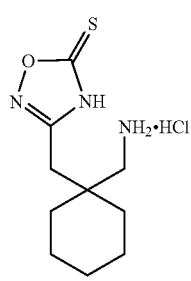

can be synthesized by the general route outlined in Scheme 5b.

Scheme 5b

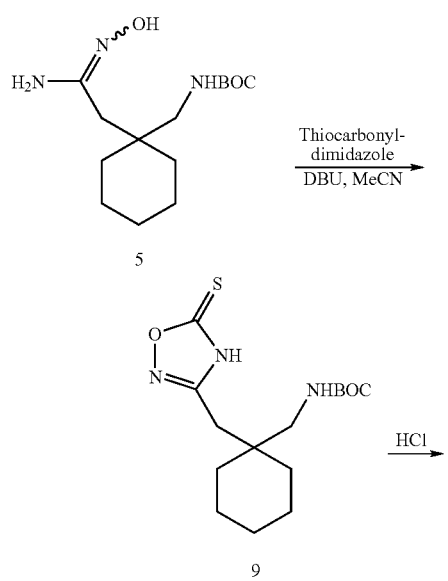

-continued

Heterocycles such as

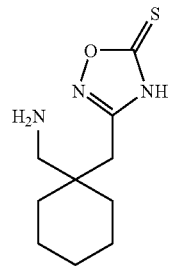

can be synthesized by the general route shown in Scheme 6 below:

Scheme 6

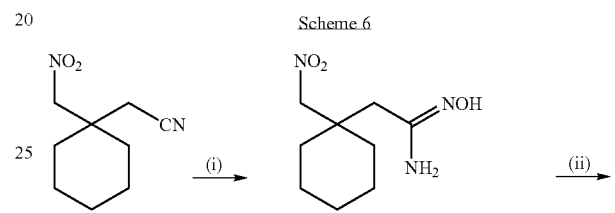

(i) NH$_2$OH•HCl, Et$_3$N;
(ii) 1,1'-thiocarbonyldiimidazole followed by DBU or DBN;
(iii) Fe/HCl.

Compound 1 [(nitromethyl-cyclohexyl)acetonitrile] can be treated with hydroxylamine hydrochloride in the presence of a base such as triethylamine to give compound 2.

The heterocyclic compound 3 can be prepared from compound 2 by treatment with 1,1'-thiocarbonyldiimidazole followed by a base such as 1,8-diazabicyclo-[4,5,0]-undec-7-ene (DBU) or 1,5-diazabicyclo[2.2.2]octane] (DBN).

The nitro compound (compound 3) can be converted to the required amine by reduction, for example, with iron and hydrochloric acid.

Heterocycles such as

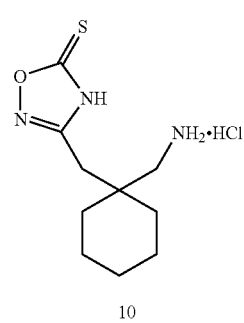

can be synthesized following the general route as shown in Scheme 7.

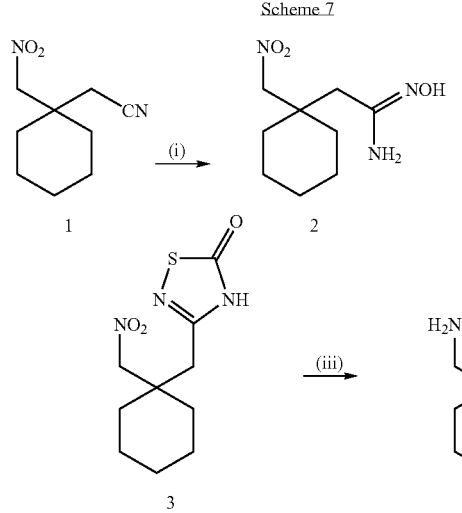

(i) NH$_2$OH•HCl, Et$_3$N;
(ii) 1,1'-thiocarbonyldiimidazole followed by silica gel or BF$_3$•OEt$_2$;
(iii) Fe/HCl.

Compound 1 [(nitromethyl-cyclohexyl)acetonitrile] can be treated with hydroxylamine hydrochloride in the presence of a base such as triethylamine to give compound 2.

The heterocyclic compound 3 can be prepared from compound 2 by treatment with 1,1'-thiocarbonyldiimidazole followed by treatment with silica gel or boron trifluoride etherate.

The nitro compound (compound 3) can be converted to the required amine by reduction, for example, with iron and hydrochloric acid.

Heterocycles such as

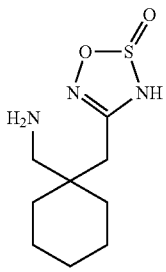

can be synthesized following the general route outlined in Scheme 8:

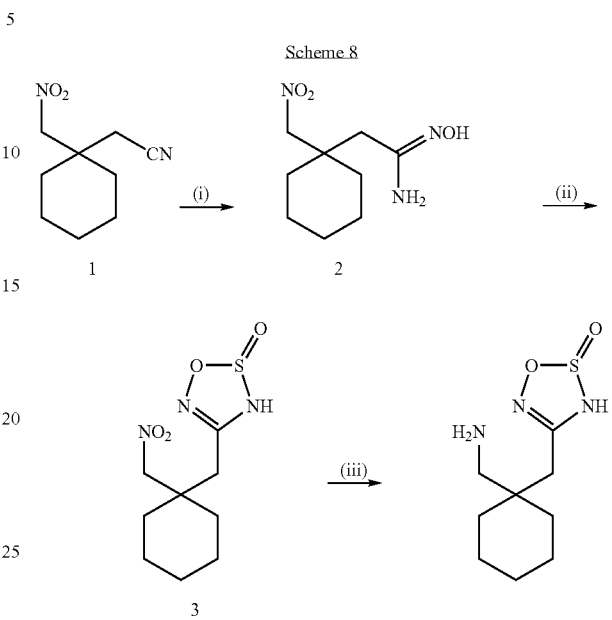

(i) NH$_2$OH•HCl, Et$_3$N;
(ii) Pyridine, SOCl$_2$;
(iii) Fe/HCl.

Compound 1 [(nitromethyl-cyclohexyl)acetonitrile] can be treated with hydroxylamine hydrochloride in the presence of a base such as triethylamine to give compound 2.

The heterocyclic compound 3 can be prepared from compound 2 by treatment with thionyl chloride in the presence of a base such as pyridine.

The nitro compound (compound 3) can be converted to the required amine by reduction, for example, with iron and hydrochloric acid.

The following examples are illustrative of the preparation of compounds of Formulas III, IIIC, IIIF, IIIG, or IIIH; they are not intended to limit the scope.

EXAMPLE 1

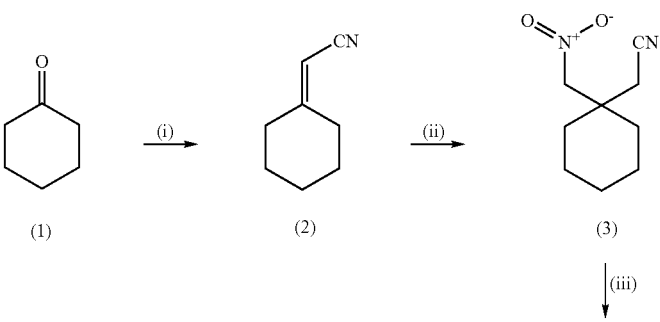

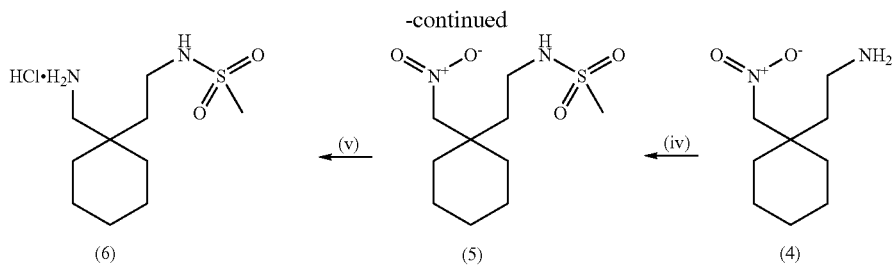

Reagents:
(i) Diethylcyanomethyl phosphonate, NaH, tetrahydrofuran;
(ii) Nitromethane, tetrabutylammonium fluoride, tetrahydrofuran;
(iii) Borane methyl sulphide, toluene;
(iv) Triethylamine, methanesulphonyl chloride, tetrahydrofuran;
(v) 10% Pd—C, hydrogen gas, methanol than HCl.

Cyclohexylidene-Acetonitrile (2)

Sodium hydride (60% in oil, 0.80 g, 20 mmol) was suspended in 50 mL tetrahydrofuran and chilled in ice under nitrogen. Diethylcyanomethyl phosphonate (3.85 g, 22 mmol) was added dropwise in 10 mL tetrahydrofuran and stirring continued for 15 minutes to give a clear solution. Cyclohexanone (1.90 g, 19 mol) was added in 5 mL tetrahydrofuran and the reaction mixture allowed to warm up to room temperature. The liquor was decanted and the residue washed three times with ether. The liquor and washings were combined, washed with dilute hydrochloric acid and water, dried over magnesium sulphate, filtered, and evaporated to dryness. The residue was purified by chromatography on silica eluting with heptane/ethyl acetate 4:1 to give the required product as a colorless oil (1.5 g, 67%).

$^1$H NMR 400 MHz (CDCl$_3$): δ 1.50 (m, 6H), 2.25 (t, J=5.6 Hz, 2H), 2.49 (t, J=6.8 Hz, 2), 5.04 (s, 1H). IR vmax 2933, 2859, 2217, 1633, 1449

(1-Nitromethyl-cyclohexyl)-acetonitrile (3)

The nitrile (compound 2, 0.78 g, 6.44 mmol), nitromethane (0.80 g, 13.11 mmol) and tetrabutyl ammonium fluoride (1.0 M in tetrahydrofuran, 10 mL, 10 mmol) were heated in 20 mL tetrahydrofuran to 70° C. overnight. The reaction mixture was diluted with ethyl acetate and washed with dilute hydrochloric acid and water, dried over magnesium sulphate, filtered, and evaporated to dryness. The residue was purified by chromatography on silica eluting with heptane/ethyl acetate 3:1 to give the required product as a yellow oil (0.83 g, 71%).

$^1$H NMR 400 MHz (CDCl$_3$): δ 1.57 (s, 10H), 2.63 (s, 2H), 4.52 (s, 2H). Analysis calculated for C$_9$H$_{13}$N$_2$O$_2$: C, 59.32; H, 7.74; N, 15.37. Found: C, 59.40; H, 7.65; N, 15.18.

2-(1-Nitromethyl-cyclohexyl)-ethylamine (4)

Borane methyl sulphide (2.0 M in toluene, 1.3 mL, 2.6 mmol) was added to compound 3 (0.4 g, 2.2 mmol) in toluene (10 mL) under nitrogen. After heating to 60° C. for 3 hours, the mixture was allowed to cool, and 15 mL methanol was added followed by 15 mL 4 M HCl in dioxane. After reflux for 1 hour, the mixture was evaporated to dryness. Crystallization from ethyl acetate gave the required product as colorless crystals (0.23 g, 47%); mp 170–173° C.

$^1$H NMR 400 MHz (d$_6$_DMSO): δ 1.30–1.50 (m, 10H), 1.64–1.69 (m, 2H), 2.82–2.86 (m, 2H), 4.75 (s, 2H), 7.89 (s, 3H). Analysis calculated for C$_9$H$_{18}$N$_2$O$_2$·HCl·0.2H$_2$O: C, 47.77; H, 8.64; N, 12.38. Found: C, 47.80; H, 8.66; N, 12.64.

N-[2-(1-Nitromethyl-cyclohexyl)-ethyl]-methane-sulfonamide (5)

Triethylamine (0.64 g, 6.3 mmol) was added dropwise to a mixture of the amine hydrochloride salt (compound 4, 0.70 g, 3.1 mmol) and methane sulfonyl chloride (0.36 g, 6.3 mmol) in tetrahydrofuran (35 mL). After stirring at room temperature for 2 hours, the mixture was filtered, diluted with ethyl acetate, and washed with dilute hydrochloric acid, saturated sodium bicarbonate solution, and water, dried over magnesium sulphate, filtered, and evaporated to dryness. The residue was crystallized from ethyl acetate/heptane to give colorless crystals (0.39 g, 47%); mp 86–88° C.

$^1$H NMR 400 MHz (d$_6$_DMSO): δ 1.35–1.50 (m, 10H), 1.55–1.60 (m, 2H), 2.89 (s, 3H), 2.99–3.06 (m, 2H), 4.55 (s, 2H), 6.93 (t, J=6 Hz, 1H). Analysis calculated for C$_{10}$H$_{20}$N$_2$O$_4$S: C, 45.44; H, 7.63; N, 10.60; S, 12.13. Found: C, 45.77; H, 7.64; N, 10.58; S, 12.17.

N-[2-(1-Aminomethyl-cyclohexyl)-ethyl]-methane-sulfonamide hydrochloride (6)

Ten percent Palladium on carbon was added under nitrogen to a solution of compound 5 (0.35 g, 1.3 mmol) in methanol (50 mL). The mixture was shaken under 40 psi hydrogen for 6 hours and then filtered through keiselguhr. The filtrate was evaporated to dryness. 4N HCl in dioxane was added followed by ether to give the product as a colorless crystalline solid (0.33 g, 92%); mp 196–199° C.

$^1$H NMR 400 MHz (d$_6$_DMSO): δ 1.25–1.45 (m, 10H), 1.55–1.60 (m, 5H), 2.70–2.75 (m, 2H), 2.90–2.95 (m, 5H), 6.86 (t, J=6.0 Hz, 1H), 7.86 (bs, 3H). Analysis calculated for C$_{10}$H$_{22}$N$_2$O$_2$S·HCl·0.25H$_2$O: C, 43.63; H, 8.60; N, 10.17. Found: C, 43.43; H, 8.64; N, 9.95.

EXAMPLE 2

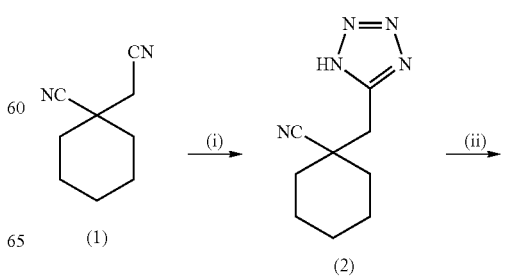

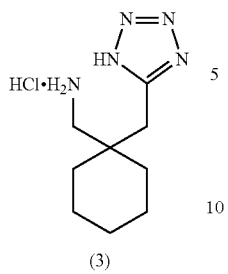

Reagents:
(i) Trimethylsilylazide, trimethylaluminium (2 M in hexanes), toluene;
(ii) Raney Nickel, hydrogen gas, methanol then HCl.

1-(1H-Tetrazol-5-ylmethyl)-cyclohexane-carbonitrile (2)

To a solution of the bis nitrile (Griffiths G., Mettler H., Mills L. S., and Previdoli F., *Helv. Chim. Acta,* 74:309 (1991)) (1.48 g, 10 mmol) in toluene (20 mL) under nitrogen was added trimethylsilylazide (1.15 g, 10 mmol) followed by trimethylaluminium (5 mL, 2.0 M in hexanes, 10 mmol). After heating to 90° C. overnight the mixture was allowed to cool and added carefully to ethyl acetate, ice and 6N hydrochloric acid. The aqueous phase was extracted with ethyl acetate, and the extracts washed with water, dried over magnesium sulphate, and evaporated to dryness. Crystallization gave the required compound (158 mg, 8%).

C-[1-(1H-Tetrazol-5-ylmethyl)-cyclohexyl]-methylamine hydrochloride (3)

The tetrazole (compound 8, 158 mg, 0.83 mmol) in methanol was added to a washed suspension of Raney nickel in methanol. The mixture was shaken under 40 psi hydrogen for 3.5 hours and then filtered to remove the catalyst and evaporated to dryness. The residue was partitioned between ethyl acetate and dilute hydrochloric acid. The aqueous phase was separated and evaporated to dryness. Recrystallization from methanol/ether gave the required product (44 mg, 23%); mp 176–179° C.

$^1$H NMR 400 MHz (d$_6$-DMSO): δ 1.20–1.60 (m, 10H), 2.84 (s, 2H), 3.07 (s, 2H), 8.06 (bs, 3H).

EXAMPLE 3

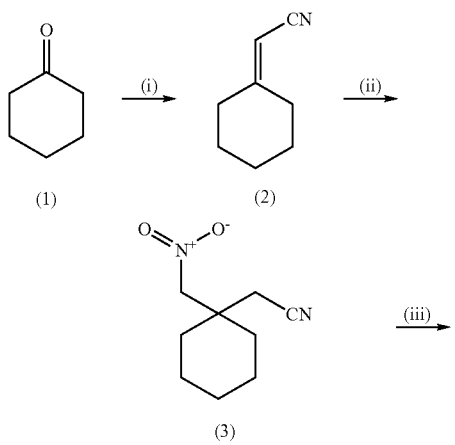

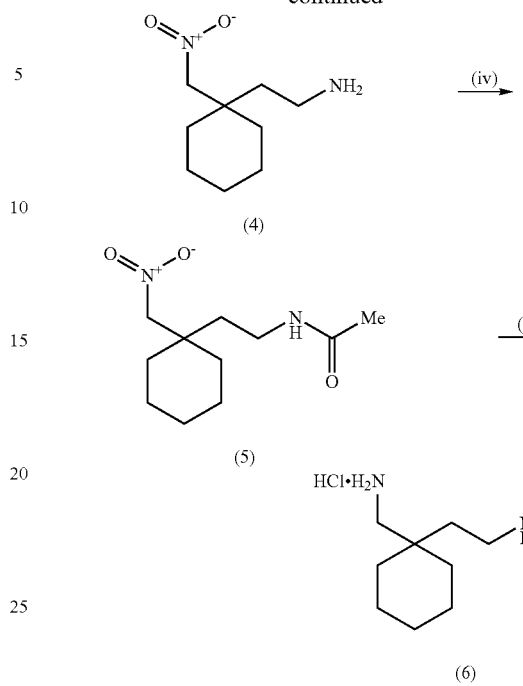

Reagents:
(i) Diethylcyanomethyl phosphonate, NaH, tetrahydrofuran;
(ii) Nitromethane, tetrabutylammonium fluoride, tetrahydrofuran;
(iii) Borane methyl sulphide, toluene;
(iv) Triethylamine, acetyl chloride, tetrahydrofuran;
(v) 10% Pd—C, hydrogen gas, methanol then HCl

Cyclohexylidene-Acetonitrile (2)

Sodium hydride (60% in oil, 0.80 g, 20 mmol) was suspended in 50 mL tetrahydrofuran and chilled in ice under nitrogen. Diethylcyanomethyl phosphonate (3.85 g, 22 mmol) was added dropwise in 10 mL tetrahydrofuran and stirring continued for 15 minutes to give a clear solution. Cyclohexanone (1.90 g, 19 mmol) was added in 5 mL tetrahydrofuran and the reaction mixture allowed to warm up to room temperature. The liquor was decanted and the residue washed three times with ether. The liquor and washings were combined, washed with dilute hydrochloric acid and water, dried over magnesium sulphate, filtered, and evaporated to dryness. The residue was purified by chromatography on silica eluting with heptane/ethyl acetate 4:1 to give the required product as a colorless oil (1.5 g, 67%).

$^1$H NMR 400 MHz (CDCl$_3$): δ 1.50 (m, 6H), 2.25 (t, J=5.6 Hz, 2H), 2.49 (t, J=6.8 Hz, 2H), 5.04 (s, 1H). IR vmax 2933, 2859, 2217, 1633, 1449.

(1-Nitromethyl-cyclohexyl)-acetonitrile (3)

The nitrile (compound 2, 0.78 g, 6.44 mmol), nitromethane (0.80 g, 13.11 mmol) and tetrabutyl ammonium fluoride (1.0 M in tetrahydrofuran, 10 mL, 10 mmol) were heated in 20 mL tetrahydrofuran to 70° C. overnight. The reaction mixture was diluted with ethyl acetate and washed with dilute hydrochloric acid and water, dried over magnesium sulphate, filtered, and evaporated to dryness. The residue was purified by chromatography on silica eluting with heptane/ethyl acetate 3:1 to give the required product as a yellow oil (0.83 g, 71%).

¹H NMR 400 MHz (CDCl₃): δ 1.57 (s, 10H), 2.63 (s, 2H), 4.52 (s, 2H). Analysis calculated for $C_9H_{13}N_2O_2$: C, 59.32; H, 7.74; N, 15.37. Found: C, 59.40; H, 7.65; N, 15.18.

2-(1-Nitromethyl-cyclohexyl)-ethylamine (4)

Borane methyl sulphide (2.0 M in toluene, 1.3 mL, 2.6 mmol) was added to compound 3 (0.4 g, 2.2 mmol) in toluene (10 mL) under nitrogen. After heating to 60° C. for 3 hours, the mixture was allowed to cool, and 15 mL methanol was added followed by 15 mL 4 M HCl in dioxane. After reflux for 1 hour, the mixture was evaporated to dryness. Crystallization from ethyl acetate gave the required product as colorless crystals (0.23 g, 47%); mp 170–173° C.

¹H NMR 400 MHz (d₆DMSO): δ 1.30–1.50 (m, 10H), 1.64–1.69 (m, 2H), 2.82–2.86 (m, 2H), 4.75 (s, 2H), 7.89 (s, 3H). Analysis calculated for $C_9H_{18}N_2O_2 \cdot HCl \cdot 0.2H_2O$: C, 47.77; H, 8.64; N, 12.38. Found: C, 47.80; H, 8.66; N, 12.64.

N-[2-(1-Nitromethyl-cyclohexyl)-ethyl]-acetamide (5)

The amine hydrochloride salt (compound 4, 0.50 g, 2.25 mmol) was reacted with acetyl chloride (0.20 g, 2.55 mmol) and triethylamine (0.45 g, 4.45 mmol) in tetrahydrofuran following the procedure described in Example 1, Step 4. Purification by chromatography on silica eluting with ethyl acetate gave the required product as a crystalline solid (0.35 g, 69%); mp 68–70° C.

¹H NMR 400 MHz (CDCl₃): δ 1.40–1.60 (m, 10H), 1.60–1.65 (m, 2H), 1.98 (s, 3H), 3.30–3.40 (m, 2H), 4.40 (s, 2H), 5.59 (bs, 1H).

N-[2-(1-Aminomethyl-cyclohexyl)-ethyl]-acetamide hydrochloride (6)

Compound 5 (0.30 g, 1.3 mmol) was hydrogenated in the presence of 10% palladium on carbon following the procedure described in Example 1, Step 5 to give the product as the hydrochloride salt (0.35 g, 100%).

¹H NMR 400 MHz (d₆DMSO): δ 1.20–1.40 (m, 10H), 1.40–1.50 (m, 2H), 1.81 (s, 3H), 2.75 (q, J=6.0 Hz, 2H), 2.95–3.05 (m, 2H), 7.99 (bs, 3H), 8.06 (t, J=4.8 Hz, 1H). IR vmax 3265, 2929, 1628, 1553, 1446, 1373, 1298.

EXAMPLE 4

3-(1-Aminomethyl-cyclohexylmethyl)-4H-[1,2,4]oxadiazol-5-one; hydrochloride [1-(tert-Butoxycarbonylamino-methyl)-cyclohexyl]-acetic acid (2)

A solution of Gabapentin (1) (9.37 g, 0.0547 mol) in 125 mL 1N NaOH and 50 mL THF was cooled to 0° C. and a solution of di-tert-butyl dicarbonate (13.1 g, 0.06 mol) in 200 mL THF was slowly added. The reaction mixture was stirred at room temperature 2 hours and concentrated on a rotary evaporator to remove THF. The concentrate was saturated with KH₂PO₄ and extracted 3×EtOAc. The EtOAc extracts were washed 2× brine and dried over MgSO₄. Evaporation yielded 14.8 g (100%) white solid, mp 109–111° C.

¹ HNMR (CDCl₃) δ 1.2–1.4 (m, 19H), 2.27 (s, 2H), 3.11 (d, 2H, J=6.84 Hz), 4.95 (broad, 1H). MS (APCI) m/z 272 (M+1). Analysis calculated for $C_{14}H_{25}NO_4$: C, 61.97; H, 9.29; N, 5.16. Found: C, 62.36; H, 9.27; N, 5.19.

(1-Carbamoylmethyl-cyclohexylmethyl)-carbamic acid tert-butyl ester (3)

[1-(tert-Butoxycarbonylamino-methyl)-cyclohexyl]-acetic acid (2) (152 g, 0.56 mol) was taken up in 1 L THF and triethylamine (66.2 g, 0.65 mol) and cooled to –10° C. Over a 1-hour period, isobutyraldehyde was added (84.7 g, 0.62 mol), and the heterogeneous mixture was stirred at 0° C. for 15 minutes. Ammonia gas was bubbled into the cold reaction mixture for 30 minutes, and the mixture was allowed to warm to room temperature. After 16 hours stirring, the reaction mixture was evaporated to dryness on a rotary evaporator, and the residue was taken up in water, extracted 3×EtOAc, washed 2× brine and dried over MgSO₄. Evaporation yielded an oil which was crystallized from pentane to yield 116.5 g (77%) white crystals; mp 123–125° C.

¹HNMR (CDCl₃) δ 1.2–1.6 (m, 19H), 2.12 (s, 2H), 3.13 (d, 2H, J=7.08 Hz), 4.97 (s, 1H), 5.43 (s, 1H), 7.43 (s, 1H). MS (APCI) 271 m/z. (M+1). Analysis calculated for $C_{14}H_{26}N_2O_3$: C, 62.19; H, 9.69; N, 10.36. Found: C, 62.00; H, 9.72; N, 9.96.

(1-Cyanomethyl-cyclohexylmethyl)-carbamic acid tert-butyl ester (4)

Cyanuric chloride (39.5 g, 0.214 mol) was added to (1-carbamoylmethyl-cyclohexylmethyl)-carbamic acid tert-butyl ester (3) (116 g, 0.429 mol) in 400 mL DMF. An ice-water bath was used to moderate the exotherm, and the reaction mixture was stirred at room temperature for 1.5 hours. The mixture was poured into ice-water containing 120 g (1.43 mol) NaHCO₃ and was extracted 4× EtOAc. The extracts were washed 1× water, 2× brine and dried over Na₂SO₄. Evaporation yielded an oil which was taken up in 3:1 hexane/EtOAc and filtered through silica gel. Evaporation yielded white crystals (86.5 g, 80%); mp 54–58° C.

¹HNMR (CDCl₃) δ 1.3–1.5 (m, 19H), 2.30 (s, 2H), 3.15 (d, 2h, J=7.00 Hz), 4.60 (broad, 1H). MS (APCI) m/z 253 (M+1). Analysis calculated for $C_{14}H_{24}N_2O_2$: C, 66.63; H, 9.59; N, 11.10. Found: C, 66.64; H, 9.52; N, 10.80.

[1-(N-Hydroxycarbamimidoylmethyl)-cyclohexylmethyl]-carbamic acid tert-butyl ester (5)

A suspension of hydroxylamine hydrochloride (69.5 g, 1.00 mol) in DMSO (300 mL) was cooled in ice-water, and triethylamine (106.7 g, 1.05 mol) was added. The resulting exotherm brought the temperature to 20° C. The mixture was stirred at this temperature 15 minutes, and triethylamine hydrochloride was filtered off and washed with THF. The filtrate was concentrated to remove THF, and (1-cyanomethyl-cyclohexylmethyl)-carbamic acid tert-butyl ester (4) (50.4 g, 0.2 mol) was added, and the mixture was heated at 75° C. for 15 hours. After cooling, the reaction mixture was diluted with water (1 L) and extracted 3× EtOAc. The EtOAc extracts were washed 1× saturated KH₂PO₄, 1× saturated NaHCO₃, 2× brine and dried over Na₂SO₄. Evaporation yielded a gummy solid which was triturated in Et₂O to give white crystals, 25.2 g (44%); mp 125–127° C.

¹HNMR (CDCl₃) δ 1.3–1.5 (m 19H), 1.99 (s, 2H), 3.12 (d, 2H J=6.84 Hz), 4.93 (t, 1H, J=6.84 Hz), 5.40 (s, 1H). MS (APCI) m/z 286 (M+1). Analysis calculated for $C_{14}H_{27}N_3O_3$: C, 58.92; H, 9.54; N, 14.72. Found: C, 58.96; H, 9.80; N, 14.65.

BOC-Gabapentin amidoxime carbamate (6)

A solution of [1-(N-Hydroxycarbamimidoylmethyl)-cyclohexylmethyl]-carbamic acid tert-butyl ester (5) (25.1 g, 0.088 mol) and pyridine (7.82 g, 0.099 mol) in DMF (200 mL) was cooled in ice-water as isobutyraldehyde (12.32 g, 0.09 mol) was added dropwise. After 15 minutes, the bath was removed and the mixture was stirred at room temperature 2 hours, diluted with water, and extracted 3× EtOAc. The extracts were washed 1× water, 2× brine and dried over $Na_2SO_4$. Evaporation yielded an oil, 34 g (100%) which was used without further purification. MS (APCI) m/z 386 (M+1).

[1-(5-Oxo-4,5-dihydro-[1,2,4]oxadiazol-3-ylmethyl)-cyclohexylmethyl]-carbamic acid tert-butyl (7)

BOC-Gabapentin amidoxime carbamate (33.88 g, 0.088 mol) was taken up in xylene (250 mL) and heated under reflux 2.5 hours. The xylene was evaporated off and the residue taken up in $Et_2O$ and extracted 3×75 mL 1N NaOH. The alkaline extracts were acidified with saturated $KH_2PO_4$ and extracted 3×$Et_2O$. The $Et_2O$ extracts were washed 1× saturated $KH_2PO_4$, 2× brine and dried over $Na_2SO_4$. Evaporation yielded 17.9 g (65%) of a cream-colored solid, mp 140–143° C.

[1] HNMR ($CDCl_3$) δ 1.0–1.6 (m, 19H), 2.42 (s, 2H), 3.00 (d, 2H, J=7.32 Hz), 4.86 (t, 1H, J=7.08 Hz), 11.30 (s, 1H). MS (APCI) m/z 312 (M+1). Analysis calculated for $C_{15}H_{25}N_3O_4$: C, 57.86; H, 8.09; N, 13.49. Found: C, 58.21; H, 8.31; N, 13.30.

3-(1-Aminomethyl-cyclohexylmethyl)-4H-[1,2,4]oxadiazol-5-one; hydrochloride (8)

A solution of BOC-Gabapentin oxadiazolone (17.7 g, 0.0568 mol) in 4 M HCl in dioxane (200 mL) was allowed to stand 1.5 hours. Concentration to half volume followed by addition of $Et_2O$ gave a precipitate which was filtered off and recrystallized from MeOH to give white crystals (12.98 g, 92.7%), mp 209–212° C.

[1] HNMR (DMSO-$d_6$) δ 1.2–1.5 (m, 10H), 2.64 (s, 4H), 2.79 (s, 2H), 7.98 (s, 3H), 12.35 (s, 1H). MS (APCI) m/z 212 (M+1). Analysis calculated for $C_{10}H_{17}N_3O_2 \cdot HCl$: C, 48.49; H, 7.32; N, 16.96; Cl, 14.31. Found: C, 48.71; H, 7.18; N, 17.03; Cl, 14.32.

EXAMPLE 5

[1-(5-Thioxo-4,5-dihydro-[1,2,4]oxadiazol-3-ylmethyl)-cyclohexylmethyl]-carbamic acid tert-butyl ester (9)

A mixture of [1-(N-Hydroxycarbamimidoylmethyl)-cyclohexylmethyl]-carbamic acid tert-butyl ester (4.85 g, 0.017 mol), 90% 1,1□-thiocarbonyldiimidazole (3.96 g, 0.02 mol) and DBU (10.39 g, 0.068 mol) in MeCN (150 mL) was stirred at room temperature 19 hours. The reaction mixture was evaporated to dryness, suspended in saturated $KH_2PO_4$ and extracted 3× EtOAc. The EtOAc extracts were washed 2× saturated $KH_2PO_4$, 2× brine and dried over $Na_2SO_4$. Evaporation followed by filtration through silica gel, eluting with 3:1 EtOAc/hexane yielded, upon evaporation, a solid which was recrystallized from $Et_2O$/hexane to give a pale pink solid, 2.6 g (47%), mp 160–161° C.

[1] HNMR ($CDCl_3$) δ 1.1–1.6 (m, 19H), 2.53 (s, 2H), 3.00 (d, 2H, J=7.33 Hz), 4.90 (t, 1H, J=7.08 Hz), 12.88 (s, 1H). MS (APCI) m/z 328 (M+1). Analysis calculated for $C_{15}H_{25}N_3O_3S$: C, 55.02; H, 7.70; N, 12.83; S, 9.79. Found: C, 55.34; H, 7.80; N, 12.72; S, 9.43.

3-(1-Aminomethyl-cyclohexylmethyl)-4H-[1,2,4]oxadiazole-5-thione; hydrochloride (10)

[1-(5-Thioxo-4,5-dihydro-[1,2,4]oxadiazol-3-ylmethyl)-cyclohexylmethyl]-carbamic acid tert-butyl ester (9)

(2.5 g, 0.0076 mol) was taken up in 4 M HCl in 1,4-dioxane (75 mL) and stirred at room temperature. The precipitate which formed was filtered off and recrystallized from MeOH-$Et_2O$ to yield 1.31 g (66%) white solid, mp 210–212° C.

[1] HNMR (DMSO-$d_6$) δ 1.2–1.5 (m, 10H), 2.79–2.85 (m, 4H), 7.99 (s, 3H). MS (APCI) m/z 228 (M+1). Analysis calculated for $C_{10}H_{17}N_3OS \cdot HCl$: C, 45.53; H, 6.88; N, 15.93; S, 12.16; Cl, 13.44. Found: C, 45.92; H, 6.71; N, 15.83; S, 11.81; Cl, 13.48.

EXAMPLE 6

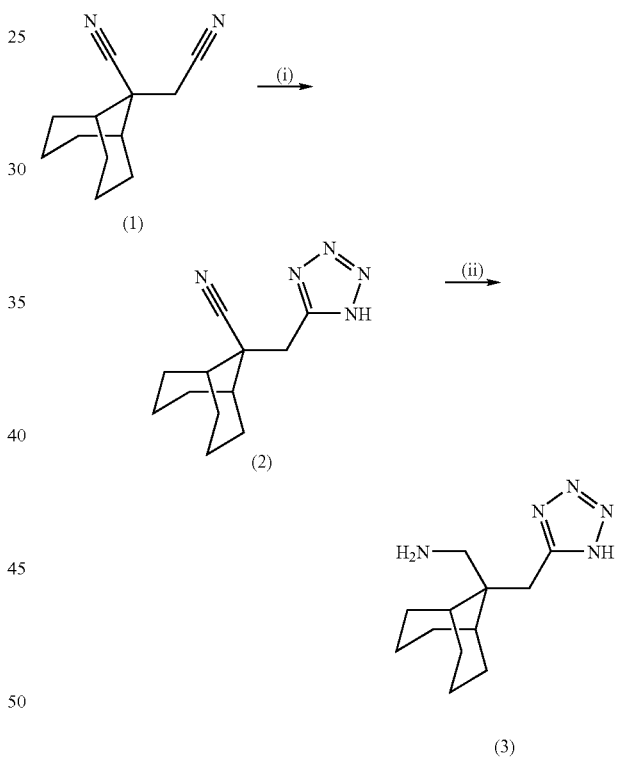

Reagents:
(i) Trimethylsilylazide, dibutyl tin oxide, toluene
(ii) Nickel catalyst, Methanol

Synthesis of 9-(1H-Tetrazol-5-ylmethyl)-bicyclo[3.3.1]nonane-9-carbonitrile (2)

To a solution of the bis nitrile (ref WO 9733859) (1.2 g, 6.38 mmol) in toluene (10 mL) was added trimethylsilylazide (1.48 g, 12.87 mmol) followed by dibutyl tin oxide (0.16 g, 0.64 mmol). After heating to 95° for 3 days the mixture was diluted with ethyl acetate, washed with 1N HCl and water, dried over magnesium sulphate, and evaporated to dryness. Crystallization gave the required compound (0.3 g, 20%); mp 189–191° C.

400 MHz NMR (d$_6$DMSO) □ 1.50–1.70 (m, 4H), 1.75–2.10 (m, 10H), 3.48 (s, 2H).

Synthesis of C-[9-(1H-Tetrazol-5-ylmethyl)-bicyclo[3.3.1]non-9-yl]-methylamine hydrochloride (3)

The tetrazole obtained in Step 1 (0.60 g, 2.59 mmol) in methanol (100 mL) was added to a washed suspension of nickel catalyst in methanol. The mixture was shaken under 40 psi hydrogen overnight and then filtered to remove the catalyst and evaporated to dryness. The residue was dissolved in methanol and ethereal hydrogen chloride added. Addition of ether and filtration gave the required product (0.19 g, 22%). mp 232–236° C.

400 MHz NMR (d$_6$DMSO) ⸹, 1.75–1.95 (m, 4H), 2.05–2.15 (m, 2H), 3.13 (s, 2H), 3.29 (s, 2H), 8.0 (bs, 3H).

EXAMPLE 7

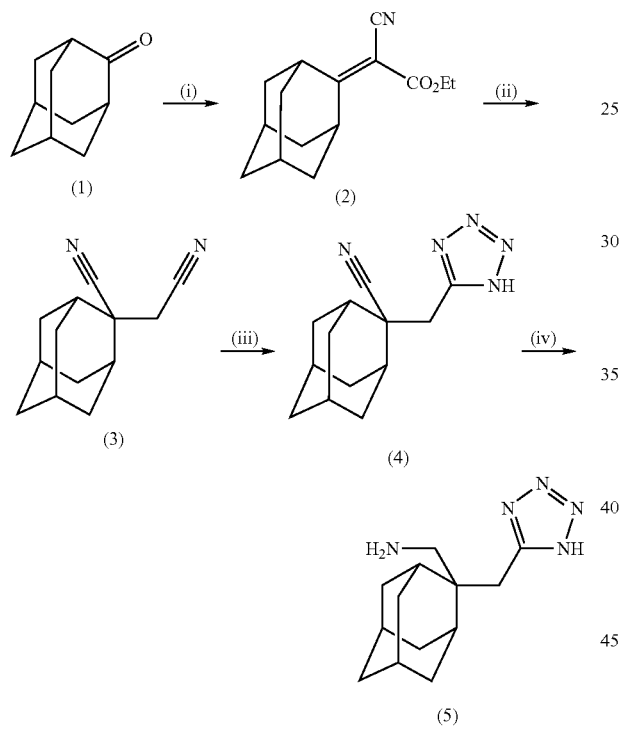

Reagents:
(i) Ethylcyanoacetate, NaH, THF;
(ii) KCN, EtOH, water, reflux;
(iii) Trimethylsilylazide, dibutyltin oxide, toluene;
(iv) Nickel catalyst, Methanol Synthesis of 2-(1H-Tetrazol-5-ylmethyl)-adamantane-2-carbonitrile (4)

Prepared in the same manner as 9-(1H-Tetrazol-5-ylmethyl)-bicyclo[3.3.1]nonane-9-carbonitrile in Example 4.

Synthesis of C-[2-(1H-Tetrazol-5-ylmethyl)-adamantan-2-yl]-methylamine hydrochloride (5)

The nitrile obtained in Step 3 was prepared in an analogous manner to (0.47 g, 1.9 mmol) was shaken with nickel catalyst (one spatula full, washed) under 50 psi hydrogen overnight. Filtration through kieselguhr and evaporation followed by treatment with methanol and ethereal hydrogen chloride gave the required product which was crystallized from methanol and acetonitrile (25 mg, 5%); mp 250–252° C.

400 MHz NMR □ 1.49 (s, 2H), 1.54 (d, J=13.7 Hz, 2H), 1.59 (d, J=13.7 Hz), 1.67 (s, 2H), 1.83 (s, 1H), 1.90 (s, 1H), 1.97 (d, J=12.9 Hz, 2H), 2.19 (d, J=12.7 Hz, 2H), 3.15 (s, 2H), 3.34 (s, obscured by water), 7.99 (bs, 3H).

Mass Spec ES⁺ 248 (100%, (M+H)⁺).

EXAMPLE 8

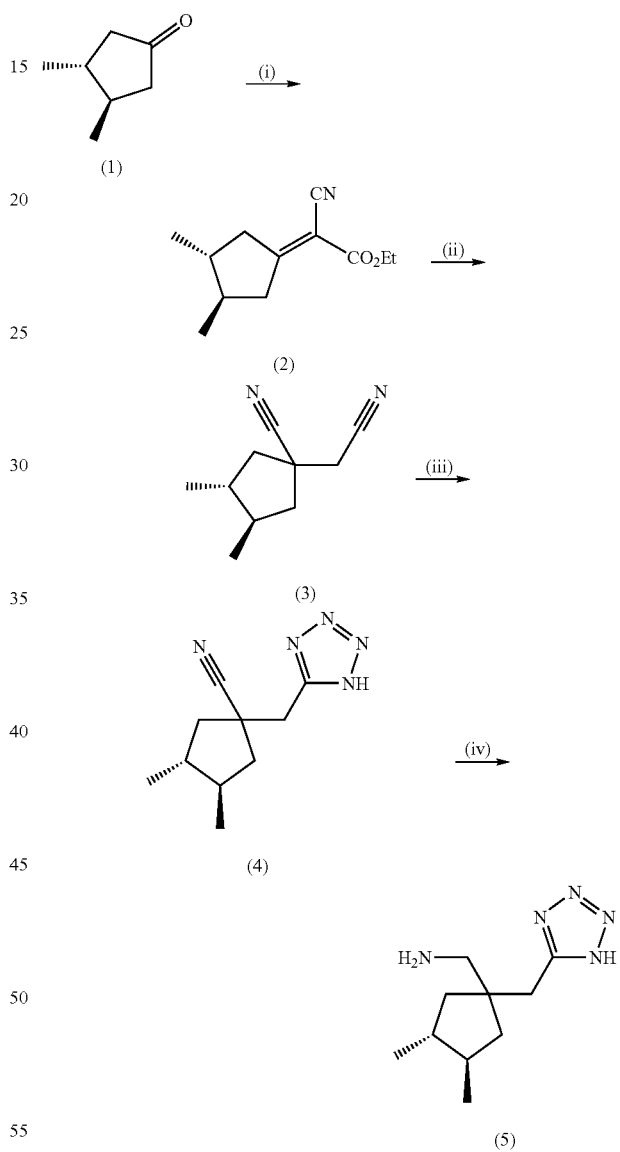

Reagents:
(i) Ethyl cyanoacetate, ammonium acetate, acetic acid, toluene
(ii) Potassium cyanide, aqueous ethanol
(iii) Trimethylsilylazide, dibutyltin oxide, toluene
(iv) nickel catalyst, methanol Synthesis of (trans)Cyano-(3,4-dimethyl-cyclopentylidene)-acetic acid ethyl ester (2)

Trans-3,4-dimethyl cyclopentanone (2.91 g, 25.94 mmol), ethyl cyanoacetate (2.93 g, 25.93 mmol), ammonium acetate (0.20 g, 2.60 mmol), and acetic acid (0.31 g, 5.17 mmol)

were heated together in refluxing toluene under a Dean-Stark trap for 24 hours. After cooling and filtration through kieselguhr, evaporation gave the required product as an off-white solid (5.0 g, 93%).

400 MHz NMR ☐ 1.08 (d, J=6.0 Hz, 3H), 1.09 (d, J=6.4 Hz, 3H), 1.34 (t, J=7.2 Hz, 3H), 1.55–1.70 (m, 2H), 2.30–2.45 (m, 2H), 3.08 (dd, J=20.0 Hz, 8.0 Hz, 1H), 3.43 (dd, J=20.0 Hz, 7.0 Hz, 1H), 4.26 (q, J=7.1 Hz, 2H).

Mass Spec ES+ 208.19 (M+H)+, 225.19, 230.16 (100%, (M+Na)+).

Synthesis of (trans)1-Cyanomethyl-3,4-dimethyl-cyclopentanecarbonitrile (3)

The product from Step 1 (5.0 g, 24.1 mmol) was refluxed with potassium cyanide (1.57 g, 24.2 mmol) in ethanol/10% water (50 mL) overnight. Evaporation to dryness and purification by chromatography eluting with ethyl acetate/heptane 1:1 gave the required product as a yellow oil 2.9 g (74%). tlc rf 0.45 ethyl acetate/heptane 1:1.

400 MHz NMR ☐ 1.05 (d, J=8.4 Hz, 3H), 1.07 (d, J=8.8 Hz, 3H), 1.49 (dd, J=13.2, 11.6 Hz, 1H), 1.60–1.70 (m, 1H), 1.75–1.90 (m, 1H), 1.96 (dd, J=13.6, 14.8 Hz, 1H), 2.19 (dd, J=14.0, 8.4 Hz, 1H), 2.48 (dd, J=13.2, 6.4 Hz, 1H), 2.73 (s, 2H).

Synthesis of (trans)3,4-Dimethyl-1-(1H-tetrazol-5-ylmethyl)-cyclopentanecarbonitrile (4)

The bis-nitrile from Step 2 (1.62 g, 10 mmol) was heated with trimethylsilyl azide (2.84 g, 24.7 mmol) and di-butyl tin oxide (0.24 g, 0.96 mmol) in toluene (50 mL) to 100° C. overnight. The reaction mixture was diluted with ethyl acetate and washed with dilute hydrochloric acid and water. The solution was dried over magnesium sulphate and evaporated to dryness. Purification by chromatography eluting with ethyl acetate gave the required product as a colorless oil 0.94 g, (46%).

Mass Spec ES+ 206.23 (M+H)+, 228.26 (M+Na)+.

400 MHz NMR CDCl3 ☐ 1.04 (d, J=7.2 Hz, 3H), 1.05 (d, J=6.4 Hz), 1.56 (dd, J=11.6, 11.6 Hz, 1H), 1.55–1.65 (m, 1H), 1.65–1.75 (m, 1H), 1.83 (dd, J=13.6, 9.2 Hz, 1H), 2.27 (dd, J,=14.0, 8.0 Hz), 2.35 (dd, J=13.0, 6.8 Hz, 1H), 3.36 (s, 2H).

Synthesis of (trans)C-[3,4-Dimethyl-1-(1H-tetrazol-5-ylmethyl)-cyclopentyl]-methylamine hydrochloride (5)

The tetrazole obtained in Step 3 (0.90 g, 0.44 mmol) and nickel catalyst (one spatula full, washed) were shaken together in methanol (200 mL) overnight. The mixture was filtered through kieselguhr and evaporated to dryness. The residue was treated with methanol and ethereal hydrogen chloride and then stirred with di-tertiarybutyl dicarbonate (0.80 g, 3.67 mmol) and sodium bicarbonate (0.80 g, 9.52 mmol) in aqueous dioxane (1:1, 20 mL) overnight. The mixture was diluted with ethyl acetate and the aqueous phase separated, acidified, and extracted 3× with ethyl acetate. The extracts were dried over magnesium sulphate, filtered and evaporated to give a colorless oil. This oil was stirred with 4 M hydrogen chloride in dioxane (5 mL) overnight and then evaporated to dryness to give the required product 0.24 g (76%).

400 MHz d6DMSO ☐ 0.88 (d, J=6.4 Hz, 3H), 0.89 (d, J=5.6 Hz, 3H), 1.15–1.25 (m, 3H), 1.35–1.45 (m, 1H), 1.70–1.80 (m, 2H), 2.82 (d, J=13.2 Hz, 1H), 2.89 (d, J=13.2 Hz, 1H), 3.04 (d, 15.2 Hz, 1H), 3.05 (d, J=15.2 Hz, 1H).

Mass Spec ES+ 210 100%, (M+H)+. Elemental analysis calculated for C10H19N5·HCl·0.5H2O: C, 47.14; H, 8.31; N, 27.49. Found: C, 47.23; H, 7.97; N, 27.16.

Compounds of Formula IV wherein $R^1$ and $R^2$ are as defined above may be prepared according to the following methods.

General Synthetic Schemes

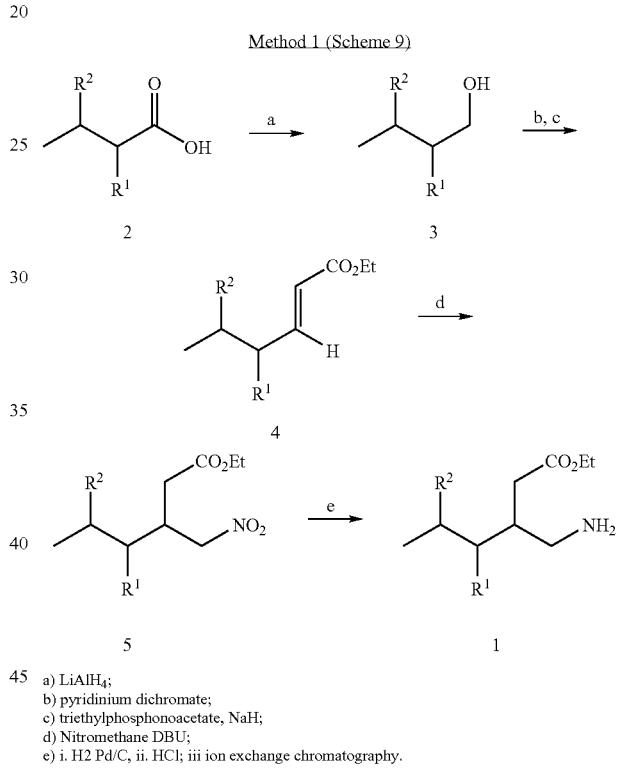

Method 1 (Scheme 9)

a) LiAlH4;
b) pyridinium dichromate;
c) triethylphosphonoacetate, NaH;
d) Nitromethane DBU;
e) i. H2 Pd/C, ii. HCl; iii ion exchange chromatography.

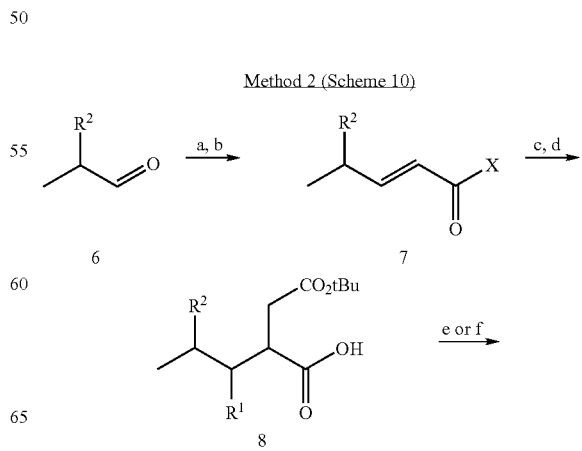

Method 2 (Scheme 10)

-continued

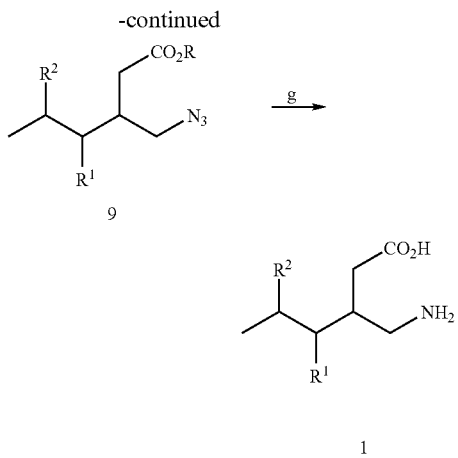

X = OEt or chiral oxazolidine auxiliary.
a) Triethyphosphonoacetate, NaH;
b) i. NaOH, ii. Pivaloyl chloride, Et$_3$N, XH;
c) R$^1$MgBr, CuBr$_2$ DMS;
d) NaHMDS, BrCH$_2$CO$_2$tBu;
e) R = tBU i. LiOH, H$_2$O$_2$; ii. BH$_3$, iii. TsCl, ET$_3$N, iv. NaN$_3$, DMSO;
f) R = Et i. LiOH, H$_2$O$_2$; ii. BH$_3$, iii. PTSA, THF; iv HBr EtOH, v. NaN$_3$ DMSO
g) i. H$_2$ Pd/C; ii. HCl, iii. Ion exchange chromatography.

SPECIFIC EXAMPLES

Synthesis of Example 9

3-Aminomethyl-5-methylheptanoic acid

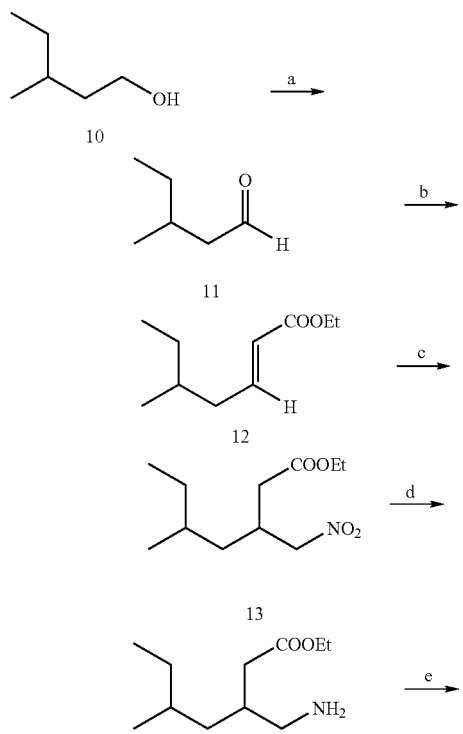

-continued

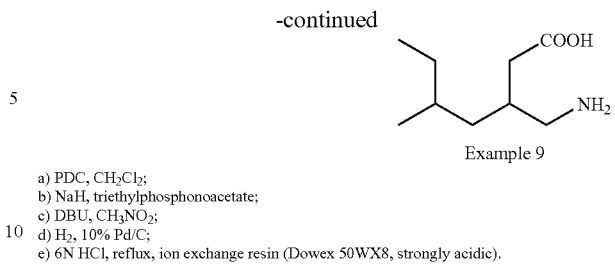

Example 9 a) PDC, CH$_2$Cl$_2$;
b) NaH, triethylphosphonoacetate;
c) DBU, CH$_3$NO$_2$;
d) H$_2$, 10% Pd/C;
e) 6N HCl, reflux, ion exchange resin (Dowex 50WX8, strongly acidic).

3-Methyl-1-pentanal 11

To a stirred suspension of pyridinum dichromate (112.17 g, 298.1 mmol) in dichloromethane 500 mL was added 3-methyl-1-pentanol 10 (15 g, 146.79 mmol). After stirring for 2.5 hours, ether 400 mL was added, and stirring was continued for another 5 minutes. The filtrate from the mixture was concentrated to a small volume and applied to a column of Florisil. The compound was eluted with petroleum ether, and further chromatographed on silica gel column using 10% ether in petroleum ether as eluent gave 11 (6.5 g, 44%).

$^1$H-NMR (CDCl$_3$) δ 9.72, (d, —CHO), 2.38 (dd, 1H, —CH$_2$CHO), 2.19 (dd, 1H, —CH$_2$CHO), 1.95 (m, 1H, C$_2$H$_5$(CH$_3$)CHCH$_2$), 1.4–1.0 (m), 0.9–0.8 (m).

Ethyl 5-methyl-2-heptenoate 12

Sodium hydride (60% dispersion, 2.4 g, 65 mmol) was washed with hexane and suspended in dimethoxyethane 60 mL. While cooling in ice water bath triethyl phosphonoacetate was slowly added, calcd. 5 minutes. The reaction was stirred for 15 minutes at 0° C. and a solution of 3-methyl-1-pentanal 11 (6.5 g, 65 mmol) in methoxyethane 20 mL was added. After refluxing overnight, it was concentrated, water and hexane were added, the organic phase was separated, and the aqueous portion discarded. The solution was washed twice with brine and dried on magnesium sulfate. The solvent was evaporated to give 12 (6.75 g, 61%). $^1$H-NMR (CDCl$_3$) δ 6.89 (m, 1H, —CH$_2$CH:CHCOOEt), 5.77 (d, 1H, —CH$_2$CH:CH:CHCOOEt), 4.16 (q, 2H, —COOCH$_2$CH$_3$), 2.15 and 1.98 (1H each and a multiplet, —CH$_2$CH:CHCOOEt), 1.48 (m, 1H, C$_2$H$_5$(CH$_3$)CHCH$_2$), 1.30–1.10 (m), and 0.83.

Ethyl 5-methyl-3-nitromethylheptanoate 13

Ethyl 5-methyl-2-heptanoate 12 (6.75 g, 39.70 mmol), DBU (6.0 g, 39.7 mmol), nitromethane (21.97 g, 359.9 mmol) in acetonitrile 80 mL was stirred at room temperature under nitrogen atmosphere overnight. The mixture was concentrated to an oil. A solution of the oil in ether was washed with 1N HCl, brine and dried. It was evaporated to give a light oil which was chromatographed on silica gel, eluting with 5% to 10% ether in Pet. ether to give 13 (3.6 g, 42%). $^1$H-NMR (CDCl$_3$) δ 4.49–4.39 (m), 4.12–4.07 (m), 3.61 (m), 2.32 (m), 1.36–1.18 (m), 0.86–0.79.

3-Aminomethyl-5-methylheptanoic acid
(example 9)

Ethyl 5-methyl-3-nitromethylheptanoate 13 (3.6 g) was hydrogenated in ethanol in the presence of 20% Pd/C and evaporated to give 14. Six normal hydrochloric acid 30 mL was added and refluxed overnight. The solvent was evaporated at reduced pressure, and the residue was azeotroped with toluene. Aqueous solution of the residue was applied to Dowex 50WX 8–100 ion exchange resin that had been washed to neutral pH with HPLC grade water. The column was eluted with water until eluent was neutral pH, and then with 0.5N. NH$_4$OH solution to give factions containing 3-aminomethyl-5-methylheptanoic acid. The fractions were combined and further chromatographed on a C$_{18}$ column. The compound was eluted with 40% water in methanol and crystallized from methanol-ether to give Example 9 630 mg. $^1$H-NMR (CD$_3$OD) δ 2.83 (m, 1H), 2.75 (m, 1H), 2.35 (m, 1H), 2.15 (m, 1H), 1.95 (1H, bs), 1.38 (1H, m), 1.3–1.15 (m, 2H), 1.14–0.95 (m, 2H). 0.80 (m, 2CH$_3$). MS found molecular ion at (M+1) 174 and other ions at 156, 139, and 102. Anal. Calcd. for C$_9$H$_{19}$NO$_2$: C, 62.39; H, 11.05; N, 8.08. Found C, 62.00; H, 10.83; N, 7.98.

In a similar way the following examples can be prepared.
3-Aminomethyl-5-methyl-heptanoic acid;
3-Aminomethyl-5-methyl-octanoic acid;
3-Aminomethyl-5-methyl-nonanoic acid;
3-Aminomethyl-5-methyl-decanoic acid;
3-Aminomethyl-5-methyl-undecanoic acid;
3-Aminomethyl-5-methyl-dodecanoic acid;
3-Aminomethyl-5-methyl-tridecanoic acid;
3-Aminomethyl-5-cyclopropyl-hexanoic acid;
3-Aminomethyl-5-cyclobutyl-hexanoic acid;
3-Aminomethyl-5-cyclopentyl-hexanoic acid;
3-Aminomethyl-5-cyclohexyl-hexanoic acid;
3-Aminomethyl-5-trifluoromethyl-hexanoic acid;
3-Aminomethyl-5-phenyl-hexanoic acid;
3-Aminomethyl-5-(2-chlorophenyl)-hexanoic acid;
3-Aminomethyl-5-(3-chlorophenyl)-hexanoic acid;
3-Aminomethyl-5-(4-chlorophenyl)-hexanoic acid;
3-Aminomethyl-5-(2-methoxyphenyl)-hexanoic acid;
3-Aminomethyl-5-(3-methoxyphenyl)-hexanoic acid;
3-Aminomethyl-5-(4-methoxyphenyl)-hexanoic acid; and
3-Aminomethyl-5-(phenylmethyl)-hexanoic acid.

Synthesis of Example 10

(3R,4S)3-Aminomethyl-4,5-dimethyl-hexanoic acid

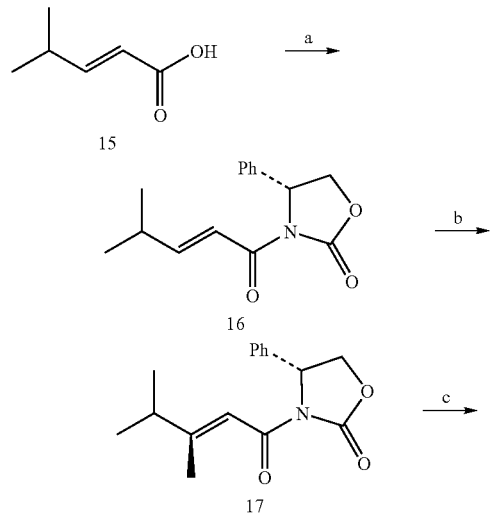

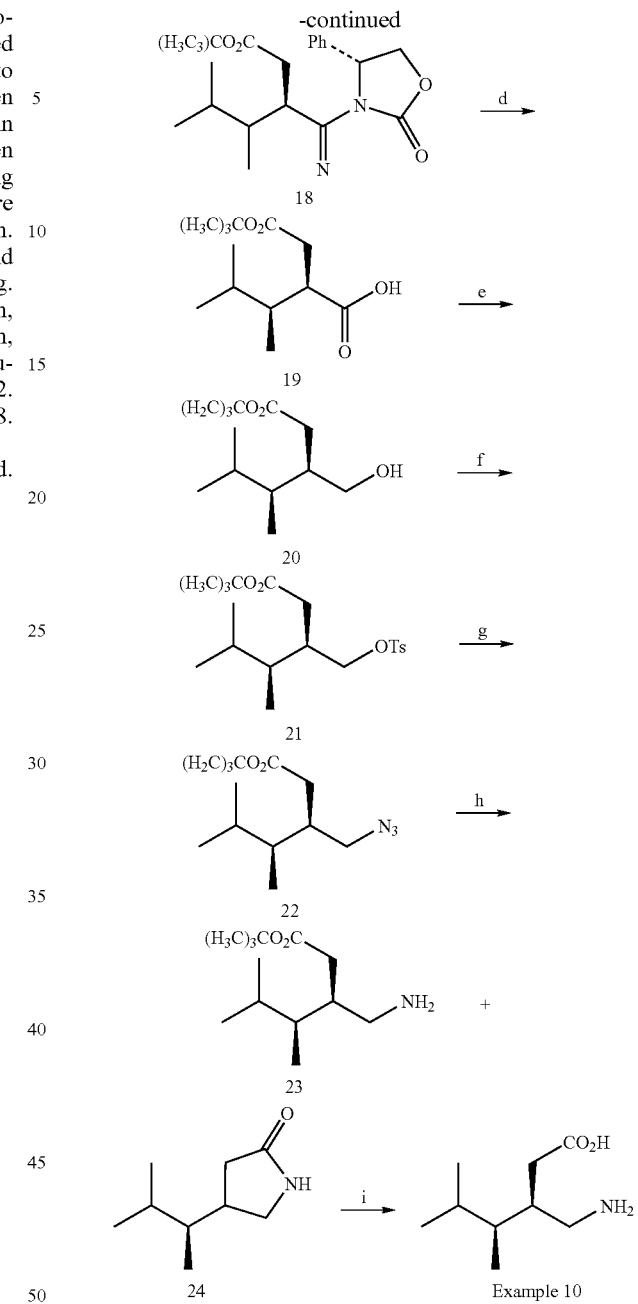

Reagents and Conditions:
a) (R)-(-)-4-phenyl-2-oxazolidinone, (CH$_3$)$_3$CCOCl, Et$_3$N, LiCl, THF, -20 to 23° C.;
b) MeMgCl, CuBrSMe$_2$, THF, -35° C.;
c) NaHMDS, BrCH$_2$CO$_2$tBu, THF, -78° C. to -40° C.;
d) LiOH, H$_2$O$_2$, THF, H$_2$O, 25° C.;
e) BH$_3$SMe$_2$, THF, 0 to 25° C.;
f) pTsCl, pyridine, 25° C.;
g) NaN$_3$, DMSO, 60° C.;
h) Raney nickel, MeOH, H$_2$; i) 3M HCl, reflux, ion exchange resin (Dower 50WX8, strongly acidic).

[R-(E)]3-(4-Methyl-pent-2-enoyl)-4-phenyl-oxazolidin-2-one 16

Trimethylacetyl chloride (7.8 g, 0.065 mol) was added to acid 14 (6.9 g, 0.06 mol) and triethylamine (18 g, 0.187 mol) in THF (200 mL) at −20° C. After 1 hour, lithium chloride (2.35 g, 0.55 mol) and (R)-(−)-4-phenyl-2-oxazolidinone (8.15 g, 0.05 mol) were added and the thick suspension warmed to room temperature. After 20 hours, the suspension was filtered and the filtrate concentrated. The resultant solid was recrystallized from hexane/ethyl acetate (5:1) to give the oxazolidinone 16 as a white solid (8.83 g, 68%). $^1$H NMR (CDCl$_3$) δ 7.35 (m, 5H), 7.18 (dd, 1H, J=15.4 and 1.2 Hz), 7.02 (dd, 1H, J=15.4 and 6.8 Hz), 5.45 (dd, 1H, J=8.8 and 3.9 Hz), 4.68 (t, 1H, J=8.8 Hz), 4.22 (dd, 1H, J=8.8 and 3.9 Hz), 2.50 (m, 1H), 1.04 (d, 1H, J=1.4 Hz), 1.02 (d, 1H, J=1.4 Hz). MS, m/z (relative intensity): 260 [M+H, 100%].

(3R,3R*)3-(3,4-Dimethyl-pentanoyl)-4-phenyl-oxazolidin-2-one 17

To copper(I) bromide-dimethyl sulphide complex in THF (45 mL) at −20° C. was added methylmagnesium chloride (as a 3 M solution in THF). After 20 minutes, the oxazolidinone 16 (3.69 g, 0.014 mol) in THF (20 mL) was added dropwise over 10 minutes. After 2.5 hours, the reaction was quenched through the addition of a saturated aqueous solution of ammonium chloride. The resultant two layers were separated and the aqueous phase extracted with ether. The combined organic phases were washed with 1 M hydrochloric acid, then with 5% aqueous ammonium hydroxide. The organic phases were dried (MgSO$_4$) and concentrated to give the oxazolidinone 17 as a white solid (3.39 g, 88%). $^1$H NMR (CDCl$_3$) δ 7.30 (m, 1H), 5.40 (dd, 1H, J=8.8 and 3.7 Hz), 4.63 (t, 1H, J=8.8 Hz), 4.21 (dd, 1H, J=8.8 and 3.7 Hz), 2.85 (dd, 1H, J=16.1 and 5.6 Hz), 2.8 (dd, 1H, J=16.1 and 8.5 Hz), 1.90 (m, 1H), 1.56 (m, 2H), 0.83 (d, 3H, J=6.8 Hz), 0.78 (d, 3H, J=6.8 Hz), 0.75 (d, 3H, J=6.8 Hz). MS, m/z (relative intensity): 276 [M+H, 100%].

[3R-(3R*(R*),4S*)]-4,5-Dimethyl-3-(2-oxo-4-phenyl-oxazolidine-3-carbonyl)-hexanoic acid tert-butyl ester 18

Sodium bis(trimethylsilyl)amide (14.4 mL, 0.014 mol of a 1 M solution in THF) was added to a solution of the oxazolidinone 17 (3.37 g, 0.012 mol) in THF (35 mL) at −78° C. After 35 minutes, tert-butyl bromoacetate (3.5 g, 0.018 mol) was added and the solution immediately warmed to −40° C. After 3 hours, the reaction was quenched through the addition of a saturated aqueous solution of ammonium chloride. The resultant two layers were separated and the aqueous phase extracted with ether. The combined organic phases were dried (MgSO$_4$) and concentrated. Flash chromatography (9:1 to 5:1 hexane/ethyl acetate gradient) gave the ester 18 (3.81 g, 82%) as a white solid. $^1$H NMR (CDCl$_3$) δ 7.35 (m, 5H), 5.37 (dd, 1H, J=8.4 and 3.1 Hz), 4.67 (t, 1H, J=8.7 Hz), 4.41 (dt, 1H, J=12.0 and 3.5 Hz), 4.25 (dd, 1H, J=8.68 and 3.1 Hz), 2.65 (dd, 1H, J=16.9 and 12.0 Hz), 2.25 (dd, 1H, J=16.9 and 3.5 Hz), 1.6 (m, 1H), 1.45 (m, 1H), 1.23 (s, 9H), 1.02 (d, 1H, J=6.5 Hz), 0.93 (d, 1H, J=6.7 Hz), 0.80 (d, 1H, J=7.0 Hz). MS, m/z (relative intensity): 429 [M−H+CH$_3$CN, 100%], 388 [M−H, 20%].

(3R,4S)-2-(1,2-Dimethyl-propyl)-succinic acid 4-tert-butyl ester 19

To the oxazolidinone 18 (3.62 g, 9.3 mmol) in THF (54 mL)/water (15 mL) was added a premixed solution of lithium hydroxide (20 mL of a 0.8 M aqueous solution, 0.016 mol)/H$_2$O$_2$ (5.76 mL of a 30% aqueous solution). After 7 hours, the solution was diluted with water and sodium bisulfite added (~10 g). After stirring for a further 0.5 hours, the two layers were separated and the aqueous phase extracted with ether. The aqueous phase was then rendered acidic (pH 2) with 1 M hydrochloric acid and extracted with ether. The combined organic phases were dried (MgSO$_4$) and concentrated. Flash chromatography (5:1 hexane/ethyl acetate) gave the acid 19 (2.1 g, 95%) as a colorless oil. $^1$H NMR (CDCl$_3$) δ 3.0 (m, 1H), 2.55 (dd, 1H, J=16.6 and 11.2 Hz), 2.27 (dd, 1H, J=16.6 and 3.4 Hz), 1.70 (m, 1H), 1.53 (m, 1H), 1.45 (m, 1H), 1.43 (s, 9H), 0.95 (d, 1H, J=6.8 Hz), 0.90 (d, 1H, J=6.6 Hz), 0.83 (d, 1H, J=6.8 Hz). MS, m/z (relative intensity): 243 [M−H, 100%].

(3R,4S)-3-Hydroxymethyl-4,5-dimethyl-hexanoic acid tert-butyl ester 20

Borane-methyl sulfide complex (16 mL, 0.032 mol of a 2 M solution in THF) was added to a stirred solution of the acid 19 (1.96 g, 8 mmol) in THF (20 mL) at 0° C. After 20 hours, methanol was added until effervescence ceased and the solution concentrated. Flash chromatography (5:1 hexane/ethyl acetate gradient) gave the alcohol 20 (1.29 g, 70%) as a colorless oil. $^1$H NMR (CDCl$_3$) δ 3.62 (m, 1H), 2.32 (m, 1H), 2.14 (m, 1H), 1.6 (m, 1H), 1.45 (s, 9H), 1.35 (m, 1H), 0.93 (d, 1H, J=6.8 Hz), 0.86 (d, 1H, J=6.8 Hz), 0.77 (d, 1H, J=6.9 Hz). MS, m/z (relative intensity): 175 [M−tBu, 100%].

(3R,4S)-4,5-Dimethyl-3-(toluene-4-sulfonyloxymethyl)-hexanoic acid tert-butyl ester 21 p-Toluenesulfonyl chloride (847 mg, 4.4 mmol) was added to a stirred solution of the alcohol 6 (850 mg, 3.7 mmol), DMAP (10 mg, 0.08 mmol) and triethylamine (1.23 mL, 8.88 mmol) in CH$_2$Cl$_2$ (20 mL) at 0° C. and the solution warmed to room temperature. After 15 hours, the solution was washed with 1N hydrochloric acid then with brine. The combined organic phases were dried (MgSO$_4$) and concentrated. Flash chromatography (100 to 92% hexane/ethyl acetate gradient) gave the tosylate 7 (1.22 g, 86%) as a thick gum. $^1$H NMR (CDCl$_3$) δ 7.80 (d, 2H, J=8.2 Hz), 7.25 (d, 2H, J=8.2 Hz), 3.92 (m, 1H), 2.38 (s, 3H), 2.20 (m, 2H), 1.95 (m, 1H), 1.40 (m, 1H), 1.32 (s, 9H), 1.27 (m, 1H), 0.78 (d, 1H, J=6.6 Hz), 0.73 (d, 1H, J=6.6 Hz), 0.63 (d, 1H, J=7.1 Hz). MS, m/z (relative intensity): 311 [85%], 198 [100%], 157 [95%].

(3R,4S)-3-Azidomethyl-4,5-dimethyl-hexanoic acid tert-butyl ester 22

A solution of the tosylate 21 (1.19 g, 3.1 mmol) and sodium azide (402 mg, 6.2 mmol) in DMSO (15 mL) was warmed to 60° C. for 2.5 hours. Water (100 mL) was added and the solution extracted with ether. The combined organic phases were dried (MgSO$_4$) and concentrated. Flash chromatography (9:1 hexane/ethyl acetate) gave the azide 22 (628 mg, 80%) as a colorless oil. $^1$H NMR (CDCl$_3$) δ 3.4 (dd, 1H, J=12.21 and 6.11 Hz), 3.3 (dd, 1H, J=21.11 and 6.59 Hz), 2.30 (dd, 1H, J=15.14 and 3.66 Hz), 2.25 (m, 1H), 2.05 (dd, 1H, J=15.14 and 9.04 Hz), 1.55 (m, 1H), 1.45 (s, 9H), 1.35 (m, 1H), 0.95 (d, 1H, J=6.59 Hz), 0.90 (d, 1H, J=6.83 Hz), 0.80 (d, 1H, J=7.08 Hz). MS (m/z): (relative intensity): 228 [M−N$_2$, 35%], 172 [M−N$_2$.tBu, 100%].

(3R,4S)-3-Aminomethyl-4,5-dimethyl-hexanoic acid tert-butyl ester 23 and [4R-[4R*(S*)]]-4-(1,2-Dimethyl-propyl)-pyrrolidin-2-one 24

The azide 8 (640 mg, 2.5 mmol) and Raney nickel (1 g) in methanol (50 mL) were shaken under an atmosphere of hydrogen for 4 hours. The solution was filtered and the filtrate concentrated to give a mixture of the amine 23 and lactam 24 which was used without further purification in the next step.

(3R,4S)-3-Aminomethyl-4,5-dimethyl-hexanoic acid
Example 10

A solution of the amine 23 and lactam 24 (500 mg) in 3 M hydrochloric acid were heated to reflux for 9 hours, then stirred at room temperature for 15 hours. The solution was concentrated and the resultant solid subjected to a sequential purification which involved ion exchange chromatography (Dowex 50WX8, strongly acidic), oxalate salt formation then further purification by ion exchange chromatography (Dowex 50WX8, strongly acidic) to give the Example 10 (343 mg) as a white solid. $^1$H NMR (D$_2$O) δ 2.87 (m, 2H), 2.22 (dd, 1H, J=15.4 and 3.4 Hz), 2.12 (m, 1H), 1.93 (dd, 1H, J=15.4 and 9.5 Hz), 1.38 (m, 1H), 1.12 (m, 1H), 0.77 (d, 1H, J=6.6 Hz), 0.74 (d, 1H, J=6.6 Hz), 0.70 (d, 1H, J=6.8 Hz). MS, m/z (relative intensity): 174 [M+H, 100%].

In a similar way, the following examples can be prepared:
3-Aminomethyl-4,5-dimethyl-hexanoic acid;
(3R,4S)-3-Aminomethyl-4,5-dimethyl-hexanoic acid MP;
(3S,4S)-3-Aminomethyl-4,5-dimethyl-hexanoic acid;
(3R,4R)-3-Aminomethyl-4,5-dimethyl-hexanoic acid MP;
3-Aminomethyl-4-isopropyl-hexanoic acid;
3-Aminomethyl-4-isopropyl-heptanoic acid;
3-Aminomethyl-4-isopropyl-octanoic acid;
3-Aminomethyl-4-isopropyl-nonanoic acid;
3-Aminomethyl-4-isopropyl-decanoic acid; and
3-Aminomethyl-4-phenyl-5-methyl-hexanoic Method 3 (Scheme 11)

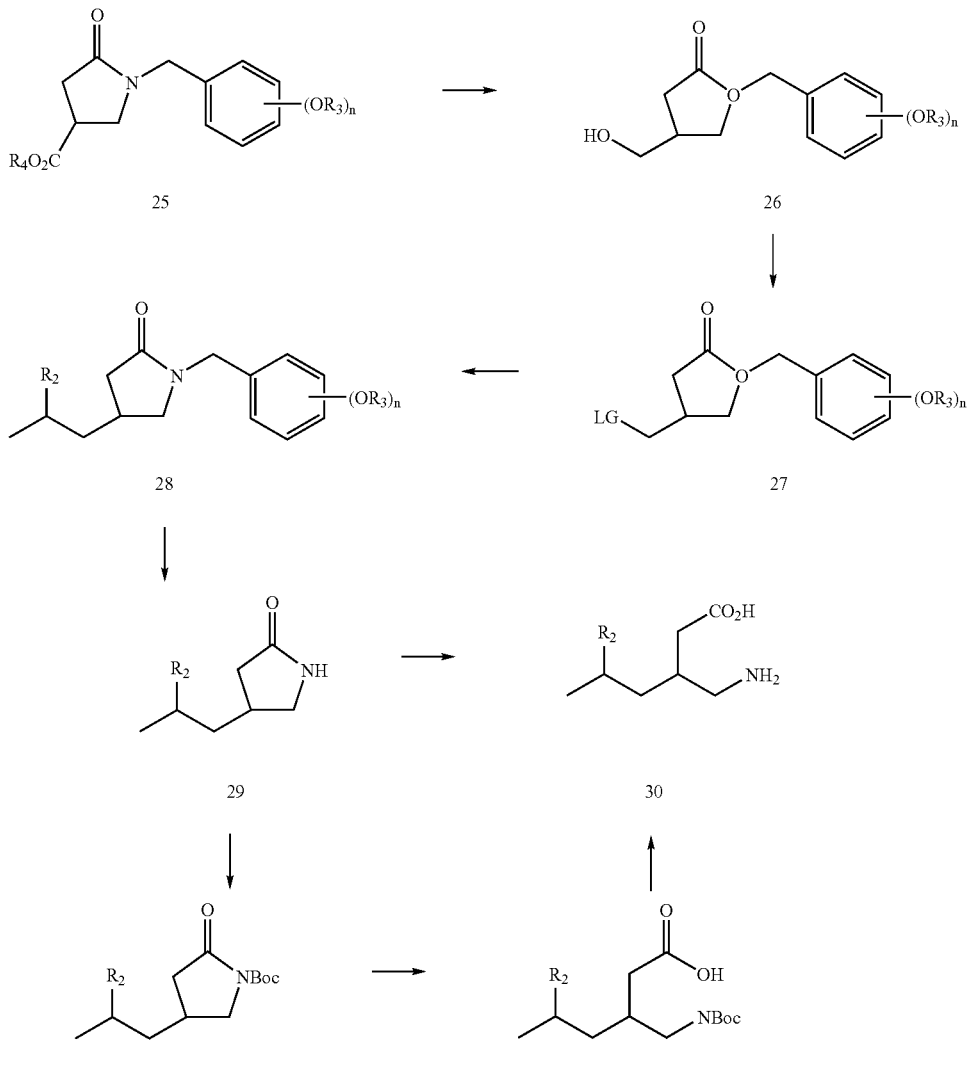

where
R$_3$ = OMe or H
R$_4$ = Me, Et
n = 0 to 2

A compound of structure 30 could be prepared from a compound of structure 29 by treatment with an aqueous acid such as hydrochloric acid and alike at a temperature between room temperature and reflux. As an alternative, a compound of structure 30 can be prepared from a compound of structure 32 by treatment with trifluoroacetic acid in a solvent such as CH$_2$Cl$_2$ or EtOAc and alike. Compound 32 could be prepared by base mediate hydrolysis of a Boc protected lactam such as compound 31 which itself could be prepared from a compound of structure 29 by treatment with di-tert-butyl dicarbonate in a solvent such as THF and alike. The treatment of the Boc-lactam 31 with aqueous sodium hydroxide for example would give rise to the acid 32.

A compound of structure 29 could be prepared from compound of structure 28 (n=0) by treatment with sodium or lithium metal in ammonia. Preferably, the reaction is carried out with sodium metal in ammonia. Alternatively, a compound of structure 29 could be prepared from compound of structure 28 (n=1 or 2) by treatment with ceric ammonium nitrate in a mixture of acetonitrile and water. Other methods known in the literature for the removal of substituted alkoxy benzyl groups from nitrogen are described in Green, *Protective Groups in Organic Synthesis*, Wiley, 2 ed, 1991 and could be utilized.

A compound of structure 28 could be prepared from a compound of structure 27 (where LG is a suitable leaving group such as a halide or an alkyl sulphonate, preferably an iodide would be used) by carbon-carbon bond forming reactions known in the art. Several methods exist in the literature for the coupling of organohalides or organoalkyl sulphonates with organometallic reagents in the presence of various metal salts as summarized in *Comprehensive Organic Synthesis*, volume 3:413 which could be utilized. For example, a compound of structure 28 could be prepared from a compound of structure 27 (where LG is iodide) by treatment with a suitable secondary halide (chloride or iodide) in the presence of magnesium metal, iodine and copper bromide dimethylsulphide in a solvent such as tetrahydrofuran and alike. Alternatively the method according to El Marini, *Synthesis,* 1992:1104 could be used. Hence, a compound of structure 28 could be prepared from a compound of structure 27 (where LG is iodide) by treatment with suitable methyl-substituted secondary halide such as an iodide in the presence of magnesium, iodine and lithium tetrachlorocuprate in a solvent such as tetrahydrofuran and alike.

A compound of structure 27 incorporates a suitable leaving group, which would undergo nucleophilic substitution with suitable nucleophile. Examples of such leaving groups include halides such as chloride, bromide, or iodide, and sulphonic esters such as mesylate, tosylate, triflate, nosylate, and alike. A compound of structure 27 (where LG=iodide) could be prepared from a compound of structure 26 through treatment with iodine, triphenylphosphine, and imidazole in a solvent such as toluene and alike.

A compound of structure 26 could be prepared from compound of structure 25 by treatment with a metal borohydride, such as sodium borohydride in a solvent such as tetrahydrofuran or DME and alike.

Compound 25 could be prepared in a similar fashion to the procedures of Zoretic et al, *J. Org. Chem.,* 1980; 45:810–814 or Nielsen et al *J. Med. Chem.,* 1990; 33:71–77 using an appropriate benzylamine, such as but not limited to benzylamine, 4-methoxybenzylamine or 2,4-dimethoxybenzylamine.

As an alternative approach, a compound of structure 26 could be treated with sodium metal and ammonia to give 4-hydroxymethyl-pyrrolidinone which could be iodinated affording 4-iodomethyl-pyrrolidinone. 4-iodomethyl-pyrrolidinone could then be coupled with organometallic reagents according to the above procedures avoiding protection of the lactam nitrogen as below.

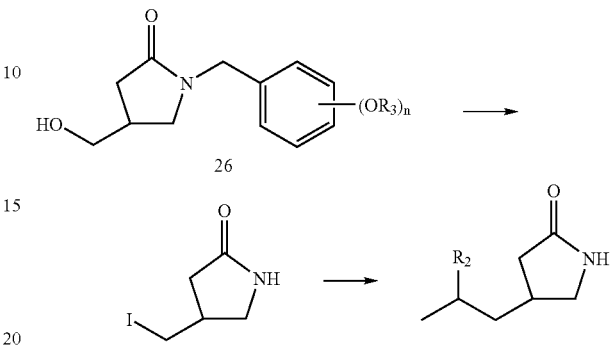

Analogous to the above methods a lactam of structure 33 (see Nielsen et. al., *J. Med. Chem.,* 1990; 33:71–77 for general method of preparation) could be employed thus establishing fixed stereochemistry at C3 of the final amino acids.

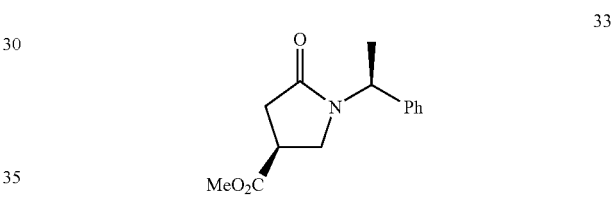

Compounds which could be prepared in this manner include:
3-Aminomethyl-5-methyl-6-phenyl-hexanoic acid;
3-Aminomethyl-6-(4-chloro-phenyl)-5-methyl-hexanoic acid;
3-Aminomethyl-6-(3-chloro-phenyl)-5-methyl-hexanoic acid;
3-Aminomethyl-6-(2-chloro-phenyl)-5-methyl-hexanoic acid;
3-Aminomethyl-6-(4-fluoro-phenyl)-5-methyl-hexanoic acid;
3-Aminomethyl-6-(3-fluoro-phenyl)-5-methyl-hexanoic acid;
3-Aminomethyl-6-(2-fluoro-phenyl)-5-methyl-hexanoic acid;
3-Aminomethyl-5-methyl-7-phenyl-heptanoic acid;
3-Aminomethyl-7-(4-chloro-phenyl)-5-methyl-heptanoic acid;
3-Aminomethyl-7-(3-chloro-phenyl)-5-methyl-heptanoic acid;
3-Aminomethyl-7-(2-chloro-phenyl)-5-methyl-heptanoic acid;
3-Aminomethyl-7-(4-fluoro-phenyl)-5-methyl-heptanoic acid;
3-Aminomethyl-7-(3-fluoro-phenyl)-5-methyl-heptanoic acid;
3-Aminomethyl-7-(2-fluoro-phenyl)-5-methyl-heptanoic acid;
(3S)-3-Aminomethyl-6-cyclopropyl-5-methyl-hexanoic acid;

(3S)-3-Aminomethyl-6-cyclobutyl-5-methyl-hexanoic acid;
(3S)-3-Aminomethyl-6-cyclopentyl-5-methyl-hexanoic acid;
(3S)-3-Aminomethyl-6-cyclohexyl-5-methyl-hexanoic acid;
(3S)-3-Aminomethyl-7-cyclopropyl-5-methyl-heptanoic acid;
(3S)-3-Aminomethyl-7-cyclobutyl-5-methyl-heptanoic acid;
(3S)-3-Aminomethyl-7-cyclopentyl-5-methyl-heptanoic acid;
(3S)-3-Aminomethyl-7-cyclohexyl-5-methyl-heptanoic acid;
(3S)-3-Aminomethyl-8-cyclopropyl-5-methyl-octanoic acid;
(3S)-3-Aminomethyl-8-cyclobutyl-5-methyl-octanoic acid;
(3S)-3-Aminomethyl-8-cyclopentyl-5-methyl-octanoic acid;
(3S)-3-Aminomethyl-8-cyclohexyl-5-methyl-octanoic acid;
(3S)-3-Aminomethyl-5-methyl-heptanoic acid;
(3S)-3-Aminomethyl-5-methyl-octanoic acid;
(3S)-3-Aminomethyl-5-methyl-nonanoic acid;
(3S)-3-Aminomethyl-5-methyl-decanoic acid;
(3S)-3-Aminomethyl-5-methyl-undecanoic acid;
(3S)-3-Aminomethyl-5,7-dimethyl-octanoic acid;
(3S)-3-Aminomethyl-5,8-dimethyl-nonanoic acid;
(3S)-3-Aminomethyl-5,9-dimethyl-decanoic acid;
(3S)-3-Aminomethyl-5,6-dimethyl-heptanoic acid;
(3S)-3-Aminomethyl-5,6,6-trimethyl-heptanoic acid;
(3S)-3-Aminomethyl-5-cyclopropyl-hexanoic acid;
(3S)-3-Aminomethyl-6-fluoro-5-methyl-hexanoic acid;
(3S)-3-Aminomethyl-7-fluoro-5-methyl-heptanoic acid;
(3S)-3-Aminomethyl-8-fluoro-5-methyl-octanoic acid;
(3S)-3-Aminomethyl-7,7,7-trifluoro-5-methyl-heptanoic acid;
(3S)-3-Aminomethyl-8,8,8-trifluoro-5-methyl-octanoic acid;
(3S)-3-Aminomethyl-5-methyl-hept-6-enoic acid;
(3S)-3-Aminomethyl-5-methyl-oct-7-enoic acid;
(3S)-3-Aminomethyl-5-methyl-non-8-enoic acid;
(E)-(3S)-3-Aminomethyl-5-methyl-oct-6-enoic acid;
(Z)-(3S)-3-Aminomethyl-5-methyl-oct-6-enoic acid;
(E)-(3S)-3-Aminomethyl-5-methyl-non-6-enoic acid;
(Z)-(3S)-3-Aminomethyl-5-methyl-non-6-enoic acid;
(E)-(3S)-3-Aminomethyl-5-methyl-non-7-enoic acid;
(Z)-(3S)-3-Aminomethyl-5-methyl-non-7-enoic acid;
(E)-(3S)-3-Aminomethyl-5-methyl-dec-7-enoic acid;
(Z)-(3S)-3-Aminomethyl-5-methyl-dec-7-enoic acid;
3-Aminomethyl-6-cyclopropyl-5-methyl-hexanoic acid;
3-Aminomethyl-6-cyclobutyl-5-methyl-hexanoic acid;
3-Aminomethyl-6-cyclopentyl-5-methyl-hexanoic acid;
3-Aminomethyl-6-cyclohexyl-5-methyl-hexanoic acid;
3-Aminomethyl-7-cyclopropyl-5-methyl-heptanoic acid;
3-Aminomethyl-7-cyclobutyl-5-methyl-heptanoic acid;
3-Aminomethyl-7-cyclopentyl-5-methyl-heptanoic acid;
3-Aminomethyl-7-cyclohexyl-5-methyl-heptanoic acid;
3-Aminomethyl-8-cyclopropyl-5-methyl-octanoic acid;
3-Aminomethyl-8-cyclobutyl-5-methyl-octanoic acid;
3-Aminomethyl-8-cyclopentyl-5-methyl-octanoic acid;
3-Aminomethyl-8-cyclohexyl-5-methyl-octanoic acid;
3-Aminomethyl-5-methyl-heptanoic acid;
3-Aminomethyl-5-methyl-octanoic acid;
3-Aminomethyl-5-methyl-nonanoic acid;
3-Aminomethyl-5-methyl-decanoic acid;
3-Aminomethyl-5-methyl-undecanoic acid;
3-Aminomethyl-5,7-dimethyl-octanoic acid;
3-Aminomethyl-5,8-dimethyl-nonanoic acid;
3-Aminomethyl-5,9-dimethyl-decanoic acid;
3-Aminomethyl-5,6-dimethyl-heptanoic acid;
3-Aminomethyl-5,6,6-trimethyl-heptanoic acid;
3-Aminomethyl-5-cyclopropyl-hexanoic acid;
3-Aminomethyl-6-fluoro-5-methyl-hexanoic acid;
3-Aminomethyl-7-fluoro-5-methyl-heptanoic acid;
3-Aminomethyl-8-fluoro-5-methyl-octanoic acid;
3-Aminomethyl-7,7,7-trifluoro-5-methyl-heptanoic acid;
3-Aminomethyl-8,8,8-trifluoro-5-methyl-octanoic acid;
3-Aminomethyl-5-methyl-hept-6-enoic acid;
3-Aminomethyl-5-methyl-oct-7-enoic acid;
3-Aminomethyl-5-methyl-non-8-enoic acid;
(E)-3-Aminomethyl-5-methyl-oct-6-enoic acid;
(Z)-3-Aminomethyl-5-methyl-oct-6-enoic acid;
(E)-3-Aminomethyl-5-methyl-non-6-enoic acid;
(Z)-3-Aminomethyl-5-methyl-non-6-enoic acid;
(E)-3-Aminomethyl-5-methyl-non-7-enoic acid;
(Z)-3-Aminomethyl-5-methyl-non-7-enoic acid;
(E)-3-Aminomethyl-5-methyl-dec-7-enoic acid; and
(Z)-3-Aminomethyl-5-methyl-dec-7-enoic acid.

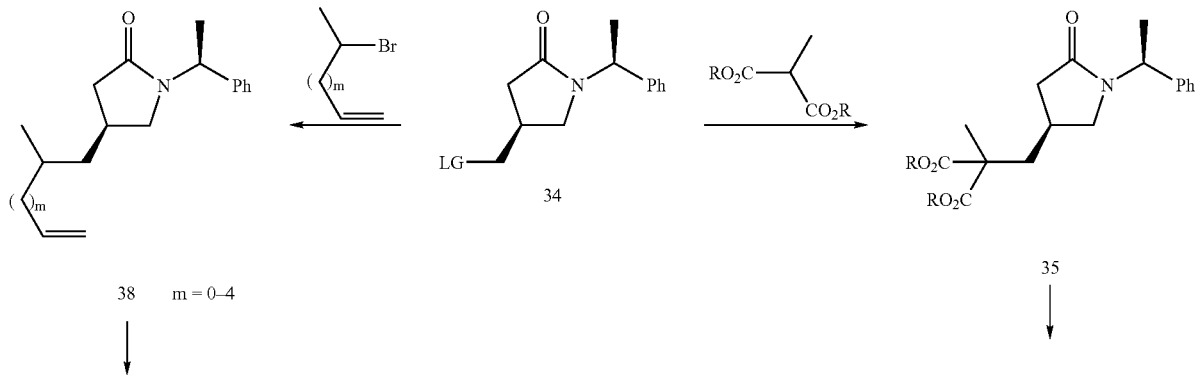

Method 4 (Scheme 12)

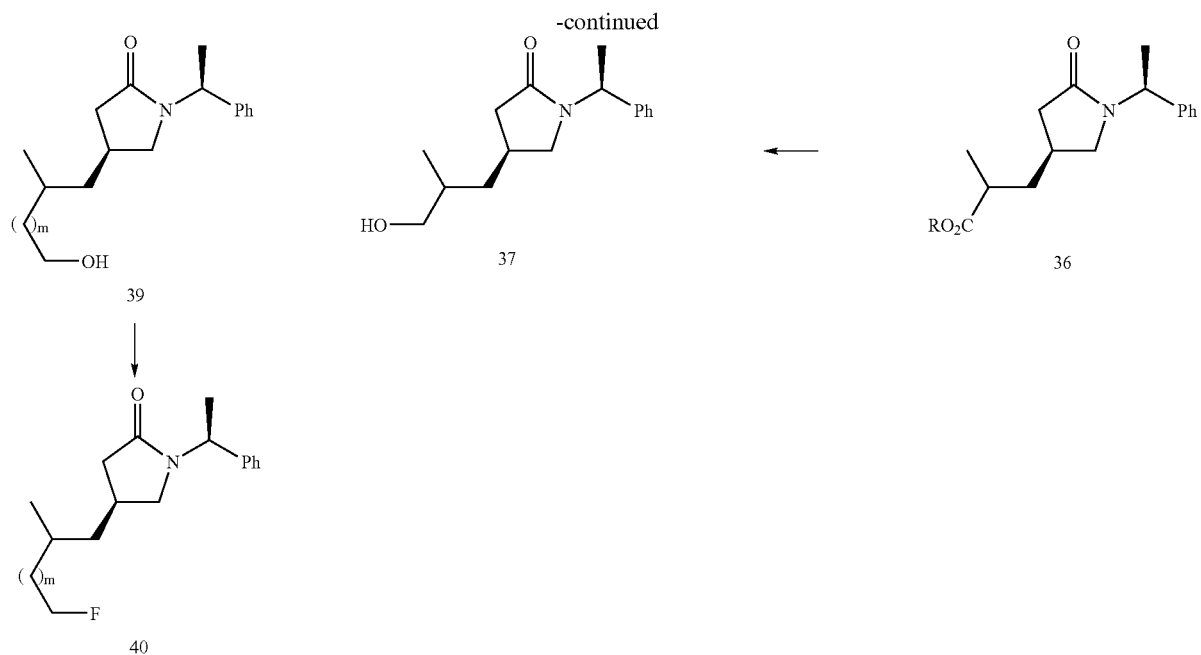

A compound of structure 40 could be prepared from compound of structure 39 through treatment with diethylaminosulphur trifluoride in a solvent such as methylene chloride at a temperature between −78° C. and room temperature. Other methods for the fluorination of alcohols are known and could be utilized as exemplified in Wilkinson, *Chem. Rev.* 1992; 92:505–519. Compounds of structure 40 can be converted to the requisite □-amino acid as described in method 3 above.

A compound of structure 39 could be prepared from compound of structure 38 through treatment with osmium tetroxide and sodium periodate in a solvent such as THF and water and reduction of the resultant intermediate with sodium borohydride in a solvent such as ethanol.

Compounds of structures 38 and 34 could be prepared from compound of structure 33 according to the principles described in method 3.

An alternative procedure for the synthesis of alcohol 39 (n=0) involves the treatment of a compound of structure 36 with a metal borohydride, such as sodium borohydride in a solvent such as tetrahydrofuran or DME and alike to give a compound of structure 37, the fluorination of which could be achieved in a similar manner to the preparation of a compound of structure 40. A compound of structure 36 could be prepared from compound of structure 35 through treatment with sodium or lithium chloride in aqueous DMSO at a temperature between room temperature and reflux. Preferably the reaction is carried out using sodium chloride in aqueous DMSO at reflux. A compound of structure 35 could be prepared from compound of structure 34 through treatment with a suitable methyl malonic acid diester, such as dimethyl methylmalonate and alike with sodium hydride in a solvent such as DMSO or THF and alike. Preferably the reaction is carried out by adding NaH to a solution of dimethyl methylmalonate in DMSO followed by the addition of the lactam 34 (where LG is preferably iodide or as defined in method 3) pre-dissolved in DMSO.

Compounds 39 and 37 can be converted to the free amino acids bearing a hydroxyl group by the methods described above.

The following compounds could be prepared in this manner:
(3S)-3-Aminomethyl-6-fluoro-5-methyl-hexanoic acid;
(3S)-3-Aminomethyl-6-fluoro-5-methyl-hexanoic acid;
(3S)-3-Aminomethyl-7-fluoro-5-methyl-heptanoic acid;
(3S)-3-Aminomethyl-8-fluoro-5-methyl-octanoic acid;
(3S)-3-Aminomethyl-9-fluoro-5-methyl-nonanoic acid;
(3S)-3-Aminomethyl-7-hydroxy-5-methyl-heptanoic acid; and
(3S)-3-Aminomethyl-6-hydroxy-5-methyl-hexanoic acid.

Method 5 (Scheme 13)

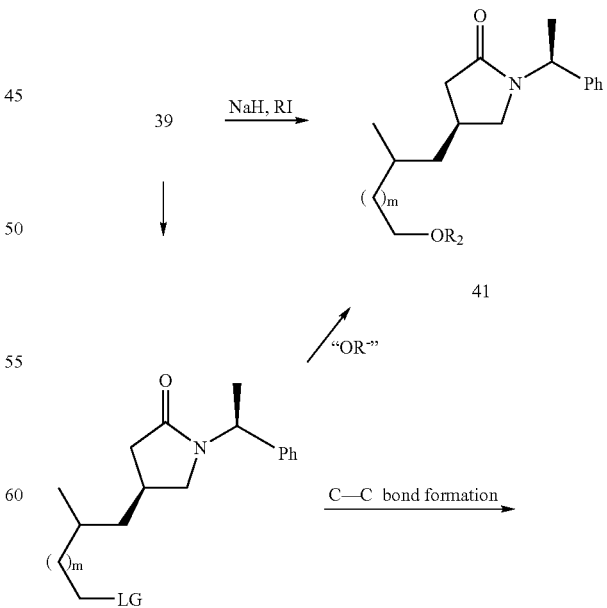

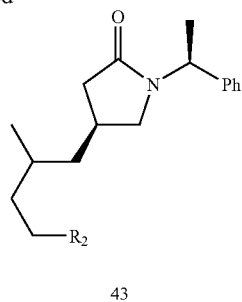

43 compound of structure 41 could be prepared from compound of structure 39 through treatment with a suitable alkyl iodide (or alkyl sulphonate), such as methyl iodide and alike, and a base such as n-butyl lithium or sodium hydride and alike, in a solvent such as DMSO or THF and alike. Preferably the reaction is carried out by adding NaH to a solution of the alcohol in DMSO followed by the addition of the alkyl iodide and heating of the reaction mixture at a temperature between room temperature and reflux. The conversion of compounds of structure 41 to the □-amino acids has been described above.

Alternatively, compounds of structure 41 could be derived from compounds of structure 42 (where LG=iodide, bromide or an sulphonic acid ester, as exampled in method 3) by treatment of an appropriate alkoxy anion in a solvent such as DMSO or THF and alike. A compound of structure 42 would also serve as a substrate for carbon-carbon bond forming procedures as outlined in method 3.

Compounds which could be prepared in this manner include:

(3S)-3-Aminomethyl-7-hydroxy-5-methyl-heptanoic acid;
(3S)-3-Aminomethyl-7-methoxy-5-methyl-heptanoic acid;
(3S)-3-Aminomethyl-7-ethoxy-5-methyl-heptanoic acid;
(3S)-3-Aminomethyl-5-methyl-7-propoxy-heptanoic acid;
(3S)-3-Aminomethyl-7-fluoromethoxy-5-methyl-heptanoic acid;
(3S)-3-Aminomethyl-7-(2-fluoro-ethoxy)-5-methyl-heptanoic acid;
(3S)-3-Aminomethyl-5-methyl-7-(3,3,3-trifluoro-propoxy)-heptanoic acid;
(3S)-3-Aminomethyl-6-hydroxy-5-methyl-hexanoic acid;
(3S)-3-Aminomethyl-6-methoxy-5-methyl-hexanoic acid;
(3S)-3-Aminomethyl-6-ethoxy-5-methyl-hexanoic acid;
(3S)-3-Aminomethyl-5-methyl-6-propoxy-hexanoic acid;
(3S)-3-Aminomethyl-6-fluoromethoxy-5-methyl-hexanoic acid;
(3S)-3-Aminomethyl-6-(2-fluoro-ethoxy)-5-methyl-hexanoic acid; and
(3S)-3-Aminomethyl-5-methyl-6-(3,3,3-trifluoro-propoxy)-hexanoic acid.

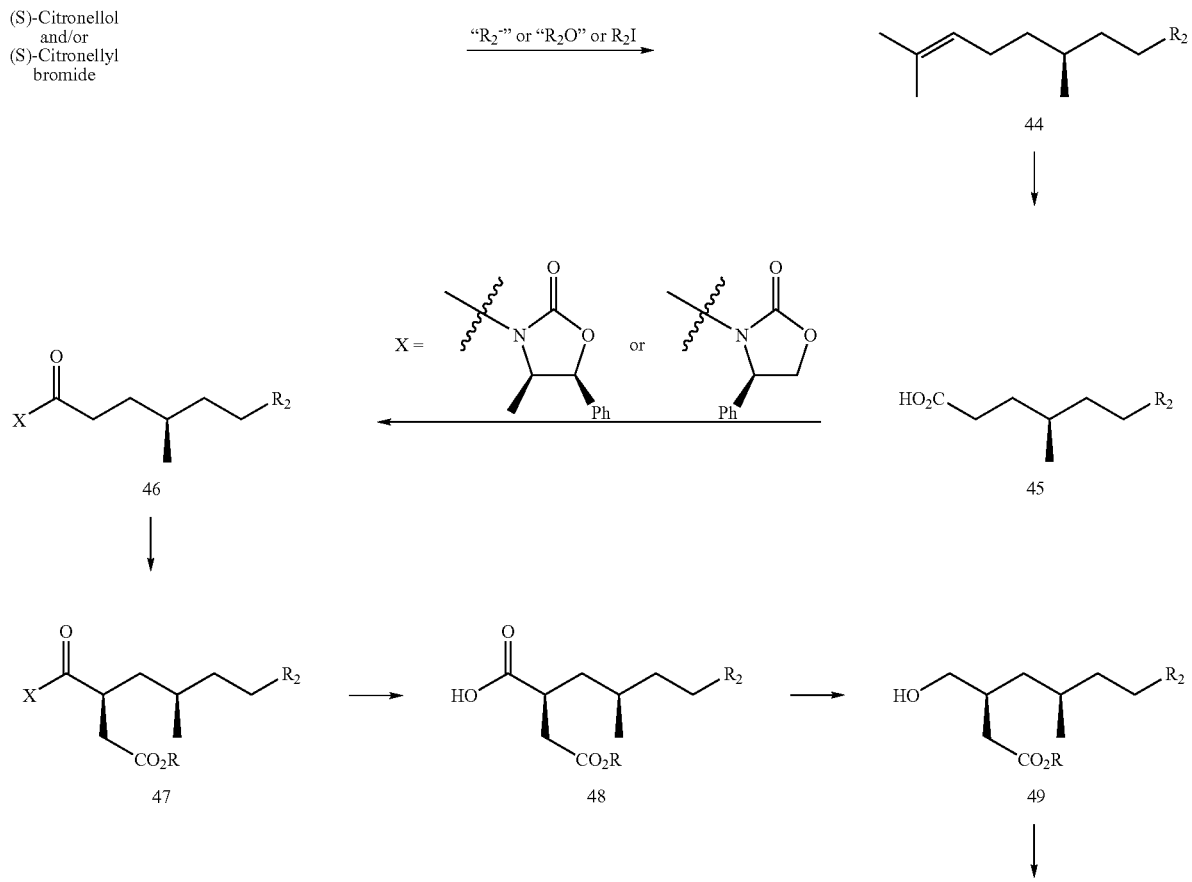

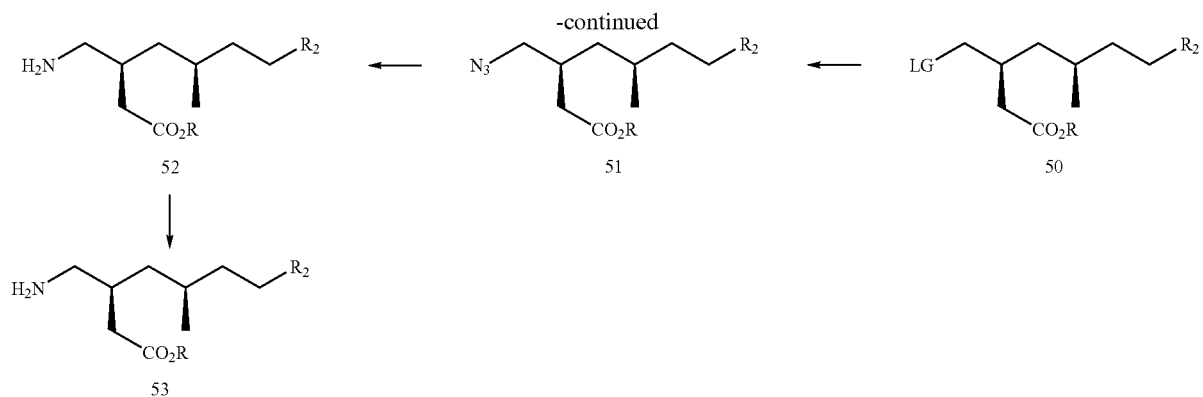

Compounds of structure 53 could be prepared from a compound of structure 45 as shown above and by the general procedures described in Hoekstra et. al., *Organic Process Research and Development*, 1997; 1:26–38.

Compounds of structure 45 can be prepared from compounds of structure 44 by treatment with a solution of chromium trioxide in water/sulfuric acid. Alternative methods of cleaving the olefin in 44 could be utilized as detailed in Hudlicky, *Oxidations in Organic Chemistry*, ACS Monograph 186, ACS 1990:77.

Compounds of structure 44 (where $R_2$=alkyl, branched alkyl, cycloalkyl, alkyl-cycloalkyl) could be prepared from (S)-citronellyl bromide by carbon-carbon bond forming reactions known in the art and as described in method 3. The substitution of the halide in (S)-citronellyl bromide with alkoxy anions could also be used to provide compounds of structure 44 where R=alkoxy or phenoxy ethers (and appropriate substitutions thereof as according to Formula 1). Alternatively (S)-citronellol could be utilized to afford compounds of structure 44 by treatment of (S)-citronellol with a base such as sodium hydride, and treatment of the resultant alkoxide with an appropriate alkyl halide to afford ethers. In another method (S)-citronellyl bromide (or an appropriate sulphonic ester such as, but not limited to, methanesulfonic acid (S)-3,7-dimethyl-oct-6-enyl ester) could be reduced with an appropriate metal borohydride or with an aluminum hydride species, such as LAH, to provide (R)-2,6-dimethyl-oct-2-ene.

To one skilled in the art it will be appreciated that rational choice of either R- or S-citronellol or R- or S-citronellyl bromide would give rise to the requisite isomer at C5 of the final amino acid.

Compounds which could be prepared in this manner include:

(3S,5S)-3-Aminomethyl-7-methoxy-5-methyl-heptanoic acid;
(3S,5S)-3-Aminomethyl-7-ethoxy-5-methyl-heptanoic acid;
(3S,5S)-3-Aminomethyl-5-methyl-7-propoxy-heptanoic acid;
(3S,5S)-3-Aminomethyl-7-isopropoxy-5-methyl-heptanoic acid;
(3S,5S)-3-Aminomethyl-7-tert-butoxy-5-methyl-heptanoic acid;
(3S,5S)-3-Aminomethyl-7-fluoromethoxy-5-methyl-heptanoic acid;
(3S,5S)-3-Aminomethyl-7-(2-fluoro-ethoxy)-5-methyl-heptanoic acid;
(3S,5S)-3-Aminomethyl-5-methyl-7-(3,3,3-trifluoro-propoxy)-heptanoic acid;
(3S,5S)-3-Aminomethyl-7-benzyloxy-5-methyl-heptanoic acid;
(3S,5S)-3-Aminomethyl-5-methyl-7-phenoxy-heptanoic acid;
(3S,5S)-3-Aminomethyl-7-(4-chloro-phenoxy)-5-methyl-heptanoic acid;
(3S,5S)-3-Aminomethyl-7-(3-chloro-phenoxy)-5-methyl-heptanoic acid;
(3S,5S)-3-Aminomethyl-7-(2-chloro-phenoxy)-5-methyl-heptanoic acid;
(3S,5S)-3-Aminomethyl-7-(4-fluoro-phenoxy)-5-methyl-heptanoic acid;
(3S,5S)-3-Aminomethyl-7-(3-fluoro-phenoxy)-5-methyl-heptanoic acid;
(3S,5S)-3-Aminomethyl-7-(2-fluoro-phenoxy)-5-methyl-heptanoic acid;
(3S,5S)-3-Aminomethyl-7-(4-methoxy-phenoxy)-5-methyl-heptanoic acid;
(3S,5S)-3-Aminomethyl-7-(3-methoxy-phenoxy)-5-methyl-heptanoic acid;
(3S,5S)-3-Aminomethyl-7-(2-methoxy-phenoxy)-5-methyl-heptanoic acid;
(3S,5S)-3-Aminomethyl-5-methyl-7-(4-trifluoromethyl-phenoxy)-heptanoic acid;
(3S,5S)-3-Aminomethyl-5-methyl-7-(3-trifluoromethyl-phenoxy)-heptanoic acid;
(3S,5S)-3-Aminomethyl-5-methyl-7-(2-trifluoromethyl-phenoxy)-heptanoic acid;
(3S,5S)-3-Aminomethyl-5-methyl-7-(4-nitro-phenoxy)-heptanoic acid;
(3S,5S)-3-Aminomethyl-5-methyl-7-(3-nitro-phenoxy)-heptanoic acid;
(3S,5S)-3-Aminomethyl-5-methyl-7-(2-nitro-phenoxy)-heptanoic acid;
(3S,5R)-3-Aminomethyl-7-cyclopropyl-5-methyl-heptanoic acid;
(3S,5R)-3-Aminomethyl-7-cyclobutyl-5-methyl-heptanoic acid;
(3S,5R)-3-Aminomethyl-7-cyclopentyl-5-methyl-heptanoic acid;
(3S,5R)-3-Aminomethyl-7-cyclohexyl-5-methyl-heptanoic acid;
(3S,5R)-3-Aminomethyl-8-cyclopropyl-5-methyl-octanoic acid;
(3S,5R)-3-Aminomethyl-8-cyclobutyl-5-methyl-octanoic acid;

(3S,5R)-3-Aminomethyl-8-cyclopentyl-5-methyl-octanoic acid;
(3S,5R)-3-Aminomethyl-8-cyclohexyl-5-methyl-octanoic acid;
(3S,5R)-3-Aminomethyl-5-methyl-heptanoic acid;
(3S,5R)-3-Aminomethyl-5-methyl-octanoic acid;
(3S,5R)-3-Aminomethyl-5-methyl-nonanoic acid;
(3S,5R)-3-Aminomethyl-5-methyl-decanoic acid;
(3S,5R)-3-Aminomethyl-5-methyl-undecanoic acid;
(3S,5R)-3-Aminomethyl-5,9-dimethyl-decanoic acid;
(3S,5R)-3-Aminomethyl-5,8-dimethyl-nonanoic acid;
(3S,5S)-3-Aminomethyl-7-fluoro-5-methyl-heptanoic acid;
(3S,5R)-3-Aminomethyl-8-fluoro-5-methyl-octanoic acid;
(3S,5R)-3-Aminomethyl-8,8,8-trifluoro-5-methyl-octanoic acid;
(3S,5R)-3-Aminomethyl-5-methyl-7-phenyl-heptanoic acid;
(3S,5R)-3-Aminomethyl-7-(4-chloro-phenyl)-5-methyl-heptanoic acid;
(3S,5R)-3-Aminomethyl-7-(3-chloro-phenyl)-5-methyl-heptanoic acid;
(3S,5R)-3-Aminomethyl-7-(2-chloro-phenyl)-5-methyl-heptanoic acid;
(3S,5R)-3-Aminomethyl-7-(4-methoxy-phenyl)-5-methyl-heptanoic acid;
(3S,5R)-3-Aminomethyl-7-(3-methoxy-phenyl)-5-methyl-heptanoic acid;
(3S,5R)-3-Aminomethyl-7-(2-methoxy-phenyl)-5-methyl-heptanoic acid;
(3S,5R)-3-Aminomethyl-7-(4-fluoro-phenyl)-5-methyl-heptanoic acid;
(3S,5R)-3-Aminomethyl-7-(3-fluoro-phenyl)-5-methyl-heptanoic acid;
(3S,5R)-3-Aminomethyl-7-(2-fluoro-phenyl)-5-methyl-heptanoic acid; and
(3S,5R)-3-Aminomethyl-5,10-dimethyl-undecanoic acid.

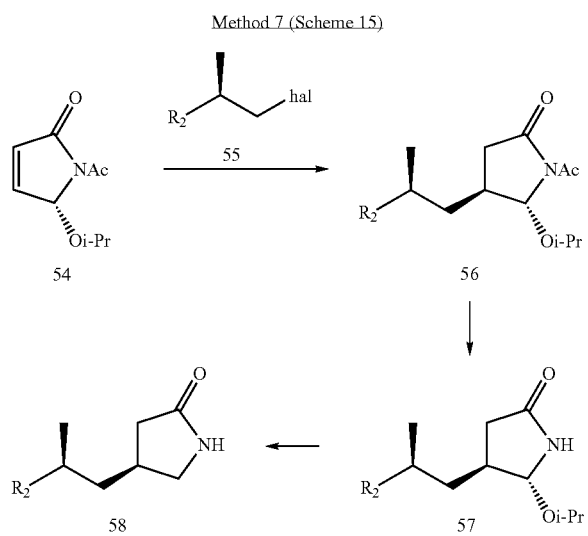

Method 7 (Scheme 15)

A compound of structure 58 can be prepared from a compound of structure 57 by treatment with borontrifluoride diethyletherate and triethylsilane in a solvent such as $CH_2Cl_2$. Alternatively the method described in Meyers, *J. Org. Chem.*, 1993; 58:36–42, could be utilized thus treating a compound of structure 57 with sodium cyanoborohydride in a solvent such as THF/methanol with 3% HCl in methanol.

A compound of structure 57 can be prepared from a compound of structure 56 by treatment with dimethylamine in a solvent such as DMF and alike according to the procedure of Koot, *Tetrahedron Lett.*, 1992; 33:7969–7972.

A compound of structure 56 can be prepared from a compound of structure 54 by treatment of a suitable primary halide 55 (iodide, bromide, or chloride) under standard transmetallation conditions with tBuLi and treatment of the resultant organometallic reagent with suitable copper salt, such as but not limited to, copper bromide or copper iodide. The resultant organo-cuprate is added to lactam (see Koot et al, *J. Org. Chem.*, 1992; 57:1059–1061 for the preparation of the chiral lactam 54) in a solvent such as THF and alike. The procedure of Koot, *Tetrahedron Lett.*, 1992; 33:7969–7972 exemplifies this method.

To one skilled in the art it will be appreciated that rational choice of either R- or S-primary halides 55 would give rise to the requisite isomer at C5 of the final amino acid.

Compounds which could be prepared in this manner include:
(3S,5S)-3-Aminomethyl-5-methoxy-hexanoic acid;
(3S,5S)-3-Aminomethyl-5-ethoxy-hexanoic acid;
(3S,5S)-3-Aminomethyl-5-propoxy-hexanoic acid;
(3S,5S)-3-Aminomethyl-5-isopropoxy-hexanoic acid;
(3S,5S)-3-Aminomethyl-5-tert-butoxy-hexanoic acid;
(3S,5S)-3-Aminomethyl-5-fluoromethoxy-hexanoic acid;
(3S,5S)-3-Aminomethyl-5-(2-fluoro-ethoxy)-hexanoic acid;
(3S,5S)-3-Aminomethyl-5-(3,3,3-trifluoro-propoxy)-hexanoic acid;
(3S,5S)-3-Aminomethyl-5-phenoxy-hexanoic acid;
(3S,5S)-3-Aminomethyl-5-(4-chloro-phenoxy)-hexanoic acid;
(3S,5S)-3-Aminomethyl-5-(3-chloro-phenoxy)-hexanoic acid;
(3S,5S)-3-Aminomethyl-5-(2-chloro-phenoxy)-hexanoic acid;
(3S,5S)-3-Aminomethyl-5-(4-fluoro-phenoxy)-hexanoic acid;
(3S,5S)-3-Aminomethyl-5-(3-fluoro-phenoxy)-hexanoic acid;
(3S,5S)-3-Aminomethyl-5-(2-fluoro-phenoxy)-hexanoic acid;
(3S,5S)-3-Aminomethyl-5-(4-methoxy-phenoxy)-hexanoic acid;
(3S,5S)-3-Aminomethyl-5-(3-methoxy-phenoxy)-hexanoic acid;
(3S,5S)-3-Aminomethyl-5-(2-methoxy-phenoxy)-hexanoic acid;
(3S,5S)-3-Aminomethyl-5-(4-nitro-phenoxy)-hexanoic acid;
(3S,5S)-3-Aminomethyl-5-(3-nitro-phenoxy)-hexanoic acid;
(3S,5S)-3-Aminomethyl-5-(2-nitro-phenoxy)-hexanoic acid;
(3S,5S)-3-Aminomethyl-6-methoxy-5-methyl-hexanoic acid;
(3S,5S)-3-Aminomethyl-6-ethoxy-5-methyl-hexanoic acid;
(3S,5S)-3-Aminomethyl-5-methyl-6-propoxy-hexanoic acid;
(3S,5S)-3-Aminomethyl-6-isopropoxy-5-methyl-hexanoic acid;
(3S,5S)-3-Aminomethyl-6-tert-butoxy-5-methyl-hexanoic acid;

(3S,5S)-3-Aminomethyl-6-fluoromethoxy-5-methyl-hexanoic acid;
(3S,5S)-3-Aminomethyl-6-(2-fluoro-ethoxy)-5-methyl-hexanoic acid;
(3S,5S)-3-Aminomethyl-5-methyl-6-(3,3,3-trifluoro-propoxy)-hexanoic acid;
(3S,5S)-3-Aminomethyl-5-methyl-6-phenoxy-hexanoic acid;
(3S,5S)-3-Aminomethyl-6-(4-chloro-phenoxy)-5-methyl-hexanoic acid;
(3S,5S)-3-Aminomethyl-6-(3-chloro-phenoxy)-5-methyl-hexanoic acid;
(3S,5S)-3-Aminomethyl-6-(2-chloro-phenoxy)-5-methyl-hexanoic acid;
(3S,5S)-3-Aminomethyl-6-(4-fluoro-phenoxy)-5-methyl-hexanoic acid;
(3S,5S)-3-Aminomethyl-6-(3-fluoro-phenoxy)-5-methyl-hexanoic acid;
(3S,5S)-3-Aminomethyl-6-(2-fluoro-phenoxy)-5-methyl-hexanoic acid;
(3S,5S)-3-Aminomethyl-6-(4-methoxy-phenoxy)-5-methyl-hexanoic acid;
(3S,5S)-3-Aminomethyl-6-(3-methoxy-phenoxy)-5-methyl-hexanoic acid;
(3S,5S)-3-Aminomethyl-6-(2-methoxy-phenoxy)-5-methyl-hexanoic acid;
(3S,5S)-3-Aminomethyl-5-methyl 6-(4-trifluoromethyl-phenoxy)-hexanoic acid;
(3S,5S)-3-Aminomethyl-5-methyl 6-(3-trifluoromethyl-phenoxy)-hexanoic acid;
(3S,5S)-3-Aminomethyl-5-methyl 6-(2-trifluoromethyl-phenoxy)-hexanoic acid;
(3S,5S)-3-Aminomethyl-5-methyl 6-(4-nitro-phenoxy)-hexanoic acid;
(3S,5S)-3-Aminomethyl-5-methyl 6-(3-nitro-phenoxy)-hexanoic acid;
(3S,5S)-3-Aminomethyl-5-methyl 6-(2-nitro-phenoxy)-hexanoic acid;
(3S,5S)-3-Aminomethyl-6-benzyloxy-5-methyl-hexanoic acid;
(3S,5R)-3-Aminomethyl-6-cyclopropyl-5-methyl-hexanoic acid;
(3S,5R)-3-Aminomethyl-6-cyclobutyl-5-methyl-hexanoic acid;
(3S,5R)-3-Aminomethyl-6-cyclopentyl-5-methyl-hexanoic acid;
(3S,5R)-3-Aminomethyl-6-cyclohexyl-5-methyl-hexanoic acid;
(3S,5R)-3-Aminomethyl-5-methyl-heptanoic acid;
(3S,5R)-3-Aminomethyl-5-methyl-octanoic acid;
(3S,5R)-3-Aminomethyl-5-methyl-nonanoic acid;
(3S,5R)-3-Aminomethyl-5-methyl-decanoic acid;
(3S,5R)-3-Aminomethyl-5-methyl-undecanoic acid;
(3S,5R)-3-Aminomethyl-5-methyl-dodecanoic acid;
(3S,5R)-3-Aminomethyl-5,7-dimethyl-octanoic acid;
(3S,5R)-3-Aminomethyl-5,8-dimethyl-nonanoic acid;
(3S,5R)-3-Aminomethyl-5,9-dimethyl-decanoic acid;
(3S,5R)-3-Aminomethyl-5,10-dimethyl-undecanoic acid;
(3S,5S)-3-Aminomethyl-5,6-dimethyl-heptanoic acid;
(3S,5S)-3-Aminomethyl-5,6,6-trimethyl-heptanoic acid;
(3S,5S)-3-Aminomethyl-5-cyclopropyl-hexanoic acid;
(3S,5S)-3-Aminomethyl-6-fluoro-5-methyl-hexanoic acid;
(3S,5S)-3-Aminomethyl-7-fluoro-5-methyl-heptanoic acid;
(3S,5R)-3-Aminomethyl-8-fluoro-5-methyl-octanoic acid;
(3S,5S)-3-Aminomethyl-7,7,7-trifluoro-5-methyl-heptanoic acid;
(3S,5R)-3-Aminomethyl-8,8,8-trifluoro-5-methyl-octanoic acid;
(3S,5S)-3-Aminomethyl-5-methyl-6-phenyl-hexanoic acid;
(3S,5S)-3-Aminomethyl-6-(4-chloro-phenyl)-5-methyl-hexanoic acid;
(3S,5S)-3-Aminomethyl-6-(3-chloro-phenyl)-5-methyl-hexanoic acid;
(3S,5S)-3-Aminomethyl-6-(2-chloro-phenyl)-5-methyl-hexanoic acid;
(3S,5S)-3-Aminomethyl-6-(4-methoxy-phenyl)-5-methyl-hexanoic acid;
(3S,5S)-3-Aminomethyl-6-(3-methoxy-phenyl)-5-methyl-hexanoic acid;
(3S,5S)-3-Aminomethyl-6-(2-methoxy-phenyl)-5-methyl-hexanoic acid;
(3S,5S)-3-Aminomethyl-6-(4-fluoro-phenyl)-5-methyl-hexanoic acid;
(3S,5S)-3-Aminomethyl-6-(3-fluoro-phenyl)-5-methyl-hexanoic acid;
(3S,5S)-3-Aminomethyl-6-(2-fluoro-phenyl)-5-methyl-hexanoic acid;
(3S,5R)-3-Aminomethyl-5-methyl-7-phenyl-heptanoic acid;
(3S,5R)-3-Aminomethyl-7-(4-chloro-phenyl)-5-methyl-heptanoic acid;
(3S,5R)-3-Aminomethyl-7-(3-chloro-phenyl)-5-methyl-heptanoic acid;
(3S,5R)-3-Aminomethyl-7-(2-chloro-phenyl)-5-methyl-heptanoic acid;
(3S,5R)-3-Aminomethyl-7-(4-methoxy-phenyl)-5-methyl-heptanoic acid;
(3S,5R)-3-Aminomethyl-7-(3-methoxy-phenyl)-5-methyl-heptanoic acid;
(3S,5R)-3-Aminomethyl-7-(2-methoxy-phenyl)-5-methyl-heptanoic acid;
(3S,5R)-3-Aminomethyl-7-(4-fluoro-phenyl)-5-methyl-heptanoic acid;
(3S,5R)-3-Aminomethyl-7-(3-fluoro-phenyl)-5-methyl-heptanoic acid;
(3S,5R)-3-Aminomethyl-7-(2-fluoro-phenyl)-5-methyl-heptanoic acid;
(3S,5S)-3-Aminomethyl-5-methyl-hept-6-enoic acid;
(3S,5R)-3-Aminomethyl-5-methyl-oct-7-enoic acid;
(3S,5R)-3-Aminomethyl-5-methyl-non-8-enoic acid;
(E)-(3S,5S)-3-Aminomethyl-5-methyl-oct-6-enoic acid;
(Z)-(3S,5S)-3-Aminomethyl-5-methyl-oct-6-enoic acid;
(Z)-(3S,5S)-3-Aminomethyl-5-methyl-non-6-enoic acid;
(E)-(3S,5S)-3-Aminomethyl-5-methyl-non-6-enoic acid;
(E)-(3S,5R)-3-Aminomethyl-5-methyl-non-7-enoic acid;
(Z)-(3S,5R)-3-Aminomethyl-5-methyl-non-7-enoic acid;
(Z)-(3S,5R)-3-Aminomethyl-5-methyl-dec-7-enoic acid; and
(E)-(3S,5R)-3-Aminomethyl-5-methyl-undec-7-enoic acid.

Method 8 (Scheme 16)

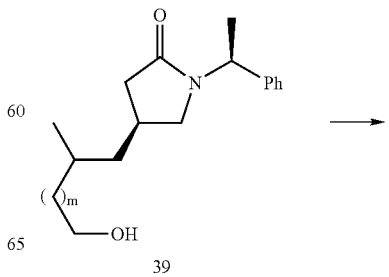

39

-continued

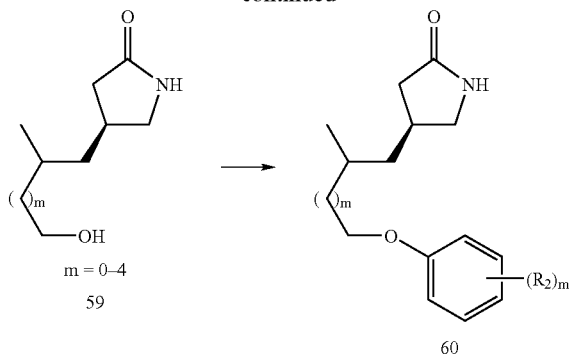

m = 0–4
59
60

A compound of structure 60 can be prepared from a compound of structure 59 through treatment with an appropriately substituted phenol (including phenol itself) under conditions described by Mitsunobu, *Synthesis,* 1981:1.

A compound of structure 59 could be prepared from compound of structure 39 by treatment with sodium or lithium metal and alike in ammonia. Preferably, the reaction is carried out with sodium metal in ammonia.

The direct hydrolysis of compound 60 would give rise to the desired amino acid or the approach via hydrolysis of the Boc protected lactam could be utilized.

Compounds which could be prepared in this manner include:
(3S)-3-Aminomethyl-5-methyl-7-phenoxy-heptanoic acid;
(3S)-3-Aminomethyl-7-(4-chloro-phenoxy)-5-methyl-heptanoic acid;
(3S)-3-Aminomethyl-7-(3-chloro-phenoxy)-5-methyl-heptanoic acid;
(3S)-3-Aminomethyl-7-(2-chloro-phenoxy)-5-methyl-heptanoic acid;
(3S)-3-Aminomethyl-7-(4-fluoro-phenoxy)-5-methyl-heptanoic acid;
(3S)-3-Aminomethyl-7-(3-fluoro-phenoxy)-5-methyl-heptanoic acid;
(3S)-3-Aminomethyl-7-(2-fluoro-phenoxy)-5-methyl-heptanoic acid;
(3S)-3-Aminomethyl-7-(4-methoxy-phenoxy)-5-methyl-heptanoic acid;
(3S)-3-Aminomethyl-7-(3-methoxy-phenoxy)-5-methyl-heptanoic acid;
(3S)-3-Aminomethyl-7-(2-methoxy-phenoxy)-5-methyl-heptanoic acid;
(3S)-3-Aminomethyl-5-methyl-7-(4-trifluoromethyl-phenoxy)-heptanoic acid;
(3S)-3-Aminomethyl-5-methyl-7-(3-trifluoromethyl-phenoxy)-heptanoic acid;
(3S)-3-Aminomethyl-5-methyl-7-(2-trifluoromethyl-phenoxy)-heptanoic acid;
(3S)-3-Aminomethyl-5-methyl-7-(4-nitro-phenoxy)-heptanoic acid;
(3S)-3-Aminomethyl-5-methyl-7-(3-nitro-phenoxy)-heptanoic acid;
(3S)-3-Aminomethyl-5-methyl-7-(2-nitro-phenoxy)-heptanoic acid;
(3S)-3-Aminomethyl-6-(3-chloro-phenoxy)-5-methyl-hexanoic acid;
(3S)-3-Aminomethyl-6-(2-chloro-phenoxy)-5-methyl-hexanoic acid;
(3S)-3-Aminomethyl-6-(4-fluoro-phenoxy)-5-methyl-hexanoic acid;
(3S)-3-Aminomethyl-6-(3-fluoro-phenoxy)-5-methyl-hexanoic acid;
(3S)-3-Aminomethyl-6-(2-fluoro-phenoxy)-5-methyl-hexanoic acid;
(3S)-3-Aminomethyl-6-(4-methoxy-phenoxy)-5-methyl-hexanoic acid;
(3S)-3-Aminomethyl-6-(3-methoxy-phenoxy)-5-methyl-hexanoic acid;
(3S)-3-Aminomethyl-6-(2-methoxy-phenoxy)-5-methyl-hexanoic acid;
(3S)-3-Aminomethyl-5-methyl 6-(4-trifluoromethyl-phenoxy)-hexanoic acid;
(3S)-3-Aminomethyl-5-methyl 6-(3-trifluoromethyl-phenoxy)-hexanoic acid;
(3S)-3-Aminomethyl-5-methyl 6-(2-trifluoromethyl-phenoxy)-hexanoic acid;
(3S)-3-Aminomethyl-5-methyl 6-(4-nitro-phenoxy)-hexanoic acid;
(3S)-3-Aminomethyl-5-methyl 6-(3-nitro-phenoxy)-hexanoic acid;
(3S)-3-Aminomethyl-5-methyl 6-(2-nitro-phenoxy)-hexanoic acid;
(3S)-3-Aminomethyl-5-methyl-6-phenoxy-hexanoic acid; and
(3S)-3-Aminomethyl-6-(4-chloro-phenoxy)-5-methyl-hexanoic acid.

Method 9 Synthesis of C-4 substituted analogs (Scheme 17)

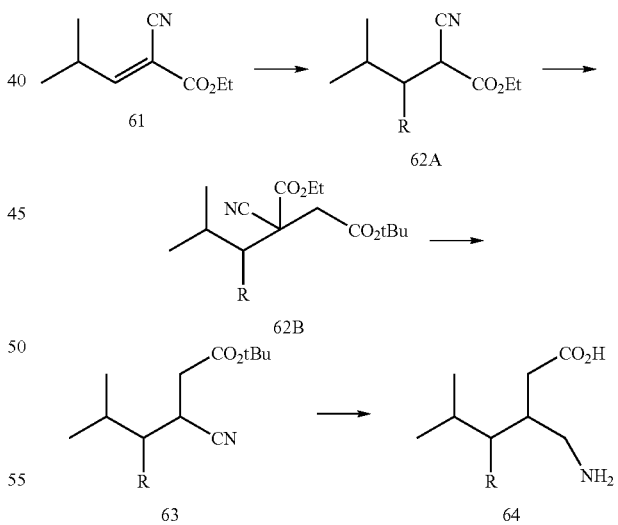

A compound of structure 64 could be prepared from compound of structure 63 by treatment of 63 with hydrogen at 50 psi in the presence of a catalyst such as such as Raney nickel in the presence of a base such as triethyl amine in an organic solvent for example methanol. The resulting product is then treated with an aqueous acid such as 6N HCl at a temperature between room temperature and reflux. The resulting mixture could be subjected to ion exchange chromatography to isolate the product 64.

A compound of structure 63 can be prepared from a compound of structure 62B by treatment with an appropriate base, such as but not limited to sodium hydride, n-butyl lithium and alike, and an alkylating reagent such as t-butyl-bromoacetate or benzylbromoacetate in a solvent such as DMSO or THF an alike. Preferably, the reaction is carried out by treating a solution of a compound of structure 62B in THF with sodium hydride and alkylation of the resultant anion with t-butylbromoacetate.

A compound of structure 62B can be prepared from a compound of structure 62A by treatment with sodium chloride in a solvent such as aqueous DMSO at a temperature between 50° C. and reflux.

A compound of structure 62A can be prepared from a compound of structure 61 by treatment with an appropriate alkylmetalhalide such as an alkyl lithium reagent or an organomagnesium halide in a solvent such as THF or ether in the presence of a copper salt, such as but not limited to copper iodide, copper bromide dimethylsulphide. Alternatively, the reaction may be carried out by the treatment of the nitrile in a solvent such as ether at, or below, room temperature with an alkylmagnesium chloride.

A compound such as 61 can be prepared according to known literature procedures between the condensation of isobutylaldheyde and methylcyanoacetate.

Method 10: C-4 Substitution (Scheme 18)

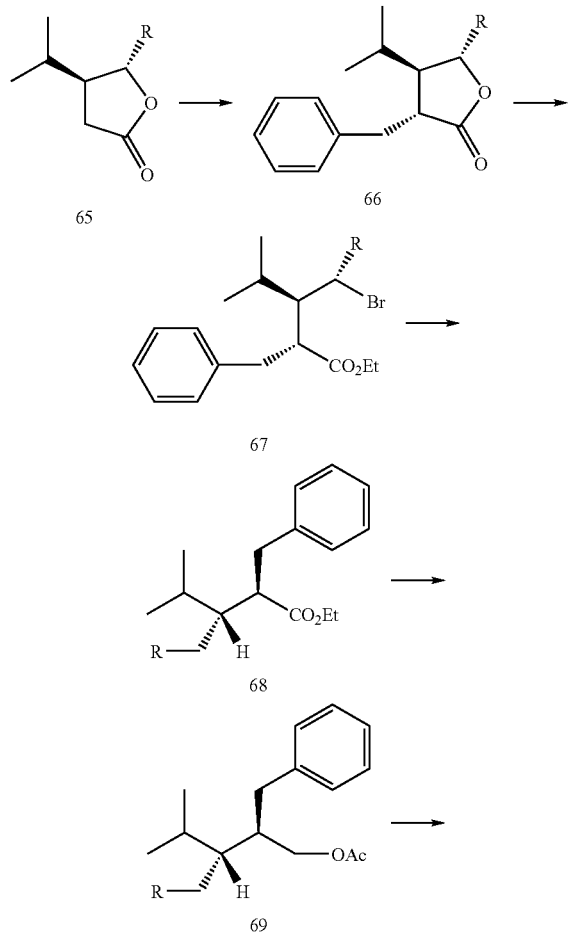

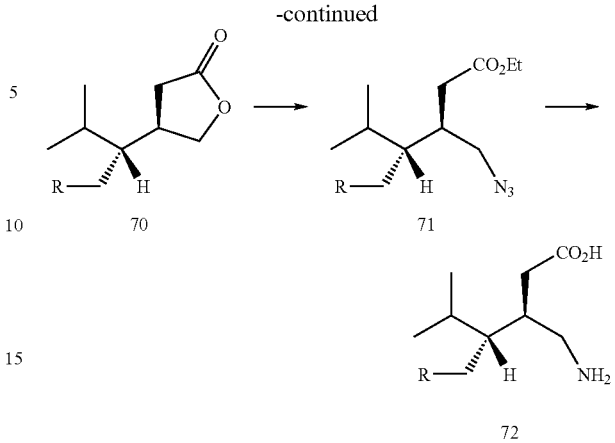

Doubly branched 3-substituted alpha2delta ligands 72 can be prepared in two steps from the azide 71 through hydrogenation of the azide 71 in the presence of a noble metal catalyst such as 5% palladium on carbon and hydrolysis of the resulting lactam with a strong acid such as 6 N HCl at reflux. The final product 72 can then be isolated using ion exchange chromatography.

Compound 71 can be prepared in two steps by treatment of a lactone such as 70 with HBr in a solvent such as ethanol at a temperature such as 0° C. and reacting the resulting bromide with sodium azide in a solvent such as dimethyl sulfoxide at a temperature between 10° C. and 80° C.

Lactone 70 can be prepared in two steps by oxidation of a compound such as 69 with an oxidant such as sodium periodate in the presence of a catalytic amount of ruthenium trichloride in a solvent such as acetonitrile at a temperature between 0° C. and 100° C. and treatment of the resulting compound with potassium carbonate in methanol followed at a temperature between 25° C. and 70° C. and then treatment with an acid such as p-toluene sulfonic acid in a solvent such as THF at reflux or an aqueous acid such as HCl in water at ambient temperature.

A compound such as 69 can be prepared by a reduction of a compound such as 68 with a hydride reducing agent such as lithium aluminum hydride in a solvent such as ether or THF and reaction of the resulting alcohol with an acylating agent such as acetic anhydride in the presence of a base such as triethyl amine or pyridine or the like.

Compounds of structure 68 can be prepared by reaction of a compound such as 67 with hydrogen at approximately 50 psi in the presence of a noble metal catalyst such as 5% palladium on carbon in a solvent such as ethanol. A compound of the formula 67 can be prepared by reaction of a compound of structure 66 with a solution of ethanol saturated with hydrogen bromide gas. A compound such as 66 can be prepared from a compound such as 65 by treatment of a compound such as one with a strong base such as lithium diisopropyl amine in a solvent such as THF at a temperature such as −78° C. and reaction of the resulting anion with a compound such as benzyl bromide or benzyl iodide. Compounds of the structure 66 (R=H or lower alkyl) can be prepared in optical form from methods known in the literature (Davies, *J. Org. Chem.*, 1999; 64(23): 8501–8508; Koch *J. Org. Chem.*, 1993; 58(10):2725–37; Afonso, *Tetrahedron*, 1993; 49(20):4283–92; Bertus, *Tetrahedron*, Asymmetry 1999; 10(7):1369–1380; Yamamoto, *J, Am. Chem. Soc.*, 1992; 114(20):7652–60).

SPECIFIC EXAMPLES

EXAMPLE 11

Synthesis of 3-Aminomethyl-5-methyl-octanoic acid

1-Benzyl-4-(2-methyl-pentyl)-pyrrolidin-2-one 76

To a suspension of magnesium turnings (0.50 g, 0.021 mol) in 15 mL of dry THF under nitrogen, was added an iodine crystal and 2-bromopentane (2.88 g, 0.019 mol). After an exothermic reaction which was periodically cooled in an ice bath, the reaction was stirred at room temperature

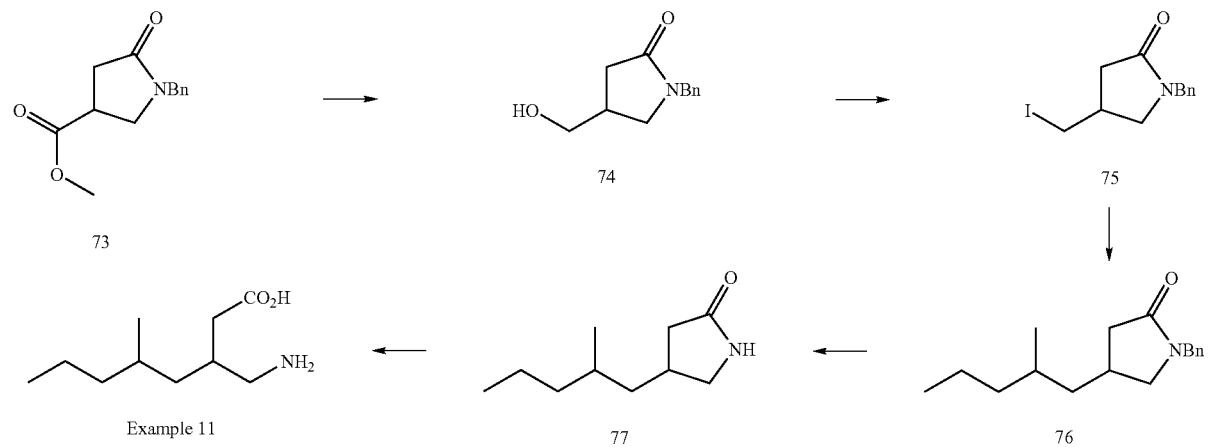

1-Benzyl-4-hydroxymethyl-pyrrolidine-2-one 74

Sodium borohydride (8.0 g, 0.211 mol) was added to a solution of methyl-1-benzyl-5-oxo-3-pyrrolidnecarboxylate 73 (See Zoretic et al, *J. Org. Chem.*, 1980; 45:810–814 for general method of synthesis) (32.0 g, 0.137 mol) in 1,2-dimethoxyethane (600 mL) and refluxed for 19 hours. The reaction was cooled to room temperature and 200 mL of water was added. The reaction was quenched with 1 M citric acid and concentrated under reduced pressure. The residue was extracted with dichloromethane, dried over magnesium sulfate, and evaporated to dryness to give 17.47 g, 62% of the alcohol 74 as clear oil. $^1$H NMR (CDCl$_3$) δ 7.30 (m, 5H), 4.38 (d, 1H, J=14.7), 4.46 (d, 1H, J=14.7), 3.56 (m, 2H), 3.36 (m, 1H), 3.10 (m, 1H), 2.52 (m, 2H), 2.26 (m, 1H). MS, m/z (relative intensity): 207 [M+2H, 66%]. IR (KBr) 3345, 2946, 2866, 1651, 1445, 1025, 737, and 698 cm$^{-1}$.

1-Benzyl-4-iodomethyl-pyrrolidin-2-one 75

To alcohol lactam 74 (11.18 g, 0.056 mol) in 210 mL toluene was added in turn, triphenylphosphine (20.0 g, 0.076 mol), imidazole (10.8 g, 0.159 mol), and iodine (19.0 g, 0.075 mol). After stirring the suspension for 1.5 hours, the supernatant was poured into another flask. The sticky yellow residue was washed twice with ether and the solutions were combined. The solvent was evaporated and the residue was chromatographed on silica, eluting with 1:1 acetone/hexane to give 7.92 g, 46% of the iodolactam 75 as yellow oil. $^1$H NMR (CDCl$_3$) δ 7.25 (m, 5H), 4.38 (d, 1H, J=14.6), 4.46 (d, 1H, J=14.6), 3.38 (dd, 1H, J=7.8 and 2.2), 3.20 (dd, 1H, J=5.6 and 4.4), 3.12 (dd, 1H, J=7.3 and 2.4), 2.96 (dd, 1H, J=5.8 and 4.4), 2.60 (m, 2H), 2.22 (dd, 1H, J=10.5 and 9.7). MS, m/z (relative intensity): 224 [M–H–Bn, 94%], 317 [M+2H, 64%]. IR 3027, 2917, 1688, 1438, 1267, and 701 cm$^{-1}$.

for 2 hours. Eight milliliters of Li$_2$CuCl$_4$ (made from 84 mg LiCl and 134 mg CuCl$_2$ in 10 mL of dry THF) was added at 0° C. followed by dropwise addition of 1-Benzyl-4-iodomethyl-pyrolidine-2-one 75 in 15 mL dry THF, and the resulting suspension was let stir at 0° C. for 3 hours. Stirring was continued at room temperature for 1 hour before quenching with a saturated solution of ammonium chloride. Water was added to dissolve the precipitate formed, and the solution was then extracted with ether and dried over magnesium sulfate. The solvent was evaporated under vacuum and the residue chromatographed on silica eluting with 1:1 acetone/hexane to give 1.13 g, 69% of the 1-benzyl-4-(2-methyl-pentyl)-pyrrolidin-2-one 76. $^1$H NMR (CDCl$_3$) δ 7.30 (m, 5H), 4.44 (m, 2H), 3.32 (m, 1H), 2.86 (m, 1H), 2.56 (m, 1H), 2.40 (m, 1H), 2.10 (m, 1H), 1.30 (m, 6H), 1.10 (m, 1H), 0.90 (m, 6H). MS, m/z (relative intensity): 261 [M+2H, 100%], 301 [M–H+CH$_3$CN, 82%], 260 [M+H, 72%].

4-(2-Methyl-pentyl)-pyrrolidin-2-one 77

A 250 mL 3-neck flask equipped with a dry ice condenser was chilled to –78° C. Ammonia (80 mL) was condensed into the flask and 1-benzyl-4-(2-methyl-pentyl)-pyrrolidin-2-one 76 (1.67 g, 0.006 mol) in 15 mL THF was added. Freshly cut sodium beads were added until a deep blue color persisted. The cooling bath was removed and the reaction stirred at reflux (–33° C.) for 1 hour. The reaction was quenched with ammonium chloride and the excess ammonia was allowed to evaporate. The resulting residue was diluted with water, extracted with dichloromethane, and dried over magnesium sulfate. Evaporation of the solvent followed by chromatography on silica eluting with 1:1 acetone/hexane gave 0.94 g, 86% of the 4-(2-Methyl-pentyl)-pyrrolidin-2-one 77. $^1$H NMR (CDCl$_3$) δ 6.25 (br, 1H), 3.44 (m, 1H), 2.95 (m, 1H), 2.54 (m, 1H), 2.40 (m, 1H), 1.98 (m, 1H), 1.30 (m, 6H), 0.80 (m, 6H). MS, m/z (relative intensity): 212 [M+2H+CH$_3$CN, 100%], 171 [M+2H, 72%], 170 [M+1H, 65%].

3-Aminomethyl-5-methyl-octanoic acid (Example 11)

The 4-(2-methyl-pentyl)-pyrrolidin-2-one 77 (0.94 g, 0.007 mol) was dissolved in 70 mL of 6N HCl and refluxed for 20 hours. The solution was evaporated under vacuum and an aqueous solution of the residue was applied to Dowex 50WX 8-100 (strongly acidic) ion exchange resin that had been washed with HPLC grade water. The column was eluted, first with water until the eluent was at constant pH, and then with 5% ammonium hydroxide solution. The ammonium hydroxide fractions were evaporated and azeotroped with toluene. The white solid was washed with acetone filtered and dried in a vacuum oven for 24 hours to give the amino acid 0.61 g, 59%. $^1$H NMR (CD$_3$OD) δ 3.00 (m, 1H), 2.85 (m, 1H), 2.48 (m, 1H), 2.30 (m, 1H), 2.14 (brm, 1H), 1.60 (brm, 1H), 1.38 (m, 4H), 1.18 (m, 2H), 0.60 (m, 6H). MS, m/z (relative intensity): 188 [M+H, 100%].

EXAMPLE 12

Synthesis of 3-Aminomethyl-5,7-dimethyl-octanoic acid

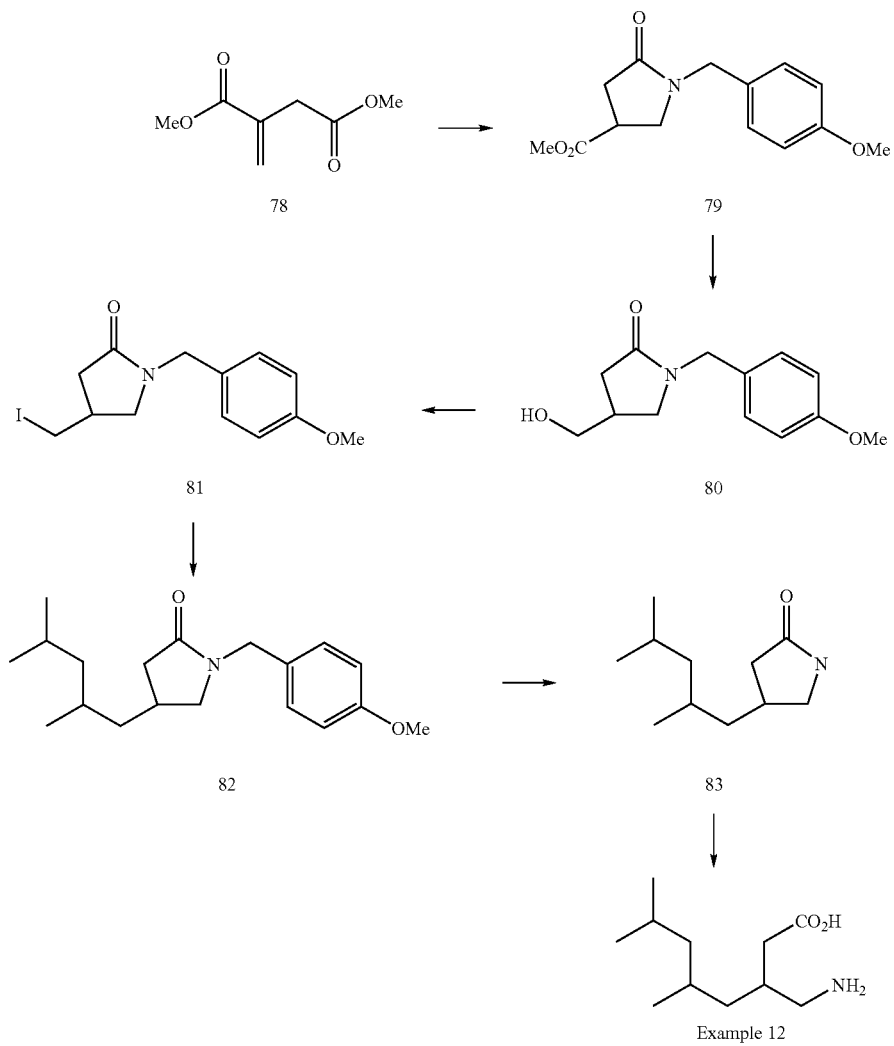

1-(4-Methoxy-benzyl)-5-oxo-pyrrolidine-3-carboxylic acid methyl ester 79

To 4-methoxybenzylamine (42 g, 0.306 mol) in methanol (40 mL) at 0° C. was added the dimethyl itaconate (48 g, 0.306 mol) in methanol (13 mL). The solution was stirred at room temperature for 4 days. 1N HCl was added to the solution followed by ether. The two layers were separated and the aqueous phase extracted with ether. The combined organic phases were dried (MgSO$_4$). Upon filtration of the drying agent the desired material 79 precipitated from solution that was collected and dried under vacuum. 23.26 g, 29%. MS, m/z (relative intensity): 264 [M+H, 100%]. Anal. Calcd for C$_{14}$H$_{17}$N$_1$O$_4$: C, 63.87; H, 6.51; N, 5.32. Found: C, 63.96; H, 6.55; N, 5.29.

4-Hydroxymethyl-1-(4-methoxy-benzyl)-pyrrolidine-2-one 80

NaBH$_4$ (15 g, 0.081 mol) was added in portions to ester 79 in ethanol (600 mL) at room temperature. After 4.5 hours water (~200 mL) was carefully added to the reaction and the solution stirred at room temperature overnight. The resultant solid was removed by filtration and the filtrate concentrated to give alcohol 80 as an oil. 15.33 g, 81%. MS, m/z (relative intensity): 235 [M+H, 100%].

4-Iodomethyl-1-(4-methoxy-benzyl)-pyrrolidin-2-one 81

To alcohol 80 (12.9 g, 0.055 mol) in PhMe was added triphenylphosphine (20 g, 0.077 mol), imidazole (10.8 g, 0.16 mol), and iodine (19 g, 0.075 mol). The suspension was stirred at room temperature 5 hours. A saturated aqueous solution of sodium thiosulphate was added and the two layers separated. The aqueous phase was extracted with ether and the combined organic phases washed with brine, dried (MgSO$_4$) and concentrated. Flash chromatography (6:1 to 4:1 toluene/acetone) of the residue gave iodide 81 as an oil. 11.9 g, 63%. MS, m/z (relative intensity): 346 [M+H, 100%].

4-(2,4-Dimethyl-pentyl)-1-(4-methoxy-benzyl)-pyrrolidin-2-one 82

A procedure similar to the preparation of 1-benzyl-4-(2-methyl-pentyl)-pyrrolidin-2-one 76 was utilized to give 4-(2,4-dimethyl-pentyl)-1-(4-methoxy-benzyl)-pyrrolidin-2-one as an oil. 1.22 g, 29%. MS, m/z (relative intensity): 304 [M+H, 100%].

4-(2,4-Dimethyl-pentyl)-pyrrolidin-2-one 83

To the lactam (1.17 g, 3.86 mmol) in MeCN (20 mL) at 0° C. was added ceric ammonium nitrate (4.2 g, 7.7 mmol) in H$_2$O (10 mL). After 50 minutes a further portion of ceric ammonium nitrate (2.1 g, 3.86 mmol) was added, and after 1 hour the mixture was absorbed onto silica and flash chromatographed to give an oil. MS, m/z (relative intensity): 183 [M+H, 100%].

3-Aminomethyl-5,7-dimethyl-octanoic acid (Example 12)

A procedure similar to the preparation of 3-aminomethyl-5-methyl-octanoic acid (Example 3) was utilized to give the amino acid as a solid. MS, m/z (relative intensity): 202 [M+H, 100%].

EXAMPLE 13

Synthesis of (S)-3-Aminomethyl-5-methyl-octanoic acid

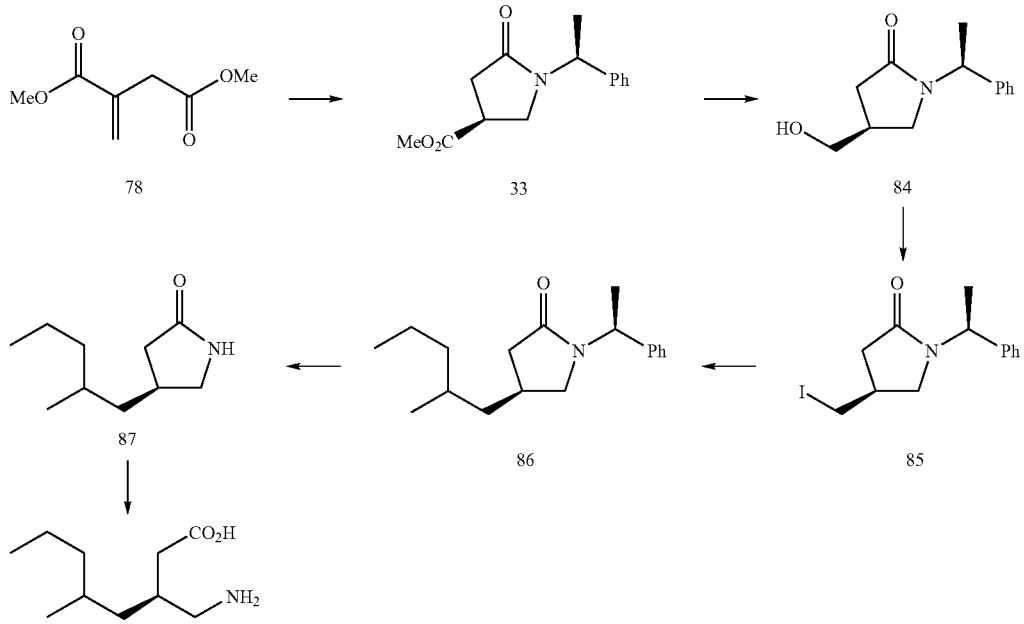

Example 13

(S)-4-Hydroxymethyl-1-((S)-1-phenyl-ethyl)-pyrrolidin-2-one 84

To the ester 33 (49 g, 0.198 mol) in EtOH (600 mL) was added sodium borohydride (22 g, 0.595 mol). After 7 hours, 1 M citric acid was carefully added and, after effervescence had ceased, water was added to fully quench the reaction. The ethanol was removed under reduced pressure and ethyl acetate added. The resultant two layers were separated, the aqueous phase was extracted with EtOAc, and the combined organic phases dried (MgSO$_4$) and concentrated to give a heavy oil. MS, m/z (relative intensity): [M+H, 100%].

(S)-4-Iodomethyl-1-((S)-1-phenyl-ethyl)-pyrrolidin-2-one 85

A procedure similar to the iodination of compound 80 was utilized giving iodide 85 as an oil. 35.2 g, 56%. Anal. Calcd for $C_{13}H_{16}I_1N_1O_1$: C, 47.43; H, 4.90; N, 4.25. Found: C, 47.41; H, 4.83; N, 4.17.

4-(2-Methyl-pentyl)-1-((S)-1-phenyl-ethyl)-pyrrolidin-2-one 86

A procedure similar to the preparation of 1-benzyl-4-(2-methyl-pentyl)-pyrrolidin-2-one 76 was utilized to give 2.71 g, 81.0% of 86 as an oil. MS, m/z (relative intensity): 274 [M+1H, 100%], 315 [M+H+CH$_3$CN, 65%].

(S)-4-(2-Methyl-pentyl)-pyrrolidin-2-one 87

A procedure similar to the preparation of 4-(2-methyl-pentyl)-pyrrolidin-2-one 77 was used to give 1.14 g, 72.8% of 87 as an oil. MS, m/z (relative intensity): 170 [M+1H, 10%], 211 [M+1H+CH$_3$CN, 90%].

EXAMPLE 13

(S)-3-Aminomethyl-5-methyl-octanoic acid

A procedure similar to the preparation of 3-aminomethyl-5-methyl-octanoic acid (Example 11) was used to give the amino acid (example 5) 0.88 g, 74.3%. $^1$H NMR (CD$_3$OD) δ 2.95 (m, 1H), 2.80 (m, 1H), 2.40 (m, 1H), 2.25 (m, 1H), 2.05 (brm, 1H), 1.50 (brm, 1H), 1.30 (m, 4H), 1.10 (m, 2H), 0.90 (m, 6H). MS, m/z (relative intensity): 188 [M+1H, 100%], 186 [M−1H, 100%], 229 [M+1H+CH$_3$CN, 30%].

EXAMPLE 14

Synthesis of (S)-3-Aminomethyl-7-methoxy-5-methyl-heptanoic acid

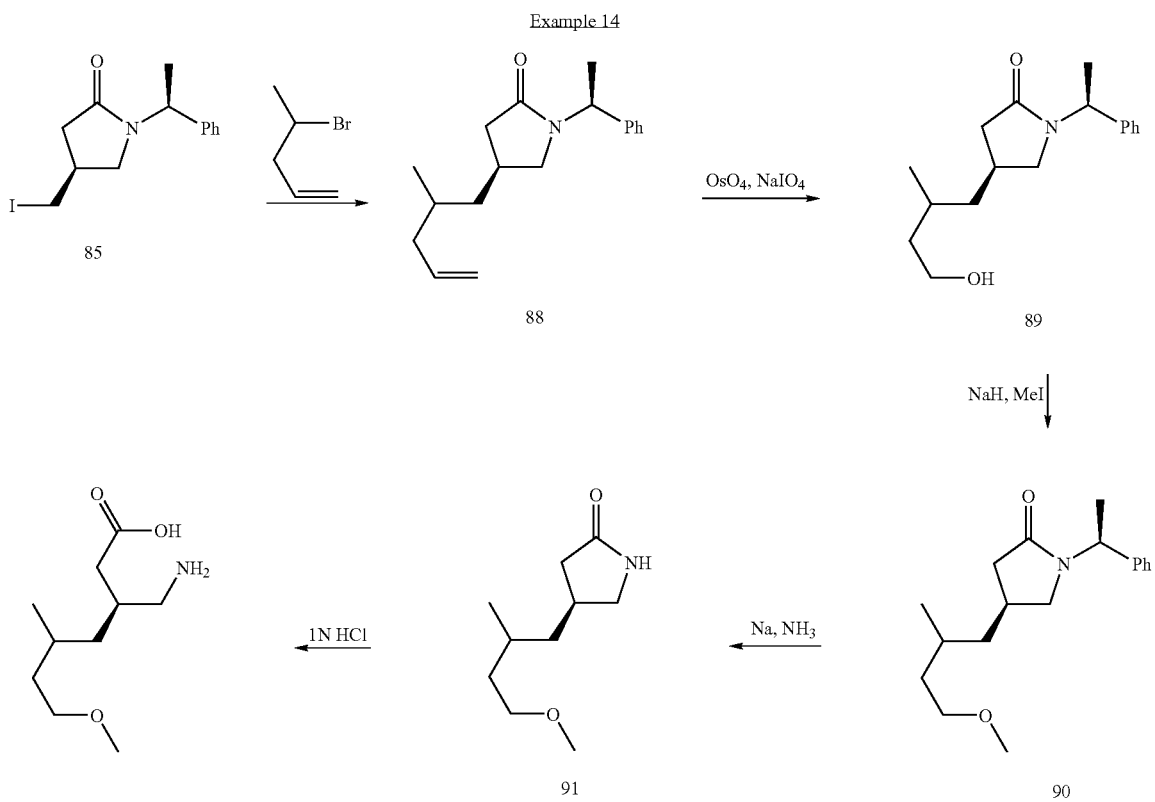

Example 14

(S)-4-(2-Methyl-pent-4-enyl)-1-((S)-1-phenyl-ethyl)-pyrrolidin-2-one 88

A procedure similar to the preparation of 1-benzyl-4-(2-methyl-pentyl)-pyrrolidin-2-one 76 was followed giving the adduct 88 as an oil. 6 g, 74%. MS, m/z (relative intensity): 272 [M+H, 100%].

(S)-4-(4-Hydroxy-2-methyl-butyl)-1-((S)-1-phenyl-ethyl)-pyrrolidin-2-one 89

OsO$_4$ (2 mL of a 4% wt solution in t-BuOH) was added to the alkene 88 (5.8 g, 0.021 mol) in THF/H$_2$O (3:1, 100 mL). After 1 hour, sodium periodate (11.4 g, 0.053 mol) was added. After 2 hours, the suspension was filtered and the solids washed with dichloromethane. The filtrate was concentrated and the residue azeotroped with toluene. The residue was dissolved in ethanol and sodium borohydride (2.5 g) added. The suspension was stirred at room temperature overnight. 1N citric acid was added and the mixture diluted with ether. The resultant two layers were separated and the aqueous phase was extracted with ether and the combined organic dried (MgSO$_4$) and concentrated. Flash chromatography (1:1 hexane/EtOAc) of the residue gave an oil. 4.2 g, 73%. MS, m/z (relative intensity): 276 [M+H, 100%].

(S)-4-(4-Methoxy-2-methyl-butyl)-1-((S)-1-phenyl-ethyl)-pyrrolidin-2-one 90

To alcohol 89 (2 g, 7.66 mmol) in DMSO (60 mL) at room temperature was added NaH (368 mg, 60% in oil). After 30 minutes the methyl iodide (1.08 g, 7.66 mmol) was added and the solution stirred at room temperature overnight, upon which the reaction was diluted with water (500 mL). The solution was extracted with ether, and the combined organic extracts were dried (MgSO$_4$) and concentrated. Flash chromatography (90% to 50% hexane/acetone) of the residue gave the product 90 as an oil (1.1 g, 52%). MS m/z 290 (M+H, 100%).

(S)-4-(4-Methoxy-2-methyl-butyl)-pyrrolidin-2-one 91

A procedure similar to the synthesis of 4-(2-methyl-pentyl)-pyrrolidin-2-one 77 was utilized giving lactam 91 as an oil. MS m/z 186 (M+H, 100%).

EXAMPLE 14

(S)-3-Aminomethyl-7-methoxy-5-methyl-heptanoic acid

A procedure similar to the synthesis of example 3 was followed. The resultant amino acid isolated from ion-exchange chromatography was recrystallized from methanol/ethyl acetate to give the example 6 as a white solid. MS m/z 204 (M+H, 100%). Anal. Calcd for C$_{10}$H$_{21}$N$_1$O$_3$: C, 59.09; H, 10.41; N, 6.89. Found: C, 58.71; H, 10.21; N, 6.67.

EXAMPLE 15

Synthesis of (S)-3-Aminomethyl-6-fluoro-5-methyl-hexanoic acid

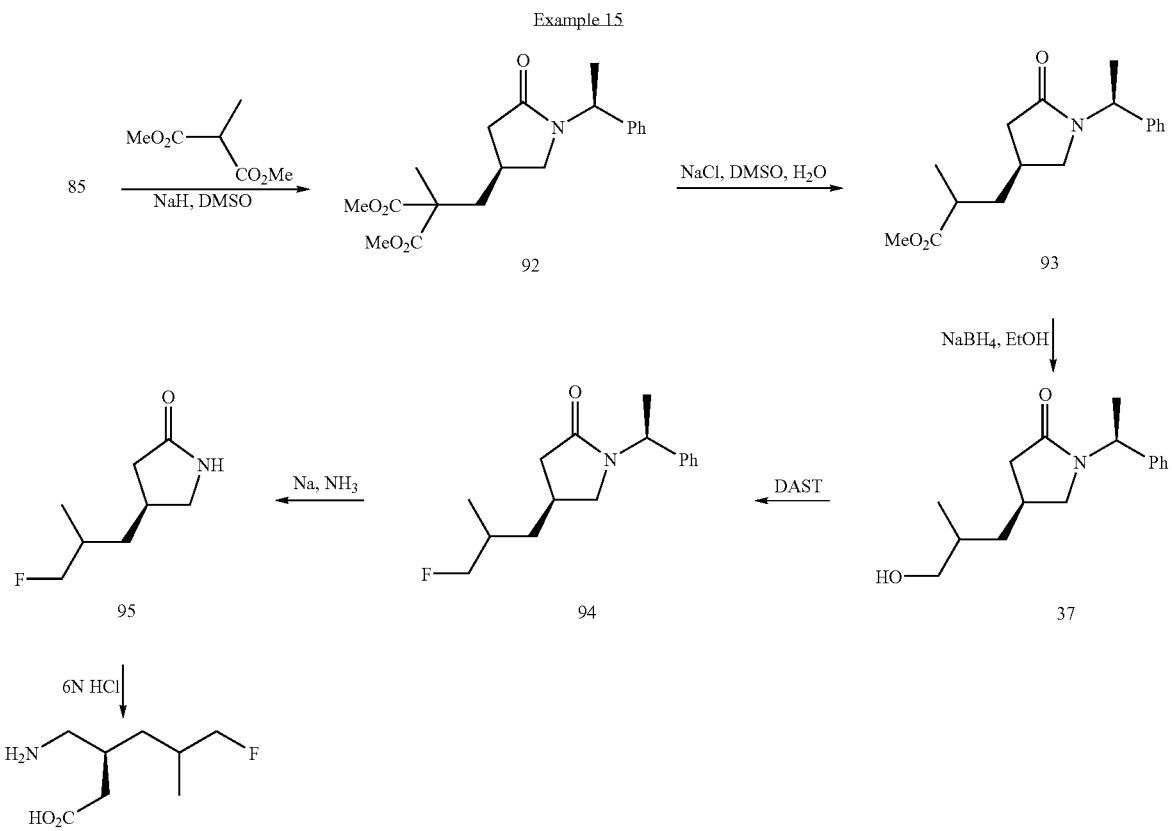

2-Methyl-2-[(S)-5-oxo-1-((S)-1-phenyl-ethyl)-pyrrolidin-3-ylmethyl]-malonic acid dimethyl ester 92

To dimethyl methylmalonate (1.06 g, 7.29 mmol) in DMSO (7 mL) at room temperature was added NaH (291 mg of a 60% dispersion in oil). After the effervescence had ceased the lactam 85 (2 g, 7.29 mol) in DMSO (5 mL) was added. After 1 hour water was added and the aqueous solution extracted with ether. The combined organic extracts were dried (MgSO$_4$) and concentrated. Flash chromatography (1:1 hexane/acetone) of the residue gave the product as an oil (1.7 g, 81%). MS m/z 348 (M+H, 100%).

2-Methyl-3-[(S)-5-oxo-1-((S)-1-phenyl-ethyl)-pyrrolidin-3-yl]-propionic acid methyl ester 93

The ester 92 (483 mg, 1.4 mmol), NaCl (104 mg, 1.8 mmol), water (105 μL) and DMSO (5 mL) were heated to reflux for 2 hours. The solution was cooled to room temperature water was added and the aqueous solution extracted with ether. The combined organic extracts were dried (MgSO$_4$) and concentrated. Flash chromatography (80% to 66% hexane/acetone) of the residue gave the product as an oil (160 mg, 40%). MS m/z 290 (M+H, 100%).

(S)-4-(3-Hydroxy-2-methyl-propyl)-1-((S)-1-phenyl-ethyl)-pyrrolidin-2-one 37

To the ester 93 (4.82 g, 0.017 mol) in EtOH (100 mL) was added NaBH$_4$ (3.7 g, 0.10 mol) and the mixture heated to reflux for 2.5 hours. The solution was cooled to 0° C. and 1 M citric acid carefully added followed by water. The solution was concentrated to half volume added and extracted with ether. The combined organic extracts were dried (MgSO$_4$) and concentrated. Flash chromatography (1:1 hexane/acetone) of the residue gave the product as an oil (2.6 g, 59%). MS m/z 262 (M+H, 100%).

(S)-4-(3-Fluoro-2-methyl-propyl)-1-((S)-1-phenyl-ethyl)-pyrrolidin-2-one 94

To DAST (1 g, 6.2 mmol) in CH$_2$Cl$_2$ (20 mL) at −78° C. was added the alcohol 37 in CH$_2$Cl$_2$ (10 mL). After 1 hour at −78° C. the solution was warmed to room temperature. After 7 hours the solution was carefully quenched with a saturated aqueous solution of sodium bicarbonate and the two layers separated. The organic phase was dried (MgSO$_4$) and concentrated. Flash chromatography (90% to 66% hexane/acetone) of the residue gave the product as an oil (600 mg, 37%). MS m/z 264 (M+H, 100%).

(S)-4-(3-Fluoro-2-methyl-propyl)-pyrrolidin-2-one 95

A procedure similar to the preparation of 4-(2-methylpentyl)-pyrrolidin-2-one 77 was utilized affording the lactam as an oil (242 mg, 68%). MS m/z 159 (M, 100%).

EXAMPLE 15

(S)-3-Aminomethyl-6-fluoro-5-methyl-hexanoic acid

A procedure similar to the synthesis of example 11 was followed. The resultant amino acid isolated from ion-exchange chromatography was recrystallized from methanol/ethyl acetate to give example 15 as a white solid. MS m/z 177 (M, 100%). Anal. Calcd for C$_8$H$_{16}$F$_1$N$_1$O$_2$:0.02H$_2$O: C, 54.11; H, 9.10; N, 7.89. Found: C, 53.75; H, 9.24; N, 7.72.

EXAMPLE 16

Synthesis of (S)-3-Aminomethyl-6-methoxy-5-methyl-hexanoic acid

Example 16

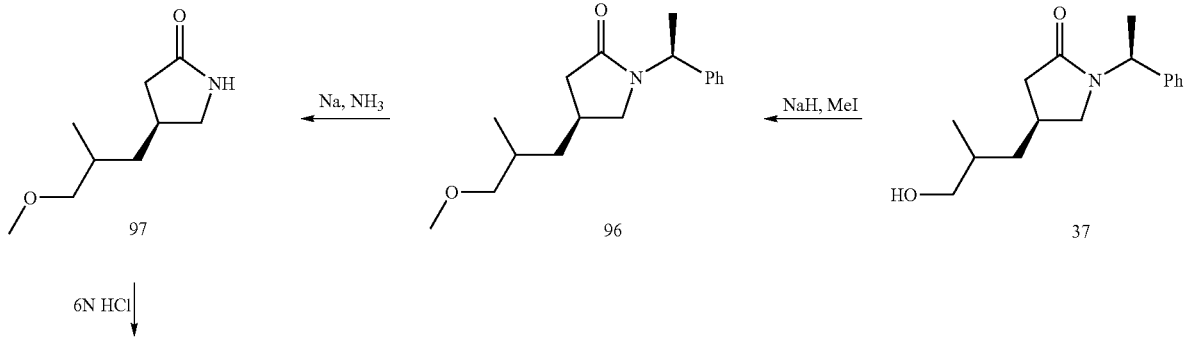

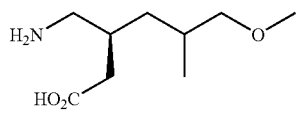

(S)-4-(3-Methoxy-2-methyl-propyl)-1-((S)-1-phenyl-ethyl)-pyrrolidin-2-one 96

A procedure similar to the synthesis of (S)-4-(4-methoxy-2-methyl-butyl)-1-((S)-1-phenyl-ethyl)-pyrrolidin-2-one 90 was utilized giving ether 96 as an oil (90 mg, 37%). MS m/z 276 (M+H, 100%).

(S)-4-(3-Methoxy-2-methyl-propyl)-pyrrolidin-2-one 97

A procedure similar to the synthesis of 4-(2-methyl-pentyl)-pyrrolidin-2-one 77 was utilized giving 97 as an oil (760 mg, 93%). MS m/z 171 (M+H, 100%).

EXAMPLE 16

(S)-3-Aminomethyl-6-methoxy-5-methyl-hexanoic acid

A procedure similar to the synthesis of example 11 was followed. The resultant amino acid isolated from ion-exchange chromatography was recrystallized from methanol/ethyl acetate to give Example 16 as a white solid. MS m/z 190 (M+H, 100%). Anal. Calcd for $C_9H_{19}N_1O_3$: C, 57.12; H, 10.12; N, 7.40. Found: C, 57.04; H, 10.37; N, 7.30. A second batch precipitated from the mother liquors (1:5 ratio of C5 isomers by $^1$H NMR). MS m/z 190 (M+H, 100%).

EXAMPLE 17

Synthesis of (3S,5R)-3-Aminomethyl-5-methyl-octanoic acid hydrochloride

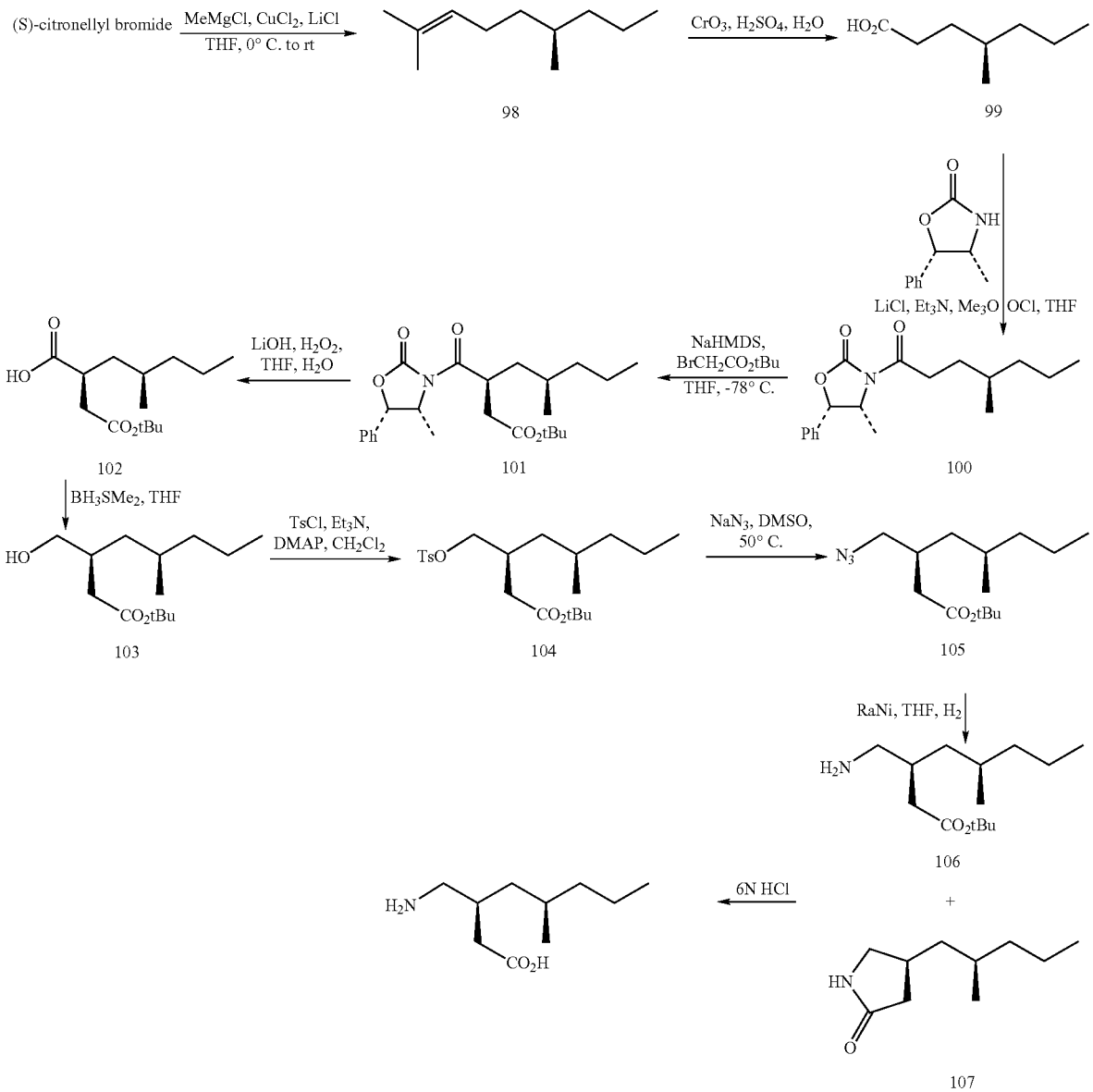

Example 17

(R)-2,6-Dimethyl-non-2-ene 98

To (S)-citronellyl bromide (50 g, 0.228 mol) in THF (800 mL) at 0° C. was added LiCl (4.3 g) followed by $CuCl_2$ (6.8 g). After 30 minutes methylmagnesium chloride (152 mL of a 3 M solution in THF, Aldrich) was added and the solution warmed to room temperature. After 10 hours the solution was cooled to 0° C. and a saturated aqueous solution of ammonium chloride carefully added. The resultant two layers were separated and the aqueous phase extracted with ether. The combined organic phases were dried ($MgSO_4$) and concentrated to give an oil. 32.6 g; 93%. Used without further purification. $^{13}C$ NMR (100 MHz; $CDCl_3$) 131.13, 125.28, 39.50, 37.35, 32.35, 25.92, 25.77, 20.31, 19.74, 17.81, 14.60.

(R)-4-Methyl-heptanoic acid 99

To alkene 98 (20 g, 0.13 mol) in acetone (433 mL) was added a solution of $CrO_3$ (39 g, 0.39 mol) in $H_2SO_4$ (33 mL)/$H_2O$ (146 mL) over 50 minutes. After 6 hours a further amount of $CrO_3$ (26 g, 0.26 mol) in $H_2SO_4$ (22 mL)/$H_2O$ (100 mL) was added. After 12 hours the solution was diluted with brine and the solution extracted with ether. The combined organic phases were dried ($MgSO_4$) and concentrated. Flash chromatography (gradient of 6:1 to 2:1 hexane/EtOAc) gave the product 99 as an oil. 12.1 g; 65%. MS, m/z (relative intensity): 143 [M–H, 100%].

(4R,5S)-4-Methyl-3-((R)-4-methyl-heptanoyl)-5-phenyl-oxazolidin-2-one 100

To the acid 99 (19 g, 0.132 mol) and triethylamine (49.9 g, 0.494 mol) in THF (500 mL) at 0° C. was added trimethylacetylchloride (20 g, 0.17 mol). After 1 hour LiCl (7.1 g, 0.17 mol) was added followed by the oxazolidinone (30 g, 0.17 mol). The mixture was warmed to room temperature and after 16 hours the filtrate was removed by filtration and the solution concentrated under reduced pressure. Flash chromatography (7:1 hexane/EtOAc) gave the product 100 as an oil. 31.5 g; 79%. $[\square]_D$=5.5 (c 1 in $CHCl_3$). MS, m/z (relative intensity): 304 [M+H, 100%].

(3S,5R)-5-Methyl-3-((4R,5S)-4-methyl-2-oxo-5-phenyl-oxazolidine-3-carbonyl)-octanoic acid tert-butyl ester 101

To oxazolidinone 100 (12.1 g, 0.04 mol) in THF (200 mL) at −50° C. was added NaHMDS (48 mL of a 1 M solution in THF). After 30 t-butylbromoacetate (15.6 g, 0.08 mol) was added. The solution was stirred for 4 hours at −50° C. and then warmed to room temperature. After 16 hours a saturated aqueous solution of ammonium chloride was added and the two layers separated. The aqueous phase was extracted with ether and the combined organic phases dried ($MgSO_4$) and concentrated. Flash chromatography (9:1 hexane/EtOAc) gave the product 101 as a white solid 12 g; 72%. $[\square]_D$=30.2 (c 1 in $CHCl_3$). $^{13}C$ NMR (100 MHz; $CDCl_3$) 176.47, 171.24, 152.72, 133.63, 128.87, 125.86, 80.85, 78.88, 55.34, 39.98, 38.77, 38.15, 37.58, 30.60, 28.23, 20.38, 20.13, 14.50, 14.28.

(S)-2-((R)-2-Methyl-pentyl)-succinic acid 4-tert-butyl ester 102

To ester 101 (10.8 g, 0.025 mol) in $H_2O$ (73 mL) and THF (244 mL) at 0° C. was added a premixed solution of LiOH (51.2 mL of a 0.8 M solution) and $H_2O_2$ (14.6 mL of a 30% solution). After 4 hours a further 12.8 mL LiOH (0.8 M solution) and 3.65 mL of $H_2O_2$ (30% solution) was added. After 30 minutes sodium bisulfite (7 g), sodium sulfite (13 g), and water (60 mL) was added followed by hexane (100 mL) and ether (100 mL). The two layers were separated and the aqueous layer extracted with ether. The combined organic phases were concentrated to an oil that was dissolved in heptane (300 mL). The resultant solid was filtered off and the filtrate dried ($MgSO_4$) and concentrated to afford an oil (6 g, 93%) which was used without further purification. MS, m/z (relative intensity): 257 [M+H, 100%].

(3S,5R)-3-Hydroxymethyl-5-methyl-octanoic acid tert-butyl ester 103

To acid 102 (3.68 g, 0.014 mol) in THF (100 mL) at 0° C. was added $BH_3.Me_2$ (36 mL of a 2 M solution in THF, Aldrich) upon which the solution was warmed to room temperature. After 15 hours ice was carefully added (in order to control the effervescence) to the solution followed by brine. The solution was extracted with ether and the combined organic phases dried ($MgSO_4$) and concentrated under reduced pressure. Flash chromatography (4:1 hexane/EtOAc) gave alcohol 103 as an oil (2.0 g, 59%). $^{13}C$ NMR (100 MHz; $CDCl_3$) 173.56, 80.85, 65.91, 39.74, 39.20, 38.90, 35.65, 29.99, 28.31, 20.18, 19.99, 14.56.

(3S,5R)-5-Methyl-3-(toluene-4-sulfonyloxymethyl)-octanoic acid tert-butyl ester 104

To alcohol 103 (1.98 g, 8.1 mmol) in $CH_2Cl_2$ (40 mL) at room temperature was added triethylamine (2.4 g, 0.024 mol), DMAP (20 mg) and tosyl chloride (2.3 g, 0.012 mol). After 14 hours 1N HCl was added and the two layers separated. The aqueous phase was extracted with ether and the combined organic phases dried ($MgSO_4$) and concentrated. Flash chromatography (95% hexane/EtOAc) gave tosylate 104 as an oil (2.94 g, 91%). $^{13}C$ NMR (100 MHz; $CDCl_3$) 171.60, 144.92, 133.07, 130.02, 128.12, 80.80, 72.15, 39.73, 38.09, 37.89, 32.67, 29.71, 28.22, 21.83, 20.10, 19.54, 14.49.

(3S,5R)-3-Azidomethyl-5-methyl-octanoic acid tert-butyl ester 105

Tosylate 104 (2.929, 7.3 mmol) and sodium azide (1.43 g, 0.02 mol) were warmed to ~50° C. in DMSO (30 mL). After 2 hours the solution was cooled to room temperature and diluted with water. The solution was extracted with ether and the combined organic phases dried ($MgSO_4$) and concentrated to give an oil 1.54 g, 79%. Further purification by flash chromatography (95% hexane/EtOAc) gave an oil. $[\alpha]_D$=−8.3 (c 1 in $CHCl_3$). $^{13}C$ NMR (100 MHz; $CDCl_3$) 172.01, 80.73, 54.89, 39.73, 39.46, 39.00, 33.40, 29.85, 28.30, 20.15, 19.82, 14.52.

(S)-4-((R)-2-Methyl-pentyl)-pyrrolidin-2-one 107 and (3S,5R)-3-aminomethyl-5-methyl-octanoic acid tert-butyl ester 106

Azide 105 was treated with 5% Pd/C and shaken under an atmosphere of hydrogen for 20 hours where upon a further 200 mg of 5% Pd/C added. After 6 hours the filtrate was concentrated to afford an oil which by $^1H$ NMR was found to be a mixture of primary amine 106 and lactam 107 (1.75 g) which was used without further purification.

EXAMPLE 17

(3S,5R)-3-Aminomethyl-5-methyl-octanoic acid hydrochloride

The mixture of the amine 106 and the lactam 107 (1.74 g) was treated with 3N HCl (40 mL) and the solution warmed to 50° C. for 4 hours then cooled to room temperature. After 12 hours the solution was concentrated and the residue recrystallized from ethyl acetate to give the amino acid as a white solid 605 mg. MS, m/z (relative intensity): 188 [M+H, 100%]. Anal. Calcd for $C_{10}H_{21}N_1O_2 \cdot H_1Cl_1$ C, 53.68; H, 9.91; N, 6.26. Found: C, 53.83; H, 10.12; N, 6.07.

EXAMPLE 18

Synthesis of (3S,5R)-3-Aminomethyl-5-methyl-heptanoic acid

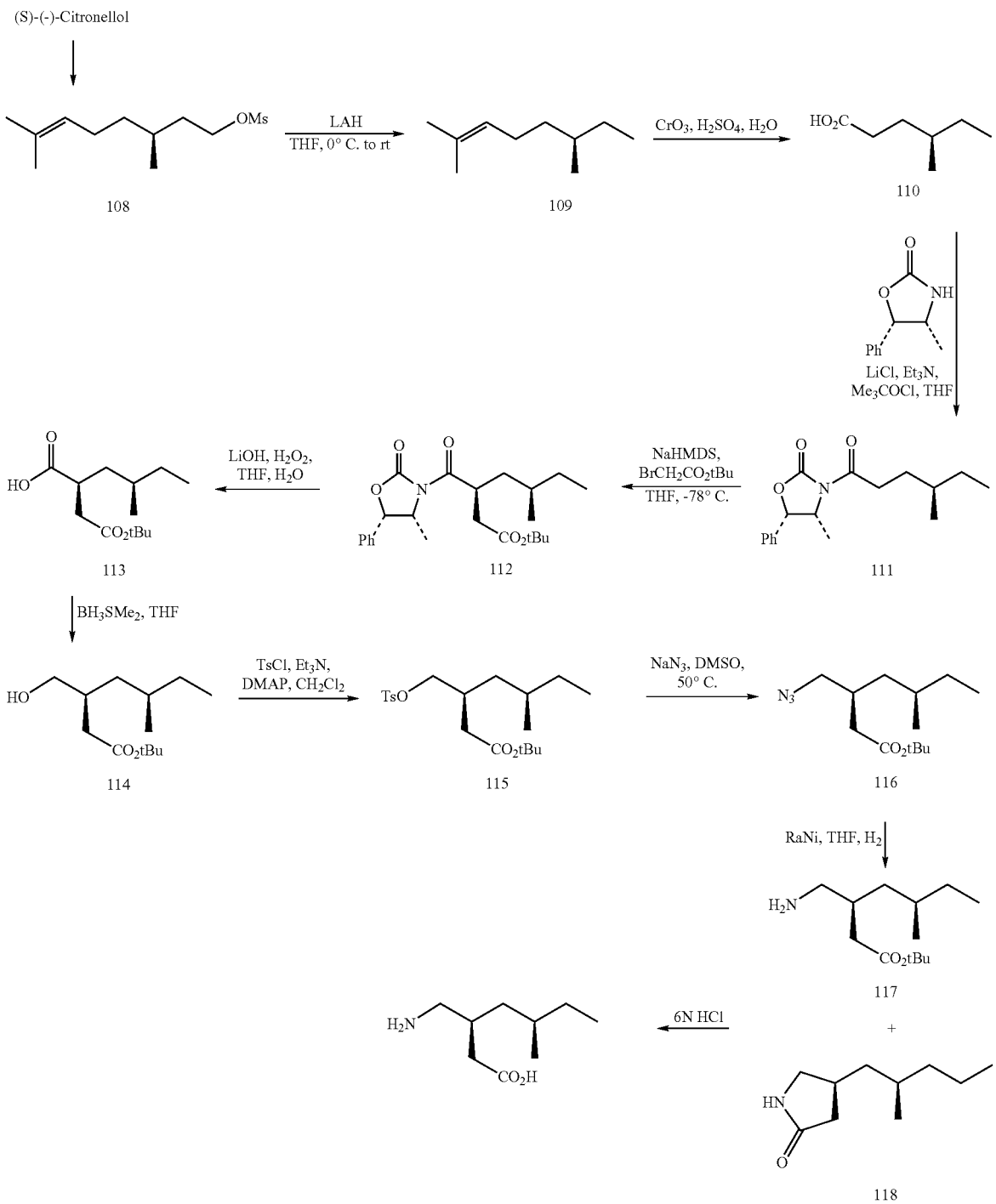

Methanesulfonic acid (S)-3,7-dimethyl-oct-6-enyl ester 108

To S-(−)-citronellol (42.8 g, 0.274 mol) and triethylamine (91 mL, 0.657 mol) in CH$_2$Cl$_2$ (800 mL) at 0° C. was added methanesulphonyl chloride (26 mL, 0.329 mol) in CH$_2$Cl$_2$ (200 mL). After 2 hours at 0° C. the solution was washed with 1N HCl then brine. The organic phase was dried (MgSO$_4$) and concentrated to afford an oil (60.5 g, 94%) which was used without further purification. $^1$H NMR (400 MHz; CDCl$_3$) 5.05 (1H, m), 4.2 (2H, m), 2.95 (3H, s), 1.98 (2H, m), 1.75 (1H, m), 1.6 (3H, s), 1.5 (4H, m), 1.35 (2H, m), 1.2 (1H, m), 0.91 (3H, d, J=6.5 Hz).

(R)-2,6-Dimethyl-oct-2-ene 109

To alkene 108 (60 g, 0.256 mol) in THF (1 L) at 0° C. was added lithium aluminum hydride (3.8 g, 0.128 mol). After 7 hours, a further 3.8 g of lithium aluminum hydride was added and the solution warmed to room temperature. After 18 hours, a further 3.8 g of lithium aluminum hydride was added. After a further 21 hours, the reaction was carefully quenched with 1N citric acid and the solution diluted further with brine. The resultant two phases were separated and the organic phase was dried (MgSO$_4$) and concentrated to afford an oil which was used without further purification. MS, m/z (relative intensity): 139 [M−H, 100%].

(R)-4-Methyl-hexanoic acid 110

A procedure similar to the synthesis of (R)-4-methyl-heptanoic acid 99 was utilized giving the acid as an oil (9.3 g, 56%). MS, m/z (relative intensity): 129 [M−H, 100%].

(4R,5S)-4-Methyl-3-((R)-4-methyl-hexanoyl)-5-phenyl-oxazolidin-2-one 111

A procedure similar to the synthesis of (4R,5S)-4-methyl-3-((R)-4-methyl-heptanoyl)-5-phenyl-oxazolidin-2-one 100 was utilized giving oxazolidinone 111 as an oil (35.7 g, 95%). MS, m/z (relative intensity): 290 [M+H, 100%].

(3S,5R)-5-Methyl-3-[1-((4R,5S)-4-methyl-2-oxo-5-phenyl-oxazolidin-3-yl)-methanoyl]-heptanoic acid tert-butyl ester 112

A procedure similar to the preparation of (3S,5R)-5-methyl-3-((4R,5S)-4-methyl-2-oxo-5-phenyl-oxazolidine-3-carbonyl)-octanoic acid tert-butyl ester 101 was followed giving 112 as an oil (7.48 g; 31%).

(S)-2-((R)-2-Methyl-butyl)-succinic acid 4-tert-butyl ester 113

To ester 112 (7.26 g, 0.018 mol) in H$_2$O (53 mL) and THF (176 mL) at 0° C. was added a premixed solution of LiOH (37 mL of a 0.8 M solution) and H$_2$O$_2$ (10.57 mL of a 30% solution) and the solution warmed to room temperature. After 2 hours sodium bisulfite (7 g), sodium sulfite (13 g), and water (60 mL) was added and the two layers were separated and the aqueous layer extracted with ether. The combined organic phases were concentrated to an oil that was dissolved in heptane (200 mL). The resultant solid was filtered off and the filtrate dried (MgSO$_4$) and concentrated to afford an oil (4.4 g) that was used without further purification.

(3S,5R)-3-Hydroxymethyl-5-methyl-heptanoic acid tert-butyl ester 114

A procedure similar to the preparation of (3S,5R)-3-hydroxymethyl-5-methyl-octanoic acid tert-butyl ester 103 was utilized giving alcohol 114 as an oil (2.68 g, 69%). MS, m/z (relative intensity): 216 [89%], 174 [M−(CH$_3$)$_3$C, 100%].

(3S,5R)-5-Methyl-3-(toluene-4-sulfonyloxymethyl)-heptanoic acid tert-butyl ester 115

To 114 alcohol (2.53 g, 0.011 mmol) in CH$_2$Cl$_2$ (140 mL) at 0° C. was added pyridine (2.6 g, 0.033 mol), DMAP (100 mg), and tosyl chloride (3.15 g, 0.016 mol) and the solution warmed to room temperature for 3.5 hours whereupon more DMAP and TsCl (3.15 g) were added. After 14 hours 1N HCl was added and the two layers separated. The organic phase was washed with brine then or dried (MgSO$_4$) and concentrated. Flash chromatography (95% to 86% hexane/EtOAc) gave tosylate 115 as an oil (1.53 g, 36%). $^{13}$C NMR (100 MHz; CDCl$_3$) 130.03, 128.12, 72.18, 37.89, 37.71, 32.67, 31.49, 29.88, 28.22, 21.83, 19.07, 11.37.

(3S,5R)-3-Azidomethyl-5-methyl-heptanoic acid tert-butyl ester 116

A procedure similar to the preparation of (3S,5R)-3-azidomethyl-5-methyl-octanoic acid tert-butyl ester 105 was utilized giving an oil 0.956 g, 97%. MS, m/z (relative intensity): 228 [M−N$_2$, 80%].

(S)-4-((R)-2-Methyl-butyl)-pyrrolidin-2-one 118 and (3S,5R)-3-Aminomethyl-5-methyl-heptanoic acid tert-butyl ester 117

Azide 116 (689 mg) was treated with 20% Pd/C (90 mg) in THF (20 mL) and shaken under an atmosphere of hydrogen for 36 hours. The catalyst was removed by filtration and the resultant oil used without further purification.

EXAMPLE 18

(3S,5R)-3-Aminomethyl-5-methyl-heptanoic acid

The mixture of amine 117 and lactam 118 was treated with 6N HCl and the solution warmed to 50° C. for 17 hours then cooled to room temperature and concentrated. The resultant oil was subjected to ion-exchange chromatography (Dowex, strongly acidic resin) using 5% ammonium hydroxide to give a cream solid which was recrystallized from methanol/ethyl acetate to give (3S,5R)-3-aminomethyl-5-methyl-heptanoic acid, example 10. MS, m/z (relative intensity): 174 [M+H, 100%]. Anal. Calcd for C$_{19}$H$_{19}$N$_1$O$_2$. C, 62.39; H, 11.05; N, 8.08. Found: C, 62.23; H, 11.33; N, 7.89.

EXAMPLE 19

Synthesis of (3S,5S)-3-Aminomethyl-5-methyl-octanoic acid

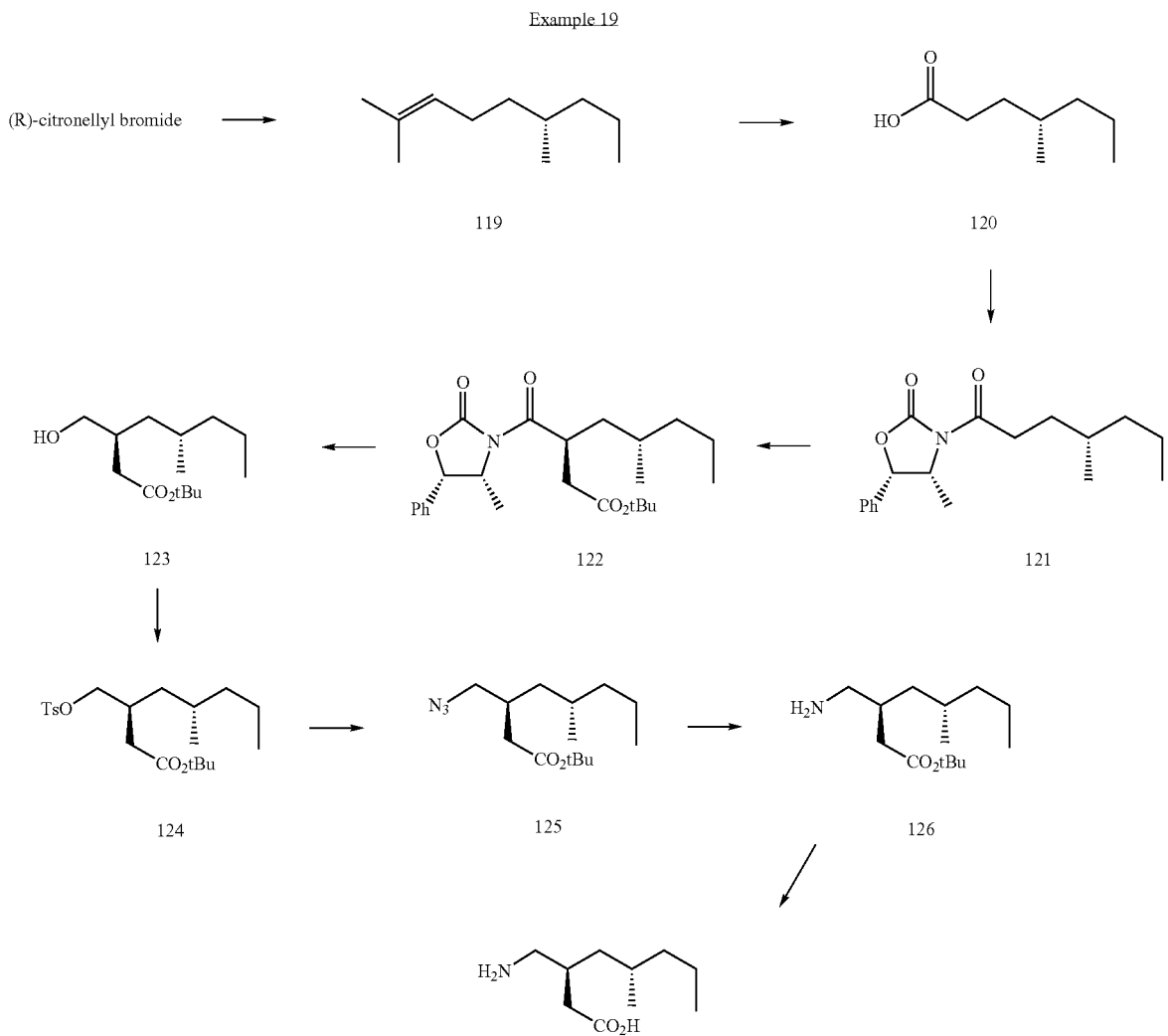

(S)-2,6-Dimethyl-non-2-ene 119

CuCl$_2$ (5.36 g, 39.7 mmol) and LiCl (3.36, 80.0 mmol) were stirred together in dry THF (40 mL) for 15 minutes. The resulting solution was added to methylmagnesium chloride, 3.0 M in THF (168 mL) at 0° C. under nitrogen atmosphere and stirred at that temperature for 15 minutes. To the reaction suspension was added slowly (R)-(−)-Citronellyl bromide (55.16 g, 251.8 mmol) in THF (100 mL), and stirred at 0° C. for 2.5 hours. It was warmed to room temperature and stirring was continued for an additional 1 hour. The mixture was cooled to 0° C. and quenched with saturated ammonium chloride solution. The suspension was then extracted into ether, washed with water, and dried over MgSO$_4$. The solution was concentrated under reduced pressure to afford 36.3 g; 94% of (S)-2,6-Dimethyl-non-2-ene as an oil. MS, m/z (relative intensity): 153 [M−1H, 100%], 194 [M−1H+CH$_3$CN, 45%].

(S)-4-Methyl-heptanoic acid 120

To the (S)-2,6-Dimethyl-non-2-ene 119 (39.0 g, 253.2 mmol) in acetone (1 L) at 0° C. was added Jones reagent (2.7 M, 600 mL) dropwise over 1.5 hours and let stir at room temperature for 18 hours. The reaction mixture was poured into a saturated solution of Na$_2$SO$_4$ and extracted into ether. It was washed with brine and concentrated in vacuo. The oily residue was dissolved in methanol (70 mL) and 1 M NaOH (700 mL) and then stirred for 30 minutes. The aqueous solution was washed with CH$_2$Cl$_2$, acidified with 10% HCl and extracted into CH$_2$Cl$_2$. The solution was dried over MgSO$_4$ and concentrated to dryness to give 24.22 g; 66% of (S)-4-Methyl-heptanoic acid as an oil. MS, m/z (relative intensity): 143 [M−1H, 100%].

(4R,5S)-4-Methyl-3-((S)-4-methyl-heptanoyl)-5-phenyl-oxazolidin-2-one 121

A procedure similar to the preparation of (4R,5S)-4-methyl-3-((R)-4-methyl-heptanoyl)-5-phenyl-oxazolidin-2-one 100 was utilized giving (4R,5S)-4-methyl-3-((S)-4-methyl-heptanoyl)-5-phenyl-oxazolidin-2-one 121 6.2 g;

80.0%, as an oil. MS, m/z (relative intensity): 304 [M+1H, 90%], 355 [M+1H+CH$_3$CN, 60%].

(3S,5S)-5-Methyl-3-((4R,5S)-4-methyl-2-oxo-5-phenyl-oxazolidine-3-carbonyl)-octanoic acid tert-butyl ester 122 n-BuLi, 1.6 M in Hexane (18.0 mL, 30.1 mmol) was added dropwise to a solution of diisopropylamine (4.6 mL, 32.6 mmol) in dry THF (50 mL) under nitrogen at −5° C. keeping the temperature below 0° C. during addition. The mixture was let stir at −5° C. for 20 minutes and then cooled to −78° C. 121 (7.6 g, 25.1 mmol) in dry THF (12 mL) was added to the LDA solution and stirred at −78° C. for 30 minutes. t-Butylbromo acetate (4.8 mL, 32.6 mmol) as added to the reaction and stirring at −78° C. was continued for 2 hours. It was let warm to room temperature before stirring for an additional 18 hours. The reaction was quenched with a saturated solution NaH$_2$PO$_4$, extracted into ethyl acetate, and dried over MgSO$_4$. The solution was concentrated to give a solid residue which was dissolved in hot hexane. The hexane solution was allowed to cool to room temperature before cooling further in an ice bath. The resulting precipitate was collected and allowed to air dry to give 122 as a fluffy white solid. 4.3 g; 41%. MS, m/z (relative intensity): 362 [M−C(CH$_3$)$_3$+1H, 100%], 418 [M+1H, 20%].

(S)-2-((S)-2-Methyl-pentyl)-succinic acid 4-tert-butyl ester and (3S,5S)-3-Hydroxymethyl-5-methyl-octanoic acid tert-butyl ester 123

To the ester 122 in a mixture of THF (203.0 mL) and water (61.0 mL) at 0° C. was added a premixed solution of 30% H$_2$O$_2$ (12.2 mL) and LiOH (0.8 M, 42.7 mL). The resulting solution was stirred at 0° C. for 4 hours. To the reaction was added sodium bisulfite (7 g), sodium sulfite (13 g), and water (60 mL). A 1:1 mixture of ether/hexane (200 mL) was then added and the organic phase was separated. The aqueous phase was extracted with ether and the combined organic extract was dried over MgSO$_4$ and concentrated in vacuo. The residue was dissolved in heptane and let stir for 5 minutes. The resulting precipitate was filtered and the filtrate was concentrated to dryness to give as an oil.

(3S,5S)-3-Hydroxymethyl-5-methyl-octanoic acid tert-butyl ester 123

A procedure similar to the preparation of (3S,5R)-3-hydroxymethyl-5-methyl-octanoic acid tert-butyl ester 103 was followed giving 123 as an oil. 4.0 g; 76.0%. MS, m/z (relative intensity): 230 [M−C(CH$_3$)$_3$+1H+CH$_3$CN, 100%], 189 [M−C(CH$_3$)$_3$+1H, 70%].

(3S,5S)-5-Methyl-3-(toluene-4-sulfonyloxymethyl)-octanoic acid tert-butyl ester 124

A: procedure similar to the preparation of (3S,5R)-5-methyl-3-(tolunen-4-sulfonyloxymethyl)-octanoic acid tert-butyl ester 104 was followed giving 6.9 g of 124. MS, m/z (relative intensity): 343 [M−C(CH$_3$)$_3$+1H, 70%], 384 [M−C(CH$_3$)$_3$+1H+CH$_3$CN, 100%].

(3S,5S)-3-Azidomethyl-5-methyl-heptanoic acid tert-butyl ester 125

A procedure similar to the preparation of (3S,5R)-3-azidomethyl-5-methyl-octanoic acid tert-butyl ester 105 was followed giving 2.9 g; 66% of 125 as an oil. MS, m/z (relative intensity): 212 [M−C(CH$_3$)$_3$−1H, 45%].

(3S,5S)-3-Aminomethyl-5-methyl-octanoic acid tert-butyl ester 126

A mixture of 125 (2.8 g, 10.4 mmol) and 10% Pd/C (1.0 g) in methanol (50.0 mL) was hydrogenated at 41 PSI for 96 hours. The solution was filtered to give 1.7 g of crude 126 which was used in the next step without further purification. MS, m/z (relative intensity): 244 [M+1H, 100%], 285 [M+1H+CH$_3$CN, 25%].

EXAMPLE 19

(3S,5S)-3-Aminomethyl-5-methyl-octanoic acid

A procedure similar to the preparation of example 18 (3S,5R)-3-aminomethyl-5-methyl-heptanoic acid was followed giving example 19. 380 mg; 29.0%. $^1$H NMR (CD$_3$OD) δ 2.90 (dd, J=3.9, 8.8 Hz, 1H), 2.80 (dd, J=7.6, 5.1 Hz, 1H), 2.40 (dd, J=3.2, 12.51 Hz, 1H), 2.20 (dd, J=8.8, 6.8 Hz, 1H), 2.05 (m, 1H), 1.55 (m, 1H), 1.30 (m, 3H), 1.10 (m, 2H), 0.85 (m, 6H); MS, m/z (relative intensity): 187 [M+1H, 100%], 211 [M+1H+CH$_3$CN, 30%].

EXAMPLE 20

Synthesis of
(3S,5S)-3-Aminomethyl-5-methyl-heptanoic acid

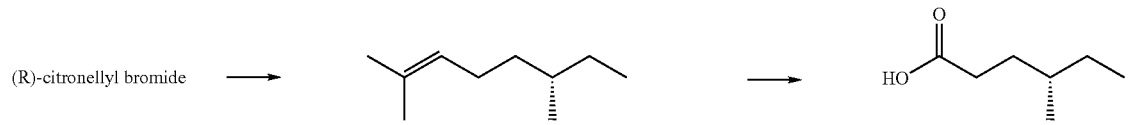

Example 20

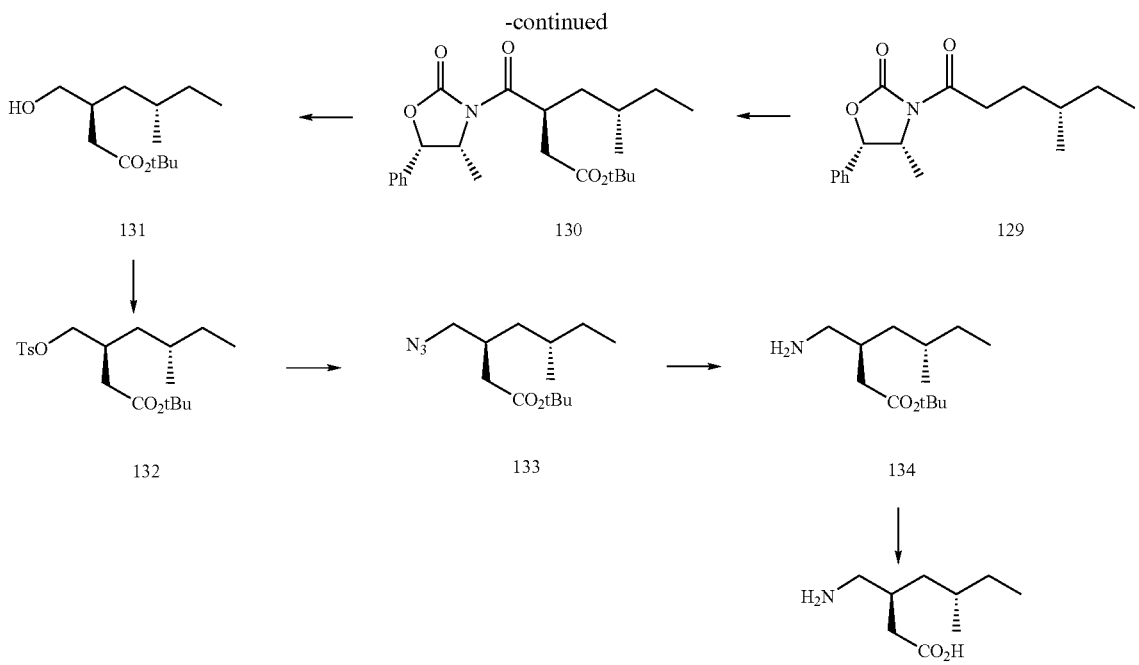

(S)-2,6-Dimethyl-oct-2-ene 127

(R)-(−)-Citronellyl bromide (49.1 g, 224.2 mmol) was dropwise added to a solution of LAH 1.0 M in THF (336 mL, 336 mmol) at 0° C. over a 45-minute period. Stirring was continued for an additional 4 hours at 0° C. The reaction was slowly quenched with a saturated solution of ammonium chloride followed by the addition of ether (100 mL). The resulting white slurry was filtered and the filtrate was dried over $MgSO_4$. The solution was concentrated under reduced pressure to afford 26.2 g; 83% of 127 as an oil. MS, m/z (relative intensity): 180 [M−1H+$CH_3CN$, 100%], 139 [M−1H, 90%].

(S)-4-Methyl-hexanoic acid 128

A procedure similar to that used to prepare compound 120 was used giving 15.9 g of 128 as an oil. MS, m/z (relative intensity): 129 [M−1H, 100%], 170 [M−1H+$CH_3CN$, 70%].

(4R,5S)-4-Methyl-3-((S)-4-methyl-hexanoyl)-5-phenyl-oxazolidin-2-one 129

A procedure similar to that used to prepare (4R,5S)-4-Methyl-3-((S)-4-methyl-heptanoyl)-5-phenyl-oxazolidin-2-one 121 was used giving 35.0 g of crude (4R,5S)-4-methyl-3-((S)-4-methyl-hexanoyl)-5-phenyl-oxazolidin-2-one 129 as an oil. It was used in the next step without further purification. MS, m/z (relative intensity): 290 [M+1H, 100%], 331 [M+1H+$CH_3CN$, 20%].

(3S,5S)-5-Methyl-3-((4R,5S)-4-methyl-2-oxo-5-phenyl-oxazolidine-3-carbonyl)-heptanoic acid tert-butyl ester 130

A procedure similar to that used to prepare (3S,5S)-5-methyl-3-((4R,5S)-4-methyl-2-oxo-5-phenyl-oxazolidine-3-carbonyl)-octanoic acid tert-butyl ester 122 was used to give 4.6.0 g, 25.4% of 130 as a white solid. MS, m/z (relative intensity): 348 [M−C($CH_3$)$_3$+1H, 100%], 443 [M−1H+$CH_3CN$, 100%], 402 [M−1H, 55%], 404 [M+1H, 45%].

(3S,5S)-3-Hydroxymethyl-5-methyl-heptanoic acid tert-butyl ester 131

A procedure similar to that used to prepare (3S,5S)-3-Hydroxymethyl-5-methyl-octanoic acid tert-butyl ester 123 was giving 1.2 g, 52.1% of 131 as an oil. MS, m/z (relative intensity): 175 [M−C($CH_3$)$_3$+1H, 100%], 173 [M−C($CH_3$)$_3$−1H, 100%], 216 [M−C($CH_3$)$_3$+1H+$CH_3CN$, 95%].

(3S,5S)-5-Methyl-3-(toluene-4-sulfonyloxymethyl)-heptanoic acid tert-butyl ester 132

A procedure similar to the preparation of (3S,5R)-5-methyl-3-(toluene-4-sulfonyloxymethyl)-octanoic acid tert-butyl ester 104 was followed giving 2.1 g of 132 as an oil. The product was used in the next step without further purification. MS, m/z (relative intensity): 329 [M−C($CH_3$)$_3$+1H, 85%], 370 [M−C($CH_3$)$_3$+1H+$CH_3CN$, 65%].

(3S,5S)-3-Azidomethyl-5-methyl-heptanoic acid tert-butyl ester 133

A procedure similar to the preparation of (3S,5R)-3-azidomethyl-5-methyl-octanoic acid tert-butyl ester 105 was followed giving 0.76 g, 54.0% of 133 as an oil. MS, m/z (relative intensity): 198 [M−C($CH_3$)$_3$−1H, 100%]

(3S,5S)-3-Aminomethyl-5-methyl-heptanoic acid tert-butyl ester 134

A procedure similar to that used for (3S,5S)-3-aminomethyl-5-methyl-octanoic acid tert-butyl ester 126 was used giving 0.62 g of 134 as an oil. The product was used in the next step without further purification. MS, m/z (relative intensity): 230 [M+1H, 100%], 271 [M+1H+$CH_3CN$, 45%].

EXAMPLE 20

(3S,5S)-3-Aminomethyl-5-methyl-heptanoic acid

A procedure similar to that used for Example 19 was used giving (3S,5S)-3-aminomethyl-5-methyl-heptanoic acid (0.3 g, 65.1%) as a white solid. $^1$H NMR (CD$_3$OD) δ 2.80–3.00 (m, 2H), 2.40 (m, 1H), 2.20 (dd, J=8.2, 7.1 Hz, 1H), 2.05 (m, 1H), 1.30–1.50 (m, 3H), 1.00–1.20 (m, 2H), 0.9 (m, 6H); MS, m/z (relative intensity): 187 [M+1H, 100%], 211 [M+1H+CH$_3$CN, 30%]. MS, m/z (relative intensity): 174 [M+1H, 100%], 172 [M−1H, 100%], 215 [M+1H+CH$_3$CN, 20%].

EXAMPLE 21

Synthesis of (3S,5R)-3-Aminomethyl-5-methyl-nonanoic acid hydrochloride

(R)-4-Methyl-octanoic acid 136

Lithium chloride (0.39 g, 9.12 mmol) and copper (I) chloride (0.61 g, 4.56 mmol) were combined in 45 mL THF at ambient temperature and stirred 15 minutes, then cooled to 0° C. at which time ethyl magnesium bromide (1 M solution in THF, 45 mL, 45 mmol) was added. (S)-citronellyl bromide (5.0 g, 22.8 mmol) was added dropwise and the solution was allowed to warm slowly to ambient temperature with stirring overnight. The reaction was quenched by cautious addition of sat. NH$_4$Cl (aq), and stirred with Et$_2$O and sat. NH$_4$Cl (aq) for 30 minutes. The phases were separated and the organic phase dried (MgSO$_4$) and concentrated. The crude product was used without purification.

To a solution of alkene 135 (3.8 g, 22.8 mmol) in 50 mL acetone at 0° C. was added Jones' reagent (2.7 M in H$_2$SO$_4$ (aq), 40 mL, 108 mmol) and the solution was allowed to warm slowly to ambient temperature with stirring overnight. The mixture was partitioned between Et$_2$O and H$_2$O, the phases were separated, and the organic phase washed with brine, dried (MgSO$_4$), and concentrated. The residue was

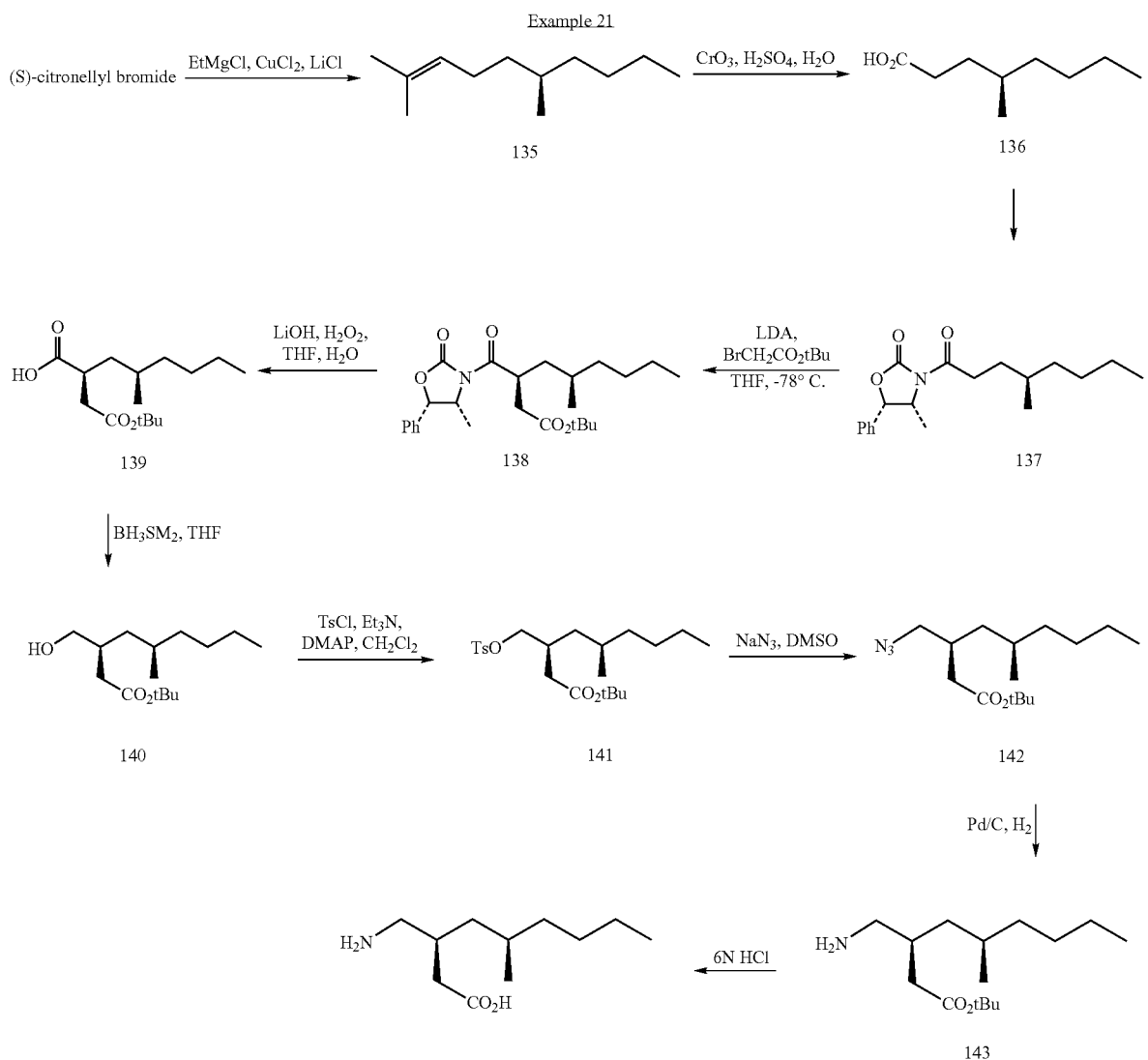

purified by flash chromatography (8:1 hexanes:EtOAc) to afford 2.14 g (59%) of acid 136 as a colorless oil: LRMS: m/z 156.9 (M+); $^1$H NMR (CDCl$_3$): ☐2.33 (m, 2H), 1.66 (m, 1H), 1.43 (m, 2H), 1.23 (m, 5H), 1.10 (m, 1H), 0.86 (m, 6H). Jones' reagent was prepared as a 2.7M solution by combining 26.7 g CrO$_3$, 23 mL H$_2$SO$_4$, and diluting to 100 mL with H$_2$O.

(4R,5S)-4-Methyl-3-((R)-4-methyl-octanoyl)-5-phenyl-oxazolidin-2-one 137

To acid 136 (2.14 g, 13.5 mmol) in 25 mL CH$_2$Cl$_2$ at 0° C. was added 3 drops DMF, followed by oxalyl chloride (1.42 mL, 16.2 mmol) resulting in vigorous gas evolution. The solution was warmed directly to ambient temperature, stirred 30 minutes, and concentrated. Meanwhile, to a solution of the oxazolidinone (2.64 g, 14.9 mmol) in 40 mL THF at −78° C. was added n-butyl lithium (1.6 M solution in hexanes, 9.3 mL, 14.9 mmol) dropwise. The mixture was stirred for 10 minutes at which time the acid chloride in 10 mL THF was added dropwise. The reaction was stirred 30 minutes at −78° C., then warmed directly to ambient temperature and quenched with sat. NH$_4$Cl. The mixture was partitioned between Et$_2$O and sat. NH$_4$Cl (aq), the phases were separated, and the organic phase dried (MgSO$_4$), and concentrated to furnish 3.2 g of oxazolidinone 137 as a colorless oil. LRMS: m/z 318.2 (M+); $^1$H NMR (CDCl$_3$): ☐7.34 (m, 5H), 5.64 (d, J=7.3 Hz, 1H), 4.73 (quint, J=6.8 Hz, 1H), 2.96 (m, 1H), 2.86 (m, 1H), 1.66 (m, 1H), 1.47 (m, 2H), 1.26 (m, 5H), 1.13 (m, 1H), 0.88 (m, 9H). The crude product was used without purification.

(3S,5R)-5-Methyl-3-((4R,5S)-4-methyl-2-oxo-5-phenyl-oxazolidine-3-carbonyl)-nonanoic acid tert-butyl ester 138

To a solution of diisopropylamine (1.8 mL, 12.6 mmol) in 30 mL THF at −78° C. was added n-butyl lithium (1.6 M solution in hexanes, 7.6 mL, 12.1 mmol), and the mixture stirred 10 minutes at which time oxazolidinone 137 (3.2 g, 10.1 mmol) in 10 mL THF was added dropwise. The solution was stirred for 30 minutes, t-butyl bromoacetate (1.8 mL, 12.1 mmol) was added quickly dropwise at −50° C., and the mixture was allowed to warm slowly to 10° C. over 3 hours. The mixture was partitioned between Et$_2$O and sat. NH$_4$Cl (aq), the phases were separated, and the organic phase dried (MgSO$_4$), and concentrated. The residue was purified by flash chromatography (16:1 to 8:1 hexanes: EtOAc) to provide 2.65 g (61%) of ester 138 as a colorless crystalline solid, mp=84–86° C. [☐]$_D^{23}$+17.1 (c=1.00, CHCl$_3$); $^1$H NMR (CDCl$_3$): ☐7.34 (m, 5H), 5.62 (d, J=7.3 Hz, 1H), 4.73 (quint, J=6.8 Hz, 1H), 4.29 (m, 1H), 2.67 (dd, J=9.8, 16.4 Hz, 1H), 2.40 (dd, J=5.1, 16.4 Hz, 1H), 1.69 (m, 1H), 1.38 (s, 9H), 1.28 (m, 7H), 1.08 (m, 1H), 0.88 (m, 9H); $^{13}$C NMR (CDCl$_3$) ☐176.45, 171.22, 152.71, 133.64, 128.86, 125.86, 80.83, 78.87, 55.33, 40.02, 38.21, 37.59, 36.31, 30.86, 29.29, 28.22, 23.14, 20.41, 14.36, 14.26. Anal. Calcd for C$_{25}$H$_{37}$NO$_5$: C, 69.58; H, 8.64; N, 3.25. Found: C, 69.37; H, 8.68; N, 3.05.

(S)-2-((R)-2-Methyl-hexyl)-succinic acid 4-tert-butyl ester 139

To a solution of ester 138 (2.65 g, 6.14 mmol) in 20 mL THF at 0° C. was added a precooled (0° C.) solution of LiOH monohydrate (1.0 g, 23.8 mmol) and hydrogen peroxide (30 wt % aqueous solution, 5.0 mL) in 10 mL H$_2$O. The mixture was stirred vigorously for 90 minutes, then warmed to ambient temperature and stirred 90 minutes. The reaction was quenched at 0° C. by addition of 100 mL 10% NaHSO$_3$ (aq), then extracted with Et$_2$O. The phases were separated, and the organic phase washed with brine, dried (MgSO$_4$), and concentrated. The crude acid 139 was used without purification.

(3S,5R)-3-Hydroxymethyl-5-methyl-nonanoic acid tert-butyl ester 140

To a solution of the crude acid 139 (6.14 mmol) in 30 mL THF at 0° C. was added borane-dimethyl sulfide complex (2.0 M solution in THF, 4.6 mL, 9.2 mmol), and the mixture was allowed to warm slowly to ambient temperature overnight. Additional BH_DMS was added until the acid was completely consumed (ca. 5 mL). The reaction was quenched by addition of MeOH, then partitioned between Et$_2$O and sat. NaHCO$_3$ (aq). The phases were separated, and the organic phase washed with brine, dried (MgSO$_4$), and concentrated to provide alcohol 140. LRMS: m/z 226.1; $^1$H NMR (CDCl$_3$): ☐3.63 (dd, J=11.0, 4.2 Hz, 1H), 3.42 (dd, J=11.0, 6.8 Hz, 1H), 2.30 (dd, J=14.9, 7.6 Hz, 1H), 2.20 (dd, J=14.9, 5.6 Hz, 1H), 2.03 (m, 2H), 1.42 (s, 9H), 1.24 (m, 6H), 1.02 (m, 2H), 0.85 (m, 6H). The crude product was used without purification.

(3S,5R)-5-Methyl-3-(toluene-4-sulfonyloxymethyl)-nonanoic acid tert-butyl ester 141

To alcohol 140 (6.14 mmol) in 30 mL CH$_2$Cl$_2$ at 0° C. was added DMAP (0.1 g), p-toluenesulfonyl chloride (1.37 g, 7.2 mmol), and then triethylamine (1.8 mL, 13 mmol) was added quickly dropwise. The mixture was warmed immediately to ambient temperature following addition and stirred overnight, and did not proceed to completion. The mixture was partitioned between Et$_2$O and 1N HCl (aq), the phases were separated, and the organic phase washed with sat. NaHCO$_3$ (aq), dried (MgSO$_4$), and concentrated to provide tosylate 141. The product was used without further purification.

(3S,5R)-3-Azidomethyl-5-methyl-nonanoic acid tert-butyl ester 142

A procedure similar to the preparation of (3S,5R)-3-azidomethyl-5-methyl-octanoic acid tert-butyl ester 105 was followed giving azide 142 as a colorless oil. LRMS: m/z 200.1; $^1$H NMR (CDCl$_3$): ☐3.31 (dd, J=12.2, 4.2 Hz, 1H), 3.19 (dd, J=12.2, 5.9 Hz, 1H), 2.22 (m, 1H), 2.10 (m, 1H), 1.39 (s, 9H), 1.21 (m, 8H), 1.00 (m, 2H), 0.81 (m, 6H).

EXAMPLE 21

(3S,5R)-3-Aminomethyl-5-methyl-nonanoic acid hydrochloride

The azide 142 (1.0 g) was hydrogenated in the presence of 20% Pd/C, EtOH, at 45 psi of H$_2$ for 15 hours to provide the crude amino ester 143 which was concentrated and used without purification. To the amino ester 143 was added 6 mL 6N HCl (aq) and the mixture was heated to reflux 90 minutes, cooled, and concentrated. Recrystallization from EtOAc:hexanes provided 0.38 g (45% from azide) of (3S, 5R)-3-aminomethyl-5-methyl-nonanoic acid hydrochloride as a colorless crystalline solid (HCl salt), and a second crop of 82 mg (10% from azide) was also obtained.

mp=146–156° C. LRMS: m/z 200.1 (M+); $^1$H NMR (CDCl$_3$): ☐2.87 (dd, J=13.2, 5.4 Hz, 1H), 2.79 (dd, J=13.2, 7.3 Hz, 1H), 2.29 (d, J=6.8 Hz, 2H), 2.08 (m, 1H), 1.31 (m, 1H), 1.09 (m, 7H0, 0.92 (m, 1H), 0.68 (m, 6H). Anal. Calcd for C$_{11}$H$_{24}$NO$_2$Cl: C, 55.57; H, 10.17; N, 5.89. Found: C, 55.69; H, 10.10; N, 5.86.

EXAMPLE 22

Synthesis of (3S,5S)-3-Aminomethyl-5-methyl-nonanoic acid t-Butyl ester 147 was prepared from oxazolidinone 146 as described above for compound 138. LRMS: m/z 348.1 (M−83).

Alcohol 149 was prepared from the t-butyl ester 147 as described above for (3S,5R)-3-hydroxymethyl-5-methyl-nonanoic acid tert-butyl ester 140. LRMS: m/z 156.9 (M−100); $^1$H NMR (CDCl$_3$): ☐3.60 (dd, J=11.0, 4.6 Hz, 1H), 3.45 (dd, J=11.0, 6.8 Hz, 1H), 2.24 (m, 2H), 2.04 (m, 2H), 1.42 (s, 9H), 1.17–1.38 (m, 7H), 1.11 (m, 1H), 0.84 (m, 6H).

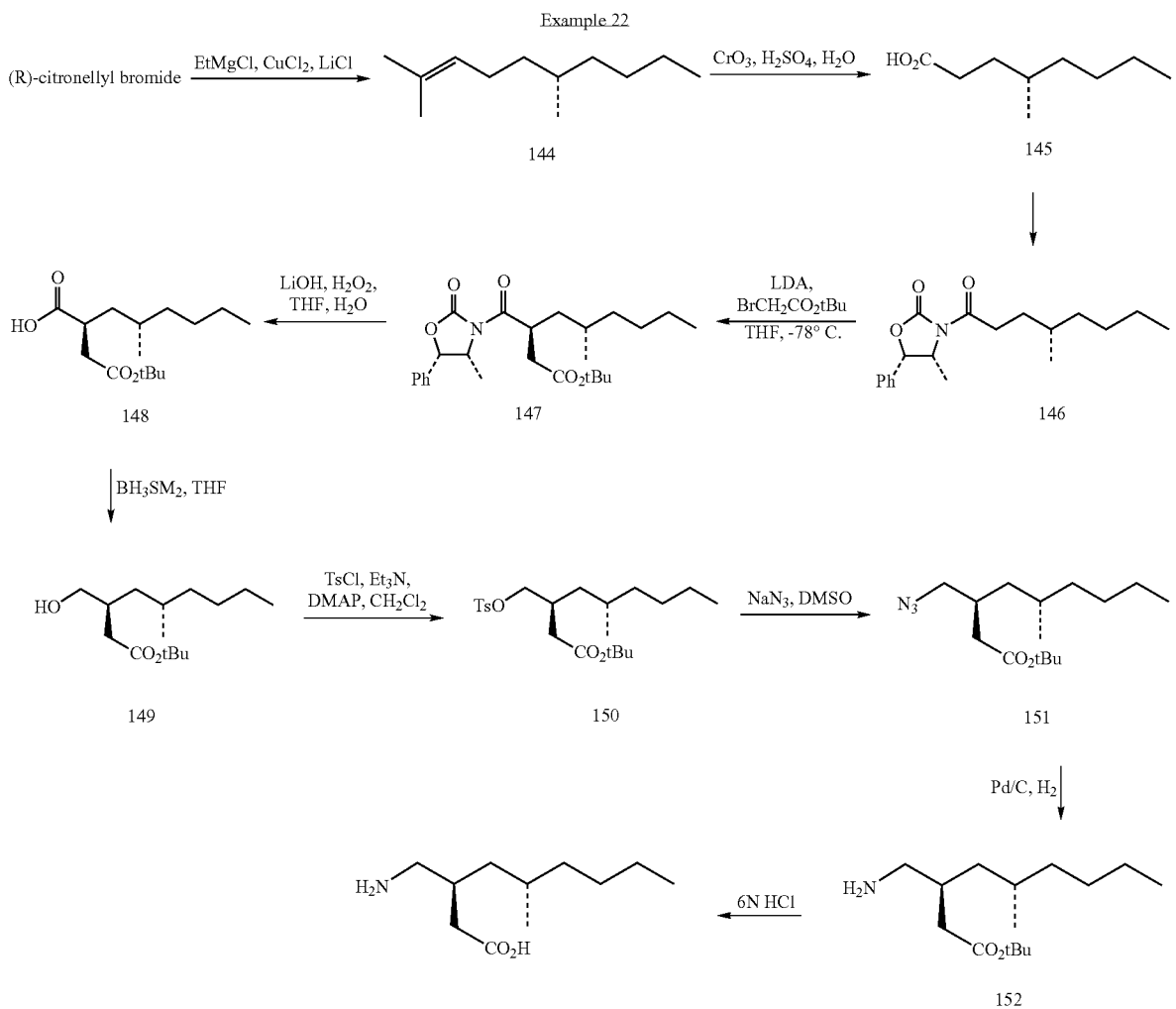

The (S)-acid 145 was prepared from (R)-citronellyl bromide according to the procedure outlined above for (R)-4-methyl-octanoic acid 136. The yield was comparable and the $^1$H NMR spectrum was identical to that of the (R)-acid enantiomer. LRMS: m/z 158.9 (M+1).

Oxazolidinone 146 was prepared from acid 145 as described above for (4R,5S)-4-methyl-3-((R)-4-methyl-octanoyl)-5-phenyl-oxazolidin-2-one 137. LRMS: m/z 290.1 (M−27); $^1$H NMR (CDCl$_3$): ☐7.38 (m, 3H), 7.28 (m, 2H), 5.64 (d, J=7.1 Hz, 1H), 4.74 (quint, J=6.8 Hz, 1H), 2.92 (m, 2H), 1.71 (m, 1H), 1.42 (m, 7H), 1.18 (m, 1H), 0.88 (m, 9H).

EXAMPLE 22

(3S,5S)-3-Aminomethyl-5-methyl-nonanoic acid (3S,5S)-3-Aminomethyl-5-methyl-nonanoic acid was obtained from 149 as described above for (3S,5R)-3-aminomethyl-5-methyl-nonanoic acid hydrochloride. The crude HCl salt thus obtained was purified by ion exchange chromatography on Dowex 50WX8 50–100 mesh, H-Form resin, using 10% NH$_4$OH as eluent to provide the free base. The waxy solid was washed twice with Et$_2$O and dried to furnish an amorphous white solid, mp 144–146° C. LRMS:

m/z 172.0 (M−28); $^1$H NMR (CDCl$_3$): ☐2.76 (d, J=5.9 Hz, 2H), 2.14 (m, 1H), 1.96 (m, 2H), 1.25 (m, 1H), 1.12 (m, 6H), 0.96 (m, 2H), 0.66 (m, 6H).

EXAMPLE 23

Synthesis of
(3S,5R)-3-Aminomethyl-5-methyl-decanoic acid wise, and the reaction allowed to warm to room temperature over 18 hours. The reaction was poured on to water/Na$_2$SO$_4$ (200 mL), and the aqueous layer extracted with ethyl acetate (4×100 mL). The combined organics were dried over MgSO$_4$, filtered, and rotovapped to give an oil. The crude oil was dissolved in CH$_2$Cl$_2$ (400 mL) and cooled to −78° C. Ozone was bubbled into reaction until blue to remove traces of the impurity (6E)(3S)-3,7-dimethylocta-1,6-diene. Dim-

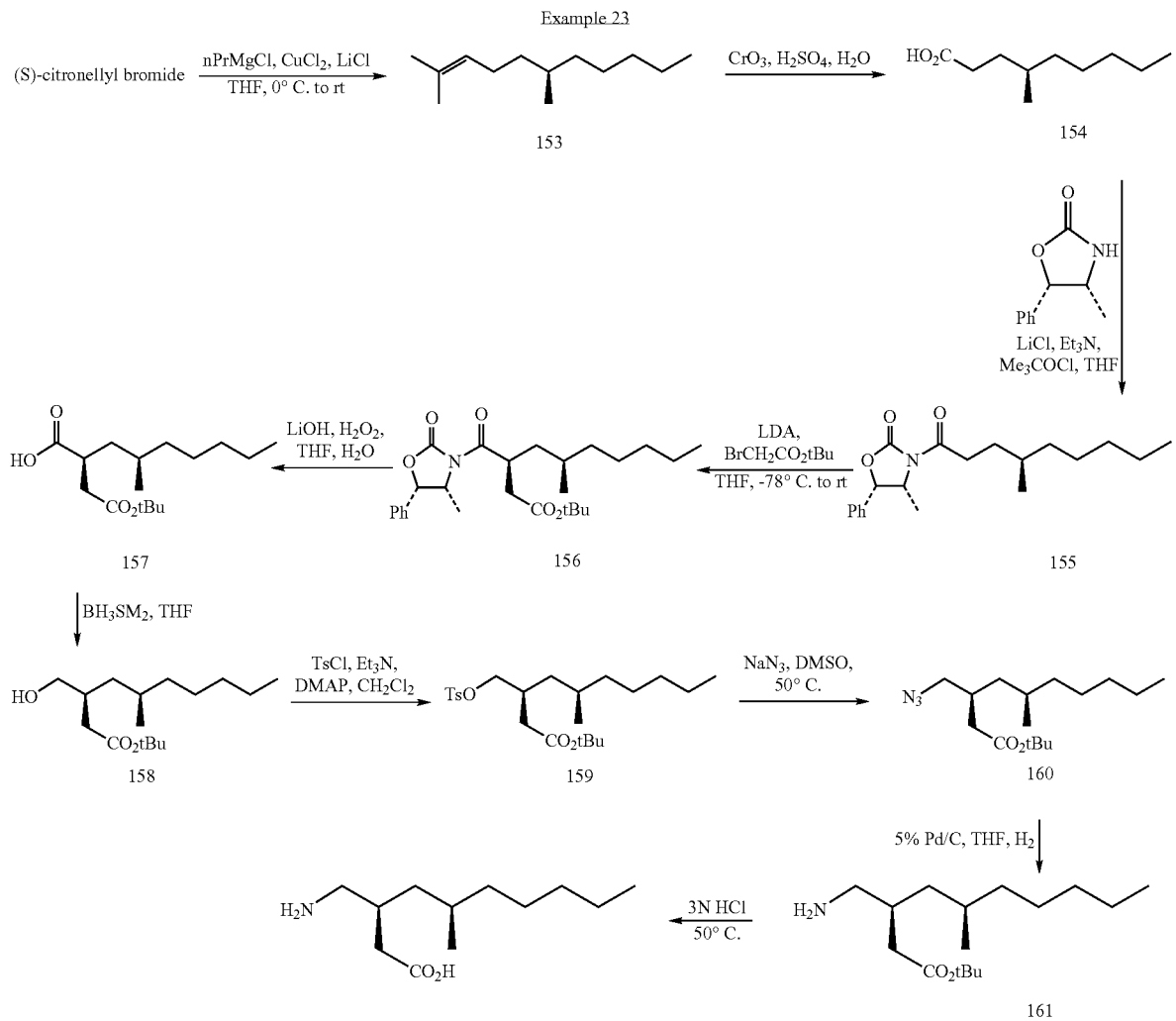

(R)-2,6-Dimethylundec-2-ene 153

A procedure similar to the preparation of (S)-2,6-dimethyl-non-2-ene 119 was used giving 153 as a colorless oil (20.16 g, 98%). $^1$H NMR (400 MHz, CDCl$_3$) δ 5.10–5.06 (m, 1H), 2.10–1.89 (m, 2H), 1.66 (s, 3H), 1.58 (s, 3H), 1.34–1.23 (m, 4H), 1.15–1.06 (m, 2H), 0.88–0.81 (m, 11H).

(R)-4-methylnonanoic acid 154

(R)-2,6-Dimethylundec-2-ene 153 (10.03 g, 55.03 mmol) was dissolved in acetone (270 mL) and cooled to 0° C. Jones reagent (CrO$_3$/H$_2$SO$_4$) (2.7 M, 120 mL) was added dropethylsulfide (5 mL) was added, and the reaction stirred at room temperature for 2 hours. The solvent was removed, and the crude material chromatographed on silica eluting with 20% EtOAc/hex to give oil. The oil was dissolved in ether (100 mL) and extracted with 10% NaOH (2×25 mL). The aqueous layers were combined and extracted with ether (50 mL). The aqueous layer was cooled to 0° C. and acidified with HCl. The acidic layer was extracted with EtOAc (3×100 mL), and the combined extracts dried over MgSO$_4$, filtered and rotovapped to give 154 as an oil (6.86 g, 54%). $^1$H NMR (400 MHz, CDCl$_3$) δ 2.40–2.25 (m, 4H), 1.70–1.62 (m, 2H), 1.47–1.11 (m, 8H), 0.87–0.84 (m, 6H); [α]$_D$=−11.4 (c1 in CHCl$_3$).

(4R,5S)-4-Methyl-3-((R)-4-methyl-nonanoyl)-5-phenyl-oxazolidin-2-one 155

Compound 154 (6.504 g, 37.76 mmol) was dissolved in THF (95 mL) and cooled to 0° C. Triethylamine (19.74 mL, 141.6 mmol) was added dropwise, followed by dropwise addition of trimethylacetyl chloride (6.98 mL, 56.64 mmol). The thick white suspension was stirred at 0° C. for 90 minutes. LiCl (1.86 g, 41.54 mmol), (4R)-4-methyl-5-phenyl-1,3-oxazolidin-2-one (6.824 g, 38.51 mmol), and THF (70 mL) were added, and the reaction warmed to room temperature overnight. The solvent was evaporated. The solids were taken up in EtOAc, filtered off, and washed generously with EtOAc. The filtrate was washed with water (2×50 mL), and brine. The organics were dried over $MgSO_4$, filtered, and rotovapped. The crude material was chromatographed on silica eluting with 10% EtOAc/hexanes to give 155 as an oil (10.974 g, 88%). $^1$H NMR (400 MHz, $CDCl_3$) δ 7.44–7.35 (m, 3H), 7.31–7.26 (m, 2H), 5.66 (d, J=7.33 Hz, 1H), 4.76 (quint, J=7.03 Hz, 1H), 3.04–2.96 (m, 1H), 2.93–2.86 (m, 1H), 1.74–1.66 (m, 1H), 1.52–1.47 (m, 1H), 1.46–1.36 (m, 2H), 1.27–1.16 (m, 2H), 0.92–0.87 (m, 8H); $[α]_D$=+34.1 (c1 in $CHCl_3$).

(3S,5R)-5-Methyl-3-((4R,5S)-4-methyl-2-oxo-5-phenyl-oxazolidine-3-carbonyl)-decanoic acid tert-butyl ester 156

A procedure similar to the preparation of (3S,5S)-5-methyl-3-((4R,5S)-4-methyl-2-oxo-5-phenyl-oxazolidine-3-carbonyl)-octanoic acid tert-butyl ester 122 was followed giving (3S,5R)-5-methyl-3-((4R,5S)-4-methyl-2-oxo-5-phenyl-oxazolidine-3-carbonyl)-decanoic acid tert-butyl ester 156 as an oil (0.668 g, 90%). $^1$H NMR (400 MHz, $CDCl_3$) δ 7.41–7.28 (m, 5H), 5.63 (d, J=7.33 Hz, 1H), 4.74 (quint, J=6.84 Hz, 1H), 4.33–4.26 (m, 1H), 2.68 (dd, J=16.4, 9.77 Hz, 1H), 2.41 (dd, J=16.6, 4.88 Hz, 1H), 1.68 (quint, J=6.6 Hz, 1H), 1.50–1.32 (m, 10H), 1.28–1.21 (m, 1H), 1.15–1.08 (m, 1H), 0.90–0.86 (m, 9H); MS (APCI) m/z 348 ($M^+$–97, 100%); $[α]_D$=+18.8 (c1 in $CHCl_3$).

(S)-2-((R)-2-Methyl-heptyl)-succinic acid 4-tert-butyl ester 157

Compound 156 (5.608 b, 12.59 mmol) was dissolved in $THF/H_2O$ (60 mL/14 mL) and cooled to 0° C. LiOH (1N, 18.89 mL) and $H_2O_2$ (35%, 4.45 mL, 50.4 mmol) were combined, and then added to the reaction dropwise keeping T<5° C. the reaction was stirred at 0° C. for 4 hours, and quenched with $Na_2SO_3$ (6.3 g) and $NaHSO_3$ (3.4 g) in 50 mL $H_2O$ added dropwise. The reaction was stirred for 15 minutes, and the layers separated. The aqueous layer was extracted with EtOAc (3×100 mL), and the combined extracts dried over $MgSO_4$, filtered, and rotovapped to give an oil. The crude material was dissolved in EtOAc (10 mL) and added dropwise to heptane (250 mL). The suspension was stirred for 20 minutes, and the solids filtered and washed with heptane. The filtrate was washed with 60° C. $H_2O$ (100 mL), dried over $MgSO_4$, filtered, and rotovapped to give 157 as an oil (3.52 g). the material was used directly in the next step.

(3S,5R)-3-Hydroxymethyl-5-methyl-decanoic acid tert-butyl ester 158

Compound 157 (3.52 g, 12.3 mmol) was dissolved in anhydrous THF (123 mL) and cooled to 0° C. Borane dimethylsulfide complex (10 M, 3.69 mL) was added dropwise, and the reaction then warmed to room temperature and stirred for 1 hour. The reaction was cooled to 0° C., and quenched with MeOH (20 mL) added dropwise. The reaction was stirred for 18 hours, and the solvent rotovapped off. The crude material was chromatographed on silica eluting with 20% EtOAc/hexanes to give 158 (2.28 g, 68%) as an oil. $^1$H NMR (400 MHz, $CDCl_3$) δ 3.65–3.59 (m, 1H), 3.43 (dd, J=11.1, 6.96 Hz, 1H), 2.31 (dd, J=14.9, 7.57 Hz, 1H), 2.21 (dd, J=15.1, 5.62 Hz, 1H), 2.06–2.02 (m, 1H), 1.43 (s, 9H), 1.40–1.25 (m, 4H), 1.07–1.13 (m, 1H), 1.03–0.96 (m, 1H), 0.86–0.84 (m, 6H); MS (APCI) m/z 216 ($M^+$–56, 100%).

(3S,5R)-5-Methyl-3-(toluene-4-sulfonyloxymethyl)-decanoic acid tert-butyl ester 159

Compound 158 (2.27 g, 8.33 mmol) was dissolved in $CH_2Cl_2$ (30 mL) and cooled to 0° C. Tosyl chloride (1.91 g, 10.0 mmol) and catalytic DMAP were added, followed by dropwise addition of triethylamine (2.55 mL, 18.33 mmol). The reaction was then stirred at 0° C. for 18 hours. The solvent was rotovapped off (removed under reduced pressure), and the crude material washed with EtOAc and filtered. The solids were washed with EtOAc, and the filtrate washed with 0.5N HCl (20 mL), brine (30 mL), dried over $MgSO_4$, filtered, and rotovapped. The oil was chromatographed on silica eluting with a 5% EtOAc/hexanes gradient to 10% EtOAc/hexanes to give 159 (3.399 g, 96%) as an oil. $^1$H NMR (400 MHz, $CDCl_3$) δ 7.75 (d, J=8.30 Hz, 2H), 7.31 (d, J=8.30 Hz, 2H), 3.99 (dd, J=9.65, 3.54 Hz, 1H), 3.89 (dd, J=9.52, 5.37 Hz, 1H), 2.42 (s, 3H), 2.28 (dd, J=14.7, 6.23 Hz, 1H), 2.19–2.14 (m, 1H), 2.10 (dd, J=14.9, 6.35 Hz, 1H), 1.38 (s, 9H), 1.31–1.17 (m, 3H), 1.08–0.81 (m, 2H), 0.79–0.76 (m, 6H); $[α]_D$=–10.1 (c1 in $CHCl_3$).

(3S,5R)-3-Azidomethyl-5-methyl-decanoic acid tert-butyl ester 160

Compound 159 (3.01 g, 7.05 mmol), sodium azide (1.26 g, 19.40 mmol) and DMSO (12 mL) were combined and heated to 60° C. for 3 hours. EtOAc (100 mL) was added to the reaction and filtered. The solids were washed with EtOAc (20 mL), and the filtrated evaporated. The crude material was chromatographed on silica eluting with 5% EtOAc/hexanes to give 160 as an oil (1.86 g, 89%).

(3S,5R)-3-Aminomethyl-5-methyl-decanoic acid tert-butyl ester 161

A solution of compound 160 (1.86 g, 6.25 mmol) in THF (50 mL) was shaken over 5% Pd/C under hydrogen and pressure for 8 hours with three purges of hydrogen. The catalyst was filtered off and the filtrate evaporated. The crude material was chromatographed on silica eluting with methanol to give 161 as an oil (1.21 g, 71%). $^1$H NMR (400 MHz, $CDCl_3$) δ 2.70 (dd, J=12.9, 4.40 Hz, 1H), 2.54 (dd, J=12.7, 6.59 Hz, 1H), 2.26 (dd, J=14.5, 6.96 Hz, 1H), 2.12 (dd, J=14.5, 6.47 Hz, 1H), 1.91 (m, 1H), 1.91 (m, 1H), 1.43 (s, 12H), 1.39–1.25 (m, 4H), 1.14–1.07 (m, 1H), 1.03–0.97 (m, 1H), 0.86–0.82 (m, 6H).

EXAMPLE 23

(3S,5R)-3-Aminomethyl-5-methyl-decanoic acid

Compound 161 (1.20 g, 4.44 mmol) was heated to 50° C. in 3N HCl (30 mL) for 4 hours. The solvent was evaporated, and the oil washed with toluene, and evaporated. The crude material was passed through an ion exchange column (Dowex 50WX8-100, strongly acidic) eluting with water, then 0.5N NH$_4$OH. Isolate (3S,5R)-3-aminomethyl-5-methyl-decanoic acid as a white solid (0.725 g, 75%): mp=174–175° C.; $^1$H NMR (400 MHz, CDCl$_3$) δ 2.83 (dd, J=12.69, 4.88 Hz, 1H), 2.70 (dd, J=13.1, 7.45 Hz, 1H), 2.08 (d, J=6.59 Hz, 2H), 1.98 (m, 1H), 1.28–1.20 (m, 1H), 1.19–1.09 (m, 2H), 0.99–0.91 (m, 2H), 0.66 (m, 6H); MS (APCI) m/z 215 (M$^+$, 10%), 174 (M$^+$–41, 100%); [α]$_D$=–5.7 (c1.025 in H$_2$O).

EXAMPLE 24

Synthesis of (3S,5S)-3-Aminomethyl-5-methyl-decanoic acid

(S)-2,6-Dimethyl-undec-2-ene 162 nPropylmagnesium chloride/ether solution (2.0 M, 228 mL) was cooled to –20° C. under a N$_2$ atmosphere. LiCl (3.87 g, 91.25 mmol), CuCl$_2$ (6.13 g, 45.63 mmol), and distilled THF (456 mL) were combined and stirred for 30 minutes. The Li$_2$CuCl$_4$ solution was added via cannula to the Grignard reagent, and the resulting solution stirred for 30 minutes at –20° C. R-(–)-Citronellyl bromide (50 g, 228.1 mmol) was dissolved in THF (60 mL) and added dropwise to the Grignard solution. The reaction was stirred at 0° C. for 1 hour. The reaction was cooled to –40° C. and quenched with NH$_4$Cl (saturated, 200 mL) added dropwise. The layers were separated and the aqueous layer extracted with ether (3×100 mL). The combined organics were dried over MgSO$_4$, filtered, and rotovapped to give an oil. The crude material was chromatographed on silica eluting with hexanes to give 162 as a colorless oil (9.15 g, 22%). $^1$H NMR (400 MHz, CDCl$_3$) δ 5.10–5.06 (m, 1H), 2.10–1.89 (m, 2H), 1.66 (s, 3H), 1.58 (s, 3H), 1.34–1.23 (m, 4H), 1.15–1.06 (m, 2H), 0.88–0.81 (m, 11H).

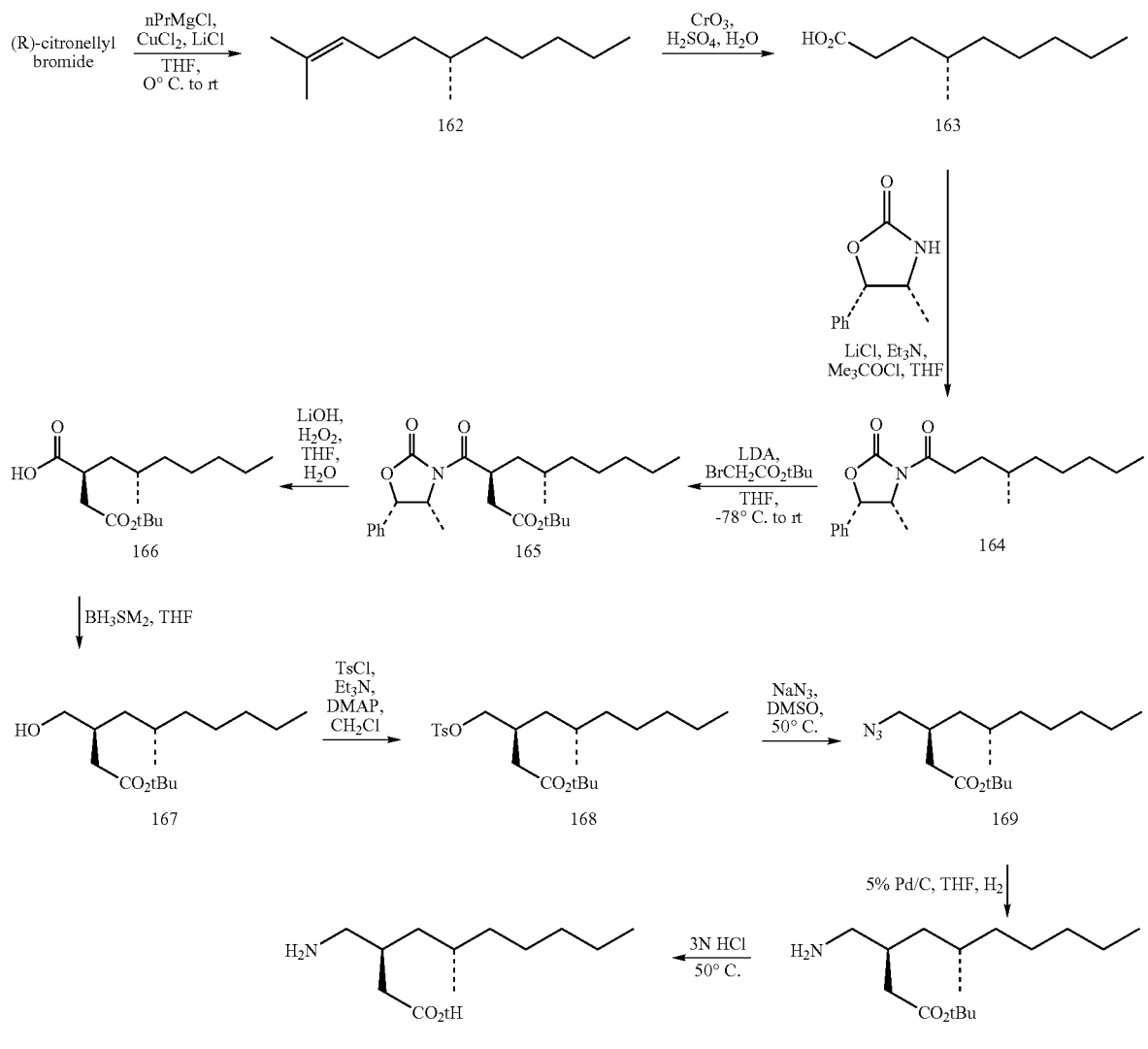

Example 24

(S)-4-Methylnonanoic acid 163

Compound 162 (7.97 g, 43.7 mmol) was dissolved in acetone (214 mL) and cooled to 0° C. Jones reagent (CrO$_3$/H$_2$SO$_4$) (2.7 M, 95 mL) was added dropwise, and the reaction allowed to warm to room temperature over 18 hours. The reaction was poured on to water/Na$_2$SO$_4$ (200 mL), and the aqueous layer extracted with ethyl acetate (4×100 mL). The combined organics were dried over MgSO$_4$, filtered, and rotovapped to give an oil. The crude oil was chromatographed on silica eluting with hexanes to give 163 as an oil (5.56 g, 74%). $^1$H NMR (400 MHz, CDCl$_3$) δ 2.40–2.25 (m, 4H), 1.70–1.62 (m, 2H), 1.47–1.11 (m, 8H), 0.87–0.84 (m, 6H); MS APCI m/z 170.9 (M$^-$1, 100%).

(4R,5S)-4-Methyl-3-((S)-4-methyl-nonanoyl)-5-phenyl-oxazolidin-2-one 164

A procedure similar to that used to prepare compound 155 was used except that (S)-4-methylnonanoic acid 163 (5.56 g, 32.27 mmol) was used as a reactant to give 164 as an oil (10.70 g 100%). $^1$H NMR (400 MHz, CDCl$_3$) δ 7.42–7.34 (m, 3H), 7.28 (d, J=6.59 Hz, 2H), 5.64 (d, J=7.33 Hz, 1H), 4.74 (quint, J=6.78 Hz, 1H), 2.94–2.85 (m, 2H), 1.73–1.67 (m, 1H), 1.47–1.43 (m, 1H), 1.39–1.22 (m, 7H), 0.90–0.84 (m, 8H).

(3S,5S)-5-Methyl-3-((4R,5S)-4-methyl-2-oxo-5-phenyl-oxazolidine-3-carbonyl)-decanoic acid tert-butyl ester 165

A procedure similar to that used to prepare compound 156 was used to give 165 as a solid (4.25 g, 61%). MS (APCI) m/z 446 (M$^+$+1, 10%), 390 (M$^+$−55, 100%, -tBu).

(S)-2-((S)-2-Methyl-heptyl)-succinic acid 4-tert-butyl ester 166

A procedure similar to that used for compound 157 was used except that ester 165 (8.42 g, 18.89 mmol) was used as a reactant to give 166 as an oil (5.81 g). The material was used directly in the next step. MS (APCI) m/z 285 (M$^-$1, 100%).

(3S,5S)-3-Hydroxymethyl-5-methyl-decanoic acid tert-butyl ester 167

A procedure similar to that used to prepare compound 158 was used except that (S)-2-((S)-2-methyl-heptyl)-succinic acid 4-tert-butyl ester 166 (5.78 g, 20.18 mmol) was used as a reactant to give 167 as an oil (4.18 g, 76%). $^1$H NMR (400 MHz, CDCl$_3$) δ 3.64–3.58 (m, 1H), 3.84–3.42 (m, 1H), 2.28–2.20 (m, 1H), 2.09–2.02 (m, 1H), 1.43 (s, 9H), 1.26–1.18 (m, 8H), 1.11–1.04 (m, 2H), 0.87–0.83 (m, 6H); MS (APCI) m/z 217 (M$^+$−55, 50%, -tBu).

(3S,5S)-5-Methyl-3-(toluene-4-sulfonyloxymethyl)-decanoic acid tert-butyl ester 168

A procedure similar to that used to prepare compound 159 was used except that (3S,5S)-3-Hydroxymethyl-5-methyl-decanoic acid tert-butyl ester 167 (4.164 g, 15.29 mmol) was used as a reactant to give 168 as an oil (4.17 g, 64%). $^1$H NMR (400 MHz, CDCl$_3$) δ 7.75 (d, J=8.30 Hz, 2H), 7.31 (d, J=8.30 Hz, 2H), 3.97 (dd, J=9.52, 4.15 Hz, 1H), 3.90 (dd, J=9.52, 5.13 Hz, 1H), 2.42 (s, 3H), 2.28, 2.19–2.13 (m, 2H), 1.37 (s, 9H), 1.27–1.01 (m, 11H), 0.85 (t, J=7.08 Hz, 3H), 0.76 (d, J=6.35 Hz, 3H).

(3S,5S)-3-Azidomethyl-5-methyl-decanoic acid tert-butyl ester 169

A procedure similar to that used to prepare compound 160 was used except (3S,5S)-5-methyl-3-(toluene-4-sulfonyloxymethyl)-decanoic acid tert-butyl ester 168 (4.155 g, 9.74 mmol) was used as a reactant to give 169 as an oil (2.77 g, 96%). MS (APCI) m/z 270 (M$^+$−27, 30%, —N$_2$), 214 (M$^+$−87, 100%, -tBu, —N$_2$).

(3S,5S)-3-Aminomethyl-5-methyl-decanoic acid tert-butyl ester 170

A procedure similar to that used to prepare compound 161 was used except that (3S,5S)-3-Azidomethyl-5-methyl-decanoic acid tert-butyl ester 169 (2.50 g, 8.405 mmol) was used as a reactant to give 170 as an oil (1.648 g, 72%). MS (APCI) m/z 272 (M$^+$+1, 100%).

EXAMPLE 24

(3S,5S)-3-Aminomethyl-5-methyl-decanoic acid

A procedure similar to that used for Example 15 was used except tert-butyl (3S,5S)-3-(aminomethyl)-5-methyldecanoate 170 (1.6 g, 6.00 mmol) was used as a reactant to give Example 16 as a white solid (72%). MS (APCI) m/z 272 (M$^+$+1, 100%). mp=174–175° C.; $^1$H NMR (400 MHz, CD$_3$OD) δ 2.91 (dd, J=12.9, 3.91 Hz, 1H), 2.83 (dd, J=12.7, 7.57 Hz, 1H), 2.43 (dd, J=15.6, 3.17 Hz, 1H), 2.19 (dd, J=15.6, 8.80 Hz, 1H), 2.08–2.04 (m, 1H), 1.53 (m, 1H), 1.38–1.27 (m, 7H), 1.78–1.03 (m, 2H), 0.90–0.86 (m, 6H), 0.66 (m, 6H); MS (APCI) m/z 216 (M$^+$+1, 100%), 214 (M$^{-1}$, 100%); [α]$_D$=+21.4 (c1 in MeOH).

EXAMPLE 25

Synthesis of (3R,4R)-3-Aminomethyl-4,5-dimethyl-hexanoic acid

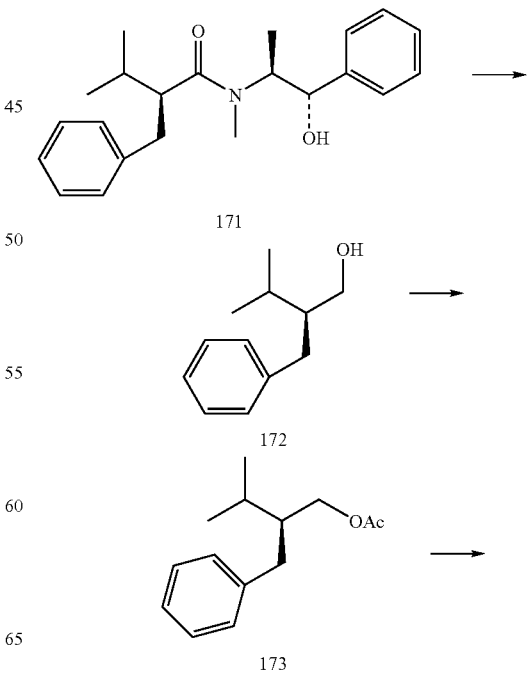

-continued

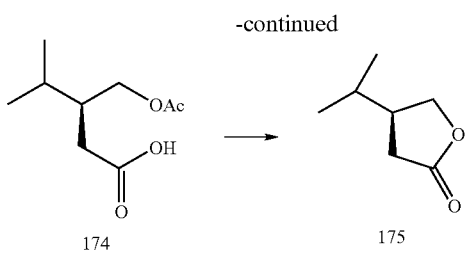
174
175

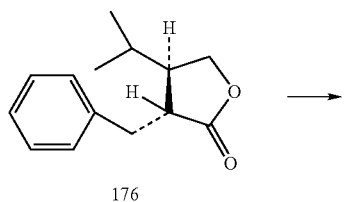
176

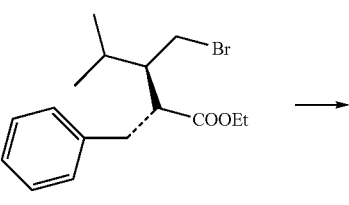
177

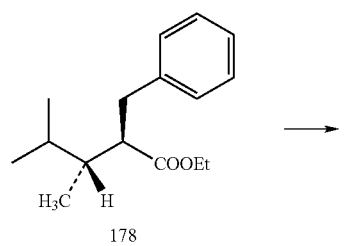
178

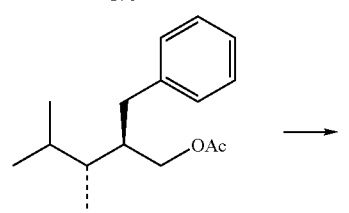
179

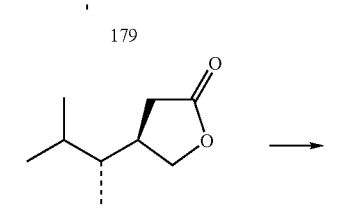
180

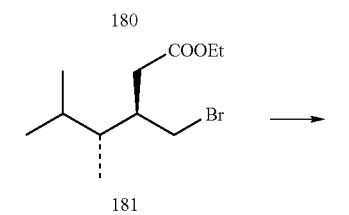
181

182

-continued

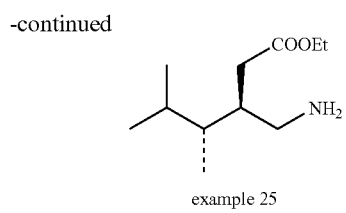
example 25

(S)-2-Benzyl-3-methyl-butan-1-ol 172

Ref. *JACS* 1997; 119:6510. Amide 171.

Large scale procedure for the synthesis of acetic acid (S)-2-benzyl-3-methyl-butyl ester 173 from 171

A of n-butyl lithium (10 M in hexane, 100 mL, 1000 mmol, 3.9 equiv.) was added to a solution of diisopropylamine (108.9 g, 150.9 mL, 1.076 mol, 4.20 equiv.) in THF (600 mL), at −78° C. The resulting solution was stirred for 10 minutes and warmed to 0° C., and held at the temperature for 10 minutes. Borane-ammonia complex (31.65 g, 1.025 mmol, and 4.0 equiv) was added in one portion, and the suspension was stirred at 0° C. for 15 minutes, and at 23° C. for 15 minutes, and then cooled to 0° C. A solution of amide 171 (86 g, 256.41 mmol, 1 equiv.) in THF was added to the cold hydride via a cannula over 3 minutes. The reaction was stirred at 23° C. for overnight, then cooled to 0° C. Excess hydride was quenched by the slow addition of 3N HCl (700 mL). The reaction mixture was diluted with more aqueous HCl (3N, 200 mL), and brine and then extracted with ether (4×15 mL). The ether solution was concentrated to a small volume, and 200 mL 2N NaOH was added, and stirred at 23° C. for 2.5 hours. More ether was added and the layers were separated. The aqueous layer was saturated with salt and extracted with ether (3×200 mL). The combined organic was washed with brine and dried on sodium sulfate. The residue was flash chromatographed (Pet. ether-25% ether-TEA) to give alcohol 172, 50 g. NMR (CDCl$_3$) δ 7.35–7.16 (m, 5H, C$_6$H$_5$), 3.55 (app. t, 2H, —CH$_2$OH), 2.71 (dd, 1H, ArCH$_2$CH—), 2.52 (dd, 1H, ArCH$_2$CH), 1.87 (m, 1H, CHCH(Me), 1.67 (m, 1H, CH(Me)$_2$), 0.98 (d, 3H, CH$_3$) and 0.96 (d, 3H, CH$_3$).

A sample 3.3 g was saved for characterization and the rest was immediately acetylated (triethylamine 50 mL, DMAP 4.6 g, acetic acid anhydride 32 mL) overnight at room temperature. Work up followed by chromatography on silica gel eluted with pet ether and then 10% ether in pet ether gave 62 g of 173. NMR (CDCl$_3$) δ 7.30–7.14 (m, 5H, C$_6$H$_5$), 3.98 (m, 2H, —CH$_2$OAc), 2.71 (dd, 1H, ArCH$_2$CH—), 2.51 (dd, 1H, ArCH$_2$CH), 1.99 (s, 3H, CH$_3$C═O), 1.82 (m, 1H, CHCH(Me) and CH(Me)$_2$), 0.97 (d, 3H, CH$_3$) and 0.95 (d, 3H, CH$_3$).

(S)-Acetoxymethyl-4-methyl-pentanoic acid 174 and (S)-4-Isopropyl-dihydro-furan-2-one 175

Acetate 173 (15 g, 68.18 mmol) was dissolved in CH$_3$CN (150 mL), carbon tetrachloride (150 mL) and HPLC grade water (300 mL) and stirred. Sodium periodate (262.50 g, 1220 mmol) was added followed by ruthenium chloride (650 mg, 3.136 mmol). After overnight stirring it was diluted with ether and water, and filtered through a pad of Celite. The organic portion was separated and the aqueous phase was further extracted with ether. After drying on magnesium sulfate the solvent was evaporated. Potassium carbonate (42 g) was added to the residue and refluxed overnight in methanol (250 mL) and cooled to room temperature. After evaporation, water was added to dissolve the solid, and conc. HCl was added to bring the pH to 2. Chloroform was added and extracted overnight. The organic phase was separated, and aqueous was further extracted with chloroform. The combined organic extracts were dried, evaporated, and the product was purified on a silica gel column and the compound was eluted with 20% ether in methylene chloride. Fractions were monitored by tlc, and spots were detected with $I_2$/KI solution. Fractions were combined to give 4.6 g of lactone 175. NMR (CDCl$_3$) δ 4.38 (dd, 1H, CH$_a$H$_b$O), 3.93 (app. t, 1H, CH$_a$H$_b$O), 2.54 (dd, 1H, CH$_c$H$_d$ C=O), 2.23 (m, 2H, CHCH(Me) and CH$_c$H$_d$ C=O), 1.60 (m, 1H, CH(Me)$_2$), 0.92 (d, 3H, CH$_3$) and 0.85 (d, 3H, CH$_3$).

(3R,4R)-3-Benzyl-4-isopropyl-dihydro-furan-2-one 176

Lithium bis(trimethylsilyl)amide (1.0 M solution in THF, 92 mL, 92 mmol) was added in 3 to 5 minutes to a solution of (S)-β-(2-propyl)-γ-butyrolactone 175 (11.68 g, 91.25 mmol) in dry THF 100 mL at −78° C. under argon atmosphere. It was stirred for 1 hour and a solution of benzyl iodide (21.87 g, 100.37 mmol) in dry THF was added rapidly. Stirring was continued for 1.5 hours and quenched at −78° C. by the addition of a solution of brine followed by ethyl acetate. The organic phase was separated and the aqueous was further extracted with ether. Chromatography on silica gel first eluted with 5% methylene chloride in pet ether, and finally with 10% ether in pet ether gave desired compound 11.6 g, 58%. NMR (CDCl$_3$) δ 7.19 (m, 5H, C$_6$H$_5$), 4.02 (app. t, 1H, CH$_a$H$_b$O), 3.87 (dd, 1H, CH$_a$H$_b$O), 2.98 (d, 2H, ArCH$_2$), 2.57 (q, 1H, BnCHC=O), 2.05 (m, 1H, CHCH(Me)$_2$), 1.55 (m, 1H, CH(Me)$_2$), 0.81 (d, 3H, CH$_3$) and 0.72 (d, 3H, CH$_3$).

(2R,3R)-2-Benzyl-3-bromomethyl-4-methyl-pentanoic acid ethyl ester 177

Lactone 176 (6.5 g, 29.8 mmol) was dissolved in absolute ethanol (80 mL) and cooled in ice bath. Anhydrous HBr was bubbled through the solution for 1 hour and stirred at room temperature overnight while maintaining reaction under dry atmosphere. It was poured onto ice cooled mixture of pet ether and brine. The organic phase was separated, and the aqueous was further extracted with pet ether. The combined organic solution was washed repeatedly with cold water and dried. Solvent was removed in vacuo to give crude compound 7.0 g. NMR (CDCl$_3$) δ 7.27 (m, 5H, C$_6$H$_5$), 4.02 (m, 2H, CH$_3$CH$_2$O), 3.70 (dd, 1H, CH$_a$H$_b$Br), 3.55 (dd, 1H, CH$_a$H$_b$Br), 2.97 (m, 2H, ArCH$_2$), 2.83 (q, 1H, BnCHC=O), 2.11 (m, 1H, CHCH(Me)$_2$), 1.97 (m, 1H, CH(Me)$_2$), 1.10 (t, 3H, CH$_3$CH$_2$O), 0.96 (d, 3H, CH$_3$) and 0.93 (d, 3H, CH$_3$).

(2R,3R)-2-Benzyl-3,4-dimethyl-pentanoic acid ethyl ester 178

Bromoester 177 (7.25 g, about 80% pure), in ethanol (100 mL) containing triethylamine (3.2 mL) was hydrogenated overnight in the presence of 20% Pd/C (1.0 g). It was filtered through a pad of Celite, and the cake was washed with ethanol. Solvent was evaporated, and the residue was taken up in ether, whereupon solid (Et$_3$N.HCl) separated. The solid was removed by filtration. The filtrate was concentrated, and the procedure was repeated to eliminate all hydrochloride salt. Product was chromatographed on a silica gel column which was eluted with pet ether to give the desired debrominated compound 3.35 g. NMR (CDCl$_3$) δ 7.21 (m, 5H, C$_6$H$_5$), 3.95 (m, 2H, CH$_3$CH$_2$O), 2.85 (m, 2H, ArCH$_2$), 2.64 (q, 1H, BnCHC=O), 1.85 (m, 1H, CHCH (Me)$_2$), 1.62 (m, 1H, CH(Me)$_2$), 1.05 (t, 3H, CH$_3$CH$_2$O), 0.95 (d, 3H, CH$_3$) 0.84 (d, 3H, CH$_3$) and 0.82 (d, 3H, CH$_3$). MS gave 290 (M+CH$_3$CN), 249 (M+1), and others at 203. Further elution with ether gave lactone (2.25 g) that was carried over from previous step.

Acetic acid (2R,3R)-2-benzyl-3,4-dimethyl-pentyl-ester 179

Ethyl ester 178 (3.20 g, 12.85 mmol) was dissolved in anhydrous ether and cooled in ice bath under inert atmosphere. Lithium aluminum hydride (500 mg, 13.15 mmol) was added, and the suspension was stirred at room temperature overnight. Excess LAH was destroyed by careful addition of ethyl acetate while the reaction was stirred in ice bath. Saturated sodium sulfate was added cautiously to coagulate the alumina that separated at room temperature as white precipitate. The reaction mixture was diluted with methylene chloride, and anhydrous sodium sulfate was added to dry the mixture. After filtration the solution was concentrated to give an oil 3.0 g.

The material (3.0 g) was dissolved in dichloromethane (30 mL) and triethylamine (2.5 mL), DMAP (200 mg), and acetic anhydride (1.5 mL) were added. It was stirred at room temperature for 3 hours, and diluted with ether. The ether solution was washed with waster, 1N HCl, saturated sodium bicarbonate, brine and dried. The solution was concentrated in vacuo to give the acetoxy compound 179 3.16 g. NMR (CDCl$_3$) δ 7.19 (m, 5H, C$_6$H$_5$), 4.03 (m, 2H, CH$_3$CH$_2$O), 2.69 (m, 2H, ArCH$_2$), 2.09 (m, 1H, BnCHCH$_2$O), 2.02 (s, 3H, CH$_3$C=O), 1.68 (m, 1H, CH$_3$CHCH(Me)$_2$), 1.23 (m, 1H, CH(Me)$_2$), 0.87 (d, 3H, CH$_3$), 0.84 (d, 3H, CH$_3$) and 0.81 (d, 3H, CH$_3$).

(R)-4-((R)-1,2-Dimethyl-propyl)-dihydro-furan-2-one 180

To a solution of aromatic compound 179 (5.0 g, 20.16 mmol) in HPLC grade acetonitrile (60 mL), carbon tetrachloride (60 mL), and water (120 mL) was added sodium periodate (86.24 g, 403.32 mmol, 20 equiv.), followed by RuCl$_3$ (414 mg, 10 mol %). The mixture was stirred vigorously overnight at room temperature, and diluted with methylene chloride (400 mL). The mixture was filtered through a pad of Celite to remove the solid precipitate. The organic portion was separated, and the aqueous was further extracted with methylene chloride. After the combined organic portions concentrated, the residue was dissolved in ether and applied to a column of Florisil. The compound was eluted with 3% methanol in ether, evaporated to a paste that was dissolved in methanol (100 mL). Potassium carbonate (8.0 g) was added, and the mixture was refluxed for 6 hours. The solvent was evaporated, and the solid residue was dissolved in water. The pH was adjusted to 2 by the careful addition of concentrated HCl while being cooled in ice water bath and stirred. Chloroform (200 mL) was added to the solution and stirred as such overnight at room temperature. The organic phase was separated, and the aqueous portion was further extracted with chloroform. After drying, the solvent was evaporated to give the lactone 180 5.0 g. NMR (CDCl$_3$) δ 4.36 (app. t, 1H, CH$_a$H$_b$O), 3.85 (app. t, 1H, CH$_a$H$_b$O), 2.46 (m, 2H, CH$_c$H$_d$ C=O), 2.13 (m, 2H, CHCH$_2$C=O), 1.60 (m, 1H, CH(Me)$_2$), 1.35 (m, 1H, CH$_3$CHCH(Me)$_2$), 0.86 (d, 3H, CH$_3$) and 0.72 (t, 3H, CH$_3$).

(3R,4R)-3-Bromomethyl-4,5-dimethyl-hexanoic acid ethyl ester 181

Lactone 180 (5.0 g) was dissolved in absolute ethanol (25 mL) and flushed with argon. While being cooled in ice water bath, anhydrous HBr gas was bubbled through the mixture for 45 minutes and allowed to stand at room temperature overnight. The mixture was poured into ice-salt water and hexane. The organic phase was separated, and the aqueous was further extracted with hexane. The combined organic extract was dried and evaporated. Flash chromatography with 10% ether in pet ether on a silica gel column gave the bromoester 181 3.54 g. NMR (CDCl$_3$) δ 4.14 (q, 2H, CH$_3$H$_2$O), 3.60 (dd, 1H, CH$_a$H$_b$Br), 3.41 (dd, 1H, CH$_c$H$_b$ Br), 2.54 (dd, 1H, Ch$_a$H$_b$C=O), 2.44 (dd, 1H, Ch$_a$H$_b$C=O), 2.22 (m, 1H, O=CCH$_2$CHCH$_2$Br), 1.67 (m, 1H, CHCH$_3$CH(Me)$_2$), 1.37 (m, 1H, CH(Me)$_2$), 1.26 (t, 3H, CH$_3$CH$_2$O), 0.94 (d, 3H, CHCH$_3$CH(Me)$_2$, 0.81 (d, 3H, ((CH$_3$)$_2$)CHCH$_3$CH) and 0.79 (d, 3H, ((CH$_3$)$_2$)CHCH$_3$CH).

(3R,4R)-3-Azidomethyl-4,5-dimethyl-hexanoic acid ethyl ester 182 and Example 25 (3R,4R)-3-Aminomethyl-4,5-dimethyl-hexanoic acid Bromoester 181 (3.54 g, 13.34 mmol), sodium azide (1.04 g, 16.13 mmol) in anhydrous DMF (8.0 mL) was stirred at room temperature overnight. Water (16 mL) and hexane were added, the organic portion was separated, and the aqueous portion was further extracted with hexane. It was dried and evaporated to give azido ester 3.0 g. NMR (CDCl$_3$) δ 4.14 (q, 2H, CH$_3$H$_2$O), 3.48 (dd, 1H, CH$_a$H$_b$N$_3$), 3.21 (dd, 1H, CH$_c$H$_b$ N$_3$), 2.34 (m 2H, Ch$_a$H$_b$C=O), 2.20 (m, 1H, O=CCH$_2$CHCH$_2$N$_3$), 1.60 (m, 1H, CHCH$_3$CH (Me)$_2$. Compound was submitted for hydrogenation (HPL, 66480×100). The hydrogenated crude was dissolved in 6N HCl and refluxed overnight. The solvent was evaporated in vacuo the residue was azeotroped with toluene. The crude was further purified by loading onto an ion exchange column chromatography (Dowex 50W×b8–100), washed to neutral eluent with HPLC grade water followed by elution of compound with 0.5N NH$_4$OH solution. Crystallization of product from methanol gave 720 mg. NMR (CD$_3$OD) δ 3.04 (dd, 1H, CH$_a$H$_b$NH$_2$), 2.82 (dd, 1H, CH$_c$H$_b$ NH$_2$), 2.52(dd, 1H, Ch$_a$H$_b$C=O), 2.40(dd, 1H, Ch$_a$H$_b$C=O), 2.07(m, 1H, O=CCH$_2$CHCH$_2$NH$_2$), 1.67(m, 1H, CHCH$_3$CH(Me)$_2$, 1.35(m, 1H, CH(Me)$_2$), 0.97(d, 3H, CHCH$_3$CH(Me)$_2$, 0.88 (d, 3H, ((CH$_3$)$_2$)CHCH$_3$CH) and 0.83(d, 3H, ((CH$_3$)$_2$) CHCH$_3$CH). [α]$_D$ −5.3(c, MeOH, 1.9 mg/mL). Anal. Calcd for C$_9$H$_{19}$NO$_2$: C, 62.39; H, 11.05; N, 8.08. Found C, 62.01; H, 11.35; N, 7.88. MS showed ions at 215 (M+CH$_3$CN), 197 (M+Na$^+$), 174 (M+H$^+$). Analysis of derivative by reverse phase HPLC, Hypersil BDS C$_{18}$ 5 micron and mobile phase 50/50 CH$_3$CN-water containing 0.1% TFA gave 99.93% purity at retention time of 8.21 minutes.

EXAMPLES 26–28

Synthesis of 3-Aminomethyl-4-isopropyl-heptanoic acid

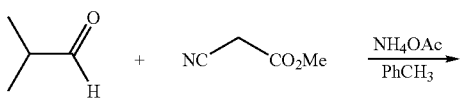

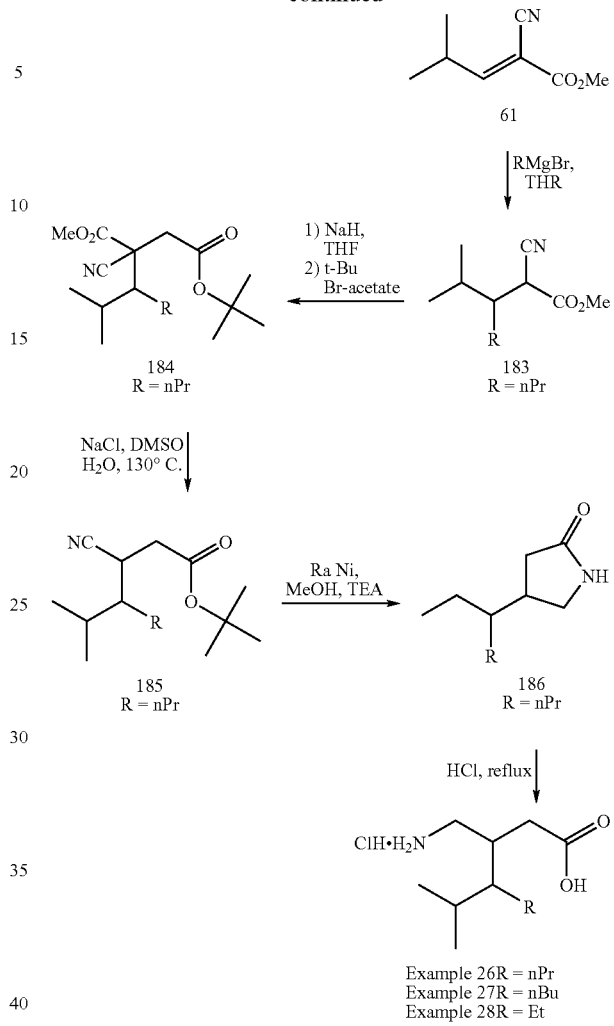

2-Cyano-4-methyl-2-pentenoic acid methyl ester 61

A solution of isobutyraldehyde (30.0 g, 416 mmol), methyl-cyano-acetate (20.6 g, 208 mmol), ammonium hydroxide (3.2 g, 41.6 mmol) and acetic acid (5.0 g, 83.2 mmol) in 500 mL of toluene is warmed to reflux under a Dean-Stark trap for 12 hours. The mixture is cooled to room temperature and extracted with saturated NaHSO$_3$ (3×100 mL), saturated NaHCO$_3$ (3×100 mL), and 100 mL of brine. The organic layer is dried over Na$_2$SO$_4$, and the solvent is evaporated. The remaining oil is distilled under high vacuum (0.5 mm Hg, B.P.=115–120° C.) to give 28.8 g of 2-cyano-4-methyl-2-pentenoic acid methyl ester 61 as an oil (90% yield).

2-Cyano-3-isopropyl-hexanoic acid methyl ester 183

A 2.0 M solution of propyl magnesium chloride in Et$_2$O (9.8 mL, 19.6 mmol) is added to a solution of 2-cyano-4-methyl-2-pentenoic acid (3.0 g, 19.6 mmol) in 50 mL of THF which is cooled in an IPA/dry ice bath to −40° C. under argon. The solution is stirred for 4 hours, and the reaction is quenched by addition of 50 mL of saturated KH$_2$PO$_4$. The THF is evaporated, and the remaining oil is chromatographed under medium pressure over silica gel with 50% CH$_2$Cl$_2$/hexane. Yield=1.9 g (50%) of 2-cyano-3-isopropyl-hexanoic acid methyl ester as an oil.

2-Cyano-2-(1-isopropyl-butyl)-succinic acid 4-tert-butyl ester 1-methyl ester 184

A solution of 2-cyano-3-isopropyl-hexanoic acid methyl ester (1.9 g, 9.6 mmol) in 10 mL of THF is added to a slurry of NaH (washed with hexane, 0.23 g, 9.6 mmol) in 20 mL of THF which is cooled in an ice water bath under argon. The solution is stirred for 10 minutes, and t-butyl bromoacetate (2.1 g, 10.6 mmol) is added. The solution is warmed to room temperature. After 12 hours, the reaction is quenched by addition of 50 mL of saturated KH$_2$PO$_4$ and the THF is evaporated. The organic products are extracted into Et$_2$O (3×50 mL), and the combined organic layers are dried over MgSO$_4$. The solvent is evaporated, and the remaining oil is chromatographed under medium pressure over silica gel in 25% hexane/CH$_2$Cl$_2$. Yield of 2-cyano-2-(1-isopropyl-butyl)-succinic acid 4-tert-butyl ester 1-methyl ester=1.3 g (42%) as an oil.

3-Cyano-4-isopropyl-heptanoic acid t-butyl ester 185

A mixture of 2-cyano-2-(1-isopropyl-butyl)-succinic acid 4-tert-butyl ester 1-methyl ester (1.3 g, 4.2 mmol), NaCl (0.25 g, 4.2 mmol), and H$_2$O (0.15 g, 8.3 mmol) in 25 mL of DMSO is warmed to 130° C. for 12 hours. The mixture is cooled to room temperature and diluted with 100 mL of brine. The organic products are extracted into Et$_2$O (3×50 mL). The organic layers are combined and washed with 50 mL of H$_2$O and 50 mL of brine. Drying over Na$_2$SO$_4$ and evaporation of the solvent gives 0.8 g (75% yield) of 3-cyano-4-isopropyl-heptanoic acid t-butyl ester as an oil.

4-(1-Isopropyl-butyl)-2-pyrrolidone 186

3-Cyano-4-isopropyl-heptanoic acid t-butyl ester (0.8 g, 3.2 mmol) is reduced under 50 psi of H$_2$ in MeOH containing TEA and Ra Ni. When the theoretical amount of H$_2$ is taken up, the catalyst is removed by filtration, and the solvent is evaporated to give 0.6 g (100% yield) of 4-(1-isopropyl-butyl)-2-pyrrolidone as an oil.

EXAMPLE 26

3-Aminomethyl-4-isopropyl-heptanoic acid 4-(1-Isopropyl-butyl)-2-pyrrolidone (0.6 g, 2.3 mmol) is warmed to reflux in 50 mL of 6.0 M HCl for 12 hours. The solution is cooled to room temperature and filtered through Celite. The filtrate is evaporated, and the solid remaining is recrystallized from MeOH/EtOAc. Yield 0.035 g (6% yield) of 3-aminomethyl-4-isopropyl-heptanoic acid as an HCl salt, mp 160–170° C. $^1$H NMR (CD$_3$OD) δ 0.9 (m, 9H), 1.30 (m, 5H), 1.78 (m, 1H), 2.30 (m, 2H), 2.45 (m, 1H), 2.95 (m, 2H). MS (APCI, CH$_3$CN, H$_2$O) 201 (M+, 100%).

EXAMPLE 27

3-Aminomethyl-4-isopropyl-octanoic acid

Prepared according to the procedure of Example 26. Yield=0.13 g (15%) of 3-aminomethyl-4-isopropyl-octanoic acid. mp=160–170° C. $^1$H NMR (CD$_3$OD) δ 0.9 (m, 9H), 1.30 (m, 7H), 1.78 (m, 1H), 2.30 (m, 1H), 2.45 (m, 2H), 2.95 (m, 2H). MS (APCI, CH$_3$CN, H$_2$O) 198 (M−17, 100%), 216 (M$^+$, 50%).

EXAMPLE 28

3-Aminomethyl-4-isopropyl-hexanoic acid

Prepared according to the procedure of Example 26. Yield=0.11 g (42%) of 3-aminomethyl-4-isopropyl-hexanoic acid. mp=170–180° C. $^1$H NMR (CD$_3$OD) δ 0.9 (m, 9H), 1.18 (m, 1H), 1.39 (m, 3H), 1.78 (m, 1H), 2.30 (m, 1H), 2.45 (m, 1H), 2.95 (m, 2H). MS (APCI, CH$_3$CN, H$_2$O) 188 (M$^+$, 100%).

EXAMPLE 29

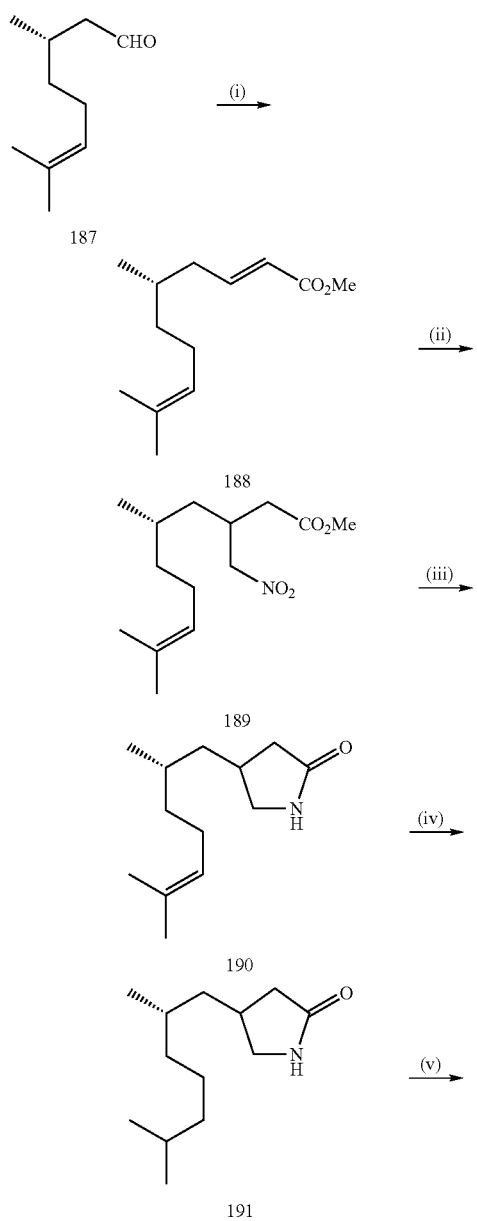

-continued

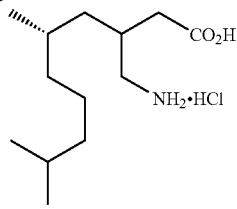

Example 29

(i) MeO₂CCH═PPh₃, THF, 40° C.;
(ii) MeNO₂, DBU;
(iii) Raney Nickel, H₂, MeOH;
(iv) Pd—C, MeOH, H₂;
(v) 6N HCl Synthesis of the Unsaturated Ester 188

(S)-(−)-citronellal 187 (2.0 mL, 11.03 mmol) was stirred at 40° C. in dry tetrahydrofuran (30 mL) with methyl triphenylphosphoranylidene acetate (3.69 g, 11.03 mmol). After 8 hours the mixture was cooled to room temperature and stirred overnight. The solvent was removed in vacuo and the residue stirred with n-pentane (50 mL). After 1 hour the solid was removed by filtration and the solvent removed in vacuo to give an oil which was purified by flash chromatography (silica, ethyl acetate:heptane 1:9) to give 2.05 g (88%) of 188 as a clear oil. $^1$H NMR (400 MHz) (CDCl₃) □0.90 (3H, d, J=6 Hz); 1.12–1.40 (2H, m); 1.60 (3H, s); 1.62 (1H, m); 1.68 (3H, s); 2.01 (3H, m); 2.21 (1H, m); 3.73 (3H, s); 5.08 (1H, m); 5.82 (1H, d, J=16 Hz); 6.94 (1H, m). MS (CI⁺)(m/z): 211(MH⁺, 75%), 179(78%), 151(100%). IR (thin film) (cm⁻¹) □: 1271, 1436, 1728, 2917.

Synthesis of the Nitroester 189

The ester 188 (2.02 g, 9.6 mmol) was dissolved in nitromethane (25 mL) with 1,8-diazabicyclo[5,4,0]undec-7-ene (1.44 mL, 9.6 mmol) and stirred at room temperature. After 23 hours the mixture was diluted with diethyl ether (150 mL) and washed with water (50 mL) and then 2N HCl (50 mL). The organic phase was collected, dried (MgSO₄), and the solvent removed in vacuo. The residue was purified by flash chromatography (silica, ethyl acetate:heptane 3:7) to give 2.26 g (87%) of 189 as a clear oil. Note that this and all subsequent compounds are equimolar mixtures of 2 diastereoisomers. $^1$H NMR (400 MHz) (CDCl₃) □0.90(2× 3H, each d, J=6 Hz); 1.09–1.58(10H, m); 1.602(6H, s); 1.685(6H, s); 1.94(4H, m); 2.42(4H, m); 2.66(2H, m); 3.70(6H, s); 4.42(4H, m); 5.07(2H, m). MS (CI⁺)(m/z): 272(MH⁺, 90%), 240(100%), 151(100%). IR (thin film) (cm⁻¹) □: 1554, 1739, 2918.

Synthesis of the Lactam 191

The nitro ester 189 (2.09 g, 7.7 mmol) was dissolved in methanol (75 mL) and shaken over Raney Nickel (catalytic, prewashed with water and then methanol) under an atmosphere of hydrogen gas (39 psi) at 35° C. After 17 hours the mixture was filtered through Celite. The solvent was removed in vacuo to give an oil. $^1$H NMR showed there had been partial reduction of the double bond so this was carried on without further purification. A sample of this partial reduced product (440 mg, 2.1 mmol) was dissolved in methanol (40 mL) and shaken over 5% Pd—C under an atmosphere of hydrogen gas. After 18 hours the catalyst was removed by filtration through Celite to obtain 442 mg (99% from partial reduced material) as a clear oil which did not need purification. Note that this and all subsequent compounds are equimolar mixtures of 2 diastereoisomers. $^1$H NMR (400 MHz) (CDCl₃) □: 0.88(18H, m); 1.04–1.58 (20H, m); 1.96(2H, m); 2.40(2H, m); 2.58(2H, m); 2.98(2H, m); (3.45(2H, m), 5.82(2H, br s). MS (CI⁺) (m/z): 212 (MH⁺, 100%).

Synthesis of Example 29

The lactam 191 (428 mg, 2.0 mmol) was heated to reflux in 6N HCl (20 mL). After 5 hours the mixture was cooled to room temperature and washed with dichloromethane (2×10 mL). The aqueous phase was collected and the solvent removed in vacuo. The residue was dissolved in water (10 mL) and freeze-dried to give 382 mg (71%) of Example 29 as a white solid. Note that this compound is an equimolar mixture of 2 diastereoisomers. $^1$H NMR (400 MHz) (d₆-DMSO) □0.82 (18H, m); 0.95–1.55 (20H, m); 2.05–2.45 (6H, m); 2.75 (4H, m); 7.98 (6H, br s). MS (CI⁺) (m/z): 230 ([MH−HCl]+, 90%), 212 (100%). Microanalysis: Calculated for C₁₃H₂₈NO₂Cl: C, 58.74; H, 10.62; N, 5.27. Found: C, 58.46; H, 10.50; N, 5.33.

To one skilled in the art, the use of (R)-(+)-citronellal would afford compounds of opposite C5-stereochemistry to Example 29.

Syntheses of compounds of Formulas (1A) or (1B) are described below in Scheme 19 and Examples 30–33.

Tetrazoles of Formula (1A) can be synthesized by the route outlined in Scheme 19.

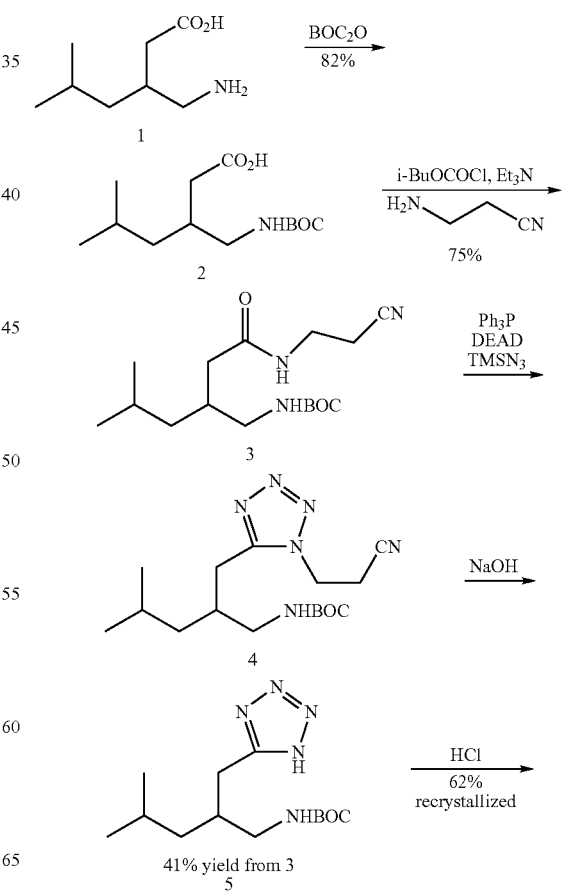

-continued

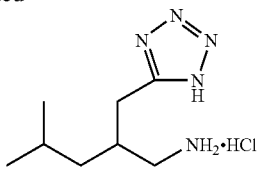

The following examples are illustrative of the instant invention, they are not intended to limit the scope.

EXAMPLE 30

4-Methyl-2-(1H-tetrazol-5-ylmethyl)-pentylamine

Compound 3 in Scheme 19 {2-[(2-Cyano-ethylcarbamoyl)-methyl]-4-methyl-pentyl}-carbamic acid tert-butyl ester A solution of compound 2 (8.0 g, 0.03 mol) (prepared in the usual manner from $(BOC)_2$ and pregabalin) was taken up in 250 mL dry THF and cooled in an ice water bath. Triethyl amine (4.62 mL, 0.033 mol) was added followed by the addition of isobutyl chloroformate (4 mL, 0.031 mol). The reaction was stirred a 0° C. for about 15 minutes during which time a precipitate formed. In a separate flask was placed 3-aminoproprionitrile fumarate (3.95 g, 0.03 mol) in 35 mL of 1 M NaOH and 300 mL of THF. This mixture was cooled to 0° C. and treated with the mixed anhydride formed above in four portions. Before each portion was added, 35 mL of 1 M NaOH was added to the mixture. The reaction was stirred for 24 hours and was then concentrated to remove THF. The resulting aqueous was extracted with three times ethyl acetate. The combined organic extracts were washed with brine, dried over magnesium sulfate. The solvents were removed under pressure to give 6.6 g green oil. MS(APCI) m/z 312 (M+1).

Compound 4 in Scheme 19 [4-Methyl-2-(1-(2-cyano-ethyl)-tetrazol-5-ylmethyl)-pentyl]-carbamic acid tert-butyl ester and compound 5 [4-Methyl-2-(1H-tetrazol-5-ylmethyl)-pentyl]-carbamic acid tert-butyl ester The cyanoamide (6.5 g, 0.0209 mol) and triphenylphosphine (11.06 g, 0.042 mol) were dissolved in 300 mL of dry THF. The solution was treated with DEAD (6.7 mL, 0.0425 mol) and $TMSN_3$ (5.75 mL, 0.043 mol). The reaction was stirred for 24 hours, and the reaction mixture was cooled to 0° C. and treated with 900 mL of an aqueous solution containing 46.9 g of $(NH_4)_2Ce(IV)NO_3$. The reaction mixture was concentrated to remove THF and extracted with three portions of $CH_2Cl_2$. The combined organic layers were dried with brine and $Na_2SO_4$, and the solvents were removed under reduced pressure to give a clear oil which was passed through a plug of silica gel to give the product admixed with triphenylphosphine oxide. This crude mixture was dissolved in 200 mL THF and 50 mL of 2N NaOH. The mixture was heated to reflux for 2 hours then stirred at room temperature overnight. The THF was removed under reduced pressure and the resulting residue diluted with water. After extraction with ether, the aqueous phase was acidified to pH 7 and extracted with 21 mL of 4N HCl. The aqueous phase was then saturated with solid $KH_2PO_4$. The aqueous mixture was extracted with $CH_2Cl_2$. The organic extracts were washed with brine and dried over $Na_2SO_4$. Evaporation if the organic solvents under reduced pressure resulted in isolation of 3.4 g of an amber oil.

4-Methyl-2-(1H-tetrazol-5-ylmethyl)-pentylamine

The material from the previous step (0.9 g, 3.18 mmol) was taken up in 20 mL of 4 M HCl in dioxane. The reaction was allowed to stand for 1 hour. A solid formed, 10 mL of ether was added, and the reaction was filtered to give Example 30 as 780 mg of a white solid; MS(APCI) m/z 184 (M+1).

EXAMPLE 31

IsobutylGABA oxadiazolonethione (G) is also named 3-(2-Aminomethyl-4-methyl-pentyl)-4H-[1,2,4]oxadiazole-5-thione; HCl

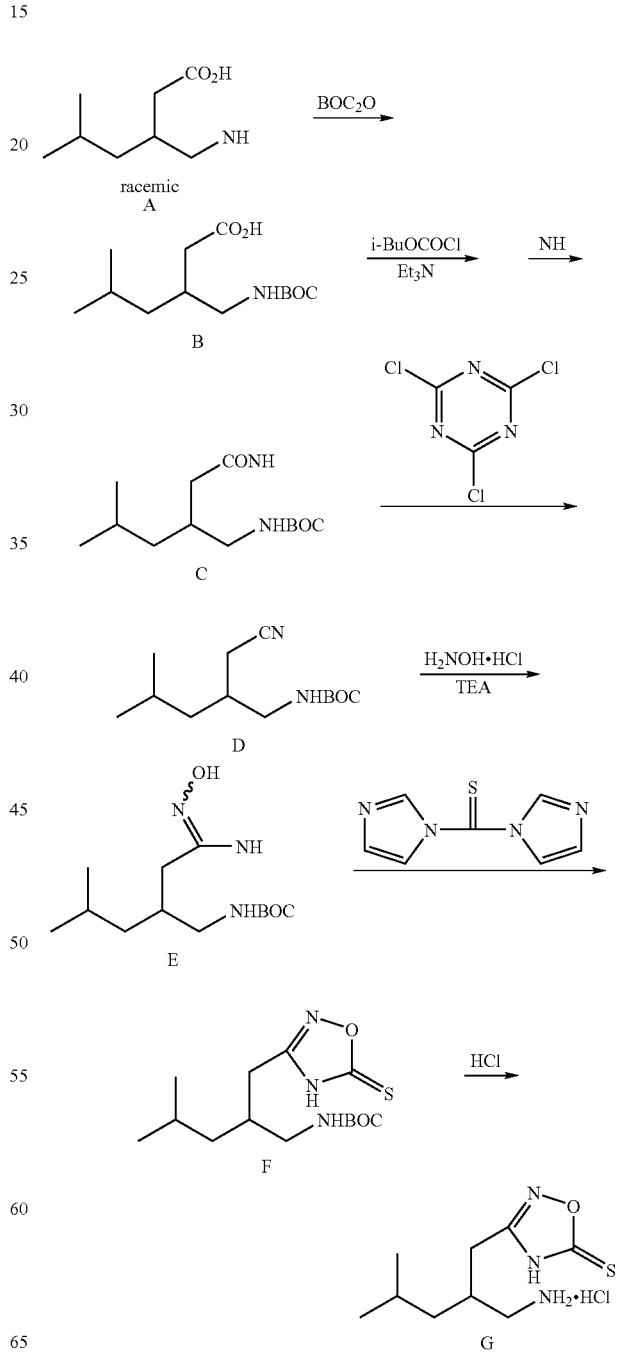

BOC-IsobutylGABA (B)

A solution of di-tert-butyl dicarbonate (13.1 g, 0.06 mol) in THF (200 mL) was added, over a 10-minute period, to a solution of isobutylGABA (9.95 g, 0.056 mol) in 1N NaOH (125 mL) and THF (50 mL) cooled in an ice-water bath. The reaction mixture was stirred at room temperature 3 hours, concentrated to remove THF, saturated with saturated $KH_2PO_4$ and extracted 3× EtOAc. The extracts were washed 2× brine, dried over $MgSO_4$, and evaporated to yield 13.8 g (95%) of a white solid, mp 84–88° C. MS (APCI) m/z 260 (M+1).

BOC-IsobutylGABA amide (C)

A solution of BOC-IsobutylGABA (6.78 g, 0.026 mol) and triethylamine (3.0 g, 0.030 mol) was cooled to 0° C. and isobutyl chloroformate (3.9 g, 0.029 mol) was slowly added. After stirring 20 minutes at 0° C., ammonia gas was bubbled into the reaction mixture for 30 minutes, and then the mixture was stirred at room temperature 18 hours. The mixture was concentrated to remove THF, suspended in water, and extracted 3× EtOAc. The extracts were washed 1×10% $Na_2CO_3$, 2× brine, and dried over $Na_2SO_4$. Evaporation yielded 4.9 g (73%) of an oil which was used without further purification. MS (APCI) m/z 259 (M+1).

BOC-IsobutylGABA nitrile (D)

A solution of BOC-IsobutylGABA amide (4.6 g, 0.0178 mol) in DMF (15 mL) was added, all at once, to cyanuric chloride (1.66 g, 0.009 mol) and stirred 30 minutes at room temperature. The reaction mixture was poured into a cold solution of NaHCO3 (4.2 g, 0.05 mol) in water (150 mL). Solid $K_2CO_3$ was added to bring the pH to 9 and the mixture was extracted 2×$CH_2Cl_2$, washed 1× brine, and dried over $Na_2SO_4$. Evaporation yielded an oil, which was filtered through silica gel, eluting with $CH_2Cl_2$_EtOAc which yielded 3.8 g oil (89%), which was used without further purification. MS (APCI) m/z 240 (M), 239 (M−1); IR (Film) 2215 $cm^{-1}$.

BOC-IsobutylGABA amidoxime (E)

A solution of hydroxylamine was prepared by adding triethylamine (7.62 g, 0.075 mol) to a suspension of hydroxylamine hydrochloride (5.21 g, 0.075 mol) in DMSO (25 mL). After 15 minutes, the triethylamine hydrochloride was filtered off, and BOC-IsobutylGABA nitrile (3.61 g, 0.015 mol) was added to the filtrate. The mixture was heated at 75° C. for 17 hours. The mixture was diluted with water and extracted 3× EtOAc. The extracts were washed 2× brine, dried over $Na_2SO_4$, and evaporated to give an oil which was filtered through a short silica gel column, eluting with $CH_2Cl_2$_EtOAc to give 3.2 g (78%) oil. $^1$H NMR (CDCl$_3$) δ 0.84 (d, 6H, J=6.35 Hz), 1.11 (m, 2H), 1.40 (s, 9H), 1.63 (m, 1H), 3.05 (m, 1H), 3.15 (m, 1H), 4.85 (m, 1H), 5.43 (m 1H); MS (APCI) 274 (M+1).

BOC-IsobutylGABA oxadiazolonethione (F)

A solution containing BOC-IsobutylGABA amidoxime (0.59, 0.00183 mol), DBU (1.129, 0.00736 mol) and 90% 1,1'-thiocarbonyldiimidazole (0.398 g, 0.002 mol) in MeCN (12 mL) was stirred at room temperature 16 hours. The reaction mixture was evaporated to dryness, taken up in EtOAc, and washed with $KHSO_4$ solution. The EtOAc layer was extracted with 1N NaOH (100 mL). The alkaline extract was washed with $Et_2O$ and acidified with saturated $KH_2PO_4$ and extracted 3× EtOAc. The extracts were washed 1× water, 1× brine and dried over $MgSO_4$. Evaporation yielded an oil, 0.25 g (43%). $^1$H NMR (CDCl$_3$) δ 0.84 (d, 6H, J=6.59 Hz), 1.1 (m, 2H), 1.41 (s, 9H), 1.65 (m, 1H), 1.85 (m, 1H), 2.60 (m, 2H), 3.1 (m, 2H), 4.94 (m, 1H), 12.8 (s, 1H). MS (APCI) 316 (M+1).

IsobutylGABA oxadiazolonethione (G) is also named 3-(2-Aminomethyl-4-methyl-pentyl)-4H-[1,2,4]oxadiazole-5-thione; HCl BOC-IsobutylGABA oxadiazolonethione (0.25 g, 0.79 mmol) was taken up in 4 M HCl in dioxane (10 mL) at room temperature for 1 hour. Evaporation followed by recrystallization of the residue from MeCN yielded Example 31 as cream-colored crystals, 0.108 g, mp 183–185° C. $^1$H NMR (DMSO-d$^6$) δ 0.84 (d, 6H, J=6.59 Hz), 1.1 (m, 2H), 1.41 (s, 9H), 1.65 (m, 1H), 0.80 (d, 6H, J=6.59 Hz), 1.06 (m, 1H), 1.25 (m, 1H), 1.55 (m, 1H), 2.1 (m, 1H), 2.7 (m, 4H), 7.95 (s, 3H); MS (APCI) 216 (M+1). Anal. Calcd for $C_9H_{17}N_3OS$—HCl: C, 42.93; H, 7.21; N, 16.69; Cl, 14.08. Found: C, 43.38; H, 7.24; N, 16.29; Cl, 14.17.

EXAMPLE 32

IsobutylGABA oxadiazolone (J) is also named 3-(2-Aminomethyl-4-methylpentyl)-4H-[1,2,4]oxadiazole-5-one HCl

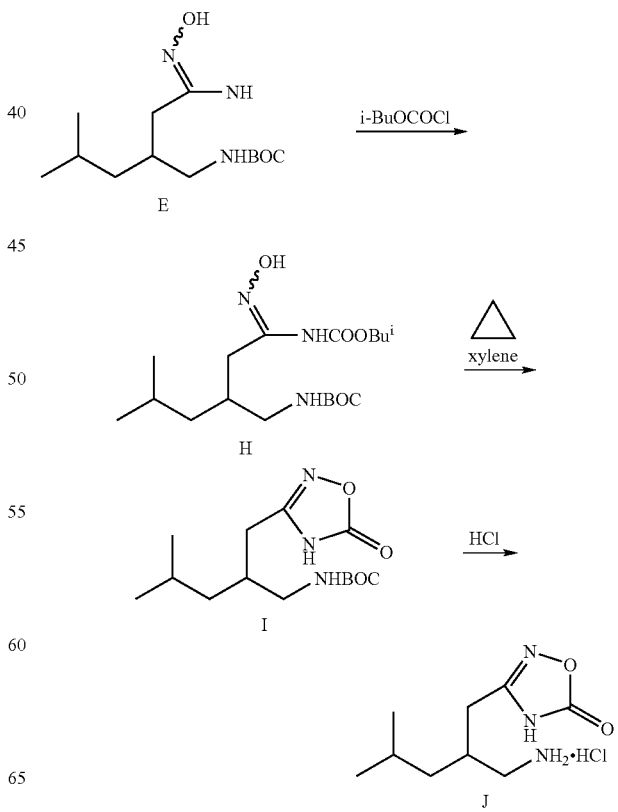

BOC-IsobutylGABA amidoxime carbamate (H)

Isobutyl chloroformate (0.253 g, 0.00185 mol) was added dropwise to a solution of BOC-IsobutylGABA amidoxime (0.5 g, 0.00183 mol) and pyridine (0.158 g, 0.002 mol) in DMF (10 mL) at 0° C. After 30 minutes at that temperature, the reaction mixture was diluted with water and extracted 3× EtOAc. The extracts were washed 1× water, 1× brine and dried over MgSO$_4$ Evaporation yielded an oil, 0.7 g (100%) which was used without further purification. MS (APCI) m/z 374 (M+1).

BOC-IsobutylGABA oxadiazolone (I)

BOC-IsobutylGABA amidoxime carbamate (0.7 g, 0.00183 mol) was taken up in xylene (20 mL) and heated under reflux 2 hours. Evaporation yielded a dark glassy oil which was taken up in Et$_2$O and extracted with 1N NaOH. The alkaline phase was acidified with saturated KH$_2$PO$_4$ and extracted 3× EtOAc. The extracts were washed with brine, dried over MgSO$_4$ and evaporated to yield a brown oil, 0.25 g (46%), which was used without further purification. MS (APCI) m/z 300 (M+1).

IsobutylGABA oxadiazolone (J) is also named 3-(2-Aminomethyl-4-methylpentyl)-4H-[1,2,4]oxadiazole-5-one; HCl BOC-IsobutylGABA oxadiazolone (0.25 g, 0.835 mmol) was taken up in 4 M HCl in dioxane and allowed to stand 2.5 hours. Evaporation followed by recrystallization of the residue from MeCN-Et$_2$O yielded Example 32 as a tan solid, 53 mg (27%), mp 181–184° C. $^1$H NMR (DMSO-d$^6$) δ 0.80 (d, 6H, J=6.35 Hz), 1.1 (m, 2H), 1.25 (s, 9H), 1.60 (m, 1H), 2.10 (m, 1H), 2.5–2.8 (m, 4H), 7.95 (s, 3H), 12.39 (s, 1H). MS (APCI) 216 (M+1). Anal. Calcd for C$_9$H$_{17}$N$_3$O$_2$·HCl: C, 45.86; H, 7.70; N, 17.83; Cl, 15.04. Found: C, 45.40; H, 7.55; N, 16.79; Cl, 15.81.

EXAMPLE 33

Preparation of (2-Aminomethyl-4-methyl-pentyl)-phosphonic acid (9)

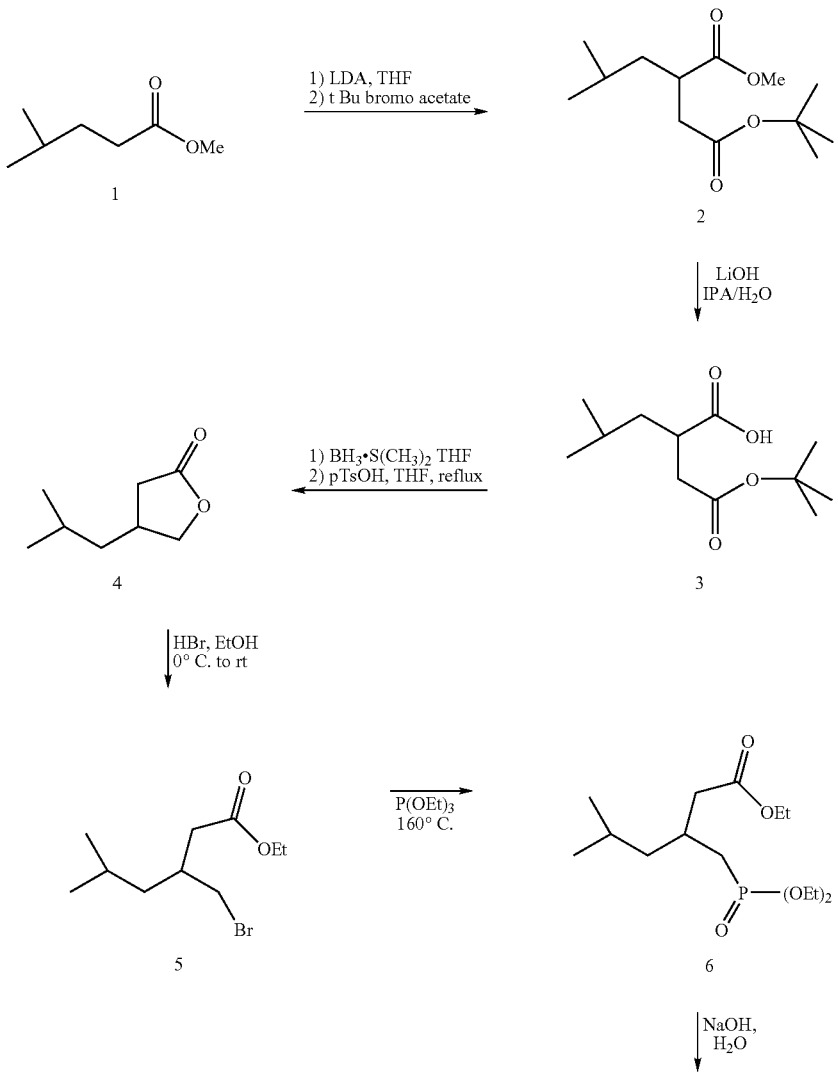

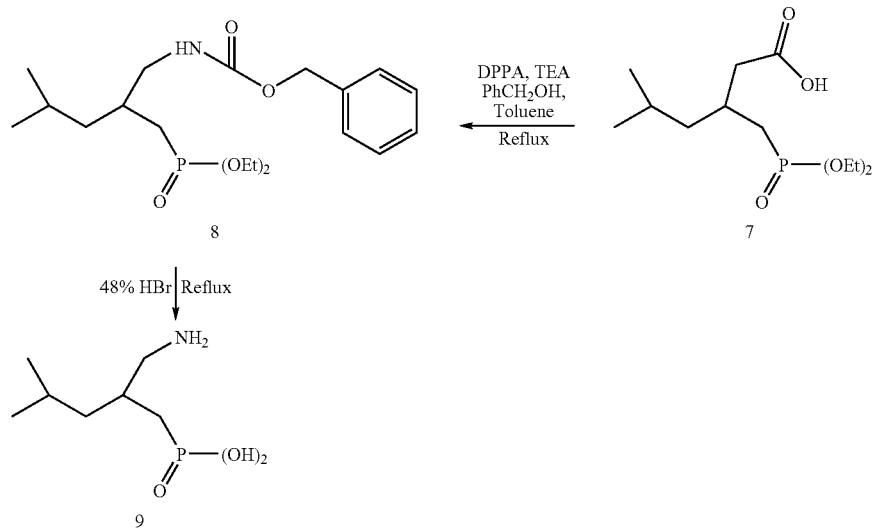

Preparation of 2-Isobutyl-succinic acid-4-t-butyl ester-1-methyl ester (2): 4-Methylpentanoic acid methyl ester (10.0 g, 76.8 mmol) is added to a solution of LDA in 150 mL of THF at −78° C. under Ar. After 15 minutes, the anion solution is added by cannula to a solution of t-butyl bromoacetate (22.5 g, 115.2 mmol) in 50 mL of THF at −78° C., and the solution is stirred for 45 minutes. The reaction mixture is then warmed to room temperature, and treated with 100 mL of saturated $KH_2PO_4$. The THF is evaporated, and the organics are extracted into $Et_2O$ (3×50 mL). The $Et_2O$ is washed with 10% $Na_2S_2O_3$ and dried with $MgSO_4$. The solvent is evaporated, and the remaining oil is distilled under vacuum (0.1 mm Hg) to give 11.1 g (59% yield) of 2-isobutyl-succinic acid-4-t butyl ester-1-methyl ester boiling at 65° C. to 72° C. NMR ($H^1$, 400 MHz, $CDCl_3$) δ 0.9 (6H, m); δ 1.2 (1H, m); δ 1.4 (9H, s); δ 1.5 (2H, m); δ 2.3 (1H, dd); δ 2.5 (1H, dd); δ 2.8 (1H, m); δ 3.6 (3H, s).

Preparation of 2-Isobutyl-succinic acid-4-t-butyl ester (3)

2-Isobutylsuccinic acid-4-t-butyl ester-l-methyl ester (11.1 g, 45.4 mmol) and $LiOH.H_2O$ (2.0 g, 47.7 mmol) are stirred in 180 mL of 3:1 $IPA/H_2O$ at room temperature overnight. The reaction mixture is extracted with $Et_2O$ (3×25 mL). The aqueous phase is acidified to pH=4, with saturated $KH_2PO_4$ and extracted with $Et_2O$ (3×50 mL). The $Et_2O$ is dried over $MgSO_4$, and evaporated to give 8.0 g (77% yield) of 2-isobutyl-succinic acid-4-t-butyl ester as an oil. NMR ($H^1$, 400 MHz, $CDCl_3$) δ 0.9 (6H, m); δ 1.3 (1H, m); δ 1.4 (9H, s); δ 1.6 (2H, m); δ 2.3 (1H, dd); δ 2.6 (1H, dd); δ 2.8 (1H, m).

Preparation of 4-Isobutyl-dihydro-furan-2-one (4)

A solution of 2-isobutyl-succinic acid-4-t-butyl ester (8.0 g, 34.7 mmol) in 100 mL of THF is cooled to 0° C. under Ar and borane dimethyl sulphide complex (2.6 g, 34.7 mmol) is added. The reaction mixture is stirred at 0° C. for 10 minutes, and at room temperature overnight. The solution is cooled to 0° C. and 100 mL of MeOH is added. The solvents are evaporated, and the remaining oil is dried under hi-vacuum for 2 hours. The oil remaining is taken up in 100 mL of THF, and a catalytic amount of p-toluene sulfonic acid is added. The solution is warmed to reflux overnight. After being cooled to room temperature, the solvent is evaporated, and the oil is taken up in $Et_2O$ (100 mL). The $Et_2O$ solution is extracted with 2.0N $Na_2CO_3$ (2×50 mL) followed by 100 mL of brine and dried over $MgSO_4$. Evaporation of $Et_2O$ followed by medium pressure chromatography (MPLC) of the remaining oil in 20% EtOAc/Hexanes gives 4.4 g (89% yield) of 4-isopropyl-dihydro-furan-2-one as an oil. NMR ($H^1$, 400 MHz, $CDCl_3$) δ 0.9 (6H, m); δ 1.3 (2H, dd); δ 1.5 (1H, m); δ 2.1 (1H, m); δ 2.6 (2H, m); δ 3.6 (1H, m); δ 4.4 (1 H, m).

Preparation of 3-Bromomethyl-3-isobutyl-propionic acid ethyl ester (5)

A solution of 4-isopropyl-dihydro-furan-2-one (4.4 g, 30.9 mmol) in absolute EtOH (50 mL) is cooled to 0° C. and saturated with HBr by passing HBr gas through it for 10 minutes. The solution is warmed to room temperature and stirred for 2.5 hours. It is diluted with 150 mL of brine and extracted with $Et_2O$ (3×100 mL). Drying over $MgSO_4$ followed by evaporation of the solvent gives 4.9 g (63% yield) of 3-bromomethyl-3-isobutyl-propionic acid ethyl ester as an oil. NMR ($H^1$, 300 MHz, $CDCl_3$) δ 0.9 (6H, d); δ 8 1.3 (5H, m); δ 1.6 (1H, m); δ 2.3 (1 H, m); 8 2.5 (1H, dd); δ 3.2 (1H, dd); δ 3.6 (1H, dd); δ 4.1 (2H, q).

Preparation of 3-(Diethoxy-phosphorylmethyl)-5-methyl-hexanoic acid ethyl ester (6)

3-Bromomethyl-3-isobutyl-propionic acid ethyl ester (4.6 g, 18.3 mmol) is warmed in a 170° C. oil bath under Ar. Triethyl phosphite (3.6 g, 22 mmol) is added dropwise over 2 hours. When addition is complete, the oil bath temperature is raised to 190° C. for 4 hours. The reaction mixture is cooled to room temperature, and the product is purified by MPLC in EtOAc to give 2.7 g (48% yield) of 3-(diethoxy-phosphorylmethyl)-5-methyl-hexanoic acid ethyl ester. NMR ($H^1$, 400 MHz, $CDCl_3$) δ 0.8 (6H, d); δ 1.2 (5H, m); δ 1.3 (6H, m); δ 1.6 (1H, m); δ 1.7 (1H, d); δ 1.8 (1H, d); δ 2.3 (2H, m); δ 2.5 (1H, dd); δ 4.1 (6H, m).

Preparation of 3-(Diethoxy-phosphorylmethyl)-5-methyl-hexanoic acid (7)

3-(Diethoxy-phosphorylmethyl)-5-methyl-hexanoic acid ethyl ester (1.0 g, 3.2 mmol) and NaOH (1.8 mL, 2.0 M) are combined in 10 mL of EtOH at 0° C. After 15 minutes, the reaction mixture is warmed to room temperature and stirred overnight. The EtOH is evaporated, and 50 mL of 2.0 M NaOH is added. The solution is extracted with $Et_2O$ (2×50 mL), and then acidified to pH=1 with concentrated HCl. The acidic solution is extracted with EtOAc (3×50 mL), and the combined extracts are dried over $MgSO_4$ and evaporated to give 0.65 g (72% yield) of 3-(diethoxy-phosphorylmethyl)-5-methyl-hexanoic acid as an oil. NMR ($H^1$, 400 MHz, $CDCl_3$) δ 0.9 (6H, d); δ 1.3 (8H, m); δ 1.6 (1H, m); δ 1.8 (2H, m); δ 2.3 (1 H, m); δ 2.5 (2H, m); δ 4.1 (4H, m).

Preparation of [2-(Benzyloxycarbonylamino-methyl)-4-methyl-pentyl)phosphonic acid diethyl ester (8)

A solution 3-(Diethoxy-phosphorylmethyl)5-methyl-hexanoic acid (0.65 g, 2.3 mmol), diphenyl-di-phosphoryl-azide (0.76 g, 2.8 mmol), triethyl amine (0.47 g, 4.6 mmol), and benzyl alcohol (0.5 g, 4.6 mmol) in 100 mL of toluene is warmed to reflux overnight. The toluene is evaporated, and the remaining oil is taken up in 50 mL of EtOAc. The EtOAc solution is washed with 1.0N HCl (2×50 mL), saturated $NaHCO_3$ (2×50 mL), and 50 mL of brine. Drying over $Na_2SO_4$ followed by evaporation of the solvent gives an oil which is purified by MPLC in EtOAc. Yield of [2-(benzyloxycarbonylamino-methyl)-4-methyl-pentyl]-phosphonic acid diethyl ester=0.46 g (52%). NMR ($H^1$, 400 MHz, $CDCl_3$) δ 0.9 (6H, m); δ 1.1–1.4 (9H, m); 1.7 (2H, m); δ 2.0 (1H, m); δ 3.1 (1H, m); δ 3.3 (1H, m); δ 4.1 (4H, q); δ 5.0 (2H, s); δ 5.7 (1H, bs); δ 7.3 (5H, m).

Preparation of (2-Aminomethyl-4-methyl-pentyl)-phosphonic acid (9)

A solution of 2-(benzyloxycarbonylamino-methyl)-4-methyl-pentyl]-phosphonic acid diethyl ester (0.46 g, 1.2 mmol) in 20 mL of 47% aqueous HBr is warmed at reflux overnight. The solution is cooled to room temperature, and the $H_2O$ is evaporated. The remaining solid is taken up in 10 mL of $H_2O$, filtered through Celite® 545, and passed through a Dowex® 50 ion exchange column (Bed Volume=30 mL). The column is eluted with 200 mL of $H_2O$, 150 mL of 3% $NH_4OH$, and 150 mL of 10% $NH_4OH$. The basic eluates are combined and evaporated to give 0.14 g of a white solid. After drying under vacuum at 60° C. with $P_2O_2$, the yield of 0.11 g (47%) of Example 33, (2-Aminomethyl-4-methyl-pentyl)-phosphonic acid, was obtained. NMR ($H^1$, 400 MHz, $CD_3OD$) δ 0.9 (6H, m); δ 1.2 (2H, t); δ 1.4 (1H, m); δ 1.7 (2H, m); δ 2.1 (1H, m); δ 2.7 (1H, dd); δ 3.0 (1H, dd). MS (m/e) 196 (M+1, 100%. Analysis for $C_7H_{18}NO_3P$: Calculated: C, 43.07; H, 9.29; N, 7.18. Found: C, 43.08; H, 8.62; N, 6.89.

The following examples are illustrative of the preparation of compounds of Formulas V–VIII.

EXAMPLE 34

(±)-(1α,6β)(2-Aminomethyl-octahydro-inden-2-yl)-acetic acid hydrochloride

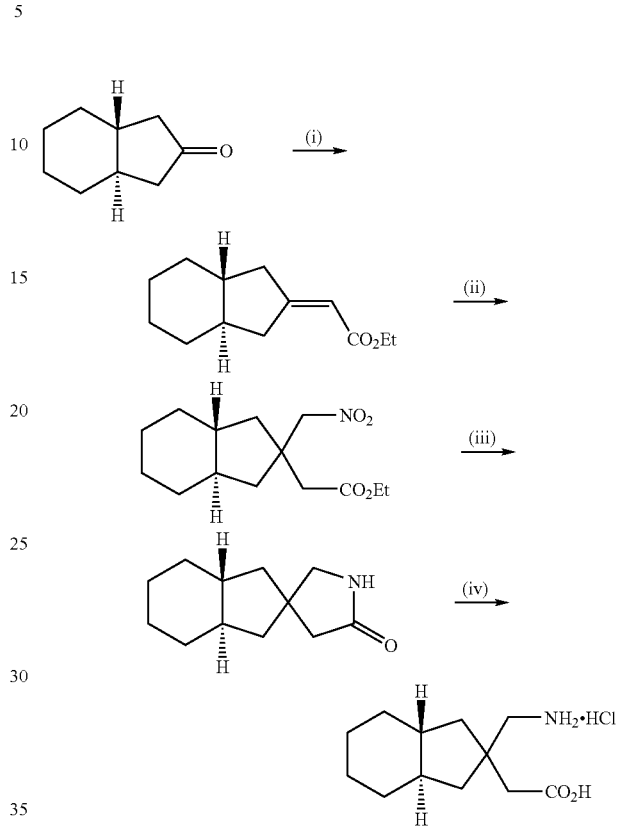

Step (i)

Sodium hydride (0.11 mg, 2.7 mmol) was stirred with THF (5 mL) at 0° C. under argon. Triethylphosphonoacetate (0.5 mL) was added dropwise and the solution stirred for 10 minutes. The ketone (0.37 g, 7.7 mmol) in THF (5 mL) was added dropwise with stirring and left to warm to room temperature. After 18 hours, the reaction mixture was separated between water (80 mL) and diethyl ether (3×20 mL). Solvent was removed in vacuo to give a yellow oil, which was purified via flash chromatography (silica, heptane/EtOAc 19:1). To give 0.34 g (62%) of the ester as a colorless oil:

$^1$H NMR ($CDCl_3$) (400 MHz): 1.05–1.29 (9H, m, ring protons+$CH_3$), 1.76–1.78 (2H, m, ring protons), 1.87–1.97 (2H, m, ring protons), 2.0–2.16 (2H, m, ring protons), 2.51–2.56 (1H, dd, J=5.7, 27.5 Hz, ring protons), 3.12–3.18 (1 H, dd, J=5.4, 18.8 Hz, ring protons), 4.12–4.20 (2H, m, $CH_2$), 5.77 (1H, s, CH). MS ($ES^+$) m/e 209 [M+H]$^+$ 100%.

Step (ii)

Ester (0.34 g, 1.63 mmol) was dissolved in THF (5 mL), with stirring under argon. Nitromethane (0.25 mL) was added and the reaction mixture heated to 60° C. TBAF (2.3 mL) was added dropwise to the hot solution over 1 hour and stirred for 4 hours. The reaction mixture was partitioned between 2N HCl and diethyl ether, and the diethyl ether layer was washed with brine. Solvent was removed in vacuo to give a yellow oil, which was purified via flash chromatography (silica, heptane/EtOAc, 19:1), to give 0.264 g (60%) of the product as a colorless oil.

¹H NMR (CDCl₃) (400 MHz): δ 0.97–1.30 (11H, m, ring protons+CH₃), 1.73–1.95 (6H, m, 2×CH+4 ring protons), 2.5 (1H, d, J=16.6 Hz, CH₂CO₂Et), 2.7 (1H, d, J=16.6 Hz, CH₂CO₂Et), 4.12–4.18 (2H, m, CH₂), 4.49–4.51 (1H, d, J=11.5 Hz, CH₂NO₂), 4.73–4.75 (1H, d, J=11.5 Hz, CH₂NO₂).

Step (iii)

Nitroester (0.24 g, 0.9 mmol) was dissolved in methanol with Nickel sponge. Reaction was hydrogenated at 50 psi, 30° C. for 15 hours. The reaction mixture was filtered through celite, and the solvent removed in vacuo to give the product 0.18 g (85%) as a yellow solid. This product was a mixture of lactam and amino ester.

Step (iv)

Amino ester was taken up in 6N HCl (5 mL) and dioxane (2.5 mL), and heated to reflux for 4 hours. The solution was washed with dichloromethane (3×5 mL), and the aqueous fraction was evaporated in vacuo to give 0.196 g (99%) of Example 34 as a colorless solid.

¹H NMR (DMSO) (400 MHz): δ 0.86–1.04 (2H, m), 1.08–1.17 (6H, m), 1.60–1.78 (6H, m), 2.35–2.39 (1H, d, J=16 Hz, CH₂CO₂H), 2.46 (1H, m, CH₂CO₂H), 2.83–2.87 (1H, d, J=13 Hz, CH₂NH₂), 2.97–3.00 (1H, d, J=13 Hz, CH₂NH₂), 7.91 (2H, bs, NH₂). MS (ES⁺) m/e 212 [M+H]⁺ 100%. HPLC, Prodigy C18 column, 5% methanol/acetonitrile. Retention time=3.00 minutes, and a purity of 99%.

EXAMPLE 35

(±)-(1α,5β)(2-Aminomethyl-octahydro-pentalen-2-yl)-acetic acid hydrochloride

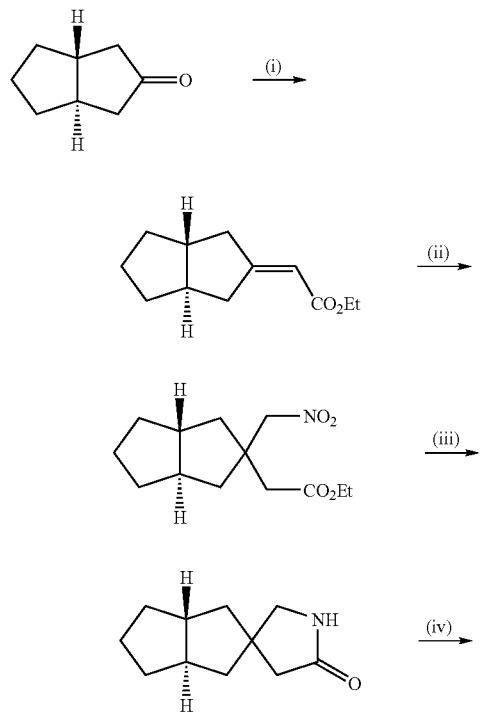

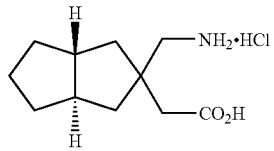

Step (i)

Sodium hydride (0.6 g, 14.5 mmol) was stirred with THF (50 mL) at 0° C. under argon. Triethylphosphonoacetate (2.9 mL) was added dropwise and the solution stirred for 10 minutes. The ketone (1.8 g, 14.5 mmol) in THF (10 mL) was added dropwise with stirring and left to warm to room temperature. After 18 hours, the reaction mixture was separated between water (250 mL) and diethyl ether (3×50 mL). Solvent was removed in vacuo to give a yellow oil, which was purified via flash chromatography (silica, heptane/EtOAc 19:1). To give 1.95 g (69%) of the ester was a colorless oil. ¹H NMR (CDCl₃) (400 MHz): δ 1.14–1.19 (2H, m, CH₂), 1.25–1.29 (3H, m, CH₃), 1.55–1.79 (4H, m, 2×CH₂), 2.03–2.10 (4H, m, 2×CH₂), 2.45–2.55 (1H, dd, CH), 3.05–3.15 (1H, dd, CH), 4.12–4.17 (2H, q, J=7.3, 14.4 Hz, COCH₂), 5.76 (1H, m, CH).

Step (ii)

Ester (1.9 g, 10 mmol) was dissolved in THF (15 mL), with stirring under argon. Nitromethane (1.4 mL) was added, and the reaction mixture heated to 60° C. TBAF (14 mL) was added dropwise to the hot solution over 1 hour, and stirred for 5 hours. The reaction mixture was separated between 2N HCl and diethyl ether, and then the ether layer was washed with brine. Diethyl ether was removed in vacuo to give an orange oil, which was purified via flash chromatography (silica, heptane/EtOAc, 19:1), to give 1.59 g (64%) of the product as a colorless oil. ¹H NMR (CDCl₃) (400 MHz): δ 1.14–1.31 (7H, m, CH₃+ring protons), 1.64–1.72 (5H, m, ring protons), 1.03–1.09 (1H, m, ring protons), 2.00–2.05 (2H, m, ring protons), 2.57–2.61 (1H, d, J=16.4 Hz, CH₂CO₂Et), 2.71–2.75 (1H, d, J=16.4 Hz, CH₂CO₂Et), 4.12–4.18 (2H, q, J=7.1, 14.2 Hz, OCH₂CH₃), 4.56–4.59 (1H, d, J=11.5 Hz, CH₂NO₂), 4.77–4.80 (1H, d, J=11.5 Hz, CH₂NO₂). IR (neat) 2957, 2870, 1731, 1547, 1374, 1182, 1030 cm⁻¹.

Step (iii)

Nitroester (1.59 g, 5.9 mmol) was dissolved in methanol (40 mL) with Nickel sponge. Reaction was hydrogenated at 50 psi, 30° C. for 5 hours. The reaction mixture was filtered through celite, and the solvent removed in vacuo to give the lactam 1.08 g (97%) as an off-white solid. ¹H NMR (CDCl₃) (400 MHz): δ 1.08–1.11 (2H, m, ring protons), 1.23–1.28 (2H, m, ring protons), 1.62–1.68 (4H, m), 1.82–1.89 (2H, m), 2.00–2.06 (2H, m), 2.30–2.40 (2H, m, CH₂CO), 3.29–3.30 (2H, M, CH₂NH), 5.45 (1H, bs, NH). MS (ES⁺) m/e 180 [M+H]⁺ 3%, 359 [2M+H]⁺ 21%, 381 [2M+Na]⁺ 100%.

Step (iv)

Lactam was taken up in 6N HCl (20 mL) and dioxane (8 mL), and heated to reflux for 4 hours. The solution was washed with dichloromethane (3×10 mL), and the aqueous fraction was evaporated in vacuo to give 0.65 g (84%) of Example 35 as a colorless solid. ¹H NMR (DMSO) (400 MHz): δ 1.0–1.18 (4H, m, ring protons), 1.52–1.72 (6H, m, ring protons), 1.95–2.02 (2H, m, ring protons), 2.33–2.67

(2H, m, CH$_2$CO$_2$H), 2.90–2.94 (1H, d, J=12.9 Hz, CH$_2$NH$_2$), 3.00–3.03 (1H, d, J=12.7 Hz, CH$_2$NH$_2$), 7.94 (2H, bs, NH$_2$). MS (ES$^+$) m/e 198 [M+H]$^+$ 100%. LCMS (ELSD) Prodigy ODS3 50 mm×2 mm column, 5%–50% MeCN/H$_2$O. Retention time=2.30 minutes, mass found=198. 100% purity.

EXAMPLE 36

(1α,3α,5α)(2-Aminomethyl-octahydro-pentalen-2-yl)-acetic acid hydrochloride

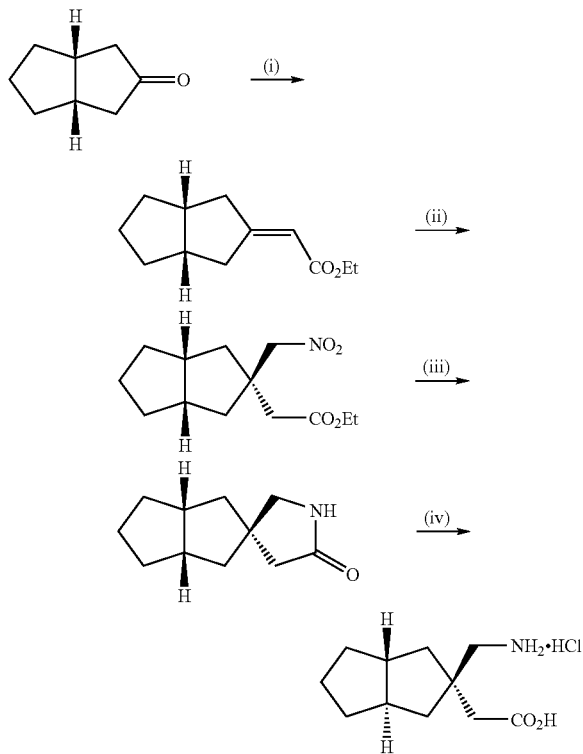

Step (i)

To a suspension of NaH (0.45 g, 11.3 mmol) in THF (25 mL), at 0° C. under argon, was slowly added (over ~10 minutes) triethylphosphonoacetate (2.3 mL, 11.6 mmol), followed by 5 (1.29 g, 10.4 mmol in 2×3 mL THF). The reaction was allowed to warm to room temperature and left to stir for 4 hours, after which it was diluted with water (100 mL), extracted with ether (2×200 mL), washed with saturated brine (50 mL), and dried (MgSO$_4$). Column chromatography (9:1 heptane/ethyl acetate) gave the product as a colorless oil, 1.75 g, 86%.

IR (thin film) (cm$^{-1}$) v=2964, 1713, 1655, 1371, 1208, 1125, 1040. $^1$H NMR (CDCl$_3$): δ 5.72 (1H, m), 4.14 (2H, q, J=7.2), 3.02–2.92 (1H, m), 2.72–2.54 (3H, m), 2.52–2.42 (1H, m), 2.28–2.20 (1H, m), 1.85–1.31 (6H, m), 1.27 (3H, t, J=7.2). (m/z AP$^+$ 195 (MI+1) at 100%.

Step (ii)

To a solution of 6 (2.75 g, 22.2 mmol) in THF (22 mL) was added TBAF (24 mL, 24.0 mmol) followed by nitromethane (4.4 mL, 8.14 mmol). The reaction was heated (oil bath at 60° C.) for 4.75 hours, after which it was diluted with ethyl acetate (100 mL) and washed with 2 M HCl (30 mL), followed by saturated brine (40 mL), dried (MgSO$_4$), and concentrated under reduced pressure. Column chromatography (9:1 heptane/ethyl acetate) gave the product as a colorless oil, 0.73 g, 20%. The product was found by $^1$H NMR to be a 9:1 mixture of diastereoisomers. $^1$H NMR (CDCl$_3$): δ 4.67 (1H, s), 4.60 (1H, s), 4.15 (2H, q, J=7.2), 4.14 (2H, q, 7.2), 2.58 (2H, s), 2.49 (2H, s), 2.12–2.0 (2H+2H, m), 1.63–1.49 (4H+4H, m), 1.44–1.36 (2H+2H, m), 1.28 (3H, t, J=7.2), 1.27 (3H, t, J=7), 1.16–1.04 (2H+2H, m).

Step (iii)

Compound 7 (0.88 g, 3.45 mmol) in methanol (100 mL) with nickel sponge catalyst underwent hydrogenation at 30° C. and a pressure of 56 psi; this was left for 5 hours. Before use, the nickel sponge catalyst was washed several times, first with water and then methanol. After hydrogenation was complete, the reaction mixture was filtered through celite and the resulting solution concentrated in vacuo to give a yellow solid, 0.62 g, 80%. $^1$H NMR (CDCl$_3$): δ 5.43 (1H, br s), 3.15 (2H, s), 2.56–2.44 (3H, m), 1.99 (2H, dd, J=12.6, 8.2), 1.64–1.50 (2H, m), 1.44–1.34 (3H, m), 1.22–1.14 (2H, m).

m/z ES$^+$ 226 (MI+1) at 100%.

Step (iv)

Compound 8 (0.61 g, 2.7 mmol) in dioxane (10 mL) and 6 M HCl (30 mL) was heated to reflux (oil bath at 100° C.) for 4 hours. After cooling, the reaction was diluted with water (40 mL) and the reaction mixture washed with dichloromethane (3×40 mL) and concentrated in vacuo to yield Example 36 as a white crystalline product as a 6:1 ratio of diastereoisomers. The product was recrystallized twice from ethyl acetate/methanol to give a 10:1 mixture of diastereoisomers.

m/z ES$^+$ 198 (MI+1) at 100%. $^1$H NMR (D$_2$O): δ 3.03 (2H, s), 2.50–2.36 (4H, m), 1.84 (2H, dd, J=12, 8), 1.41 (4H, s), 1.26 (2H, s), 1.02 (2H, m). HPLC column=Prodigy ODS 3, room temperature=0.87, Purity=100%.

EXAMPLE 37

(1α,6α,8α)(2-Aminomethyl-octahydro-inden-2-yl)-acetic acid hydrochloride

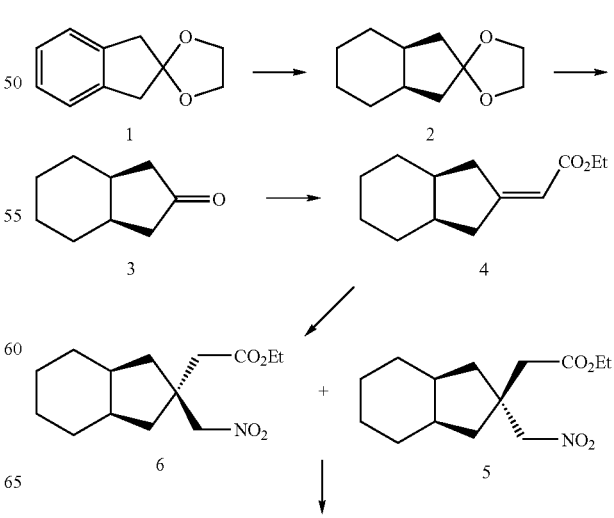

-continued

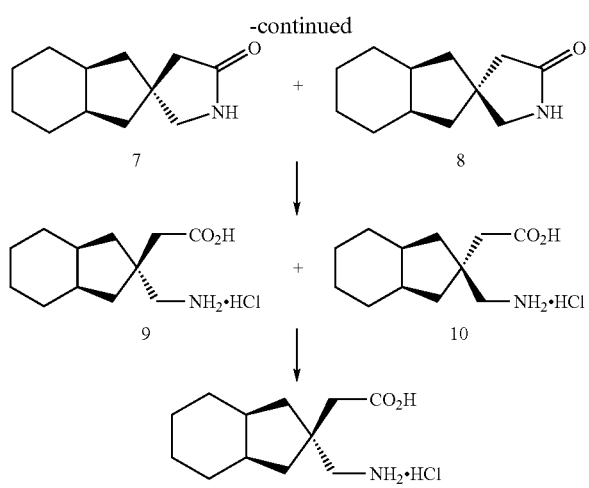

Synthesis of Compound 1

Indan-2-one (1.0 g, 7.6 mmol), ethylene glycol (0.43 mL, 7.6 mmol), and para-toluene sulphonic acid were refluxed in benzene (40 mL) using a Dean-Stark trap for 6 hours. The mixture was allowed to cool and was then diluted with ethyl acetate (100 mL) and washed with saturated sodium hydrogen carbonate solution (60 mL). The organic layer was separated off, and the aqueous layer was extracted further with ethyl acetate (2×50 mL). The combined organic fractions were washed with brine, dried ($MgSO_4$), and the solvent was evaporated under reduced pressure. The residue was chromatographed ($SiO_2$, heptane/ethyl acetate, 97:3) to give the acetal 1 (1.14 g, 85%) as a colorless oil; $R_f$(heptane/ethyl acetate, 8:2) 0.36; $v_{max}$(film)/cm$^{-1}$ 1483, 1331, 1291, 1105; $\delta_H$ (400 MHz; $CDCl_3$): 7.19–7.14 (4H, m, Ph), 4.02 (4H, s, 2×$CH_2CO_2$, 3.18 (4H, s, 2×$CH_2O$).

Synthesis of Compound 2

Acetal 1 (0.5 g, 2.84 mmol) in ethanol (50 mL) was shaken over a catalytic amount of 5% rhodium on alumina under a hydrogen atmosphere (70 Psi, 50° C.) for 16 hours. The catalyst was filtered off, and the solvent was evaporated under reduced pressure to give the acetal 2 (0.51 g, 99%) as a colorless oil; $v_{max}$(film)/cm$^{-1}$ 2923, 1449, 1337, 1192, 1115, 1089; $\delta_H$ (400 MHz; $CDCl_3$): 3.89–3.86 (4H, m, 2×$CH_2O$), 2.10–2.00 (2H, m), 1.88 (2H, dd, J=13.9, 7.6), 1.81 (2H, dd, J=13.7, 7.0), 1.56–1.26 (6H, m).

Synthesis of Compound 3

Acetal 2 (1.01 g, 5.54 mmol) was stirred in a mixture of 2N hydrochloric acid (10 mL) and acetone (10 mL) for 24 hours. After this time, tlc showed complete consumption of the starting acetal. Saturated sodium carbonate solution (20 mL) was added, and the mixture was extracted with ether (3×25 mL). The combined ether fractions were washed with brine, dried ($MgSO_4$), and the solvent was evaporated under reduced pressure. The residue was chromatographed ($SiO_2$, pentane/ether, 95:5) to give the ketone 3 (0.75 g, 97%) as a colorless oil; $R_f$ (heptane/ethyl acetate, 8:2) 0.42; $v^{max}$(film)/cm$^{-1}$ 1743 (C=O); $\delta_H$ (400 MHz; $CDCl_3$): 2.37–2.28 (2H, m), 2.20 (2H, dd, J=18.5, 7.5), 2.12 (2H, dd, J=18.7, 6.3), 1.65–1.24 (10H, m).

Synthesis of Compound 4

Triethyl phosphonoacetate (1.13 mL, 5.70 mmol) was added dropwise to a stirring suspension of sodium hydride (0.22 g of a 60% dispersion in oil, 5.43 mmol) in THF (15 mL) at 0° C. under argon. After 20 minutes, ketone 3 (0.75 g, 5.43 mmol) in THF (6 mL) was added dropwise. The mixture was allowed to warm to room temperature and stirred for 16 hours. Water (5 mL) was added, and the mixture was extracted with ether (15 mL×3). The combined organic fractions were washed with brine and dried (MgSO4). The solvent was evaporated under reduced pressure. The residue was chromatographed ($SiO_2$, heptane/ethyl acetate, 95:5) to give the ester 4 (0.81 g, 72%) as a colorless oil; $R_f$(heptane/ethyl acetate, 8:2) 0.66; $v^{max}$(film)/cm$^{-1}$ 1715 (C=O), 1652 (C=C); $\delta_H$ (400 MHz; $CDCl_3$): 5.80 (1H, quint, J=2.2, $CHCO_2Et$), 4.15 (2H, q, J=7.1, $CO_2CH_2Me$), 2.79 (1H, dd, J=19.5, 8.1), 2.69 (1H, ddt, J=19.8, 7.3, 2.3), 2.47 (1H, dd, J=17.3, 7.2), 2.34 (1H, ddt, J=17.3, 5.6, 1.8), 2.14 (1H, m), 2.02 (1H, m), 1.60–1.22 (8H, m); m/z (ES$^+$) 209 (M+H, 57%), 455 (2M+K, 67).

Synthesis of Compounds 5 and 6

Ester 4 (0.45 g, 2.16 mmol), nitromethane (0.24 mL, 4.31 mmol), and tetra-butylammonium fluoride (3.10 mmol of a 1 M solution in THF, 3.10 mmol) were heated to 65° C. in THF for 4 hours. The mixture was allowed to cool, diluted with ethyl acetate (20 mL), and acidified with dilute hydrochloric acid (15 mL). The organic layer was separated off, and the aqueous layer was further extracted with ethyl acetate (2×15 mL). The combined organic fractions were washed with brine, dried ($MgSO_4$), and the solvent was evaporated under reduced pressure. The residue was chromatographed ($SiO_2$, heptane/ethyl acetate, 98:2) to give a 9:1 ratio of nitro-esters 5 and 6 (0.35 g, 60%) as a yellow oil; $R_f$ (heptane/ethyl acetate, 9:1) 0.28; $v_{max}$(film)/cm$^{-1}$ 1732 (C=O), 1547 ($NO_2$), 1375 ($NO_2$); major isomer 5: $\delta_H$ (400 MHz; $CDCl_3$): 4.61 (2H, s, $CH_2NO_2$), 4.15 (2H, q, J=7.2, $OCH_2Me$), 2.70 (2H, s, $CH_2CO_2Et$), 2.06 (2H, m), 1.81 (2H, dd, J=13.9, 7.1), 1.56 (2H, dd, J=13.1, 6.8), 1.51–1.22 (8H, m) 1.28 (3H, t, J=7.2).

Synthesis of Compounds 7 and 8

The mixture of 5 and 6 (0.81 g, 3.01 mmol) in methanol (30 mL) was shaken over a catalytic amount of nickel sponge catalyst under a hydrogen atmosphere (50 Psi, 30° C.) for 12 hours. The mixture was filtered, and the solvent was evaporated under reduced pressure to give a 9:1 mixture of amino-esters 7 and 8 (0.42 g, 72%) as a white solid; $v_{max}$(film)/cm$^{-1}$ 3214 (NH), 1706 (C=O); major isomer 7: $\delta_H$ (400 MHz; $CDCl_3$): 5.57 (1H, br s, NH), 3.20 (2H, s, $CH_2NH$), 2.36 (2H, s, $CH_2CO$), 2.04–1.94 (2H, m), 1.77 (2H, dd, J=13.2, 7.0), 1.62 (2H, dd, J=13.4, 6.7), 1.60–1.20 (8H, m); m/z (ES$^+$) 387 (2M+H, 97%).

Synthesis of Example 37

(1α,6α,8α)(2-Aminomethyl-octahydro-inden-2-yl)-acetic acid hydrochloride

The mixture of 7 and 8 (0.42 g, 2.17 mmol) was dissolved in 1,4-dioxane (8 mL) and hydrochloric acid (20 mL of a 6N solution), and the mixture was refluxed for 6 hours. After cooling, the mixture was diluted with water (20 mL) and washed with dichloromethane (2×15 mL). The aqueous layer was evaporated under reduced pressure to give a 9:1 mixture of acids 9 and 10 (0.43 g, 79%) as a white solid. Recrystallization using ethyl acetate/methanol gave acid Example 37 exclusively (0.27 g); $\delta_H$ (400 MHz; $d_6$-DMSO): 12.3 (1H, br s, $CO_2H$), 7.94 (2H, br s, $NH_2$), 2.90 (2H, s, $CH_2NH_2$), 2.52 (2H, s, $CH_2CO_2H$), 1.97 (2H, br s), 1.65 (2H, dd, J=13.5, 6.7), 1.54–1.20 (10H, m); m/z (ES$^+$) 212 (M+H, 100%); (Found: C, 56.4; H, 8.74; N, 5.43

$C_{12}H_{21}NO_2·1HCl·0.5H_2O$ requires C, 56.1; H, 9.03; N, 5.45%); LCMS (Prodigy C18 50 mm×4.6 mmid column, 5%-50% Acetonitrile/water); Retention Time=1.53 minutes, 98% purity.

EXAMPLE 38

((1α,6α,8β)(2-Aminomethyl-octahydro-inden-2-yl)-acetic acid hydrochloride

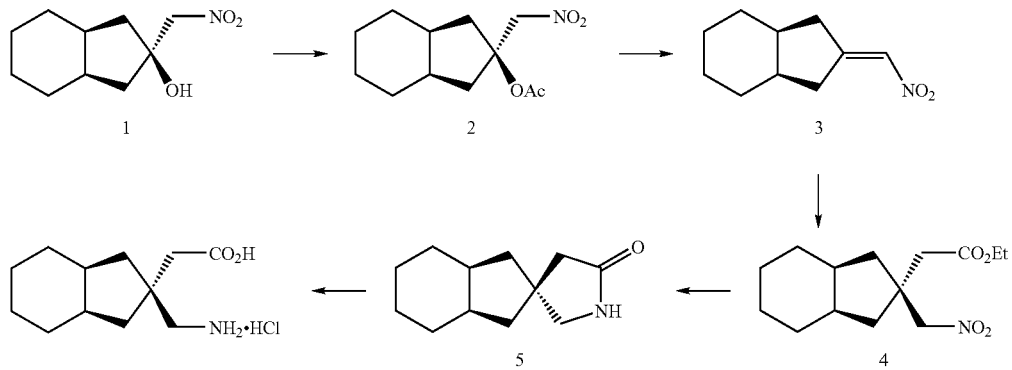

Synthesis of Compound 1 n-Butyllithium (5.1 mL of a 2.5 M solution in hexanes, 12.75 mmol) was added dropwise to a stirring mixture of nitromethane (0.34 mL, 6.3 mmol) in THF (20 mL) and HMPA (2 mL) at −78° C. under argon. The mixture was allowed to warm to −60° C. and stirred for 1 hour. The mixture was cooled to −78° C. and 3 (0.79 g, 5.73 mmol) was added. The mixture was allowed to warm to −60° C. and stirred for a further 2 hours. The mixture was quenched by addition of saturated ammonium chloride solution (5 mL). After warming to room temperature, dilute hydrochloric acid (10 mL) and ether (30 mL) were added. The organic layer was separated, and the aqueous layer was further extracted with ether (2×25 mL). The combined organic fractions were washed with brine, dried ($MgSO_4$), and the solvent was evaporated under reduced pressure. The residue was chromatographed ($SiO_2$, heptane/ethyl acetate, 95:5) to give the nitro-alcohol 1 (0.50 g, 43%) as a white solid; $R_f$ (heptane/ethyl acetate, 9:1) 0.14; $v_{max}(CH_2Cl_2)/cm^{-1}$ 3424 (OH), 1548 ($NO_2$), 1379 ($NO_2$); $\delta_H$ (400 MHz; $CDCl_3$): 4.45 (2H, s, $CH_2NO_2$), 3.26 (1H, s, OH), 2.04–1.95 (2H, m), 1.85–1.80 (4H, m), 1.64–1.24 (8H, m).

Synthesis of Compound 2

A mixture of 1 (0.50 g, 2.49 mmol) and concentrated sulphuric acid (1 drop) was heated to 50° C. in acetic anhydride (1 mL) for 5 minutes. The mixture was allowed to cool and then partitioned between ether (100 mL) and water (50 mL). The ether layer was washed with brine, dried ($MgSO_4$), and the solvent was evaporated under reduced pressure to give the nitro-acetate 2 (0.49 g, 82%) as a colorless oil; $R_f$(heptane/ethyl acetate, 9:1) 0.44; $v_{max}$(film)/$cm^{-1}$ 1739 (C=O), 1551 ($NO_2$), 1375 ($NO_2$); $\delta_H$ (400 MHz; $CDCl_3$): 4.88 (2H, s, $CH_2NO_2$), 2.38–2.00 (8H, m), 2.07 (3H, s, MeCO), 1.62–1.32 (6H, m).

Synthesis of Compound 3

Potassium methoxide (0.15 g, 2.04 mmol) in methanol (3 mL) was added dropwise to a stirring solution of 2 (0.49 g, 2.04 mmol) in methanol (5 mL) at 0° C. After 10 minutes, the mixture was partitioned between ether (100 mL) and water (50 mL). The ether layer was washed with brine, dried ($MgSO_4$) and the solvent was evaporated under reduced pressure. The residue was chromatographed ($SiO_2$, pentane/ether, 98:2) to give the nitro-alkene 3 (0.21 g, 57%) as a pale yellow oil; $R_f$ (heptane/ethyl acetate, 8:2) 0.54; $v_{max}$(film)/$cm^{-1}$ 1643 (C=C), 1509 ($NO_2$), 1342 ($NO_2$); $\delta_H$ (400 MHz; $CDCl_3$): 7.12 (1H, quint, J=2.0, $CHNO_2$), 3.01 (1H, ddt, J=20.5, 8.0, 2.1), 2.90 (1H, ddt, J=20.5, 7.3, 2.1), 2.54 (1H, ddt, J=17.8, 7.1, 2.0), 2.43 (1H, ddt, J17.7, 5.6, 1.9), 2.21 (1H, m), 2.12 (1H, m), 1.60–1:24 (8H, m).

Synthesis of Compound 4

Ethyl acetate (0.12 mL, 1.22 mmol) in THF (2 mL) was added dropwise to a stirring solution of lithium bis(trimethylsilyl)amide (1.22 mL of a 1 M solution in THF, 1.22 mmol) at −78° C. under argon. After 20 minutes, 3 (0.21 g, 1.16 mmol) in THF (1 mL) was added, and the mixture was stirred for 2 hours. The mixture was quenched by addition of saturated ammonium chloride solution (3 mL) and allowed to warm to room temperature. The mixture was diluted with ether (20 mL) and dilute hydrochloric acid (15 mL) was added. The organic layer was separated, and the aqueous layer was further extracted with ether (2×10 mL). The combined organic fractions were washed with brine, dried ($MgSO_4$), and the solvent was evaporated under reduced pressure. The residue was chromatographed ($SiO_2$, heptane/ethyl acetate, 99:1) to give the nitro-ester 4 (0.13 g, 41%) as a colorless liquid; $R_f$(heptane/ethyl acetate, 9:1) 0.32; $v_{max}$ (film)/$cm^{-1}$ 1731 (C=O), 1547 ($NO_2$), 1375 ($NO_2$); $\delta_H$ (400 MHz; $CDCl_3$): 4.73 (2H, s, $CH_2NO_2$), 4.14 (2H, q, J=7.1, $CO_2CH_2Me$), 2.58 (2H, s, $CH_2CO_2Et$), 2.07 (2H, m), 1.71–1.66 (4H, m), 1.60–1.24 (8H, m), 1.26 (3H, t, J=7.2, $CO_2CH_2Me$); m/z ($ES^+$) 270 (M+H, 100%).

Synthesis of Compound 5

4 (0.122 g, 0.45 mmol) in methanol (40 mL) was shaken over a catalytic amount of nickel sponge catalyst under a hydrogen atmosphere (60 Psi, 30° C.) for 6 hours. The mixture was filtered and the solvent was evaporated under reduced pressure to give amino-ester 5 (0.084 g, 96%) as a white solid; $v_{max}$(film)/$cm^{-1}$ 3228 (NH), 1665 (C=O); $\delta_H$ (400 MHz; $CDCl_3$): 5.49 (1H, br s, NH), 3.34 (2H, s, $CH_2NH$), 2.25 (2H, s, $CH_2CO$), 2.10–1.98 (2H, m), 1.77 (2H, dd, J=13.2, 7.1), 1.65 (2H, dd, J=13.2, 6.8), 1.62–1.20 (8H, m).

Synthesis of Example 38

(2-Aminomethyl-octahydro-inden-2-yl)-acetic acid 5 (0.083 g, 0.43 mmol) was dissolved in 1,4-dioxane (2 mL) and hydrochloric acid (8 mL of a 6N solution), and the mixture was refluxed for 5 hours. After cooling, the mixture was diluted with water (20 mL) and washed with dichloromethane (2×15 mL). The aqueous layer was evaporated under reduced pressure to give the acid 6 (0.097 g, 91%) as a white solid. This was recrystallized using ethyl acetate/methanol to give pure Example 38 (0.057 g); $\delta_H$ (400 MHz; $d_6$-DMSO): 7.90 (2H, br s, $NH_2$), 3.02 (2H, s, $CH_2NH_2$), 2.43 (2H, s, $CH_2CO_2H$), 2.00 (2H, br s), 1.53–1.24 (12H, m); m/z (ES$^+$) 212 (M+H, 100%); LCMS (Prodigy C18 50 mm×4.6 mmid column, 5%–50% Acetonitrile/water) Retention Time=1.12 minutes, 100% purity.

EXAMPLE 39

(1α,3α,5α)(3-Aminomethyl-bicyclo[3.2.0]hept-3-yl)-acetic acid hydrochloride

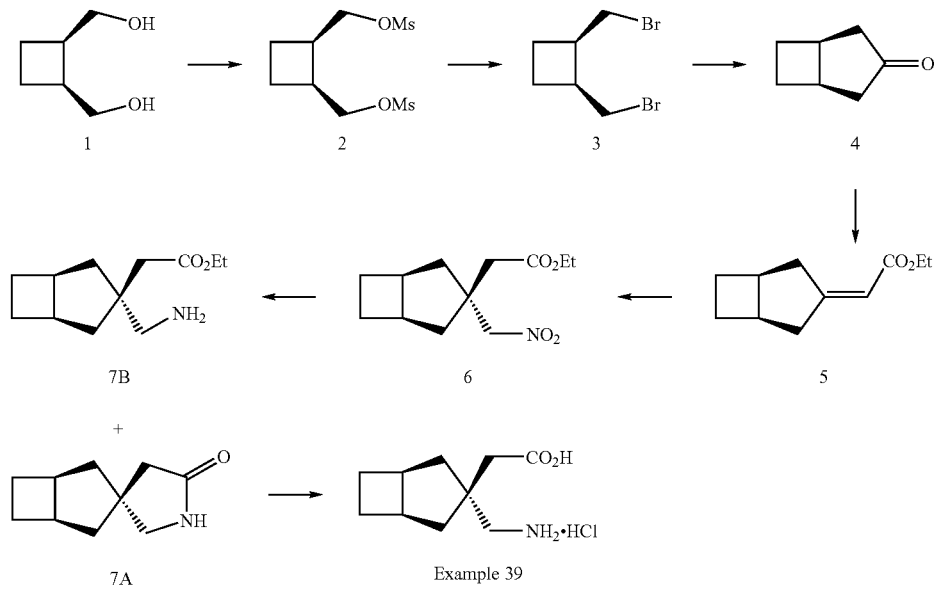

Synthesis of Compound 1

Lithium aluminum hydride (69.4 mL of a 1 M solution in ether, 69.4 mmol) was added dropwise to a stirring solution of cis-cyclobutane-1,2-dicarboxylic acid (5 g, 34.7 mmol) in THF (60 mL) at 0° C. under argon. The mixture was allowed to warm to room temperature and stirred for 16 hours. The mixture was cooled to 0° C. and quenched by careful addition of water (2.7 mL), sodium hydroxide solution (2.7 mL of a 15% w/v solution), and water (8.1 mL). The mixture was stirred for 15 minutes, and the precipitate was removed by filtration. The solvent was evaporated under reduced pressure to give the alcohol 1 as a colorless oil (4.0 g, 98%); $\delta_H$ (400 MHz; CDCl$_3$): 3.85 (2H, m), 3.6 (2H, m), 3.2 (2H, s), 2.7 (2H, m), 2 (2H, m); 1.55 (2H, m); $\delta_C$ (400 MHz; CDCl$_3$): 63.15, 37.83, 20.40.

Synthesis of Compound 2

Mesyl chloride (6.2 mL, 79.1 mmol) was added dropwise to a stirring solution of 1 (4.0 g, 34.4 mmol) in dichloromethane (150 mL) at −40° C. under argon. Triethylamine (12.0 mL, 86.0 mmol) was then added dropwise, and the mixture was allowed to warm slowly to room temperature. After stirring for 16 hours, the mixture was quenched by addition of dilute hydrochloric acid (50 mL). The organic layer was separated, and the aqueous layer was further extracted with dichloromethane (2×50 mL). The combined organic fractions were washed with brine, dried (MgSO$_4$), and the solvent was evaporated under reduced pressure. The residue was chromatographed (SiO$_2$, heptane/ethyl acetate, 6:4) to give the mesylate 2 (6.1 g, 73%) as a white solid; R$_f$(heptane/ethyl acetate, 1:1) 0.18. $\delta_H$ (400 MHz; CDCl$_3$): 4.3 (4H, m), 3.05 (6H, s), 2.9 (2H, m), 2.2 (2H, m), 1.8 (2H, m); $\delta_C$(400 MHz; CDCl$_3$): 69.51, 37.45, 35.28, 21.09.

Synthesis of Compound 3

Anhydrous lithium bromide (10.6 g, 121.8 mmol) was added to a stirring mixture of 2 (5.95 g, 24.4 mmol) in acetone (50 mL) under argon, and the mixture was refluxed for 2 hours. After cooling, the acetone was evaporated under reduced pressure, and the residue was taken up in ether (50 mL), washed with water (50 mL), brine, dried (MgSO$_4$), and the solvent was evaporated under reduced pressure. The residue was chromatographed (SiO$_2$, heptane/ethyl acetate, 95:5) to give the dibromide 3 (5.36 g, 86%) as an orange liquid; R$_f$ (heptane-ethyl acetate, 8:2), 0.82. $\delta_H$ (400 MHz; CDCl$_3$): 3.6 (2H, m), 3.45 (2H, m), 2.85 (2H, m), 2.1 (2H, m), 1.7 (2H, m; $\delta_C$(400 MHz; CDCl$_3$): 39.70, 33.79, 23.95.

Synthesis of Compound 4

To a cooled (0° C.) suspension of potassium hydride (1.58 g, 39.5 mmol) (previously washed 3 times with pentane) in tetrahydrofuran (22 mL) was added, under an argon atmosphere, a solution of methyl methylthiomethyl sulfoxide (1.36 mL, 13.04 mmol, previously dried over molecular sieves for 3 hours) in tetrahydrofuran (3 mL) over 1 hour. After stirring for a further 30 minutes, a solution of 3 (3.17 g, 13.1 mmol) in THF (2 mL) was added, at 0° C., over 1 hour. The reaction mixture was then allowed to warm up to room temperature and was stirred overnight. The mixture was quenched by addition of aqueous ammonium chloride (6 mL, 25%). After 10 minutes, the solid was filtered off and the filtrate concentrated. The residue was taken up in ether (20 mL) and 9N sulfuric acid (0.05 mL) was added. After stirring for 30 hours, saturated sodium hydrogen carbonate was added. The ether phase was separated and concentrated to 5 mL. Saturated sodium hydrogen sulphite (1.5 g) solution was added and the mixture stirred for 30 minutes. The phases were separated. The ethereal phase was stirred for further 30 minutes with a saturated sodium hydrogen sulphite (0.5 g) solution. The phases were separated, and the collected aqueous phases were treated with aqueous sodium hydroxide (5 mL, 20%) and extracted with ether. The ether phase was dried (MgSO$_4$) and evaporated under reduced pressure to give 4 as a yellow liquid (0.16 g, 11%). $\delta_H$ (400 MHz; CDCl$_3$): 3.0 (2H, m), 2.15–2.45 (6H, m), 1.65 (2H, m).

Synthesis of Compound 5

Triethyl phosphonoacetate (0.32 mL, 1.61 mmol) was added dropwise to a stirring suspension of sodium hydride (0.059 g of a 60% dispersion in oil, 1.47 mmol) in THF (2 mL) at 0° C. under argon. After 20 minutes, ketone 4 (0.16 g, 1.45 mmol) in THF (1 mL) was added dropwise. The mixture was allowed to warm to room temperature and stirred for 16 hours. Water (5 mL) was added, and the mixture was extracted with ethyl acetate. The combined organic fractions were washed with brine and dried (MgSO$_4$). The solvent was evaporated under reduced pressure. The residue was chromatographed (SiO$_2$, heptane-ethyl acetate, 95:5) to give the ester 5 (0.166 g, 0.92 mmol, 64%) as a colorless oil; $\delta_H$ (400 MHz; CDCl$_3$): 5.9 (1H, s), 4.2 (2H, q), 3.15 (1H, d), 2.9 (1H, m), 2.8 (1H, m); 2.65 (2H, m), 2.3 (1H, d), 2.15 (2H, m), 1.5 (2H, m), 1.3 (3H, t); $\delta_C$ (400 MHz; CDCl$_3$): 169.51, 166.98, 113.37, 59.62, 43.23, 38.79, 38.45, 36.20, 25.62, 24.95, 14.44.

Synthesis of Compound 6

Ester 5 (0.152 g, 0.84 mmol), nitromethane (0.092 mL, 1.7 mmol), and tetra-butylammonium fluoride (1.03 mL of a 1 M solution in THF, 1.03 mmol) were heated to 65° C. in THF (1 mL) for 4 hours. The mixture was allowed to cool, diluted with ether (30 mL), and acidified with 2N hydrochloric acid (5 mL). The organic layer was washed with brine, dried (MgSO$_4$), and the solvent was evaporated under reduced pressure. The residue was chromatographed (SiO$_2$, heptane/ether, 95:5) to give nitro-ester 6 (0.085 g, 0.35 mmol, 41%) as a colorless liquid; $\delta_H$ (400 MHz; CDCl$_3$): 4.4 (2H, s), 4.15 (2H, q), 2.75 (2H, bs), 2.7 (2H, s), 2.3 (2H, m); 2.1 (2H, m), 1.65 (4H, m), 1.15 (3H, t); $\delta_C$ (400 MHz; CDCl$_3$): 171.48, 79.68, 60.52, 50.10, 44.15, 41.06, 37.36, 25.76, 14.28.

Synthesis of Compounds 7A and 7B

Nitro-ester 6 (0.076 g, 0.31 mmol) in methanol (10 mL) was shaken over a catalytic amount of nickel sponge catalyst under a hydrogen atmosphere (50 Psi, 30° C.) for 12 hours. The mixture was filtered, and the solvent was evaporated under reduced pressure to give a mixture of lactam 7A and amino-ester 7B (0.05 g) as a white solid. This was used without further purification and characterization.

Synthesis of Example 39

7A and 7B (0.05 g) were dissolved in hydrochloric acid (2 mL of a 6N solution), and the mixture was refluxed for 4 hours. After cooling, solvent was evaporated under reduced pressure to give the acid as a white solid. This was recrystallized using ethyl acetate/methanol to give pure Example 39 (0.045 g, 0.2 mmol, 64%); $\delta_H$ (400 MHz; D$_2$O): 3 (2H, s), 2.85 (4H, m+s), 2.35 (2H, m), 2.1 (2H, m), 1.75 (4H, m). $\delta_C$ (400 MHz; D$_2$O): 167.5, 46.64, 43.89, 42.03, 40.89, 36.08, 23.91. m/z (ES$^+$) 184 (M+H, 100%).

EXAMPLE 40

(±)-(1α,5β)(3-aminomethyl-bicyclo[3.2.0]hepty-3-yl)-ascetic acid hydrochloride

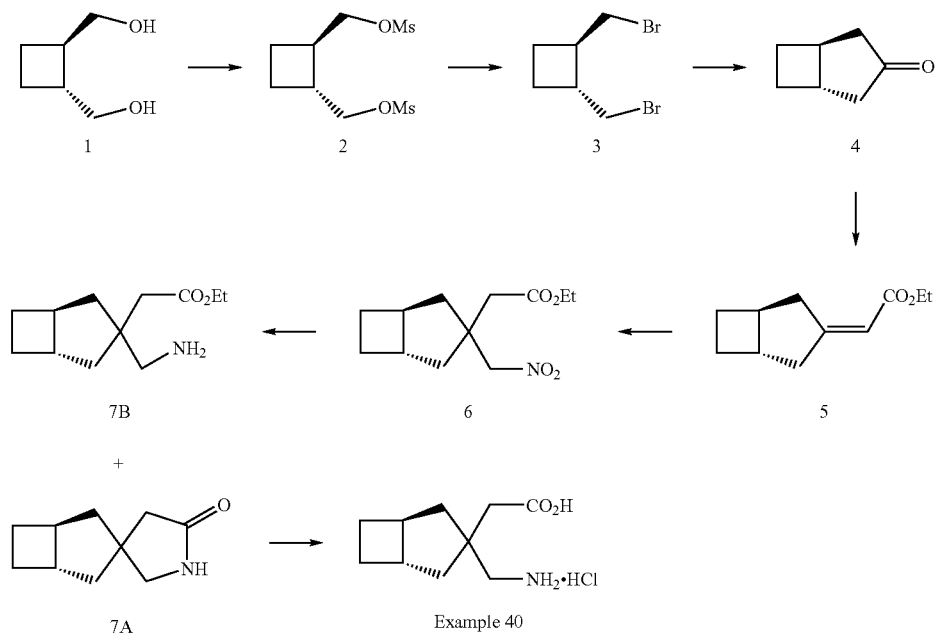

Synthesis of Compound 1

Lithium aluminum hydride (134.8 mL of a 1 M solution in ether, 134.8 mmol) was added dropwise to a stirring solution of cis-cyclobutane-1,2-dicarboxylic acid (9.71 g, 67.39 mmol) in THF (120 mL) at 0° C. under argon. The mixture was allowed to warm to room temperature and stirred for 16 hours. The mixture was cooled to 0° C. and quenched by careful addition of water (5.2 mL), sodium hydroxide solution (5.2 mL of a 15% w/v solution), and water (15.7 mL). The mixture was stirred for 15 minutes, and the precipitate was removed by filtration. The solvent was evaporated under reduced pressure to give the alcohol 1 as a pale yellow oil (6.73 g, 57.64 mmol, 85%); $\delta_H$ (400 MHz; CDCl$_3$): 3.85 (2H, m), 3.6 (2H, m), 2.9 (2H, s), 2.7 (2H, m), 2 (2H, m); 1.55 (2H, m).

Synthesis of Compound 2

Mesyl chloride (29.3 mL, 373.8 mmol) was added dropwise to a stirring solution of 1 (8.85 g, 75.8 mmol) in dichloromethane (500 mL) at −40° C. under argon. Triethylamine (63.4 mL, 454.4 mmol) was then added dropwise, and the mixture was allowed to warm slowly to room temperature. After stirring for 16 hours, the mixture was quenched by addition of dilute hydrochloric acid (100 mL). The organic layer was separated, and the aqueous layer was further extracted with dichloromethane (2×100 mL). The combined organic fractions were washed with brine, dried (MgSO$_4$), and the solvent was evaporated under reduced pressure. The residue was chromatographed (SiO$_2$, heptane-ethyl acetate, 6:4) to give the mesylate 2 (15.89 g, 58.3 mmol, 77%) as a white solid; $\delta_H$ (400 MHz; CDCl$_3$): 3.0 (6H, m), 2.6 (2H, m), 2.05 (2H, m), 1.8 (2H, m).

Synthesis of Compound 3

Anhydrous lithium bromide (25 g, 287.3 mmol) was added to a stirring mixture of 2 (15.84 g, 57.4 mmol) in acetone (150 mL) under argon, and the mixture was refluxed for 2 hours. After cooling, the acetone was evaporated under reduced pressure, and the residue was taken up in ether (100 mL), washed with water (100 mL), brine, dried (MgSO$_4$), and the solvent was evaporated under reduced pressure to give the dibromide 3 (13.5 g, 55.8 mmol, 97%) as an orange liquid; $\delta_H$ (400 MHz; CDCl$_3$): 3.5 (4H, m), 2.45 (2H, m), 2.05 (2H, m), 1.6 (2H, m).

Synthesis of Compound 4

To a cooled (0° C.) suspension of potassium hydride (1.08 g, 27 mmol) (previously washed 3 times with pentane) in THF (15 mL) was added, under an argon atmosphere, a solution of methyl methylthiomethyl sulfoxide (0.93 mL, 8.92 mmol, previously dried over molecular sieves for 3 hours) in THF (2 mL) over a period of 1 hour. After stirring for a further 30 minutes, a solution of 3 (2.16 g, 8.93 mmol) in THF (1 mL) was added, at 0° C., over a period of 1 hour. The reaction mixture was then allowed to warm up to room temperature and was stirred overnight. The mixture was quenched by addition of aqueous ammonium chloride (6 mL, 25%). After 10 minutes, the solid was filtered off and the filtrate concentrated. The residue was taken up in ether (20 mL), and 9N sulfuric acid (0.03 mL) was added. After stirring for 30 hours, saturated sodium hydrogen carbonate was added. The ether phase was separated and concentrated to 5 mL. Saturated sodium hydrogen sulphite (1.5 g) solution was added and the mixture stirred for 30 minutes. The phases were separated. The ethereal phase was stirred for further 30 minutes with a saturated sodium hydrogen sulphite (0.5 g) solution. The phases were separated, and the collected aqueous phases were treated with aqueous sodium hydroxide (5 mL, 20%) and extracted with ether. The ether phase was dried (MgSO$_4$), and the solvent was evaporated under reduced pressure to give 4 as a yellow liquid (0.141 $\delta_H$, 15%); SH (400 MHz; CDCl$_3$): 2.25 (4H, m), 2.0 (4H, m), 1.7 (2H, m).

Synthesis of Compound 5

Triethyl phosphonoacetate (0.28 mL, 1.41 mmol) was added dropwise to a stirring suspension of sodium hydride (0.052 g of a 60% dispersion in oil, 1.29 mmol) in THF (2 mL) at 0° C. under argon. After 20 minutes, ketone 4 (0.141 g, 1.28 mmol) in THF (1 mL) was added dropwise. The mixture was allowed to warm to room temperature and stirred for 16 hours. Water (5 mL) was added, and the mixture was extracted. The combined organic fractions were washed with brine and dried (MgSO$_4$). The solvent was evaporated under reduced pressure. The residue was chromatographed (SiO$_2$, heptane/ethyl acetate, 95:5) to give the ester 5 (0.092 g, 0.51 mmol, 40%) as a colorless oil; $\delta_H$ (400 MHz; CDCl$_3$): 5.85 (1H, s), 4.1 (2H, q), 3.1 (1H, d.d), 2.45 (1H, d.d), 2.2 (2H, m), 1.75 (2H, m), 1.4 (2H, m), 1.25 (3H, t); $\delta_C$ (400 MHz; CDCl$_3$): 170.53, 166.57, 115.13, 59.62, 47.06, 45.69, 39.89, 37.24, 28.52, 28.17, 14.44.

Synthesis of Compound 6

Ester 5 (0.09 g, 0.5 mmol), nitromethane (0.055 mL, 1.02 mmol), and tetra-butylammonium fluoride (0.61 mL of a 1 M solution in THF, 0.61 mmol) were heated to 65° C. in THF (1 mL) for 4 hours. The mixture was allowed to cool, diluted with ether (30 mL), and acidified with 2N hydrochloric acid (5 mL). The organic layer was washed with brine, dried (MgSO$_4$), and the solvent was evaporated under reduced pressure. The residue was chromatographed (SiO$_2$, heptane/ether, 95:5) to give nitro-ester 6 (0.063 g, 0.26 mmol, 52%) as a colorless liquid. $\delta_H$ (400 MHz; CDCl$_3$): 4.65 (2H, [AB]q), 4.15 (2H, q), 2.65 (2H, [AB]q), 1.2–1.95 (3H, t and m, 13H); $\delta_C$ (400 MHz; CDC$_{13}$): 171.28, 82.42, 60.56, 49.97, 45.80, 45.32, 42.88, 40.19, 40.09, 27.64, 14.26.

Synthesis of Compounds 7A and 7B

Nitro-ester 6 (0.063 g, 0.26 mmol) in methanol (10 mL) was shaken over a catalytic amount of nickel sponge catalyst under a hydrogen atmosphere (50 Psi, 30° C.) for 12 hours. The mixture was filtered, and the solvent was evaporated under reduced pressure to give a mixture of lactam 7A and amino-ester 7B (0.051 g) as a white solid. This was used without further purification and characterization.

Synthesis of Example 40

7A and 7B (0.051 g) were dissolved in hydrochloric acid (2 mL of a 6N solution), and the mixture was refluxed for 4 hours. After cooling, solvent was evaporated under reduced pressure to give the acid as a white solid. This was recrystallized using ethyl acetate/methanol to give pure Example 40 (0.046 g, 0.21 mmol, 81%); $\delta_H$ (400 MHz; D$_2$O): 3.3 (2H, [AB]q), 2.7 (2H, [AB]q), 2 (2H, m), 1.35–1.85 (8H, m); $\delta_C$ (400 MHz; D$_2$O): 174.8, 47.50, 46.59, 44.28, 43.61, 41.64, 38.37, 38.09, 25.88. m/z (ES+) 184 (M+H, 100%).

EXAMPLE 41

(1α,3β,5α)(3-Aminomethyl-bicyclo[3.2.0]hept-3-yl)-acetic acid hydrochloride

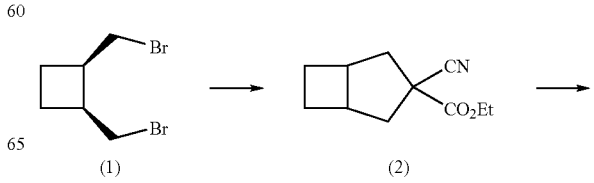

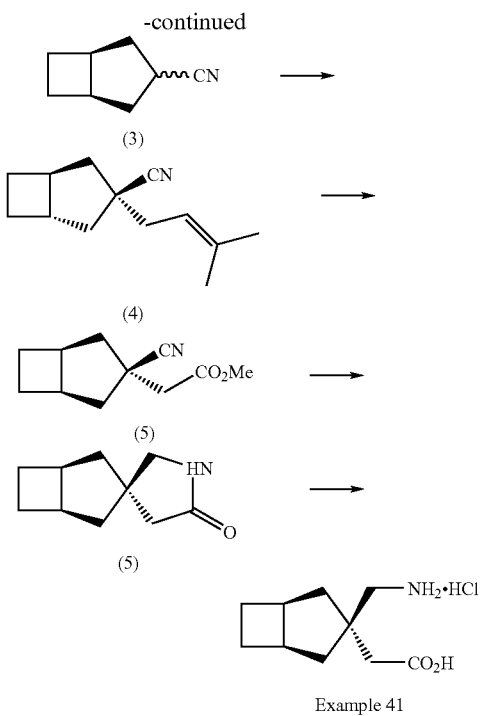

Example 41

Synthesis of Compound (2)

Dibromide 1 (5.7 g, 22.3 mmol), ethyl cyanoacetate (4.8 mL, 44.5 mmol) and potassium carbonate (6.15 g, 44.5 mmol) were stirred together in DMF (100 mL) for 48 hours. Dilute hydrochloric acid (100 mL) was added, and the mixture was extracted with ether (3×100 mL). The combined organic fractions were washed with brine, dried (MgSO$_4$), and the solvent was evaporated under reduced pressure. The residue was chromatographed (SiO$_2$, heptane-ethyl acetate, 98:2) to give the cyanoester 2 (4.3 g, 100%) as a 68:32 mixture of diastereoisomers: R$_f$(heptane-ethyl acetate, 9:1) 0.28; $v_{max}$(film)/cm$^{-1}$ 2241 (CN), 1741 (C=O); Major diastereoisomer: $\delta_H$(400 MHz; CDCl$_3$) 4.30 (2H, q, J 7.1, CO$_2$CH$_2$Me), 2.98 (2H, m), 2.56–2.22 (6H, m), 1.70 (2H, m), 1.35 (3H, t, J 7.1, Me); Minor diastereoisomer: $\delta_H$ (400 MHz; CDCl$_3$) 4.26 (2H, q, J 7.1, CO$_2$CH$_2$Me), 3.05 (2H, m), 2.56–2.22 (6H, m), 1.99 (2H, m), 1.33 (3H, t, J 7.1, Me).

Synthesis of Compound (3)

Cyanoester 2 (0.76 g, 3.91 mmol), water (0.14 mL, 7.82 mmol) and lithium chloride (0.66 g, 15.6 mmol) were heated to 150° C. in DMSO (40 mL) for 22 hours. The mixture was allowed to cool, diluted with water (150 mL), and extracted with ether (3×50 mL). The combined ether fractions were washed with brine, dried (MgSO$_4$), and the solvent was evaporated under reduced pressure. The residue was chromatographed (SiO$_2$, heptane-ethyl acetate, 95:5) to give the cyanide 3 (0.21 g, 44%) as a 60:40 mixture of diastereoisomers; R$_f$(heptane-ethyl acetate, 9:1) 0.44; $v_{max}$(film)/cm$^{-1}$ 2238 (CN); Major diastereoisomer: $\delta_H$ (400 MHz; CDCl$_3$) 2.97 (1H, m), 2.87 (2H, m), 2.32–2.18 (2H, m), 2.10–1.96 (3H, m), 1.92–1.78 (2H, m), 1.48–1.38 (1H, m); Minor diastereoisomer: $\delta_H$ (400 MHz; CDCl$_3$) 3.13 (1H, m), 2.87 (2H, m), 2.32–2.18 (2H, m), 2.10–1.96 (3H, m), 1.92–1.78 (2H, m), 1.48–1.38 (1H, m).

Synthesis of Compound (4)

Cyanide 3 (0.86 g, 7.1 mmol) in THF (30 mL) was added dropwise over 1 hour to a stirring mixture of lithium hexamethyldisilazide (7.8 mL of a 1 M solution in THF, 7.8 mmol) in THF (40 mL) at −78° C. under argon. The mixture was allowed to warm to −40° C. and stirred for 2 hours. The mixture was cooled to −78° C. and dimethylallyl bromide (1.3 mL, 10.6 mmol) was added. The mixture was stirred for a further 2 hours at −78° C. and then allowed to warm to room temperature overnight. Saturated ammonium chloride solution (20 mL) was added, and the mixture was diluted with ether (50 mL) and dilute hydrochloric acid (30 mL). The aqueous layer was further extracted with ether (2×50 mL), and the combined 15 organic fractions were washed with brine, dried (MgSO$_4$), and the solvent was evaporated under reduced pressure. The residue was chromatographed (SiO$_2$, heptane-ethyl acetate, 98:2) to give the cyanoalkene 4 (0.96 g, 72%) as a colorless oil; R$_f$(heptane-ethyl acetate, 95:5) 0.38; $v_{max}$(film)/cm$^{-1}$ 2230 (CN), 1673 (C=C); $\delta_H$ (400 MHz; CDCl$_3$) 5.27 (1H, tt, J 7.6, 1.3, CHCMe$_2$), 2.89 (2H, m), 2.30–2.22 (4H, m), 2.10 (2H, d, J 14.2), 1.94 (2H, m), 1.84–1.62 (2H, m), 1.65 (3H, s, Me), 1.55 (3H, s, Me); m/z (AP+) 190 (M+H, 100%).

Synthesis of Compound (5)

Cyanoalkene 4 (0.96 g, 5.1 mmol) and sodium hydroxide (10.2 mL of a 2.5 M solution in methanol, 25.5 mmol) were stirred together in dichloromethane (80 mL) at −78° C. Ozone was passed through the mixture which immediately went orange. After 2 hours, the mixture turned to a green color, and the solution was purged with oxygen for 5 minutes and then with nitrogen. The stirring mixture was diluted with ether (100 mL) and water (100 mL) and allowed to warm to room temperature overnight. The aqueous layer was further extracted with ether (2×50 mL), and the combined organic fractions were washed with brine, dried (MgSO$_4$), and the solvent was evaporated under reduced pressure. The residue was chromatographed (SiO$_2$, heptane-ethyl acetate, 95:5) to give the cyanoester 5 (0.70 g, 71%) as a yellow oil; R$_f$(heptane-ethyl acetate, 8:2) 0.36; $v_{max}$(film)/cm$^{-1}$ 2233 (CN), 1740 (C=O); $\delta_H$ (400 MHz; CDCl$_3$) 3.75 (3H, s, OMe), 2.94 (2H, m), 2.63 (2H, s, CH$_2$CO$_2$Me), 2.35–2.21 (4H, m), 2.00 (2H, m), 1.86 (2H, m); m/z (AP+) 194 (M+H, 95%).

Synthesis of Compound (6)

Cyanoester 5 (0.81 g, 4.2 mmol) in methanol (100 mL) was shaken over a catalytic amount of nickel sponge catalyst under a hydrogen atmosphere (60 Psi, 30° C.) for 6 hours. The mixture was filtered, and the solvent was evaporated under reduced pressure to give lactam 6 (0.64 g, 92%) as a white solid; $v_{max}$(film)/cm$^{-1}$ 1692 (C=O); $\delta_H$ (400 MHz; CDCl$_3$ 5.52 (1H, br s, NH), 3.54 (2H, s, CH$_2$NH), 2.80 (2H, m), 2.26 (2H, m), 2.16 (2H, s, CH$_2$CO), 1.93 (2H, ddd, J 13.4, 8.1, 2.4), 1.74 (2H, dd, J 13.0, 3.2), 1.64 (2H, m).

Synthesis of (1α,3β,5α)(3-Aminomethyl-bicyclo [3.2.0]hept 3-yl)-acetic acid hydrochloride Example 41

Lactam 6 (0.64 g, 3.87 mmol) was dissolved in 1,4-dioxane (4 mL) and hydrochloric acid (16 mL of a 6N solution), and the mixture was refluxed for 6 hours. After cooling, the mixture was diluted with water (20 mL) and washed with dichloromethane (2×15 mL). The aqueous layer was evaporated under reduced pressure to give acid 7 (0.67 g, 79%) as a white solid. Recrystallization using ethyl acetate/methanol gave Example 41 exclusively (0.26 g); $\delta_H$ (400 MHz; d$_6$-DMSO) 7.98 (2H, br s, NH$_2$), 3.13 (2H, s, CH$_2$NH2), 2.70 (2H, s), 2.17–2.14 (4H, m), 1.85 (2H, dd, J 13.3, 8.0), 1.63 (2H, m), 1.55 (2H, dd, J 12.9, 5.1); m/z (ES+) 184 (M+H, 100%); LCMS (Prodigy C18, 50 mm×4.6 mmid column, 5–50% Acetonitrile/water) Retention Time=2.40 minutes, 98% purity.

The following compounds are made by one of the methods of Examples 34 to 41.

(1α,5β)(3-Aminomethyl-bicyclo[3.1.0]hex-3-yl)-acetic acid,
(1α,5β)(3-Aminomethyl-bicyclo[3.2.0]hept-3-yl)-acetic acid,
(1α,5β)(2-Aminomethyl-octahydro-pentalen-2-yl)-acetic acid,
(1α,6β)(2-Aminomethyl-octahydro-inden-2-yl)-acetic acid,
(1α,7β)(2-Aminomethyl-decahydro-azulen-2-yl)-acetic acid,
(1α,5β)(3-Aminomethyl-bicyclo[3.1.0]hex-3-yl)-acetic acid,
(1α,5β)(3-Aminomethyl-bicyclo[3.2.0]hept-3-yl)-acetic acid,
(1α,5β)(2-Aminomethyl-octahydro-pentalen-2-yl)-acetic acid,
(1α,6β)(2-Aminomethyl-octahydro-inden-2-yl)-acetic acid,
(1α,7β)(2-Aminomethyl-decahydro-azulen-2-yl)-acetic acid,
(1α,3α,5α)(3-Aminomethyl-bicyclo[3.1.0]hex-3-yl)-acetic acid,
(1α,3α,5α)(3-Aminomethyl-bicyclo[3.2.0]hept-3-yl)-acetic acid,
(1α,3α,5α)(2-Aminomethyl-octahydro-pentalen-2-yl)-acetic acid,
(1α,6α,8α)(2-Aminomethyl-octahydro-inden-2 yl)-acetic acid,
(1α,7α,9α)(2-Aminomethyl-decahydro-azulen-2-yl)-acetic acid,
(1α,3β,5α)(3-Aminomethyl-bicyclo[3.1.0]hex-3-yl)-acetic acid,
(1α,3β,5α)(3-Aminomethyl-bicyclo[3.2.0]hept-3-yl)-acetic acid,
(1α,3β,5α)(2-Aminomethyl-octahydro-pentalen-2-yl)-acetic acid,
(1α,6α,8β)(2-Aminomethyl-octahydro-inden-2-yl)-acetic acid,
(1α,7α,9β)(2-Aminomethyl-decahydro-azulen-2-yl)-acetic acid,
((1R,3R,6R)-3-Aminomethyl-bicyclo[4.1.0]hept-3-yl)-acetic acid,
((1R,3S,6R)-3-Aminomethyl-bicyclo[4.1.0]hept-3-yl)-acetic acid,
((1S,3S,6S)-3-Aminomethyl-bicyclo[4.1.0]hept-3-yl)-acetic acid,
((1S,3R,6S)-3-Aminomethyl-bicyclo[4.1.0]hept-3-yl)-acetic acid,
((1R,3R,6S)-3-Aminomethyl-bicyclo[4.2.0]oct-3-yl)-acetic acid,
((1R,3S,6S)-3-Aminomethyl-bicyclo[4.2.0]oct-3-yl)-acetic acid,
((1S,3S,6R)-3-Aminomethyl-bicyclo[4.2.0]oct-3-yl)-acetic acid,
((1S,3R,6R)-3-Aminomethyl-bicyclo[4.2.0]oct-3-yl)-acetic acid,
((3αR,5R,7αS)-5-Aminomethyl-octahydro-inden-5-yl)-acetic acid,
((3αR,5S,7αS)-5-Aminomethyl-octahydro-inden-5-yl)-acetic acid,
((3αS,5S,7αR)-5-Aminomethyl-octahydro-inden-5-yl)-acetic acid,
((3αS,5R,7αR)-5-Aminomethyl-octahydro-inden-5-yl)-acetic acid,
((2R,4αS,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-decahydro-naphthalen-2-yl)-acetic acid,
((2R,4αR,8αS)-2-Aminomethyl-decahydro-naphthalen-2-yl)-acetic acid,
((2R,4αS,9αR)-2-Aminomethyl-decahydro-benzocyclohepten-2-yl-acetic acid,
((2S,4αS,9αR)-2-Aminomethyl-decahydro-benzocyclohepten-2-yl-acetic acid,
((2S,4αR,9αS)-2-Aminomethyl-decahydro-benzocyclohepten-2-yl)-acetic acid,
((2R,4αR,9αS)-2-Aminomethyl-decahydro-benzocyclohepten-2-yl)-acetic acid,
((1R,3R,6S)-3-Aminomethyl-bicyclo[4.1.0]hept-3-yl)-acetic acid,
((1R,3S,6S)-3-Aminomethyl-bicyclo[4.1.0]hept-3-yl)-acetic acid,
((1S,3S,6R)-3-Aminomethyl-bicyclo[4.1.0]hept-3-yl)-acetic acid,
((1S,3R,6R)-3-Aminomethyl-bicyclo[4.1.0]hept-3-yl)-acetic acid
((1R,3R,6R)-3-Aminomethyl-bicyclo[4.2.0]oct-3-yl)-acetic acid,
((1R,3S,6R)-3-Aminomethyl-bicyclo[4.2.0]oct-3-yl)-acetic acid,
((1S,3S,6S)-3-Aminomethyl-bicyclo[4.2.0]oct-3-yl)-acetic acid,
((1S,3R,6S)-3-Aminomethyl-bicyclo[4.2.0]oct-3-yl)-acetic acid,
((3αR,5R,7αR)-5-Aminomethyl-octahydro-inden-5-yl)-acetic acid,
((3αR,5S,7αR)-5-Aminomethyl-octahydro-inden-5-yl)-acetic acid,
((3αS,5S,7αS)-5-Aminomethyl-octahydro-inden-5-yl)-acetic acid,
((3αS,5R,7αS)-5-Aminomethyl-octahydro-inden-5-yl)-acetic acid,
((2R,4αR,8αR)-2-Aminomethyl-decahydro-naphthalen-2-yl)-acetic acid,
((2S,4αS,8αR)-2-Aminomethyl-decahydro-naphthalen-2-yl)-acetic acid,
((2S,4αR,8αS)-2-Aminomethyl-decahydro-naphthalen-2-yl)-acetic acid,
((2R,4αS,8αS)-2-Aminomethyl-decahydro-naphthalen-2-yl)-acetic acid,
((2R,4αR,9αR)-2-Aminomethyl-decahydro-benzocyclohepten-2-yl)-acetic acid,
((2S,4αR,9αR)-2-Aminomethyl-decahydro-benzocyclohepten-2-yl)-acetic acid,
((2S,4αS,9αS)-2-Aminomethyl-decahydro-benzocyclohepten-2-yl)-acetic acid, and
((2R,4αS,9αS)-2-Aminomethyl-decahydro-benzocyclohepten-2-yl)-acetic acid.

The following methods relate specifically to the preparation of Example 42, (1α,3α,5α)(3-Aminomethyl-bicyclo[3.2.0]hept-3-yl)-acetic acid.

Method 1

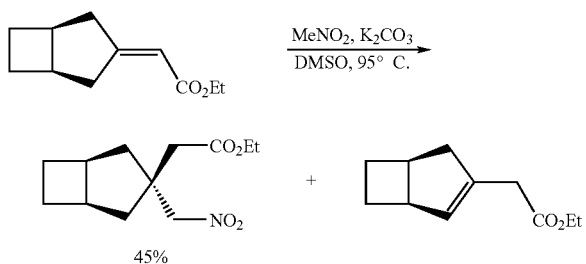

Nitromethane is added to the unsaturated ester in a solvent such as dimethylsulphoxide or N,N-dimethylformamide with a base such as potassium carbonate, sodium carbonate or cesium carbonate, at a temperature of from 0° C. to 120° C. This process achieves higher yields of the nitro ester and reduces the yield of deconjugated ester compared to previous routes.

Method 2A a) An alkyl cyanoacetate, for example ethyl cyanoacetate, is added to a mixture of cyclopentanone of formula (1) in a solvent selected from toluene, benzene, xylenes, or n-heptane to which acetic acid and β-alanine or ammonium acetate, or piperidine are added. The mixture is stirred at a temperature from 0° C. to 150° C. with removal of water by, for example, use of a Dean-Stark trap or activated molecular sieves, to produce the alkene of formula (2);

b) Adding the product of step a) above to a mixture of benzylmagnesium chloride or benzyl magnesium bromide or benzylmagnesium iodide, in a dry solvent selected from tetrahydrofuran, 1,4-dioxane, n-heptane, toluene, diethyl ether, or tert-butyl methyl ether at a temperature from −100° C. to 110° C. to produce the addition product of formula (3);

c) Adding the product of step b) above to a mixture of a base selected from potassium hydroxide, sodium hydroxide, lithium hydroxide, or cesium hydroxide in a solvent selected from ethylene glycol, 2-methoxyethyl ether, 1,4-dioxane, or diethylene glycol and stirring the mixture at a temperature from 25° C. to 250° C. to produce the carboxylic acid of formula (4);

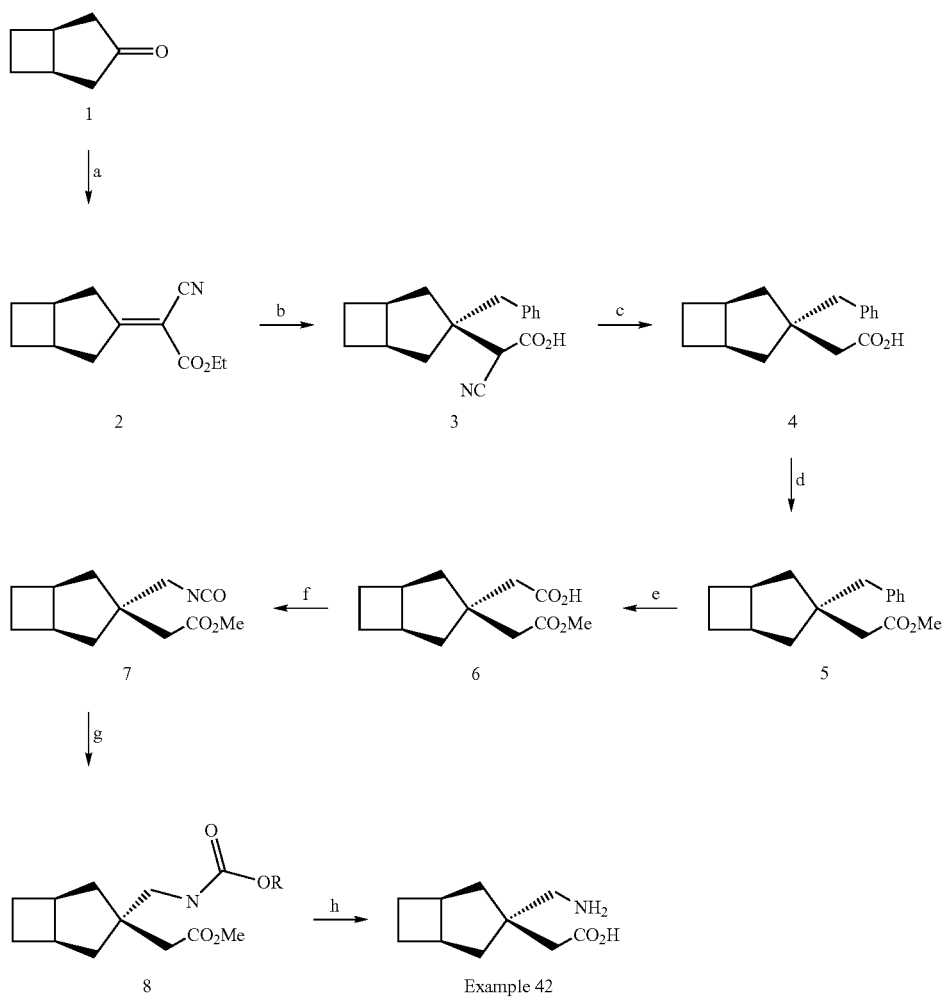

d) Adding the product of step c) above to a mixture of iodomethane in a solvent selected from dichloromethane, chloroform, tetrahydrofuran, toluene, or 1,4-dioxane to which a base such as 1,8-diazabicyclo[5.4.0]undec-7-ene (DBU), triethylamine, or 1,5-diazabicyclo[4.3.0]non-5-ene (DBN) is added and stirred at a temperature from −40° C. to 110° C. to produce the ester of formula (5); or adding the product of step c) above to a mixture of methanol and a concentrated acid such as sulphuric acid or hydrochloric acid at a temperature ranging from 0° C. to 100° C.; or adding the product of step c) above to trimethylsilyldiazomethane and methanol in benzene or toluene at a temperature from −40° C. to 100° C.; or adding the product of step c) above to diazomethane in a solvent such as benzene, toluene, dichloromethane, or diethyl ether at a temperature from −40° C. to 40° C.;

e) Adding the product of step d) above to a mixture of carbon tetrachloride or ethyl acetate and acetonitrile to which water, sodium periodate, and ruthenium (III) chloride are added, and stirred at a temperature from −40° C. to 80° C. to produce carboxylic acid of formula (6);

f) Adding the product of step e) above to a mixture of a base selected from triethylamine or diisopropylethylamine and a solvent selected from toluene, benzene, xylenes, tetrahydrofuran, diethyl ether, or n-heptane to which diphenylphosphoryl azide (DPPA) is added and stirring at a temperature from 0° C. to 150° C. to produce the isocyanate of formula (7); or adding the product of step e) above to ethyl chloroformate or isobutyl chloroformate and a base such as triethylamine or diisopropylethylamine in tetrahydrofuran or acetone or diethyl ether at a temperature of −40° C. to 78° C. followed by addition of sodium azide in water and tetrahydrofuran or acetone followed by addition of toluene or benzene and refluxing; and g) Adding the product of step f) above to a solvent selected from toluene, benzene, xylenes, or n-heptane to which methanol or tert-butanol was added to give (8) and then adding (8) to aqueous hydrochloric acid at a concentration of from 0.01 M to 12 M in the presence or absence of a solvent such as 1,4-dioxane, acetic acid or water to produce the amino acid (9); or adding the product of step f) above to a solvent selected from toluene, benzene, xylenes, or n-heptane to which benzyl alcohol was added to give (8) and then hydrogenating (8) over nickel or palladium or platinum to give lactam which was then hydrolyzed using aqueous hydrochloric acid at a concentration of from 0.01 M to 12 M in the presence or absence of a solvent such as 1,4-dioxane, acetic acid, or water to produce Example 42.

Method 2B

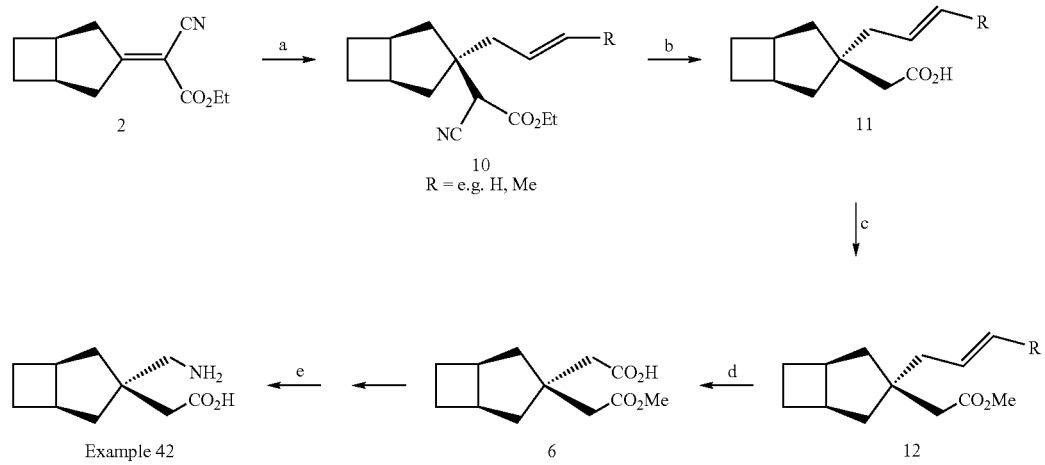

R = e.g. H, Me

Example 42 a) Cyanoester (2) is added to allylmagnesium chloride or bromide or 2-butenylmagnesium chloride in a dry solvent selected from tetrahydrofuran, 1,4-dioxane, n-heptane, toluene, diethyl ether, or tert-butyl methyl ether at a temperature from −100° C. to 110° C. to produce the addition product of formula (10);

b) Adding the product of step a) above to a mixture of a base selected from potassium hydroxide, sodium hydroxide, lithium hydroxide, or cesium hydroxide in a solvent selected from ethylene glycol, 2-methoxyethyl ether, 1,4-dioxane, or diethylene glycol and stirring the mixture at a temperature from 25° C. to 250° C. to produce the carboxylic acid of formula (11);

c) Adding the product of step b) above to a mixture of iodomethane in a solvent selected from dichloromethane, chloroform, tetrahydrofuran, toluene, or 1,4 dioxane to which a base such as 1,8-diazabicyclo[5.4.0]undec-7-ene (DBU), triethylamine, or 1,5-diazabicyclo[4.3.0]non-5-ene (DBN) was added and stirred at a temperature from −40° C. to 110° C. to produce the ester of formula (11); or adding the product of step b) above to a mixture of methanol and a concentrated acid such as sulphuric acid or hydrochloric acid at a temperature ranging from 0° C. to 100° C.; or adding the product of step b) above to trimethylsilyldiazomethane and methanol in benzene or toluene at a temperature from −40° C. to 100° C.; or adding the product of step b) above to diazomethane in a solvent such as benzene, toluene, dichloromethane, or diethyl ether at a temperature from −40° C. to 40° C.; and d) Adding the product of step c) above to a mixture of carbon tetrachloride or ethyl acetate and acetonitrile to which water, sodium periodate, and ruthenium (III) chloride were added, and stirred at a temperature from −40° C. to 80° C. to produce Example 42.

Method 2C d) The product of step c) above is ozonolyzed in a solvent such as chloroform or dichloromethane or methanol followed by addition of a quench such as triphenylphosphine or dimethylsulphide at a temperature from −100° C. to 0° C. to give (16);

e) The product of step d) above in a solvent such as methanol or ethanol was reacted with ammonia solution or ammonia gas followed by reduction using sodium borohydride,

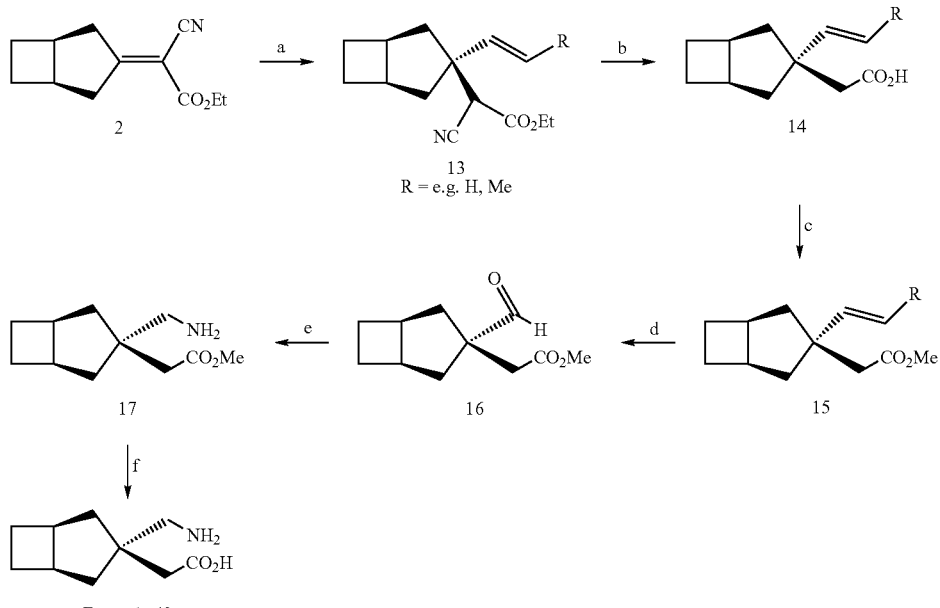

a) An organometallic reagent such as vinyl lithium or vinyl magnesium chloride or bromide in a solvent such as tetrahydrofuran or diethyl ether at a temperature from −100° C. to 0° C. is added to the cyanoester (2) to give (13);

b) Adding the product of step a) above to a mixture of a base selected from potassium hydroxide, sodium hydroxide, lithium hydroxide, or cesium hydroxide in a solvent selected from ethylene glycol, 2-methoxyethyl ether, 1,4-dioxane, or diethylene glycol and stirring the mixture at a temperature from 25° C. to 250° C. to produce the carboxylic acid of formula (14);

c) Adding the product of step b) above to a mixture of iodomethane in a solvent selected from dichloromethane, chloroform, tetrahydrofuran, toluene, or 1,4-dioxane to which a base such as 1,8-diazabicyclo[5.4.0]undec-7-ene (DBU), triethylamine, or 1,5-diazabicyclo[4.3.0]non-5-ene (DBN) is added and stirred at a temperature from −40° C. to 110° C. to produce the ester of formula (15); or adding the product of step b) above to a mixture of methanol and a concentrated acid such as sulphuric acid or hydrochloric acid at a temperature ranging from 0° C. to 100° C.; or adding the product of step b) above to trimethylsilyldiazomethane and methanol in benzene or toluene at a temperature from −40° C. to 100° C.; or adding the product of step b) above to diazomethane in a solvent such as benzene, toluene, dichloromethane, or diethyl ether at a temperature from −40° C. to 40° C.;

sodium cyanoborohydride or sodium triacetoxyborohydride, or by reduction by hydrogenation in the presence of a catalyst such as nickel, palladium, or platinum to give (17); and f) The product of step e) above is hydrolyzed using aqueous hydrochloric acid at a concentration of from 0.01 M to 12 M in the presence or absence of a solvent such as 1,4-dioxane, acetic acid, or water to produce Example 42.

Method 3

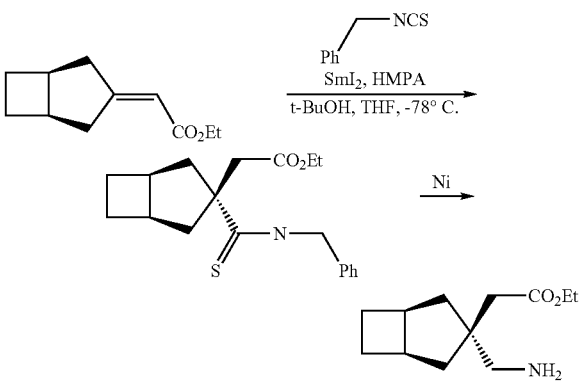

The unsaturated ester and benzyl thioisocyanate is stirred in a solvent mixture made up of tetrahydrofuran, diethyl ether, or 1,4-dioxane, a coordinating solvent such as HMPA or DMPU and an alcohol such as tert-butanol with samarium diiodide at a temperature of −100° C. to 0° C.; the resulting ester is hydrogenated in a solvent such as methanol, ethanol, ethyl acetate using a catalyst such as nickel, palladium, platinum, or rhodium at a temperature from 20° C. to 100° C. to give the amino ester.

Method 4A

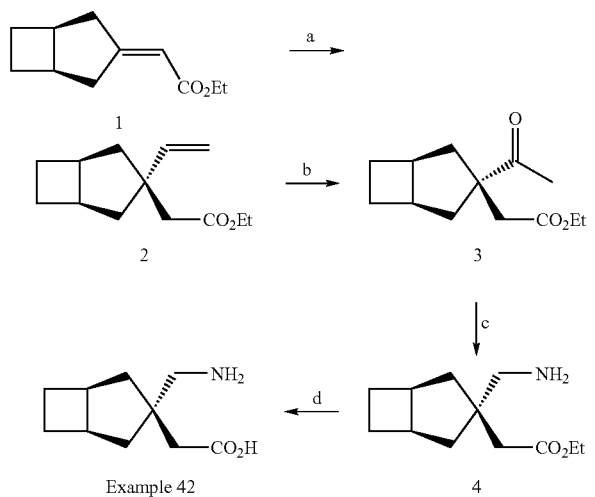

a) An organometallic reagent such as vinyl lithium or vinyl magnesium chloride or bromide is mixed with dimethylzinc, zinc chloride, copper (I) iodide, copper (I) bromide dimethyl sulphide complex, or copper (I) cyanide in the presence of a Lewis acid such as boron trifluoride etherate or aluminum chloride in a solvent such as tetrahydrofuran or diethyl ether at a temperature from −100° C. to 0° C., and the unsaturated ester (1) is added to give addition product (2);

b) The product of step a) above is ozonolyzed in a solvent such as chloroform or dichloromethane or methanol followed by addition of a quench such as triphenylphosphine or dimethylsulphide at a temperature from −100° C. to 0° C. to give (3);

c) The product of step b) above in a solvent such as methanol or ethanol was reacted with ammonia solution or ammonia gas followed by reduction using sodium borohydride, sodium cyanoborohydride or sodium triacetoxyborohydride, or by reduction by hydrogenation in the presence of a catalyst such as nickel, palladium, or platinum to give (4); and d) The product of step c) above is hydrolyzed using aqueous hydrochloric acid at a concentration of from 0.01 M to 12 M in the presence or absence of a solvent such as 1,4-dioxane, acetic acid, or water to produce Example 42.

Method 4B

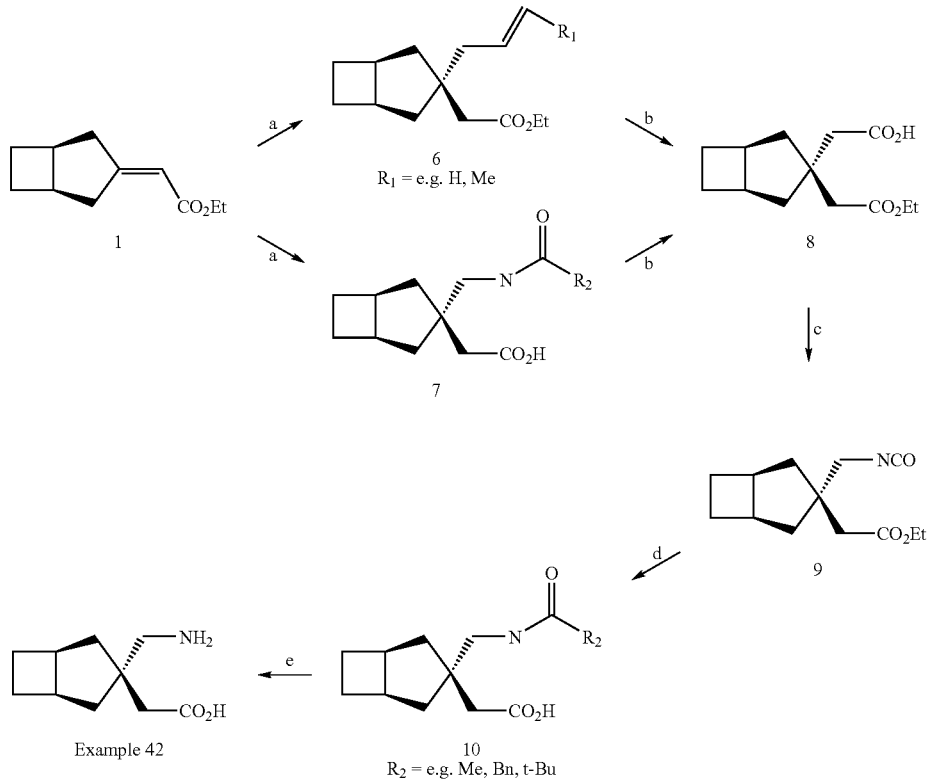

a) An organometallic reagent such as allylmagnesium chloride or bromide is mixed with dimethylzinc, zinc chloride, copper (I) iodide, copper (I) bromide dimethyl sulphide complex, or copper (I) cyanide in the presence of a Lewis acid such as boron trifluoride etherate or aluminum chloride in a solvent such as tetrahydrofuran or diethyl ether at a temperature from −100° C. to 0° C. and the unsaturated ester (1) is added to give addition product (6); or an organometallic reagent such as benzylmagnesium chloride or bromide is mixed with dimethylzinc, zinc chloride, copper (I) iodide, copper (I) bromide dimethyl sulphide complex, or copper (I) cyanide in the presence of a Lewis acid such as boron trifluoride etherate or aluminum chloride in a solvent such as tetrahydrofuran or diethyl ether at a temperature from −100° C. to 0° C., and the unsaturated ester (1) is added to give addition product (7);

b) Adding the product of step a) above to a mixture of carbon tetrachloride or ethyl acetate and acetonitrile to which water, sodium periodate, and ruthenium (III) chloride are added, and stirred at a temperature from −40° C. to 80° C. to produce carboxylic acid of formula (8);

c) Adding the product of step b) above to a mixture of a base selected from triethylamine or diisopropylethylamine and a solvent selected from toluene, benzene, xylenes, tetrahydrofuran, diethyl ether, or n-heptane to which diphenylphosphoryl azide (DPPA) is added and stirring at a temperature from 0° C. to 150° C. to produce the isocyanate of formula (9); or adding the product of step b) above to ethyl chloroformate or isobutyl chloroformate and a base such as triethylamine or diisopropylethylamine in tetrahydrofuran or acetone or diethyl ether at a temperature of −40° C. to 78° C. followed by addition of sodium azide in water and tetrahydrofuran or acetone followed by addition of toluene or benzene and refluxing;

d) Adding the product of step c) above to a solvent selected from toluene, benzene, xylenes, or n-heptane to which methanol or tert-butanol was added to give (10) and then adding (10) to aqueous hydrochloric acid at a concentration of from 0.01 M to 12 M in the presence or absence of a solvent such as 1,4-dioxane, acetic acid, or water to produce the amino acid (5); or adding the product of step c) above to a solvent selected from toluene, benzene, xylenes, or n-heptane to which benzyl alcohol was added to give (10) and then hydrogenating (10) over nickel or palladium or platinum to give lactam which was then hydrolyzed using aqueous hydrochloric acid at a concentration of from 0.01 M to 12 M in the presence or absence of a solvent such as 1,4-dioxane, acetic acid, or water to produce Example 42.

Method 5

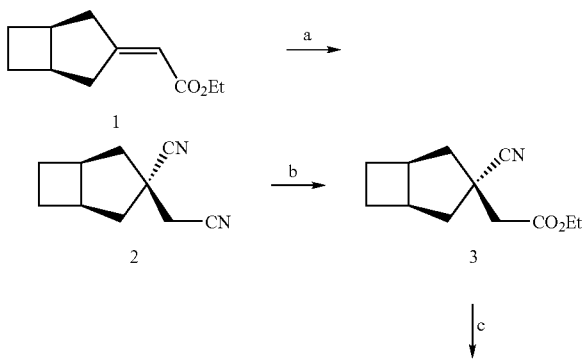

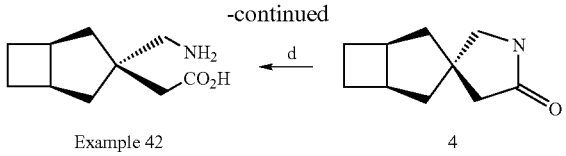

Example 42    4 a) Compound (1) and potassium cyanide or sodium cyanide and water and ethanol or methanol are refluxed together with removal of water by, for example, use of a Dean-Stark trap to give (2);

b) The product of step a) is stirred with ethanol or toluene or benzene, and the solution is saturated with gaseous hydrochloric acid at a temperature from −30° C. to 40° C. to give (3);

c) The product of step b) above is hydrogenated in methanol, ethanol, or ethyl acetate using a catalyst such as nickel, palladium, platinum, or rhodium at a temperature from 15° C. to 60° C. to give (4); and d) The product of step c) above is hydrolyzed using aqueous hydrochloric acid at a concentration of from 0.01 M to 12 M in the presence or absence of a solvent such as 1,4-dioxane, acetic acid, or water to produce Example 42.

The following examples illustrate the invention pharmaceutical compositions containing a tinnitus treating effective amount of an alpha2delta ligand, and a pharmaceutically acceptable carrier, diluent, or excipient. The examples are representative only, and are not to be construed as limiting the invention in any respect.

FORMULATION EXAMPLE 1

| Tablet Formulation: | |
| --- | --- |
| Ingredient | Amount (mg) |
| 3-(1-aminomethyl-cyclohexylmethyl)-4H-[1,2,4]oxadiazol-5-one hydrochloride | 25 |
| Lactose | 50 |
| Cornstarch (for mix) | 10 |
| Cornstarch (paste) | 10 |
| Magnesium stearate (1%) | 5 |
| Total | 100 |

3-(1-Aminomethyl-cyclohexylmethyl)-4H-[1,2,4]oxadiazol-5-one hydrochloride, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of tinnitus.

FORMULATION EXAMPLE 2

Coated Tablets:

The tablets of Formulation Example 1 are coated in a customary manner with a coating of sucrose, potato starch, talc, tragacanth, and colorant.

FORMULATION EXAMPLE 3

Injection vials:

The pH of a solution of 500 g of gabapentin and 5 g of disodium hydrogen phosphate is adjusted to pH 6.5 in 3 L of double-distilled water using 2 M hydrochloric acid. The solution is sterile filtered, and the filtrate is filled into injection vials, lyophilized under sterile conditions, and aseptically sealed. Each injection vial contains 25 mg of gabapentin.

FORMULATION EXAMPLE 4

Suppositories:

A mixture of 25 g of (1α,3α,5α)(3-aminomethyl-bicyclo[3.2.0]hept-3-yl)-acetic acid hydrochloride, 100 g of soya lecithin, and 1400 g of cocoa butter is fused, poured into molds, and allowed to cool. Each suppository contains 25 mg of (1α,3α,5α)(3-aminomethyl-bicyclo[3.2.0]hept-3-yl)-acetic acid hydrochloride.

FORMULATION EXAMPLE 5

Solution:

A solution is prepared from 1 g of 3-(2-aminomethyl-4-methyl-pentyl)-4H-[1,2,4]-oxadiazol-5-one hydrochloride, 9.38 g of $NaH_2PO_4.12H_2O$, 28.48 g of $Na_2HPO_4.12H_2O$, and 0.1 g of benzalkonium chloride in 940 mL of double-distilled water. The pH of the solution is adjusted to pH 6.8 using 2 M hydrochloric acid. The solution is diluted to 1.0 L with double-distilled water, and sterilized by irradiation. A 25 mL volume of the solution contains 25 mg of 3-(2-aminomethyl-4-methyl-pentyl)-4H-[1,2,4]-oxadiazol-5-one hydrochloride.

FORMULATION EXAMPLE 6

Ointment:

500 mg of 3-(1-aminomethyl-cycloheptylmethyl)-4H-[1,2,4]oxadiazol-5-one hydrochloride is mixed with 99.5 g of petroleum jelly under aseptic conditions. A 5 g portion of the ointment contains 25 mg of 3-(1-aminomethyl-cycloheptylmethyl)-4H-[1,2,4]oxadiazol-5-one hydrochloride.

FORMULATION EXAMPLE 7

Capsules:

2 kg of 3-(1-aminomethyl-cyclohexylmethyl)-4H-[1,2,4]oxadiazol-5-one hydrochloride are filled into hard gelatin capsules in a customary manner such that each capsule contains 25 mg of 3-(1-aminomethyl-cyclohexylmethyl)-4H-[1,2,4]oxadiazol-5-one hydrochloride.

FORMULATION EXAMPLE 8

Ampoules:

A solution of 2.5 kg of gabapentin is dissolved in 60 L of double-distilled water. The solution is sterile filtered, and the filtrate is filled into ampoules. The ampoules are lyophilized under sterile conditions and aseptically sealed. Each ampoule contains 25 mg of gabapentin.

As shown above, the invention method offers a distsinct advantage over existing treatments for diseases that comprise tinnitus, wherein the existing treatments modify pain or secondary symptoms, but do not show a disease modifying effect. The effectiveness of gabapentin, 3-(1-aminomethyl-cyclohexylmethyl)-4H-[1,2,4]oxadiazol-5-one hydrochloride, 3-(2-aminomethyl-4-methyl-pentyl)-4H-[1,2,4]oxadiazol-5-one hydrochloride, 3-(1-aminomethyl-cycloheptylmethyl)-4H-[1,2,4]oxadiazol-5-one hydrochloride, 3-(2-amino-1-cyclopentyl-ethyl)-4H-[1,2,4]oxadiazol-5-one hydrochloride, or (1α,3α,5α)(3-aminomethyl-bicyclo[3.2.0]hept-3-yl)-acetic acid hydrochloride in MIA Rat indicate that alpha2delta ligands are useful for preventing or treating tinnitus.

Having described the invention method, various embodiments of the invention are hereupon claimed.

What is claimed is:

1. A method of treating tinnitus in a mammal suffering therefrom, comprising administering a therapeutically effective amount of an alpha2delta ligand selected from
   - 3-Aminomethyl-5-methyl-octanoic acid;
   - (3S,5R)-3-Aminomethyl-5-methyl-octanoic acid;
   - (1α,3β,5α)(3-Aminomethyl-bicyclo[3.2.0]hept-3-yl)-acetic acid;
   - (1α,3α,5α)(3-Aminomethyl-bicyclo[3.2.0.]hept-3-yl)-acetic acid hydrochloride; and
   - (S,S)-(1-aminomethyl-3,4-dimethyl-cyclopentyl)-acetic acid or pharmaceutically acceptable salts thereof.

2. A method of treating tinnitus in a mammal comprising administering a pharmaceutical composition comprising a therapeutically effective amount of a compound selected from
   - 3-Aminomethyl-5-methyl-octanoic acid;
   - (3S,5R)-3-Aminomethyl-5-methyl-octanoic acid;
   - (1α,3β,5α)(3-Aminomethyl-bicyclo[3.2.0]hept-3-yl)-acetic acid;
   - (1α,3α,5α)(3-Aminomethyl-bicyclo[3.2.0.]hept-3-yl)-acetic acid hydrochloride; and
   - (S,S)-(1-aminomethyl-3,4-dimethyl-cyclopentyl)-acetic acid
   - or a pharmaceutically acceptable salt thereof, and a pharmaceutically acceptable carrier, diluent, or excipient.

* * * * *